United States Patent
Liang et al.

(10) Patent No.: US 10,973,882 B2
(45) Date of Patent: Apr. 13, 2021

(54) METHODS FOR REDUCING SEVERITY OF PULMONARY FIBROSIS

(71) Applicant: CEDARS-SINAI MEDICAL CENTER, Los Angeles, CA (US)

(72) Inventors: Carol Jiurong Liang, Encino, CA (US); Dianhua Jiang, Encino, CA (US); Paul W. Noble, Beverly Hills, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 149 days.

(21) Appl. No.: 16/150,379

(22) Filed: Oct. 3, 2018

(65) Prior Publication Data

US 2019/0099471 A1 Apr. 4, 2019

Related U.S. Application Data

(60) Provisional application No. 62/567,495, filed on Oct. 3, 2017.

(51) Int. Cl.
| | | |
|---|---|---|
| *A61K 38/20* | (2006.01) | |
| *A61K 31/728* | (2006.01) | |
| *A61K 45/06* | (2006.01) | |
| *A61P 11/00* | (2006.01) | |
| *C07K 14/54* | (2006.01) | |

(52) U.S. Cl.
CPC .......... *A61K 38/204* (2013.01); *A61K 31/728* (2013.01); *A61K 45/06* (2013.01); *A61P 11/00* (2018.01); *C07K 14/5412* (2013.01)

(58) Field of Classification Search
None
See application file for complete search history.

(56) References Cited

U.S. PATENT DOCUMENTS

| | | |
|---|---|---|
| 2015/0210769 A1 | 7/2015 | Freeman et al. |
| 2017/0247456 A1 | 8/2017 | Freeman et al. |

FOREIGN PATENT DOCUMENTS

| | | |
|---|---|---|
| WO | 2016/092082 A1 | 6/2016 |
| WO | 2017/053952 A1 | 3/2017 |

OTHER PUBLICATIONS

Lauer et al, International Journal of Cell Biology, vol. 2015, Article ID 712507, 15 pages.*
O Cantor, International Journal of COPD, 2007, vol. 3, No. 3, pp. 283-288.*
Lennon etal, The American Journal of Physiology-Lung Cellular and Molecular Physiology, 201, vol. 301, No. 2, p. L137-L147.*
Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
Moeller et al, The International Journal of Biochemistry & Cell Biology; 2008; 40(3): 362-382.*
Kobayashi etal, Respiratory Research; 2015; vol. 16:99, pp. 1-14.*
Abe, R., et al. Peripheral Blood Fibrocytes: Differentiation Pathway and Migration to Wound Sites. J Immunol. Jun. 15, 2001; 166(12): 7556-62.
Abreu, M.T. et al. Decreased expression of Toll-like receptor 4 and MD-2 correlates with intestinal epithelial cell protection against dysregulated proinflammatory gene expression in response to bacterial lipopolysaccharide. J. Immunol. 167,1609-1616 (2001).
Acharya, P.S., et al., Fibroblast migration is mediated by CD44-dependent TGF beta activation. J Cell Sci. May 1, 2008; 121(Pt 9): 1393-402.
Ahn, M-H., et al. A promoter Snp rs4073T>A in the common allele of the interleukin 8 gene is associated with the development of idiopathic pulmonary fibrosis via the IL-8 protein enhancing mode. Respir Res. Jun. 8, 2011; 12:73.
Alberts et al. Molecular Biology of the Cell. 4th Ed. New York: Garland Science; 2002. Fibroblasts and Their Transformations: The Connective-Tissue Cell Family, 1300-1301.
Alder, J.K. et al. Telomere dysfunction causes alveolar stem cell failure. Proc. Natl. Acad. Sci. USA 112, 5099-5104 (2015).
Alvarez, D. F., et al. Lung microvascular endothelium is enriched with progenitor cells that exhibit vasculogenic capacity. Am J Physiol Lung Cell Mol Physiol. 2008; 294: L419-30.
American Thoracic Society. Idiopathic pulmonary fibrosis: diagnosis and treatment. International consensus statement. The joint statement of American Thoracic Society (ATS) and the European Respiratory Society (ERS). Am. J. Respir. Crit. Care Med. 161, 646-664 (2000).
Amin, R.S. et al. Surfactant protein deficiency in familial interstitial lung disease. J. Pediatr. 139, 85-92 (2001).
Andersson-Sjoland, A., et al. Fibrocytes are a potential source of lung fibroblasts in idiopathic pulmonary fibrosis. Int J Biochem Cell Biol. 2008; 40(10) 2129-40.
Arch, R., et al. Participation in normal immune responses of a metastasis-inducing splice variant of CD44. Science. Jul. 31, 1992; 257(5070): 682-5.
Armanios, M.Y., et al. Telomerase Mutations in Families with Idiopathic Pulmonary Fibrosis. N Engl J Med. Mar. 29, 2007; 356(13): 1317-26.

(Continued)

*Primary Examiner* — Bridget E Bunner
*Assistant Examiner* — Fozia M Hamud
(74) *Attorney, Agent, or Firm* — McCarter & English, LLP; Beverly W. Lubit

(57) ABSTRACT

The described invention provides a method of treating a lung injury at risk of progressing to a fibrotic lung disease in a subject in need thereof comprising administering to the subject a composition comprising a therapeutic amount of IL-6 polypeptide, hyaluronan (HA), mimetics thereof, pharmaceutically acceptable salts thereof, or combinations thereof, wherein the therapeutic amount is effective to increase renewal of alveolar epithelial cell 2 (AEC2) stem cells, to repair the injury, to reduce lung fibrosis, or a combination thereof.

18 Claims, 46 Drawing Sheets
(6 of 46 Drawing Sheet(s) Filed in Color)

Specification includes a Sequence Listing.

(56) References Cited

OTHER PUBLICATIONS

Armstrong, L. et al. Expression of functional toll-like receptor-2 and -4 on alveolar epithelial cells. Am. J. Respir. Cell Mol. Biol. 31, 241-245 (2004).
Arora, R., et al. Multiple Roles and Interactions of Tbx4 and Tbx5 in Development of the Respiratory System. PLoS Genet 8(8): e1002866. doi:10.1371/journal.pgen.1002866 (2012).
Baarsma, H.A., et al. Activation of WNT/b-Catenin Signaling in Pulmonary Fibroblasts by TGF-b1 Is Increased in Chronic Obstructive Pulmonary Disease. PLoS One. 2011; 6(9): e25450.
Balasubramaniam, V., et al. Bone marrow-derived angiogenic cells restore lung alveolar and vascular structure after neonatal hyperoxia in infant mice. Am J Physiol Lung Cell Mol Physiol. 2010; 298: L315-L323.
Balestrini, J.L, et al. The mechanical memory of lung myofibroblastswz. Integr Biol (Camb). Apr. 2012; 4(4): 410-21.
Barkauskas, C. E., et al. Cellular Mechanisms of Tissue Fibrosis. 7. New insights into the cellular mechanisms of pulmonary fibrosis. Am J Physiol Cell Physiol. Jun. 1, 2014; 306(11): C987-96.
Barkauskas, C.E. et al. Type 2 alveolar cells are stem cells in adult lung. J. Clin. Invest. 123, 3025-3036 (2013).
Bellusci, S., et al. Fibroblast Growth Factor 10 (FGF10) and branching morphogenesis in the embryonic mouse lung. Development. Dec. 1997; 124(23): 4867-78.
Berge,SM, et al., "Pharmaceutical Salts," J Pharm Sci, 66: 1-19 (1977).
Bjermer, L., et al. Hyaluronan and type III procollagen peptide concentrations in bronchoalveolar lavage fluid in idiopathic pulmonary fibrosis. Thorax. Feb. 1989; 44(2): 126-31.
Bolaños et al., Role of Sonic Hedgehog in Idiopathic Pulmonary Fibrosis, Am J Physiol Lung Cell Mol Physiol 303, Sep. 28, 2012, 978-990.
Bournazos, S., et al. Fcy Receptor IIIb (CD16b) Polymorphisms are Associated with Susceptibility to Idiopathic Pulmonary Fibrosis. Lung. Dec. 2010; 188(6): 475-81.
Bujak, M., et al. The role of Interleukin-1 in the pathogenesis of heart disease. Arch Immulon Ther Exp (Warsz). May-Jun. 2009; 57(3): 165-76.
Camenisch, T.D., et al. Disruption of hyaluronan synthase-2 abrogates normal cardiac morphogenesis and hyaluronan-mediated transformation of epithelium to mesenchyme. J Clin Invest. Aug. 2000; 106(3): 349-60.
Cao, Z. et al. Targeting of the pulmonary capillary vascular niche promotes lung alveolar repair and ameliorates fibrosis. Nat. Med. 22, 154-162 (2016).
Chambers, R.C. Abnormal wound healing responses in pulmonary fibrosis: focus on coagulation signalling. Eur Respir Rev. 2008; 17(109): 130-137.
Chamoto, K., et al. CD341 Progenitor to Endothelial Cell Transition in Post Pneumonectomy Angiogenesis. Am J Respir Cell Mol Biol. Mar. 2012; 46(3): 283-9.
Chang, J.T. et al. Gather: a systems approach to interpreting genomic signatures. Bioinformatics. 2006; 22(23): 2926-33.
Chapman, H.A. et al. Integrin ?6?4 identifies an adult distal lung epithelial population with regenerative potential in mice. J. Clin. Invest. 121, 2855-2862 (2011).
Checa, M., et al. MMP-1 polymorphisms and the risk of idiopathic pulmonary fibrosis. Hum Genet. Dec. 2008; 124(5): 465-72.
Chen, H. et al. Airway epithelial progenitors are region specific and show differential responses to bleomycin-induced lung injury. Stem Cells 30, 1948-1960 (2012).
Then, J-H., et al. Beta-Catenin Mediates Mechanically Regulated, Transforming Growth Factor-beta1-Induced Myofibroblast Differentiation of Aortic Valve Interstitial Cells. Arterioscler Thromb Vasc Biol. Mar. 2011; 31(3): 590-7.
Cherng, S., et al. Alpha-Smooth Muscle Actin (?-SMA) . J Am Sci. 2008: 4(4): 7-9.
Chiaramonte, M.G., An IL-13 inhibitor blocks the development of hepatic fibrosis during a T-helper type 2-dominated inflammatory response et al. J Clin Invest. Sep. 1999; 104(6): 777-85.

Chiaramonte, M.G., et al. Regulation and function of the interleukin 13 receptor a2 during a T helper cell type 2- dominant immune response J Exp Med. Mar. 17, 2003; 197(6): 687-701.
Chilosi et al, Migratory marker expression in fibroblast foci of idiopathic pulmonary fibrosis, Respiratory Research Biomed Central LTD, London, GB 7:1 2006.
Chilosi, M., et al. Aberrant Wnt/beta-Catenin Pathway Activation in Idiopathic Pulmonary Fibrosis. Am J Pathol. May 2003; 162(5): 1495-502.
Cho, C. Y., et al., Dressing the Part. Dermatol Clin. Jan. 1998; 16(1): 25-47.
Chung, KF, "Cytokines as targets in chronic obstructive pulmonary disease," (2006) Curr. Drug Targets 7: 675-81.
Chung, M.P. et al. Role of Repeated Lung Injury and Genetic Background in Bleomycin-Induced Fibrosis. Am J Respir Cell Mol Biol. Sep. 2003; 29(3 Pt 1): 375-80.
Chunn, J. L. et al. Partially adenosine deaminase-deficient mice develop pulmonary fibrosis in association with adenosine elevations. Am J Physiol Lung Cell Mol Physiol. Mar. 2006; 290(3): L579-87.
Collard, H,.R., et al. Changes in Clinical and Physiologic Variables Predict Survival in Idiopathic Pulmonary Fibrosis. Am J Respir Crit Care Med. Sep. 1, 2003; 168(5): 538-42.
Collard, H.R., et al. Acute Exacerbations of Idiopathic Pulmonary Fibrosis. Am J Respir Crit Care Med. Oct. 1, 2007; 176(7): 636-43.
Collard, H.R., et al. Plasma biomarker profiles in acute exacerbation of idiopathic pulmonary fibrosis. Am J Physiol Lung Cell Mol Physiol. Jul. 2010; 299(1): L3-7.
Cortez, D.M., et al. IL-17 stimulates MMP-1 expression in primary human cardiac fibroblasts via p38 MAPK- and ERK1/2-dependent C/EBP-beta , NF-kappaB, and AP-1 activation. Am J Physiol Heart Circ Physiol. Dec. 2007; 293(6): H3356-65.
Crivellato, E. The role of angiogenic growth factors in organogenesis. Int J Dev Biol. 2011; 55(4-5): 365-75.
Cronkhite, J.T., et al. Telomere Shortening in Familial and Sporadic Pulmonary Fibrosis. Am J Respir Crit Care Med. Oct. 1, 2008; 178(7): 729-37.
Darby, I., et al. a-Smooth muscle actin is transiently expressed by myofibroblasts during experimental wound healing Lab Invest. Jul. 1990; 63(1): 21-29.
Darby, I.A., et al. Fibroblasts and myofibroblasts in wound healing. Clin Cosmet Investig Dermatol. 2014; 7: 301-11.
De Langhe, S. P., et al. Levels of mesenchymal FGFR2 signaling modulate smooth muscle progenitor cell commitment in the lung. Dev Biol. Nov. 1, 2006; 299(1): 52-62.
De Wever, O., et al. Role of tissue stroma in cancer cell invasion. J Pathol. Jul. 2003; 200(4): 429-447.
Degrendele, H.C., et al. Requirement for CD44 in Activated T Cell Extravasation into an Inflammatory Site. Science. Oct. 24, 1997; 278(5338): 672-5.
Degryse, A.L., et al. Repetitive intratracheal bleomycin models several features of idiopathic pulmonary fibrosis. Am J Physiol Lung Cell Mol Physiol. Oct. 2010; 299(4): L442-52.
Desai, T.J., et al. Alveolar progenitor and stem cells in lung development, renewal and cancer. Nature 507, 190-194 (2014).
Desmouliere, A., et al. Apoptosis Mediates the Decrease in Cellularity during the Transition between Granulation Tissue and Scar. Am J Pathol. Jan. 1995; 146(1): 56-66.
Ding, B., et al. Endothelial-Derived Angiocrine Signals Induce and Sustain Regenerative Lung Alveolarization. Cell. Oct. 28, 2011; 147(3): 539-53.
Dong, Y. et al. Blocking follistatin-like 1 attenuates bleomycin-induced pulmonary fibrosis in mice. J. Exp. Med. 212, 235-252 (2015).
Dulauroy, S. et al. Lineage tracing and genetic ablation of ADAM12+ perivascular cells identify a major source of profibrotic cells during acute tissue injury. Nat Med. Aug. 2012; 18(8): 1262-70.
Duong, H., et al. Pro-angiogenic Hematopoietic Progenitor Cells and Endothelial Colony Forming Cells in Pathological Angiogenesis of Bronchial and Pulmonary Circulation. Angiogenesis. 2011; 14(4): 411-22.

(56) References Cited

OTHER PUBLICATIONS

Eblaghie, M.C., et al. Evidence that autocrine signaling through Bmpr1a regulates the proliferation, survival and morphogeneticorphogenetic behavior of distal lung epithelial cells. Dev. Biol. 291, 67-82 (2006).

Fan, J et al. Interleukin-1 induces tubular epithelial-myofibroblast transdifferentiation through a transforming growth factor-betal-dependent mechanism in vitro. Am J Kidney Dis. Apr. 2001; 37(4): 820-31.

Flaherty, K.R., et al. Prognostic Implications of Physiologic and Radiographic Changes in Idiopathic Interstitial PneumoniaAm J Respir Crit Care Med. Sep. 1, 2003; 168(5): 543-8.

Fox, C., Drug Delivery & Development. Reversing Idiopathic Pulmonary Fibrosis. http://www.dddmag.com/news/2014/10/reversing-idiopathic-pulmonary-fibrosis, Oct. 15, 2014; downloaded from internet Aug. 15, 2018.

Franzdottir, S.R., et al. Airway branching morphogenesis in three dimensional culture. Respir Res. 2010; 11: 162.

Friedler, A. et al. (2000) Development of a Functional Backbone Cyclic Mimetic of the HIV-1 Tat Arginine-rich Motif. J. Biol. Chem. 275:23783-23789.

Friedman, S.L. Fibrogenic cell reversion underlies fibrosis regression in liver. Proc Natl Acad Sci USA. Jun. 12, 2012; 109(24): 9230-9231.

Fukata, M. et al. Cox-2 is regulated by Toll-like receptor 4 (TLR4) signaling: role in proliferation and apoptosis in the Intestine. Gastroenterology 131, 862-877 (2006).

Fukuda, Y., et al. Patterns of Pulmonary Structural Remodeling After Experimental Paraquat Toxicity. Am J Pathol. Mar. 1985; 118(3): 452-75.

Furuhashi, K.,et al., Increased expression of YKL-40, a chitinase-like protein, in serum and lung of patients with idiopathic pulmonary fibrosis. Respir Med. Aug. 2010; 104(8): 1204-10.

Gangadharan, B. et al. Murine gammaherpesvirus-induced fibrosis is associated with the development of alternatively activated macrophages. J Leukoc Biol. Jul. 2008; 84(1): 50-8.

Garcia, C.K. Idiopathic pulmonary fibrosis: update on genetic discoveries. Proc. Am. Thorac. Soc. 8, 158-162 (2011).

Gasse, P., et al. IL-1 and IL-23 Mediate Early IL-17A Production in Pulmonary Inflammation Leading to Late Fibrosis. PLoS One. 2011; 6(8): e23185.

Gasse P. et al. IL-1R1/MyD88 signaling and the inflammasome are essential in pulmonary inflammation and fibrosis in mice. J Clin Invest. Dec. 2007; 117(12): 3786-99.

Giangreco, A., et al. Molecular phenotype of airway side population cells. Am J Physiol Lung Cell Mol Physiol. 2004; 286: L624-30.

Giannone, G., et al. Substrate rigidity and force define form through tyrosine phosphatase and kinase pathways. Trends Cell Biol. Apr. 2006; 16(4): 213-23.

Gilani, S. R., et al. CD28 Down-Regulation on Circulating CD4 T-Cells Is Associated with Poor Prognoses of Patients with Idiopathic Pulmonary Fibrosis. PLoS One. Jan. 29, 2010; 5(1): e8959.

Gilbert, H.S. Myelofibrosis revisited: characterization and classification of myelofibrosis in the selling of myeloproliferative disease. Prog Clin Biol Res. 1984; 154: 3-17 (Abstract).

Goldstein R., et al., Failure of mechanical properties to parallel changes in lung connective tissue composition in bleomycin-induced pulmonary fibrosis in hamsters. Am Rev Respir Dis., 120(1):67-73, 1979.

Gonzalez, R.F., et al. HTII-280, a biomarker specific to the apical plasma membrane of human lung alveolar type II cells. J. Histochem. Cytochern. 58, 891-901 (2010).

Goodman & Gilman's The Pharmacological Basis of Therapeutics, Ed. Joel G. Hardman, Lee E. Limbird, Eds., 10th Ed., McGraw Hill, New York (2001), P. 25, 50.

Greene, K.E., et al. Serum surfactant proteins-A and -D as biomarkers in idiopathic pulmonary fibrosis. Eur Respir J. Mar. 2002; 19(3): 439-46.

Grutz, G. "New Insights into the molecular mechanism of interleukin-10 mediated immunosuppression". J. Leukocyte Biol. 77: 3-15 (2005).

Guzy, R.D. et al. Fibroblast growth factor 2 is required for epithelial recovery, but not for pulmonary fibrosis, in response to bleomycin. Am. J. Respir. Cell Mol. Biol. 52, 116-128 (2015).

Habif, TP. Dermatologic surgical procedures. In: Clinic Dermatology: A Color Guide to Diagnosis and Therapy. 3rd ed. 1996. Chapter 27, 808-810.

Harari, S., et al. IPF: new insight on pathogenesis and treatment. Allergy. May 2010; 65(5):537-53.

Hashimoto, N., et al. Bone marrow-derived progenitor cells in pulmonary fibrosis. J Clin Invest. Jan. 2004; 113(2): 243-52.

Hashimoto, N., et al. Endothelial-Mesenchymal Transition in Bleomycin-Induced Pulmonary Fibrosis. Am J Respir Cell Mol Biol. Aug. 2010; 43(2): 161-72.

He, W., et al. Matrix Metalloproteinase-7 as a Surrogate Marker Predicts Renal Wntlb-Catenin Activity in CKD. J Am Soc Nephrol. Feb. 2012; 23(2): 294-304.

Hecker L et al., NADPH Oxidase-4 Mediates Myofibroblast Activation and Fibrogenic Responses to Lung Injury. Nat Med., 15(9):1077-81, 2009.

Hegab, A. E., et al. Isolation and Characterization of Murine Multipotent Lung Stem Cells. Stem Cells Dev. 2010; 19: 523-36.

Heise, R. L., et al. Mechanical Stretch Induces Epithelial-Mesenchymal Transition in Alveolar Epithelia via Hyaluronan Activation of Innate Immunity. J Biol Chem. May 20, 2011; 286(20): 17435-44.

Hinz, B. Formation and Function of the Myofibroblast during Tissue Repair. J Invest Dermatol. Mar. 2007; 127(3): 526-37.

Hinz, B. Tissue stiffness, latent TGF-beta1 activation, and mechanical signal transduction: implications for the pathogenesis and treatment of fibrosis. Curr Rheumatol Rep. Apr. 2009; 11(2): 120-6.

Hinz, B., et al. Alpha-Smooth Muscle Actin Expression Upregulates Fibroblast Contractile Activity. Mol Biol Cell. Sep. 2001; 12(9): 2730-41.

Hinz, B., et al. Biological Perspectives the Myofibroblast One Function, Multiple Origins. Am J Pathol. Jun. 2007; 170(6): 1807-16.

Hinz, B., et al. Myofibroblast Development Is Characterized by Specific Cell-Cell Adherens Junctions. Mol Biol Cell. Sep. 2004; 15(9): 4310-20.

Hinz, B., Masters and servants of the force: The role of matrix adhesions in myofibroblast force perception and transmission. EurJ Cell Biol. Apr. 2006; 85(3-4): 175-181.

Hirano, T. et al, "Roles of STAT3 in mediating the cell growth, differentiation and survival signals relayed through the IL-6 family of cytokine receptors" (2000) Oncogene 19: 2548-56.

Schrier D. et al., The Role of Strain Variation in Murine Bleomycin-Induced Pulmonary Fibrosis. Am Rev Respir Dis., 127(1):63-6,1983.

Seibold, M.A., et al. A Common MUC5B Promoter Polymorphism and Pulmonary Fibrosis. N Engl J Med. Apr. 21, 2011; 364(16): 1503-12.

Selman, M. & Pardo, A. Idiopathic pulmonary fibrosis: an epithelial/fibroblastic cross-talk disorder. Respir Res. 2002; 3: 3.

Selman, M. et al. Idiopathic pulmonary fibrosis: pathogenesis and therapeutic approaches. Drugs 64, 405-430 (2004).

Senftleben, U et al., "Activation by IKKalpha of a second, evolutionary conserved, NF?B signaling pathway," (2001) Science 293: 1495-99.

Shan, L., et al. Centrifugal Migration of Mesenchymal Cells in Embryonic Lung. Dev Dyn. 2008; 237: 750-5.

Shannon, JM. and Deterding RR. Epithelial-mesenchymal interactions in lung development. In: Lung Growth and Development, (ed. JA McDonald) vol. 100, New York: Marcel Dekker Inc, 1997, pp. 81-118.

Shao, D.D., et al. Pivotal Advance: Th-1 cytokines inhibit, and Th-2 cytokines promote fibrocyte differentiation. J Leukoc Biol. Jun. 2008; 83(6): 1323-33.

Siegelman, M.H., et al. Activation and interaction of CD44 and hyaluronan in immunological systems. J Leukoc Biol. Aug. 1999; 66(2): 315-21.

(56) References Cited

OTHER PUBLICATIONS

Smith, M. et al. Usual interstitial pneumonia-pattern fibrosis in surgical lung biopsies. Clinical, radiological and histopathological clues to aetiology.J Clin Pathol. Oct. 2013; 66(1): 896-903.

Snider, G. et al., Chronic Interstitial Pulmonary Fibrosis Produced in Hamsters by Endotracheal Bleomycin—Lung Volumes, Volume-Pressure Relations, Carbon Monoxide Uptake, and Arterial Blood Gas Studies. Am Rev Respir Dis. 117: 289-297, 1978.

Song, J. W., et al. Acute Exacerbation of Idiopathic Pulmonary Fibrosis: Incidence, Risk Factors, and Outcome. Eur Respir J.; Feb. 2011; 37(2): 356-63.

Starcher B. et al., Increased elastin and collagen content in the lungs of hamsters receiving an intratracheal injection of bleomycin. Am Rev Respir Dis., 117(2):299-305, 1978.

Strunk, R.C., et al. Pulmonary Alveolar Type 11 Epithelial Cells Synthesize and Secrete Proteins of the Classical and Alternative Complement Pathways. J. Clin. Invest. 1988; 81: 1419-1426.

Suganuma, H., et al. Enhanced migration of fibroblasts derived from lungs with fibrotic lesions. Thorax. Sep. 1995; 50(9): 984-9.

Summer, R., et al. Isolation of an Adult Mouse Lung Mesenchymal Progenitor Cell Population. Am J Respir Cell Mol Biol. 2007; 37: 152-9.

Suzuki, T. et al., CD24 Induces Apoptosis in Human B Cells Via the Glycolipid-Enriched Membrane Domains/Rafts-Mediated Signaling System. J. Immunol. (2001) 166: 5567-77.

Tadokoro, T. et al. IL-6-STAT3 promotes regeneration of airway ciliated cells from basal stem cells. Proc. Natl. Acad. Sci. USA 111, E3641-E3649 (2014).

Takeda, K. et al, "Tageted disruption of the mouse Stat3 gene3 leads to early embryonic lethality," (1997) Proc. Natl Acad. Sci. USA 94: 3801-3804.

Takeuchi, JK et al. Tbx5 and Tbx4 genes determine the wing/leg identityof limb buds. Nature. Apr. 29, 1999; 398: 810-814.

Takeuchi, O. et al. Differential roles of TLR2 and TLR4 in recognition of Gram-negative and Gram-positive bacterial cell wall components. Immunity 11, 443-451 (1999).

Tanjore, H., et al. Contribution of Epithelial-derived Fibroblasts to Bleomycin-induced Lung Fibrosis. Am J Respir Crit Care Med. Oct. 1, 2009; 180(7): 657-65.

Tebbutt, N.C. et al. Reciprocal regulation of gastrointestinal homeostasis by SHP2 and STAT-mediated trefoil gene activation in gp130-mutant mice. Nat. Med. 8, 1089-1097 (2002).

Teder, P., et al. Resolution of Lung Inflammation by CD44. Science. Apr. 5, 2002; 296: 155-8.

Thannickal, V.J., et al. Myofibroblast Differentiation by Transforming Growth Factor-beta 1 Is Dependent on Cell Adhesion and Integrin Signaling via Focal Adhesion Kinase. J Biol Cehm. Apr. 4, 2003; 278(14): 12384-12389.

Thomas, A.Q., et al. Heterozygosity for a Surfactant Protein C Gene Mutation Associated with Usual Interstitial Pneumonitis and Cellular Nonspecific Interstitial Pneumonitis in One Kindred. Am J. Respir Crit Care Med. May 1, 2002; 165(9): 1322-8.

Thrall, R. et al., Bleomycin-induced pulmonary fibrosis in the rat: inhibition by indomethacin. Am J Pathol, 95: 117-130, 1979.

Timmermans, F., et al. Endothelial progenitor cells: identity defined?. J Cell Mol Med. 2009; 13: 87-102.

Tomasek, J.J., et al. Myofibroblasts and mechano-regulation of connective tissue remodelling. Nat Rev Mol Cell Biol. May 2002; 3(5): 349-63.

Toole, B. P. Hyaluronan: from extracellular glue to pericellular cue. Nat Rev Cancer. Jul. 2004; 4(7): 528-39.

Torry, D.J., et al. Anchorage-independent Colony Growth of Pulmonary Fibroblasts Derived from Fibrotic Human Lung Tissue. J Clin Invest. Apr. 1994; 93(4): 1525-32.

Treutlein, B. et al. Reconstructing lineage hierarchies of the distal lung epithelium using single-cell RNA-seq. Nature 509, 371-375 (2014).

Tsakiri, K.D., et al. Adult-onset pulmonary fibrosis caused by mutations in telomerase. Proc Natl Acad Sci USA. May 1, 2007; 104(18): 7552-7.

Ulloa, L. et al. Inhibition of transforming growth factor-b/SMAD signalling by the interferon-g/STAT pathway. Nature Feb. 25, 1999; 397(6721): 710-3.

Umezawa, H. et al., Studies on bleomycin Cancer 20: 891-895, 1967.

Umezawa, H., Chemistry and mechanism of action of bleomycin . . . Fed Proc, 33: 2296 2302, 1974.

Vaccaro, C.A., et al. Alveolar Wall Basement Membranes in Bleomycin-induced Pulmonary Fibrosis. Am Rev Respir Dis. Oct. 1985; 132(4): 905-12.

Valenta, T., et al. The many faces and functions of b-catenin. EMBO J. Jun. 13, 2012; 31(12): 2714-36.

Vaughan, A.E. et al. Lineage-negative progenitors mobilize to regenerate lung epithelium after major injury. Nature 517, 621-625 (2015).

Vittal, R. et al., Effects of the Protein Kinase Inhibitor, Imatinib Mesylate, on Epithelial/Mesenchymal Phenotypes: Implications for Treatment of Fibrotic Diseases. J Pharmacol Exp Ther., 321(1):35-44, 2007.

Vittal, R. et al., Modulation of Prosurvival Signaling in Fibroblasts by a Protein Kinase Inhibitor Protects against Fibrotic Tissue Injury. Am J Pathol., 166(2):367-75, 2005.

Voelkel NF and Rounds S, eds. The Pulmonary Endothelium: Function in Health and Disease. Chichester, West Sussex: Wiley-Blackwell, 2009: Chapter 4, 51-72.

Volckaert, T., et al. Parabronchial smooth muscle constitutes an airway epithelial stem cell niche in the mouse lung after injury. J Clin Invest. 2011; 121: 4409-19.

Waghray, M., et al. Hydrogen peroxide is a diffusible paracrine signal for the induction of epithelial cell death by activated myofibroblasts. FASEB J. May 2005; 19(7): 854-6.

Wang, D. et al. A pure population of lung alveolar epithelial type II cells derived from human embryonic stem cells. Proc Natl Acad Sci USA. Mar. 13, 2007; 104(11): 4449-54.

Wang, Y., et al. Genetic Defects in Surfactant Protein A2 Are Associated with Pulmonary Fibrosis and Lung Cancer. Am J Hum Genet. Jan. 2009; 84(1): 52-9.

Werner, S., et al. Regulation of Wound Healing by Growth Factors and Cytokines. Physiol Rev. Jul. 2003; 83(3): 835-870.

White, E.S., et al. Negative Regulation of Myofibroblast Differentiation by PTEN (Phosphatase and Tensin Homolog Deleted on Chromosome 10) Sem. Am J Respir Crit Care Med. Jan. 1, 2006; 173(1): 112-21.

Williams, RO et al., "Cytokine inhibitors in rheumatoid arthritis and other autoimmune diseases," (2007) Curr. Opin. Pharmacol. 7: 412-17.

Wilson, M.S., et al. Bleomycin and IL-1beta-mediated pulmonary fibrosis is IL-17A dependent. J Exp Med. Mar. 15, 2010; 207(3): 535-52.

Krizhanovsky, V., et al. Senescence of Activated Stellate Cells Limits Liver Fibrosis. Cell. Aug. 22, 2008; 134(4): 657-67.

Kuperman, D.A., et al. Direct effects of interleukin-13 on epithelial cells cause airway hyperreactivity and mucus overproduction in asthma. Nat Med. Aug. 2002; 8(8): 885-9.

Laan, M., et al. Neutrophil Recruitment by Human IL-17 Via C-X-C Chemokine Release in the Airways. J Immunol. Feb. 15, 1999; 162(4): 2347-52.

Lagares, et al. Inhibition of Focal Adhesion Kinase Prevents Experimental Lung Fibrosis and Myofibroblast Formation. Arthritis Rheum, May 2012, vol. 64, No. 5. 1653-1664.

Larsson, O., et al. Fibrotic Myofibroblasts Manifest Genome-Wide Derangements of Translational Control. PLoS One. Sep. 16, 2008; 3(9): e3220.

Latsi, P.I., et al. Fibrotic Idiopathic Interstitial Pneumonia the Prognostic Value of Longitudinal Functional Trends. Am J Respir Crit Care Med. Sep. 1, 2003; 168(5): 531-537.

Latsi,. P., et al. Analysis of IL-12 p40 subunit gene and IFN-? G5644A polymorphisms in Idiopathic Pulmonary Fibrosis. Respir Res. 2003. 4:6.

Lawrence, T., "The Nuclear Factor NF-κB pathway in inflammation," Cold Spring Harbor Perspectives in Biol. (2009) 1(6): a001651.

(56) References Cited

OTHER PUBLICATIONS

Lawson W. et al., Increased and prolonged pulmonary fibrosis in surfactant protein C-deficient mice following intratracheal bleomycin. Am J Pathol. 2005;167(5):1267-1277.
Lawson, W.E, et al. Genetic mutations in surfactant protein C are a rare cause of sporadic cases of IPF. Thorax. Nov. 2004; 59(11): 977-80.
Le, T.T. et al. Blockade of IL-6 trans-signaling attenuates pulmonary fibrosis. J. Immunol. 193, 3755-3768 (2014).
Lebleu, V.S., et al. Origin and Function of Myofibroblasts in Kidney Fibrosis. Nat Med. Aug. 2013; 19(8): 1047-53.
Lebleu, VS., et al. Identification of human epididymis protein-4 as a fibroblast-derived mediator of fibrosis. Nat Med. Feb. 2013; 19(2): 227-31.
Lee, C.G., et al. Interleukin-13 induces tissue fibrosis by selectively stimulating and activating transforming growth factor beta(1). J Exp Med. Sep. 17, 2001; 194(6): 809-821.
Lee, J.H. et al. Lung stem cell differentiation in mice directed by endothelial cells via a BMP4-NFATc1 thrombospondin-1 axis. Cell 156, 440-455 (2014).
Lee, J.H., et al. Interleukin-13 Induces Dramatically Different Transcriptional Programs in Three Human Airway Cell Types. Am J Respir Cell Mol Biol. Oct. 2001; 25(4): 474-85.
Lesley, J., et al. CD44 and Its Interaction with Extracellular Matrix. Adv Immunol. 1993; 54: 271-335.
Levick, S. P., et al. Cardiac Mast Cells Mediate Left Ventricular Fibrosis in the Hypertensive Rat Heart. Hypertension. Jun. 2009; 53(6): 1041-1047.
Levy, DE, and Lee, C-K. "What does Stat3 do?" (2002) J. Clin. Invest. 109(9): 1143-48.
Li, Y., et al. Severe lung fibrosis requires an invasive fibroblast phenotype regulated by hyaluronan and CD44. J Exp Med. Jul. 4, 2011; 208(7): 1459-1471.
Liang, J. et al. A macrophage subpopulation recruited by CC chemokine ligand 2 clears apoptotic cells in non-infectious lung injury. Am. J. Physiol. Lung Cell. Mol. Physiol. 302, L933-L940 (2012).
Liang, J. et al. Hyaluronan and TLR4 promote surfactant-protein-C-positive alveolar progenitor cell renewal and prevent severe pulmonary fibrosis in mice. Nat Med. 22 (11) :1285. Nov. 2016.
Liang, J. et al. Role of hyaluronan and hyaluronan-binding proteins in human asthma. J. Allergy Clin. Immunol. 128, 403-411.e3 (2011).
Liang, Yet al, "NF-kappaB and its regulation on the immune system," (2004) Cell. Mol. Immunol. 1(5): 343-50.
Liu, G., et al. miR-21 mediates fibrogenic activation of pulmonary fibroblasts and lung fibrosis. J Exp Med. Aug. 2, 2010; 207(8): 1589-97.
Liu, L. et al. Association of ENA-78, IP-10 and VEGF gene polymorphism with idiopathic pulmonary fibrosis. Zhonghua yi xue za zhi. Oct. 20, 2009; 89(38): 2690-4 (Abstract).
Liu, Y., et al. Activation of type II cells into regenerative stem-cell-antigen-1+ cells during alveolar repair. Am. J. Respir Cell Mol. Biol. 53, 113-124 (2015).
Liu, Y., et al. IL-13 Induces Connective Tissue Growth Factor in Rat Hepatic Stellate Cells via TGF-beta-Independent Smad Signaling. J Immunol. Sep. 1, 2011; 187(5): 2814-2823.
Loberg, RD, et al., Enhanced Glycogen Synthase Kinase-3beta Activity Mediates Hypoxia-induced Apoptosis of Vascular Smooth Muscle Cells and is Prevented by Glucose Transport and Metabolism. J. Biol. Chem. 277 (44): 41667-673 (2002).
Lok, S.S. et al.Murine gammaherpes virus as a cofactor in the development of pulmonary fibrosis in bleomycin resistant mice. Eur Respir J. Nov. 2002; 20(5): 1228-32.
Lovgren, A.K., et al. Beta-arrestin Deficiency Protects Against Pulmonary Fibrosis in Mice and Prevents Fibroblast Invasion of Extracellular Matrix. Sc. Sci Transl Med. Mar. 16, 2011; 3(74):74ra23. doi:10.1126/scitranslmed.3001564.
Lown, J.W., et al. The mechanism of the bleomycin-induced cleavage of DNA1. Biochem Biophys Res Commun. Aug. 22, 1977; 77(4): 1150-7.
Ma, G., et al. Indian hedgehog mutations causing brachydactyly type A1 impair Hedgehog signal transduction at multiple levels. Cell Res. 21: 1343-57 (2011).
Mailleuix, A. A., et al. Fgf10 expression identifies parabronchial smooth muscle cell progenitors and is required for their entry into the smooth muscle cell lineage. Development. May 2005; 132(9): 2157-66.
Martinelli, M., et al. A role for epidermal growth factor receptor in idiopathic pulmonary fibrosis onset. Mol Biol Rep. Oct. 2011; 38(7): 4613-7.
Martinez, E. Multi-protein complexes in eukaryotic gene transcription. Plant Mol. Biol. 50: 925-47 (2002).
Martinez, F.O., et al. The M1 and M2 paradigm of macrophage activation: time for reassessment. F1000Prime Rep. 2014; 6:13.
Mason, R.J. Biology of alveolar type II cells. Respirology. Jan. 2006; 11 Suppl: S12-5.
Matsumoto, K. et al. Conditional inactivation of Hast reveals a crucial role for hyaluronan in skeletal growth, patterning, chondrocyte maturation and joint formation in the developing limb. Development 136, 2825-2835 (2009).
McDonald, S. et al. Combined betaseron R (recombinant human interferon beta) and radiation for inoperable non-small cell lung cancer. Radiother Oncol. Mar. 1993; 26(3): 212-8.
McQualter, J.L., et al Concise Review: Deconstructing the Lung to Reveal Its Regenerative Potential. Stem Cells. May 2012; 30(5): 811-6.
McQualter, J.L., et al. Endogenous Fibroblastic Progenitor Cells in the Adult Mouse Lung Are Highly Enriched in the Sca-1 Positive Cell Fraction. Stem Cells. 2009; 27: 612-22.
McQualter, J.L., et al. Evidence of an epithelial stem/progenitor cell hierarchy in the adult mouse lung. Proc Natl Acad Sci USA 2010; 107: 1414-19.
Meltzer, E.B., et al., Idiopathic pulmonary fibrosis. Orphanet J Rare Dis. Mar. 26, 2008; 3: 8. doi:10.1186/1750-1172-3-8.
Mentink-Kane, M.M., et al. Accelerated and Progressive and Lethal Liver Fibrosis in Mice that Lack Interleukin (IL)-10, IL-12p40, and IL-13R ?2.Gastroenterology. Dec. 2011; 141(6): 2200-9.
Mentink-Kane, M.M., et al. Opposing roles for IL-13 and IL-13 receptor a2 in health and disease. Immunol Rev. Dec. 2004; 202: 191-202.
Mikecz, K., et al. Anti-CD44 treatment abrogates tissue oedema and leukocyte infiltration in murine arthritis . . . Nat Med. Jun. 1995; 1(6): 558-63.
Minshall, E.M., et al. Eosinophil-associated TGF-beta1 mRNA expression and airways fibrosis in bronchial asthma . . . Am J Respir Cell Mol boil. Sep. 1997; 17(3): 326-33.
Miyazaki, Y. et al. Expression of a Tumor Necrosis Factor-a Transgene in Murine Lung Causes Lymphocytic and Fibrosing Alveolitis A Mouse Model of Progressive Pulmonary Fibrosis. J Clin Invest. Jul. 1995; 96(1): 250-9.
Moeller, A., et al. Circulating Fibrocytes Are an Indicator of Poor Prognosis in Idiopathic Pulmonary Fibrosis. Am J Respir Crit Care Med. Apr. 1, 2009; 179(7): 588-94.
Hodgson, U., et al. ELMOD2 Is a Candidate Gene for Familial Idiopathic Pulmonary Fibrosis. Am J Hum Genet. Jul. 2006; 79(1): 149-54.
Hofer, C.C., et al. Infection of mice with influenza A/WNSN/33 (H1N1) virus alters alveolar type II cell phenotype. Am. J. Physiol. Lung Cell. Mol. Physiol. 308, L628-L638 (2015).
Hoffman, A.M., et al. Lung-Derived Mesenchymal Stromal Cell Post-Transplantation Survival, Persistence, Paracrine Expression, and Repair of Elastase-Injured Lung. Stem Cells Dev. 2011; 20: 1779-92.
Hogan, B.L. et al. Repair and regeneration of the respiratory system: complexity, plasticity and mechanisms of lung stem cell function. Cell Stem Cell 15, 123-138 (2014).
Holgate, St, "Cytokine and anti-cytokine therapy for the treatment of asthma and allergic disease," (2004) Cytokine 28: 152-57.
Horowitz, J.C., et al. Activation of the Pro-survival Phosphatidylinositol 3-Kinase/AKT Pathway by Transforming Growth Factor-beta1 in

(56) References Cited

OTHER PUBLICATIONS

Mesenchymal Cells Is Mediated by p38 MAPK-dependent Induction of an Autocrine Growth Factor*. J Biol Chem. Jan. 9, 2004; 279(2): 1359-67.

Horowitz, J.C., et al. Combinatorial activation of FAK and AKT by transforming growth factor-?1 confers an anoikis-resistant phenotype to myofibroblasts. Cell Signal. Apr. 2007; 19(4): 761-71.

Hu, B., et al. Gut-Enriched Kruppel-Like Factor Interaction with Smad3 Inhibits Myofibroblast Differentiation. Am J Respir Cell Mol Biol. Jan. 2007; 36(1): 78-84.

Huang, X., et al. Matrix Stiffness-Induced Myofibroblast Differentiation Is Mediated by Intrinsic Mechanotransduction. Am J Respir Cell Mol Biol. Sep. 2012; 47(3): 340-8.

Humbles, A.A., et al. A Critical Role for Eosinophils in Allergic Airways Remodeling. Science. Sep. 17, 2004; 305(5691): 1776-9.

Hung, C., et al. Role of Lung Pericytes and Resident Fibroblasts in the Pathogenesis of Pulmonary Fibrosis. Am J Respir Crit Care Med. Oct. 1, 2013; 188(7): 820-30.

Hutyrova, B., et al. Interleukin-1 Gene Cluster Polymorphisms in Sarcoidosis and Idiopathic Pulmonary Fibrosis. Am J Respir Crit Care Med. Jan. 15, 2002; 165(2): 148-51.

Ishikawa, N., et al. Utility of KL-6/MUC1 in the clinical management of interstitial lung diseases. Respir Investig. Mar. 2012; 50(1): 3-13.

Izbicki G. et al., Time course of bleomycin-induced lung fibrosis. Int J Exp Pathol., 83(3):111-9, 2002.

Jakubzick, C. et al Impact of Interleukin-13 Responsiveness on the Synthetic and Proliferative Properties of Th1- and Th2-Type Pulmonary Granuloma Fibroblasts. Am J Pathol. May 2003; 162(5): 1475-86.

Janeway's Immunology, 9th Ed. 2017, Garland Science, New York, Chapter 3, pp. 109-110.

Janick-Buckner, D. et al., Alteration of bronchoalveolar lavage cell populations following bleomycin treatment in mice. Toxicol Appl Pharmacol., 100(3):465-73, 1989.

Jeannotte, L. et al. Unsuspected effects of a lung-specific Cre deleter mouse line. Genesis 49, 152-159 (2011).

Jiang, D. et al. Inhibition of pulmonary fibrosis in mice by CXCL10 requires glycosaminoglycan binding and syndecan 4. J. Clin. Invest. 120, 2049-2057 (2010).

Jiang, D. et al. Regulation of pulmonary fibrosis by chemokine receptor CXCR3. J. Clin. Invest. 114, 291-299 (2004).

Jiang, D., et al. Hyaluronan as an Immune Regulator in Human Diseases. Physiol Rev. Jan. 2011; 91(1): 221-64.

Jiang, D., et al. Hyaluronan in tissue injury and repair. Annu. Rev. Cell Dev. Biol. 23, 435-461 (2007).

Jiang, D., et al. Regulation of lung injury and repair by Toll-like receptors and hyaluronan. Nat Med. Nov. 2005; 11(11): 1173-9.

Jiang, D., et al. The role of Toll-like receptors in noninfectious lung injury. Cell Res. 16, 693-701 (2006).

Jiang, F., et al. Gene expression profile of quiescent and activated rat hepatic stellate cells implicates Wnt signaling pathway in activation. J Hepatol. Sep. 2006; 45(3): 401-9.

Jones, L. K, et al. IL-1RI deficiency ameliorates early experimental renal interstitial fibrosis. Nephrol Dail Transplant. 2009; 24: 3024-32.

Jordana, M., et al. Heterogeneous Proliferative Characteristics of Human Adult Lung Fibroblast Lines and Clonally Derived Fibroblasts from Control and Fibrotic Tissue. Am Rev Respir Dis. Mar. 1988; 137(3): 579-84.

Kalluri, R & Weinberg, R.A.. The basics of epithelial-mesenchymal transition. J Clin Invest. Jun. 1, 2009; 119(6): 1420-28.

Kamari, Y., et al. Lack of Interleukin-1alpha or Interleukin-1beta Inhibits Transformation of Steatosis to Steatohepatitis and Liver Fibrosis in Hypercholesterolemic Mice. J Hepatol. Nov. 2011; 55(5): 1086-94.

Katzenstein, A-L., et al. Erratum to "Diagnosis of usual interstitial pneumonia and distinction from other fibrosing interstitial lung diseases". Hum Pathol. Sep. 2008; 39(9): 1275-94.

Katzenstein, A., et al. Idiopathic Pulmonary Fibrosis Clinical Relevance of Pathologic Classification. Am J Respir Crit Care Med. Apr. 2008; 157: 1301-15.

Kaviratne, M., et al. IL-13 activates a mechanism of tissue fibrosis that is completely TGF-beta independent. J Immunol. Sep. 15, 2004; 173(6): 4020-9.

Kawai, T., et al. Unresponsiveness of MyD88-deficient mice to endotoxin. Immunity 11, 115-122 (1999).

Keane, M.P. et al. The importance of balanced pro-inflammatory and antiinflammatory mechanisms in diffuse lung disease. Am J Physiol Lung Cell Mol Physiol. Jul. 2001; 281(1): L92-7.

Kidiyoor et al., Gene and Cell Therapy: Therapeutic Mechanisms and Strategies. Adult Lung Stem Cells. p. 761 (Nancy Smyth Templeton ed., 4th ed. 2015.

Kim, K.K., et al. Alveolar epithelial cell mesenchymal transition develops in vivo during pulmonary fibrosis and is regulated by the extracellular matrix. Proc Natl Acad Sci USA. Aug. 29, 2006; 103(35): 13180-5.

Kinder, B.W., et al. Baseline BAL Neutrophilia Predicts Early Mortality in Idiopathic Pulmonary Fibrosis. Chest. Jan. 2008; 133(1): 226-32.

Kinder, B.W., et al. Serum Surfactant Protein-A is a Strong Predictor of Early Mortality in Idiopathic Pulmonary Fibrosis. Chest. Jun. 2009; 135(6): 1557-63.

King, J., et al.Structural and functional characteristics of lung macro- and microvascular endothelial cell phenotypes. Microvasc Res. 2004; 67: 139-51.

King, T.E. et al. Effect of interferon gamma-1b on survival in patients with idiopathic pulmonary fibrosis (INSPIRE): a multicentre, randomised, placebo-controlled trial. Lancet 2009; 374(9685): 222-8.

Kisseleva, T., et al. Myofibroblasts revert to an inactive phenotype during regression of liver fibrosis. Proc Natl Acad Sci USA. Jun. 12, 2012; 109(24): 9448-53.

Kitani, A., et al. Transforming growth factor (TGF)-beta1-producing regulatory T cells induce Smad-mediated interleukin 10 secretion that facilitates coordinated immunoregulatory activity and amelioration of TGF-beta1-mediated fibrosis. J Exp Med. Oct. 20, 2003; 198(8): 1179-88.

Kolb, M. et al. Transient expression of IL-1? induces acute lung injury and chronic repair leading to pulmonary fibrosis. J Clin Invest. Jun. 2001; 107(12): 1529-36.

Kolodsick, J.E. et al. Protection from Fluorescein Isothiocyanate-Induced Fibrosis in IL-13-Deficient, but Not IL-4-Deficient, Mice Results from Impaired Collagen Synthesis by Fibroblasts1. J Immunol. Apr. 1, 2004; 172(7): 4068-76.

Konigshoff, M., et al. WNT1-inducible signaling protein-1 mediates pulmonary fibrosis in mice and is upregulated in humans with idiopathic pulmonary fibrosis. J Clin Invest. Apr. 2009; 119(4): 772-87.

Konishi, K., et al. Gene Expression Profiles of Acute Exacerbations of Idiopathic Pulmonary Fibrosis. Am J Respir Crit Care med. Jul. 15, 2009; 180(2): 167-75.

Korthagen, N.M. et al. Serum and BALF YKL-40 levels are predictors of survival in idiopathic pulmonary fibrosis. Respir Med. Jan. 2011; 105(1): 106-13.

Kotton, D.N. and Morrisey, E.E. Lung regeneration: mechanisms, applications and emerging stem cell populations. Nat. Med. 20, 822-832 (2014).

Kramann, R., et al. Perivascular Gli1 + Progenitors Are Key Contributors to Injury-Induced Organ Fibrosis. Cell Stem Cell. Jan. 8, 2015; 16(1): 51-66.

Krenning, G., et al. The origin of fibroblasts and mechanism of cardiac fibrosis. J Cell Physiol. Nov. 2010; 225(3): 631-7.

Wilson, M.S., et al. Colitis and Intestinal Inflammation in IL10−/− Mice Results From IL-13Ra2-Mediated Attenuation of IL-13 Activity. Gastroenterology. Jan. 2011; 140(1): 254-64.

Wipff, P., et al. Myofibroblast contraction activates latent TGF-beta1 from the extracellular matrix. J Cell Biol. Dec. 17, 2007; 179(6): 1311-23.

www.genecards.org/cgi-bin/carddisp.pl?gene=CTNNB1. printed from internet Aug. 20, 2018.

(56) References Cited

OTHER PUBLICATIONS www.genecards.org/cgi-bin/carddisp.pl?gene=TBX4. printed from the internet Apr. 18, 2019.

www.genecards.org/cgi-bin/carddisp.pl?gene=WNT1. printed from internet Aug. 20, 2018.

Wynn, T.A., et al. An IL-12-based vaccination method for preventing fibrosis induced by schistosome infection. Nature. Aug. 17, 1995; 376(6541): 594-6.

Wynn, T.A., et al. Macrophages: Master Regulators of Inflammation and Fibrosis. Semin Liver Dis. Aug. 2010; 30(3): 245-57.

Wynn, T.A., et al. Mechanisms of fibrosis: therapeutic translation for fibrotic disease. Nat Med. Jul. 6, 2012; 18(7): 1028-40.

Yamamoto, H., et al. Epithelial-vascular cross talk mediated by VEGF-A and HGF signaling directs primary septae formation during distal lung morphogenesis. Dev Biol. Aug. 1, 2007; 308(1) 44-53.

Yoder, M.C., Progenitor Cells in the Pulmonary Circulation. Proc Am Thorac Soc. 2011; 8: 466-70.

Yokoyama, A., et al. Prognostic value of circulating KL-6 in idiopathic pulmonary fibrosis. Respirology. Mar. 2006; 11(2): 164-8.

Zasloff, M. Antimicrobial peptides of multicellular organisms. Nature. Jan. 24, 2002; 415(6870): 389-95.

Zeisberg, M., et al. Cellular Mechanisms of Tissue Fibrosis. 1. Common and organ-specific mechanisms associated with tissue fibrosis. Am J Physiol Cell Physiol. Feb. 1, 2013; 304(3): C216-25.

Zhang, K., et al. Lung monocyte chemoattractant protein-1 gene expression in bleomycin-induced pulmonary fibrosis. J Immunol. Nov. 15, 1994; 153(10): 4733-41.

Zhang, S. et al. Interleukin 6 mediates the therapeutic effects of adipose-derived stromal-stem cells in lipopolysaccharide-induced acute lung injury. Stem Cells 32, 1616-1628 (2014).

Zhang, Y. et al. A Variant in the Promoter of MUC5B and Idiopathic Pulmonary Fibrosis. N Engl J Med. Apr. 21, 2011; 364(16): 1576-7.

Zhang, Y., et al. Enhanced IL-1 beta and tumor necrosis factor-alpha release and messenger Rna expression in macrophages from idiopathic pulmonary fibrosis or after asbestos exposure. J Immunol. May 1, 1993; 150(9): 4188-96.

Zhang, Y., et al., Biomarkers in idiopathic pulmonary fibrosis. Curr Opin Pulm Med. Sep. 2012; 18(5): 441-6.

Zhang. K., et al. Myofibroblasts and Their Role in Lung Collagen Gene Expression during Pulmonary Fibrosis. Am J Pathol. Jul. 1994; 145(1): 114-25.

Zhao, Y. X., et al. Secretion of complement components of the alternative pathway (C3 and factor B) by the human alveolar type II epithelial cell line A549. Int J Mol Med. 2000; 5: 415-419.

Zhou, Y., et al. Inhibition of mechanosensitive signaling in myofibroblasts ameliorates experimental pulmonary fibrosis. J Clin Invest. Mar. 2013; 123(3): 1096-108.

Zhu, F., et al. IL-17 induces apoptosis of vascular endothelial cells—A potential mechanism for human acute coronary syndrome. Clin Immunol. Nov. 2011; 141(2): 152-60.

Zorzetto, M., et al. Complement Receptor 1 Gene Polymorphisms Are Associated with Idiopathic Pulmonary Fibrosis. Am J Respir Crit Care Med. Aug. 1, 2003; 168(3): 330-4.

Zorzetto, M., et al. Nod2/CARD15 gene polymorphisms in idiopathic pulmonary fibrosis. Sarcoidosis Vasc Diffuse Lung Dis. Oct. 2005; 22(3): 180-5.

Zuo, F., et al. Gene expression analysis reveals matrilysin as a key regulator of pulmonary fibrosis in mice and humans. Proc Natl Acad Sci USA. Apr. 30, 2002; 99(9): 6292-7.

Moore, B. B. et al. Murine models of pulmonary fibrosis. Am J Physiol Lung Cell Mol Physiol. Feb. 2008; 294(2): L152-60.

Moore, B.B. et al. Animal Models of Fibrotic Lung Disease. Am J Respir Cell Mol Biol. Aug. 2013; 49(2): 167-79.

Morales-Nebreda, L.I. et al. Lung-specific loss of ?3-laminin worsens bleomycin-induced pulmonary fibrosis. Am. J. Respir. Cell Mol. Biol. 52, 503-512 (2015).

Morrisey, E.E.,et al. Preparing for the First Breath: Genetic and Cellular Mechanisms in Lung Development. Dev Cell. Jan. 19, 2010; 18(1): 8-2.

Muggia, F. et al., Pulmonary toxicity of antitumor agents. Cancer Treat Rev, 10: 221-243, 1983.

Mummert, M.E., et al. Development of a peptide inhibitor of hyaluronan-mediated leukocyte trafficking. J. Exp. Med. 192, 769-779 (2000).

Murray, L.A., et al. Hyper-responsiveness of IPF/UIP fibroblasts: interplay between TGFbeta1, IL-13 and CCL2. Int J Biochem Cell Biol. 2008; 40(10): 2174-82.

Mushiroda, T., et al. A genome-wide association study identifies an association of a common variant in TERT with susceptibility to idiopathic pulmonary fibrosis. J Med Genet. Oct. 2008; 45(10): 654-6.

Myers, J.L., et al. Epithelial Necrosis and Alveolar Collapse in the Pathogenesis of Usual Interstitial Pneumonia. Chest. Dec. 1988; 94(6): 1309-11.

National Center for Biotechnology Information Gene Expression Omnibus (http://www.ncbi.nlm.nih.gov/geo/) under accession No. GSE68704. downloaded from internet Apr. 17, 2019.

Neal, M.D. et al. Toll-like receptor 4 is expressed on intestinal stem cells and regulates their proliferation and apoptosis via the p53-upregulated modulator of apoptosis. J. Biol. Chem. 287, 37296-37308 (2012).

Nelson, A.L., "Antibody fragments," Mabs 2010, 2(1): 77-83.

Nobel, P. W., et al. Hyaluronate Activation of CD44 Induces Insulin-like Growth Factor-1 Expression by a Tumor Necrosis Factor-a-dependent Mechanism in Murine Macrophages. J Clin Invest. Jun. 1993; 91(6): 2368-77.

Noble, P.W. and Jiang, D. Matrix regulation of lung injury, inflammation and repair: the role of innate immunity. Proc. Am. Thorac. Soc. 3, 401-404 (2006).

Noble, P.W., et al. Pulmonary fibrosis: patterns and perpetrators J Clin Invest. Aug. 2012; 122(8): 2756-62.

O'Donoghue, R.J. et al. Genetic partitioning of interleukin-6 signaling in mice dissociates Stat3 from Smad3- mediated lung fibrosis. EMBO Mol. Med. 4, 939-951 (2012).

Ogawa, T., et al. Suppression of type I collagen production by microRNA-29b in cultured human stellate cells. Biochem Biophys Res Commun. Jan. 1, 2010; 391(1): 316-21.

Oh, K. et al. Epithelial transglutaminase 2 is needed for T cell interleukin-17 production and subsequent pulmonary inflammation and fibrosis in bleomycin-treated mice. J. Exp. Med. 208, 1707-1719 (2011).

Osterreicher, C.H., et al. Fibroblast-specific protein 1 identifies an inflammatory subpopulation of macrophages in Ithe liver. Proc Natl Acad Sci USA. Nov. 23, 2010; 108(1): 308-13.

Papaioannou, VE., The T-box gene family: emerging roles in development, stem cells and cancer. Development. Oct. 2014; 141(20): 3819-33.

Pardo, A.,et al. Up-Regulation and Profibrotic Role of Osteopontin in Human Idiopathic Pulmonary Fibrosis. PLoS Med. Sep. 2005; 2(9): e251.

Peterson, M.W., et al. Prognostic Role of Eosinophils in Pulmonary Fibrosis. Chest. Jul. 1987; 92(1): 51-6.

Phan, S. et al., A Comparative Study of Pulmonary Fibrosis Induced by Bleomycin and an O2 Metabolite Producing Enzyme System. Chest., 83(5 Suppl):44S-45S, 1983.

Phan, S. et al., Bleomycin-induced Pulmonary Fibrosis in Rats: Biochemical Demonstration of Increased Rate of Collagen Synthesis. Am Rev Respir Dis 121: 501-506, 1980.

Phillips, R.J., et al. Circulating fibrocytes traffic to the lungs in response to CXCL12 and mediate fibrosis. J Clin Invest. Aug. 2004; 114(3): 438-46.

Piguet, P.F., et al. Expression and Localization of Tumor Necrosis Factor-alpha and Its mRNA in Idiopathic Pulmonary Fibrosis. Am J Pathol. Sep. 1993; 143(3): 651-655.

Piguet, P.F., et al. Tumor necrosis factoricachectin plays a key role in bleomycin-induced pneumopathy and fibrosis. J Exp Med. Sep. 1, 1989; 170(3): 655-63.

(56) References Cited

OTHER PUBLICATIONS

Piguet. P.F., et al. Requirement of tumour necrosis factor for development of silica induced pulmonary fibrosis. Nature. Mar. 15, 1990; 344(6263): 245-7.

Pivarcsi, A. et al. Expression and function of Toll-like receptors 2 and 4 in human keratinocytes. Int. Immunol. 15, 721-730 (2003).

Prasse, A., et al. Serum CC-Chemokine Ligand 18 Concentration Predicts Outcome in Idiopathic Pulmonary Fibrosis. Am J Respir Crit Care Med. Apr. 15, 2009; 179(8): 717-23.

Rafii, R., et al. A review of current and novel therapies for idiopathic pulmonar fibrosis. J Thorac Dis. 2013; 5(1): 48-73.

Rafii, S. et al. Platelet-derived SDF-1 primes the pulmonary capillary vascular niche to drive lung alveolar regeneration. Nat. Cell Biol. 17, 123-136 (2015).

Raghu, G., et al. Incidence and Prevalence of Idiopathic Pulmonary Fibrosis. Am J Respir Crit Care Med. Oct. 1, 2006; 174(7): 810-6.

Rakoff-Nahoum, S., et al. Recognition of commensal microflora by toll-like receptors is required for intestinal homeostasis. Cell 118, 229-241 (2004).

Rakoff-Nahoum, S., et al. Role of toll-like receptors in spontaneous commensal-dependent colitis. Immunity 25, 319-329 (2006).

Ramalingam, T.R., et al. Unique functions of the type II interleukin 4 receptor identified in mice lacking the interleukin 13 receptor ?1 chain. Nat Immunol. Jan. 2008; 9(1): 25-33.

Ramasamy, S. K., et al. Fgf10 dosage is critical for the amplification of epithelial cell progenitors and for the formation of multiple mesenchymal lineages during lung development. Dev Biol. Jul. 15, 2007; 307(2): 237-47.

Ramirez, A.M., et al. Myofibroblast Transdifferentiation in Obliterative Bronchiolitis: TGF-beta Signaling Through Smad3-Dependent and -Independent Pathways. Am J Transplant. Sep. 2006; 6(9): 2080-8.

Ramos, C. et al. Fibroblasts from Idiopathic Pulmonary Fibrosis and Normal Lungs Differ in Growth Rate, Apoptosis, and Tissue Inhibitor of Metalloproteinases Expression. Am J Respir Cell Mol Biol. May 2001; 24(5): 591-8.

Reiman, R.M., et al. Interleukin-5 (IL-5) Augments the Progression of Liver Fibrosis by Regulating IL-13 Activity. Infect Immun. Mar. 2006; 74(3): 1471-9.

Richards,T.J., et al. Peripheral Blood Proteins Predict Mortality in Idiopathic Pulmonary Fibrosis.Am J Respir Crit Care Med. Jan. 1, 2012; 185(1): 67-76.

Roberts, S.N. et al. A novel model for human interstitial lung disease: Hapten-driven lung fibrosis in rodents. J Pathol. Jul. 1995; 176(3): 309-18.

Rock, J.R., et al. Multiple stromal populations contribute to pulmonary fibrosis without evidence for epithelial to mesenchymal transition. Proc Natl Acad Sci USA. Dec. 27, 2011; 108(52): E1475-83.

Rosas, I.O., et al. MMP1 and MMP7 as Potential Peripheral Blood Biomarkers in Idiopathic Pulmonary Fibrosis. PLoS Med. Apr. 29, 2008; 5(4): e93.

Rothman, B.L., et al. Cytokine regulation of C3 and C5 production by the human type II pneumocyte cell line, A549. J Immunol. 1990; 145: 592-598.

Satelli, A., et al. Vimentin as a potential molecular target in cancer therapy or Vimentin, an overview and its potential as a molecular target for cancer therapy. Cell Mol Life Sci. Sep. 2011; 68(18): 3033-46.

Satoh, H., et al. Increased levels of KL-6 and subsequent mortality in patients with interstitial lung diseases.J Intern Med. Nov. 2006; 260(5): 429-34.

Sausville, E., et al. A role for ferrous ion and oxygen in the degradation of DNA by bleomycin. Biochem Biophys Res Commun. Dec. 6, 1976; 73(3): 814-22.

Schniedermann, J., et al. Mouse lung contains endothelial progenitors with high capacity to form blood and lymphatic vessels BMC Cell Biol. 2010; 11:50.

Scholzen, T. and Gerdes, J., The Ki-67 protein: From the known and the unknown. J. Cell Physiol (2000) 182(3): 311-22.

Hammacher et al., Protein Sci. 3:2280-93 (1994).

Kalai et al., Blood 89:1319-33 (1997).

Simpson et al., Protein Sci. 6:929-55 (1997).

U.S. Appl. No. 16/652,966, filed Apr. 1, 2020, US-2020-0262923-A1, Pending.

Bisserier et al., Lung-targeted SERCA2a Gene Therapy: From Discovery to Therapeutic Application in Bleomycin-Induced Pulmonary Fibrosis, J. Cell Immunol. 2:149-56 (2020).

Fandino et al., GLP-1 receptor agonist ameliorates experimental lung fibrosis, Sci. Rep. 10:18091 (2020).

Khunger and Velcheti, A Case of a Patient with Idiopathic Pulmonary Fibrosis with Lung Squamous Cell Carcinoma Treated with Nivolumab. J Thorac Oncol Jul. 2017;12(7):e96-e97. (Year: 2017).

Habiel et al. Role of Immune Checkpoint Proteins in Idiopathic Pulmonary Fibrosis. (bioRxiv, Aug. 8, 2017, p. 1-35). (Year: 2017).

Ni et al. PD-1/PD-L1 Pathway Mediates the Alleviation of Pulmonary Fibrosis by Human Mesenchymal Stem Cells in Humanized Mice. American Journal of Respiratory Cell and Molecular Biology, 58 (6):684-695, Jun. 2018. (Year: 2018).

\* cited by examiner

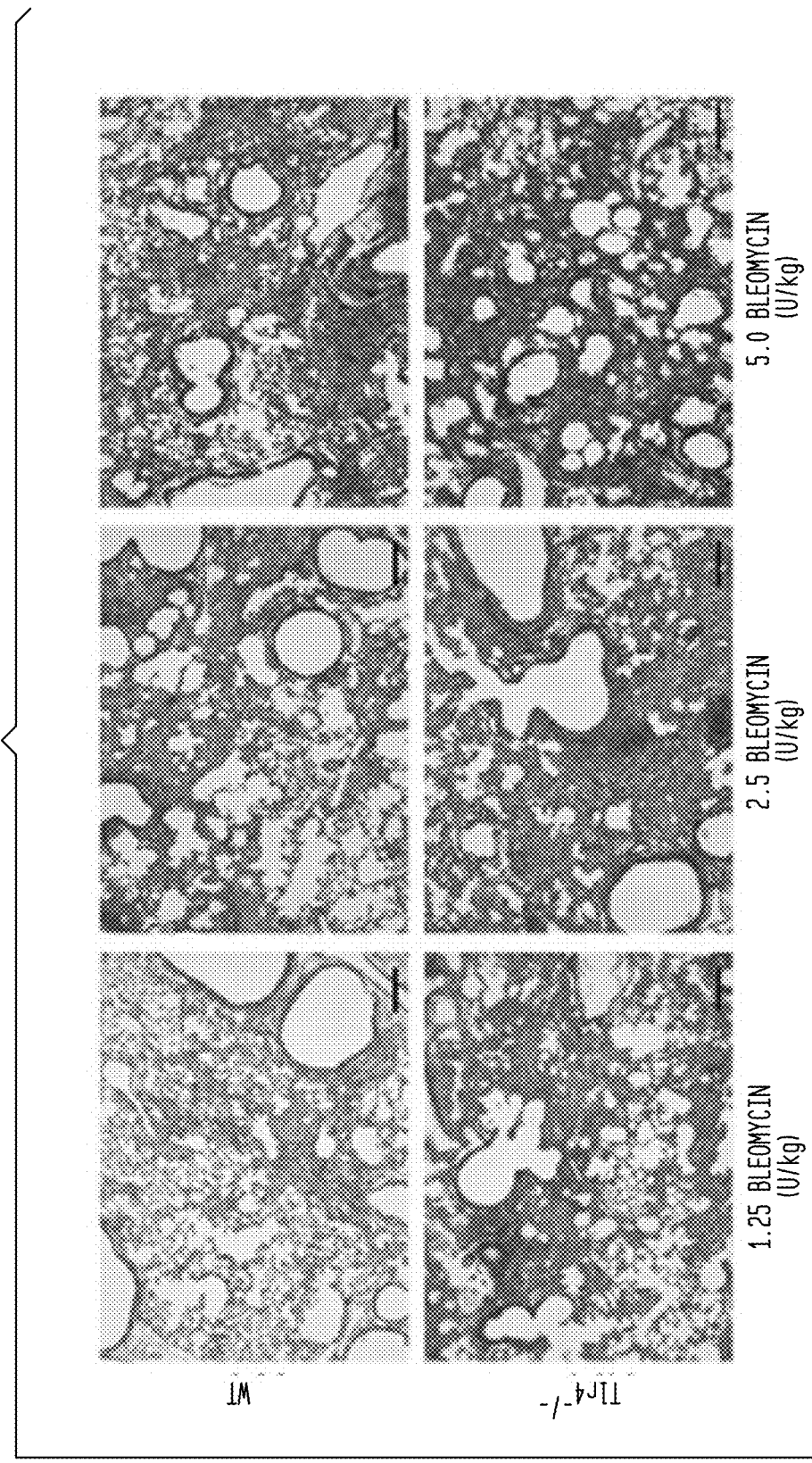

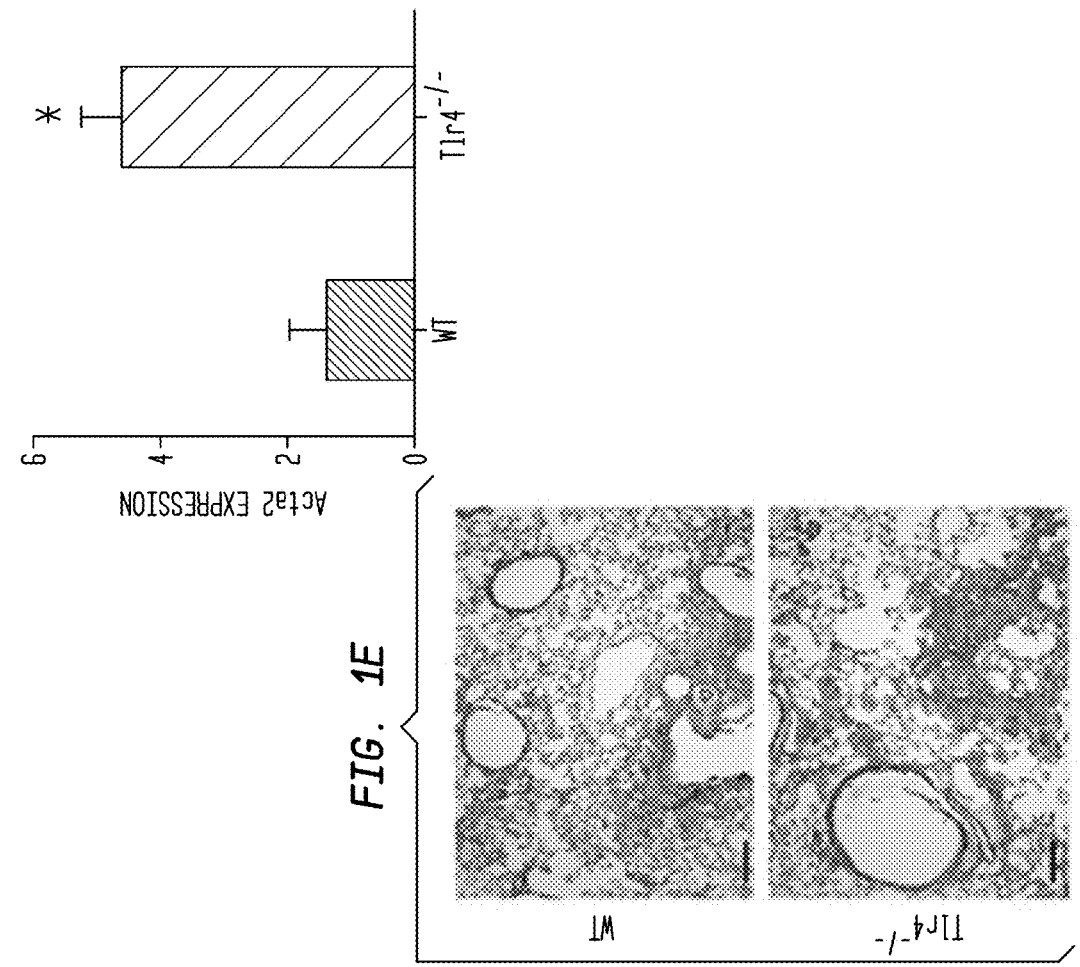

Sftpc-GFP MICE

Sftpc-GFP MICE

Sftpc-CreER; ROSA-TOMATO MICE

Sftpc-CreER; ROSA-TOMATO MICE

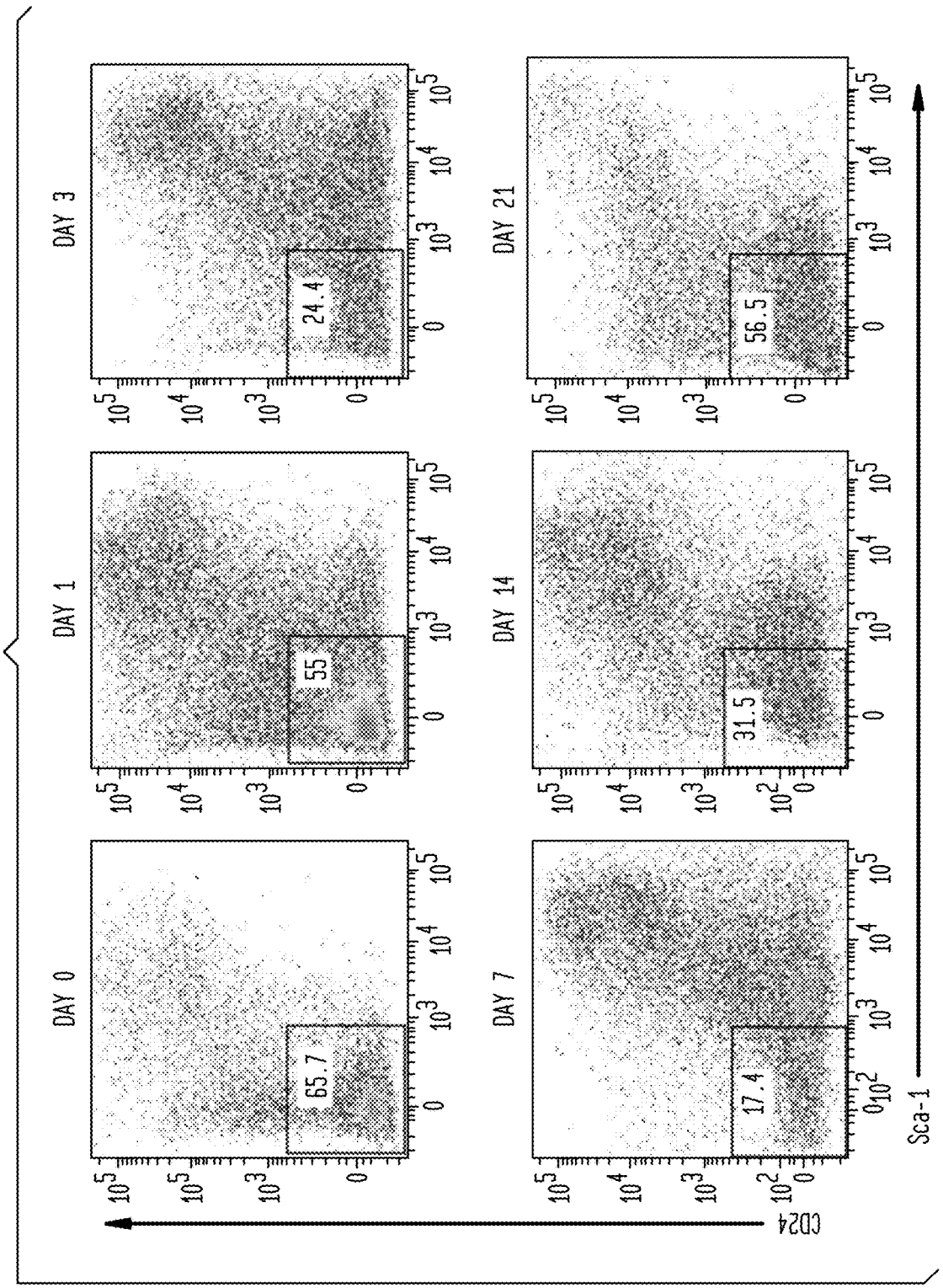

HAS2^{FLOX/FLOX}

SFTPC-CRE; HAS2^{FLOX/FLOX}

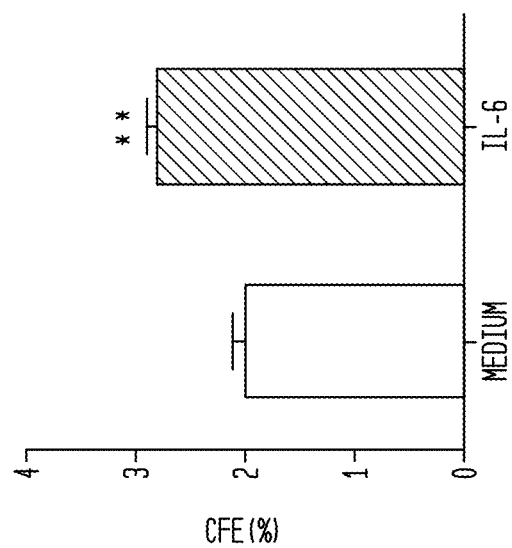
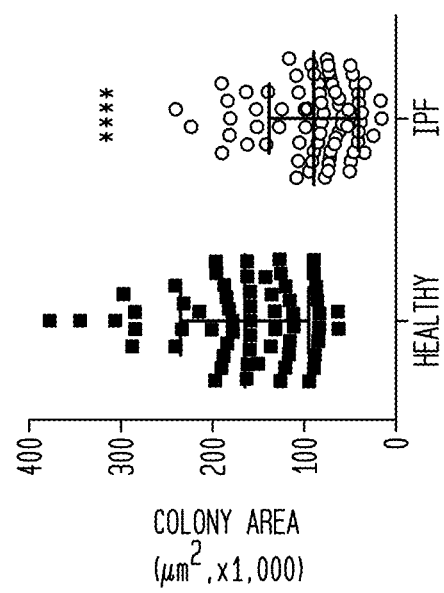
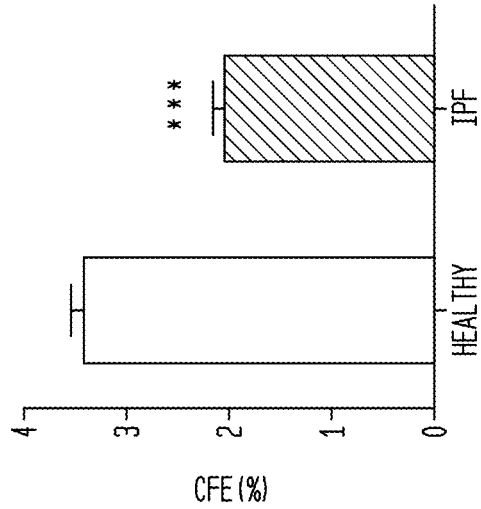
FIG. 13H
FIG. 13G
FIG. 13F

SEQUENCE LISTING

```
<160> NUMBER OF SEQ ID NOS: 13

<210> SEQ ID NO 1
<211> LENGTH: 23
<212> TYPE: PRT
<213> ORGANISM: Artificial Sequence
<220> FEATURE:
<223> OTHER INFORMATION: Mouse Tlr4 forward primer

<400> SEQUENCE: 1

Ala Ala Thr Cys Cys Thr Gly Cys Ala Thr Ala Gly Ala Gly Gly
1               5                   10                  15

Thr Ala Gly Thr Thr Cys Cys
            20

<210> SEQ ID NO 2
<211> LENGTH: 20
<212> TYPE: PRT
<213> ORGANISM: Artificial Sequence
<220> FEATURE:
<223> OTHER INFORMATION: Mouse Tlr4 reverse primer

<400> SEQUENCE: 2

Gly Thr Cys Thr Cys Cys Ala Cys Ala Gly Cys Cys Ala Cys Cys Ala
1               5                   10                  15

Gly Ala Thr Thr
            20

<210> SEQ ID NO 3
<211> LENGTH: 19
<212> TYPE: PRT
<213> ORGANISM: Artificial Sequence
<220> FEATURE:
<223> OTHER INFORMATION: Mouse Acta2 forward primer

<400> SEQUENCE: 3

Gly Cys Thr Gly Gly Thr Gly Ala Thr Gly Ala Thr Gly Cys Thr Cys
1               5                   10                  15

Cys Cys Ala

<210> SEQ ID NO 4
<211> LENGTH: 20
```

<212> TYPE: PRT
<213> ORGANISM: Artificial Sequence
<220> FEATURE:
<223> OTHER INFORMATION: Mouse Acta2 reverse primer

<400> SEQUENCE: 4

Gly Thr Cys Thr Cys Cys Ala Cys Ala Gly Cys Cys Ala Cys Cys Ala
1 5 10 15

Gly Ala Thr Thr
20

<210> SEQ ID NO 5
<211> LENGTH: 20
<212> TYPE: PRT
<213> ORGANISM: Artificial Sequence
<220> FEATURE:
<223> OTHER INFORMATION: Mouse I16 forward primer

<400> SEQUENCE: 5

Cys Thr Cys Ala Thr Thr Cys Thr Gly Cys Thr Cys Thr Gly Gly Ala
1 5 10 15

Gly Cys Cys Cys
20

<210> SEQ ID NO 6
<211> LENGTH: 22
<212> TYPE: PRT
<213> ORGANISM: Artificial Sequence
<220> FEATURE:
<223> OTHER INFORMATION: Mouse I16 reverse primer

<400> SEQUENCE: 6

Thr Gly Cys Cys Ala Thr Thr Gly Cys Ala Cys Ala Ala Cys Thr Cys
1 5 10 15

Thr Thr Thr Thr Cys Thr
20

<210> SEQ ID NO 7
<211> LENGTH: 19
<212> TYPE: PRT
<213> ORGANISM: Artificial Sequence
<220> FEATURE:
<223> OTHER INFORMATION: Mouse Gapdh forward primer

<400> SEQUENCE: 7

Ala Thr Cys Ala Thr Cys Thr Cys Cys Gly Cys Cys Cys Cys Thr Thr
1 5 10 15

Cys Thr Gly

<210> SEQ ID NO 8
<211> LENGTH: 21
<212> TYPE: PRT
<213> ORGANISM: Artificial Sequence
<220> FEATURE:
<223> OTHER INFORMATION: Mouse Gapdh reverse primer

<400> SEQUENCE: 8

Gly Gly Thr Cys Ala Thr Gly Ala Gly Cys Cys Cys Thr Thr Cys Cys
1 5 10 15

Ala Cys Ala Ala Cys
20

<210> SEQ ID NO 9
<211> LENGTH: 20

-continued

```
<212> TYPE: PRT
<213> ORGANISM: Artificial Sequence
<220> FEATURE:
<223> OTHER INFORMATION: Human HAS2 forward primer

<400> SEQUENCE: 9

Gly Cys Cys Thr Cys Ala Thr Cys Thr Gly Thr Gly Ala Gly Ala
1               5                   10                  15

Thr Gly Gly Thr
            20

<210> SEQ ID NO 10
<211> LENGTH: 20
<212> TYPE: PRT
<213> ORGANISM: Artificial Sequence
<220> FEATURE:
<223> OTHER INFORMATION: Human HAS2 reverse primer

<400> SEQUENCE: 10

Thr Cys Cys Cys Ala Gly Ala Gly Gly Thr Cys Cys Ala Cys Thr Ala
1               5                   10                  15

Ala Thr Gly Cys
            20

<210> SEQ ID NO 11
<211> LENGTH: 20
<212> TYPE: PRT
<213> ORGANISM: Artificial Sequence
<220> FEATURE:
<223> OTHER INFORMATION: Human GAPDH forward primer

<400> SEQUENCE: 11

Ala Ala Thr Gly Cys Ala Thr Cys Cys Thr Gly Cys Ala Cys Cys Ala
1               5                   10                  15

Cys Cys Ala Ala
            20

<210> SEQ ID NO 12
<211> LENGTH: 21
<212> TYPE: PRT
<213> ORGANISM: Artificial Sequence
<220> FEATURE:
<223> OTHER INFORMATION: Human GAPDH reverse primer

<400> SEQUENCE: 12

Gly Thr Ala Gly Cys Cys Ala Thr Ala Thr Thr Cys Ala Thr Thr Gly
1               5                   10                  15

Thr Cys Ala Thr Ala
            20

<210> SEQ ID NO 13
<211> LENGTH: 6114
<212> TYPE: DNA
<213> ORGANISM: Homo sapiens

<400> SEQUENCE: 13
acaccatgtt tggtaaataa gtgttttggt gttgtgcaag ggtctggttt cagcctgaag    60
ccatctcaga gctgtctggg tctctggaga ctggagggac aacctagtct agagcccatt   120
tgcatgagac caaggatcct cctgcaagag acaccatcct gagggaagag ggcttctgaa   180
ccagcttgac ccaataagaa attcttgggt gccgacgcgg aagcagattc agagcctaga   240
gccgtgcctg cgtccgtagt ttccttctag cttcttttga tttcaaatca agacttacag   300
```

```
ggagagggag cgataaacac aaactctgca agatgccaca aggtcctcct ttgacatccc     360
caacaaagag gtgagtagta ttctccccct ttctgccctg aaccaagtgg gcttcagtaa     420
tttcagggct ccaggagacc tggggcccat gcaggtgccc cagtgaaaca gtggtgaaga     480
gactcagtgg caatggggag agcactggca gcacaaggca aacctctggc acagagagca     540
aagtcctcac tgggaggatt cccaagggt cacttgggag agggcagggc agcagccaac     600
ctcctctaag tgggctgaag caggtgaaga aagtggcaga agccacgcgg tgcaaaaag     660 gagtcacaca ctccacctgg agacgccttg aagtaactgc acgaaatttg aggatggcca    720
ggcagttcta caacagccgc tcacaggag agccagaaca cagaagaact cagatgactg     780
gtagtattac cttcttcata atcccaggct tgggggctg cgatggagtc agaggaaact     840
cagttcagaa catctttggt ttttacaaat acaaattaac tggaacgcta aattctagcc     900
tgttaatctg gtcactgaaa aaaaatttt ttttttcaa aaaacatagc tttagcttat      960
tttttttctc tttgtaaaac ttcgtgcatg acttcagctt tactctttgt caagacatgc    1020
caaagtgctg agtcactaat aaaagaaaaa agaaagtaa aggaagagtg gttctgcttc    1080
ttagcgctag cctcaatgac gacctaagct gcacttttcc ccctagttgt gtcttgccat    1140
gctaaaggac gtcacattgc acaatcttaa taaggtttcc aatcagcccc acccgctctg    1200
gccccaccct caccctccaa caaagattta tcaaatgtgg gattttccca tgagtctcaa    1260
tattagagtc tcaaccccca ataaatatag gactggagat gtctgaggct cattctgccc    1320
tcgagcccac cgggaacgaa agagaagctc tatctcccct ccaggagccc agctatgaac    1380
tccttctcca caagtaagtg caggaaatcc ttagccctgg aactgccagc ggcggtcgag    1440
ccctgtgtga gggagggtg tgtggcccag ggagggctgg cgggcggcca gcagcagagg     1500
caggctccca gctgtgctgt cagctcaccc ctgcgctcgc tcccctccgg cacaggcgcc    1560
ttcggtccag ttgccttctc cctggggctg ctcctggtgt tgcctgctgc cttccctgcc    1620
ccagtacccc caggagaaga ttccaaagat gtagccgccc cacacagaca gccactcacc    1680
tcttcagaac gaattgacaa acaaattcgg tacatcctcg acggcatctc agccctgaga    1740
aaggaggtgg gtaggcttgg cgatgggtt gaagggcccg gtgcgcatgc gttccccttg     1800
cccctgcgtg tggccggggg ctgcctgcat taggaggtct ttgctgggtt ctagagcact    1860
gtagatttga ggccaacggg gccgactaga ctgacttctg tatttatcct ttgctggtgt    1920
caggaagttc cttcctttc tggaaaatgc agaatgggtc tgaaatccat gcccaccttt    1980
ggcatgagct gagggttatt gcttctcagg gcttcctttt ccctttccaa aaaattaggt    2040
ctgtgaagct ccttttttgtc cccgggcktt tggaaggact agaaaagtgc cacctgaaag    2100
gcatgttcag cttctcagag cagttgcagt acttttttggt tatgtaaact caatggctag   2160
gattcctcaa agccattcca gctaagattc atacctcaga gcccaccaaa gtggcaaatc   2220
ataaataggt taaagcatct ccccactttc aatgcaaggt atttttggtcc tgtttggtag   2280 aaagaaaaga acacaggagg ggagattggg agcccacact cgaattctgg ttctgccaaa   2340
ccagccttgt gatcttgggt aaattcccta ccacctctgg actccatcag taaaattggg    2400
cgtggactag gtgatctcat agatccttcc tgctggaaca ttctatggct tgaattatat    2460
tctcctaatt attgtcaaaa ttgctgttat taagtatcta ctgtgtgcca ggcactttaa    2520
ataaatattg tgtctaatct tcaaaacaaa tttgcaagga aggttttgg agataaggaa     2580 actgagactc aggattaagt aacacaccta aagtcacagg tgagcttgga actgaaccca    2640
agtgtgcccc cactccactg gaatttgctt gccaggatgc caatgagttg tagcttcatt    2700
```

```
tttcttagag actttcctgg ctgtggttga acaatgaaaa ggccctctag tggtgtttgt    2760
tttagggaca cttaggtgat aacaattctg gtattctttc ccagacatgt aacaagagta    2820
acatgtgtga aagcagcaaa gaggcactgg cagaaaacaa cctgaacctt ccaaagatgg    2880
ctgaaaaaga tggatgcttc caatctggat tcaatgaggt accaacttgt cgcactcact    2940
tttcactatt ccttaggcaa aacttctccc tcttgcatgc agtgcctgta tacatataga    3000
tccaggcagc aacaaaaagt gggtaaatgt aagaatgtt atgtaaattt catgaggagg     3060
ccaacttcaa gcttttttaa aggcagttta ttcttggaca ggtatggcca gagatggtgc    3120
cactgtggtg agatttaac aactgtcaaa tgtttaaaac tcccacaggt ttaattagtt     3180
catcctggga aaggtactct cagggccttt tccctctctg gctgcccctg cagggtcca    3240 ggtctgccct ccctccctgc ccagctcatt ctccacagtg ataaacctg cactgtcttc     3300 tgattatttt ataaaaggag gttccagccc agcattaaca agggcaagag tgcaggaaga    3360
acatcaaggg ggacaatcag agaaggatcc ccattgccac attctagcat ctgttgggct    3420
ttggataaaa ctaattacat ggggcctctg attgtccagt tatttaaaat ggtgctgtcc    3480
aatgtcccaa aacatgctgc ctaagaggta cttgaagttc tctagaggag cagagggaaa    3540
agatgtcgaa ctgtggcaat tttaactttt caaattgatt ctatctcctg gcgataacca    3600
attttcccac catctttcct cttaggagac ttgcctggtg aaaatcatca ctggtctttt    3660
ggagtttgag gtatacctag agtacctcca gaacagattt gagagtagtg aggaacaagc    3720
cagagctgtg cagatgagta caaaagtcct gatccagttc ctgcagaaaa aggtgggtgt    3780
gtcctcattc cctcaacttg gtgtggggga agacaggctc aaagacagtg tcctggacaa    3840
ctcagggatg caatgccact tccaaaagag aaggctacac gtaaacaaaa gagtctgaga    3900
aatagtttct gattgttatt gttaaatctt tttttgtttg tttggttggt tggctctctt    3960
ctgcaaagga catcaataac tgtattttaa actatatatt aactgaggtg gattttaaca    4020 tcaatttta atagtgcaag agatttaaaa ccaaaggcgg gggggcgggc agaaaaaagt    4080
gcatccaact ccagccagtg atccacagaa acaaagacca aggagcacaa aatgattta     4140 agattttagt cattgccaag tgacattctt ctcactgtgg ttgtttcaat tcttttttcct   4200 accttttacc agagagttag ttcagagaaa tggtcagaga ctcaagggtg gaaagaggta    4260
ccaaaggctt tggccaccag tagctggcta ttcagacagc agggagtaga cttgctggct    4320
agcatgtgga ggagccaaag ctcaataaga aggggcctag aatgaaaccc ttggtgctga    4380
tcctgcctct gccatttcta cttaagccag ggtttctcat atgttaacat gcatgggaat    4440
tccctgggca tcttcttgtg gtgtggagtc tgacttagca agcctcgggt gggtttgagg    4500
gtcaaatttc taccaggctt atatccctgg tgatgctgca gaattccagg accacacttg    4560
gaggtttaag gccttccaca agttacttat cccatatggt gggtctatgg aaaggtgttt    4620
cccagtcctc tttacaccac cggatcagtg gtctttcaac agatcctaaa gggatggtga    4680
gagggaaact ggagaaaagt atcagattta gaggccactg aagaacccat attaaaatgc    4740
ctttaagtat gggctcttca ttcatatact aaatatgaac tatgtgccag gcattatttc    4800
atatgacaga atacaaacaa ataagatagt gatgctggtc aggcttggtg gctcatgcct    4860
gtattcccta aactttggga gcctaaggtg agaactcctt gaactcctaa ggccaggagt    4920
tcaagaccag cctggataac atagcaagac cccatctcta caaaaaacca aaccaaaca    4980 aacaaaaatg atagtggtgc ttccctcagg atgcttgtgg tctaatggga gacagaacag    5040
```

```
caaagggatg attagaagtt ggttgctgtg agccaggcac agtgctgata taatcccagc    5100
gctatgggag gctgaggtgg gtggatcatt tgaggccagg agtttaagac cagcctggtc    5160
aacatggtaa aacccatct ctacttaaaa atacaaaaaa gttagccagg catggtggca    5220
tacacctgta acccagctac tcaggaggct gaggcacatg aatcacttga acccaggagg    5280
cagaggttgc tgtgcaccac tgcactccag cctgggtgac agaacgagac cttgactcaa    5340
aaaaaaaaaa aagaagtttg ttgctatgga agggtcctac tcagagcagg caccccagtt    5400
aatctcattc accccacatt tcacatttga acatcatccc atagcccaga gcatccctcc    5460
actgcaaagg atttattcaa catttaaaca atcctttta ctttcatttt ccttcaggca    5520
aagaatctag atgcaataac cacccctgac ccaaccacaa atgccagcct gctgacgaag    5580
ctgcaggcac agaaccagtg gctgcaggac atgacaactc atctcattct gcgcagcttt    5640
aaggagttcc tgcagtccag cctgagggct cttcggcaaa tgtagcatgg gcacctcaga    5700
ttgttgttgt taatgggcat tccttcttct ggtcagaaac ctgtccactg ggcacagaac    5760
ttatgttgtt ctctatggag aactaaaagt atgagcgtta ggacactatt ttaattattt    5820
ttaatttatt aatatttaaa tatgtgaagc tgagttaatt tatgtaagtc atatttatat    5880
ttttaagaag taccacttga aacattttat gtattagtt tgaaataata atggaaagtg    5940
gctatgcagt ttgaatatcc tttgtttcag agccagatca tttcttggaa agtgtaggct    6000
tacctcaaat aaatggctaa cttatacata ttttaaaga aatatttata ttgtatttat    6060
ataatgtata aatggttttt ataccaataa atggcatttt aaaaaattca gcaa          6114
```

METHODS FOR REDUCING SEVERITY OF PULMONARY FIBROSIS

This application claims the benefit of priority to U.S. Provisional Application No. 62/567,495, filed Oct. 3, 2017, the contents of which are incorporated by reference herein in their entirety.

GOVERNMENT SUPPORT

This invention was made with government support under Grant Numbers HL108793, HL060539, AI052201, and HL122068 awarded by the National Institutes of Health. The government has certain rights in the invention.

FIELD OF INVENTION

The described invention generally relates to the pathogenesis of pulmonary fibrosis and therapeutics for treating the same.

BACKGROUND

Anatomy and Physiology of the Lungs

The lungs comprise a pair of organs occupying the pulmonary cavities of the thorax, and are the organs of respiration in which aeration of the blood takes place. Normal human lungs weigh about 1 kg, of which 40% to 50% is blood. The lungs contain about 2.5 L of air at end expiration and 6 L of air at full inflation. In human lungs, the right lung is slightly larger than the left, because ⅔ of the heart is located on the left side of the body. The right lung is divided into three lobes (superior lobe, middle lobe, and inferior, or basal lobe), while the left lung is divided into two lobes (superior lobe and inferior, or basal lobe), and contains the cardiac notch, an indentation in the lung that surrounds the apex of the heart.

Each lung is surrounded by the pleura, which are double-layered serous membranes. The parietal pleura forms the outer layer of the membrane and is attached to the wall of the thoracic cavity; the visceral pleura forms the inner layer of the membrane covering the outer surface of the lungs. Between the parietal and visceral pleura is the pleural cavity, which creates a hollow space into which the lungs expand during inhalation. Serous fluid secreted by the pleural membranes lubricates the inside of the pleural cavity to prevent irritation of the lungs during breathing.

The lungs occupy the majority of the space within the thoracic cavity; they extend laterally from the heart to the ribs on both sides of the chest and continue posteriorly toward the spine. Each lung is roughly cone-shaped with the superior end of the lung forming the point of the cone and the inferior end forming the base. The superior end of the lungs narrows to a rounded tip known as the apex. The inferior end of the lungs, known as the base, rests on the dome-shaped diaphragm. The base of the lungs is concave, following the contours of the diaphragm.

Air enters the body through the nose or mouth and passes through the pharynx, larynx, and trachea. Prior to reaching the lungs, the trachea splits into the left and right bronchi, which are large, hollow tubes made of hyaline cartilage and lined with ciliated pseudostratified epithelium. The hyaline cartilage of the bronchi adds rigidity and prevents the bronchi from collapsing and blocking airflow to the lungs. The pseudostratified epithelium lines the inside of the hyaline cartilage. Each lung receives air from a single, large primary bronchus.

As the primary bronchi enter the lungs, they branch off into smaller secondary bronchi that carry air to each lobe of the lung. The secondary bronchi further branch into many smaller tertiary bronchi within each lobe. The secondary and tertiary bronchi improve the efficiency of the lungs by distributing air evenly within each lobe.

The pseudostratified epithelium that lines the bronchi contains many cilia and goblet cells. The goblet cells secrete mucus. The cilia move together to push mucus secreted by the goblet cells away from the lungs.

Particles of dust and even pathogens like viruses, bacteria, and fungi in the air entering the lungs stick to the mucus and are carried out of the respiratory tract, helping to keep the lungs clean and free of disease.

Many small bronchioles branch off from the tertiary bronchi. Bronchioles differ from bronchi both in size and in the composition of their walls. While bronchi have hyaline cartilage rings in their walls, bronchioles are comprised of elastin fibers and smooth muscle tissue. The tissue of the bronchiole walls allows the diameter of bronchioles to change to a significant degree. When the body requires greater volumes of air entering the lungs, such as during periods of physical activity, the bronchioles dilate to permit increased airflow. In response to dust or other environmental pollutants, the bronchioles can constrict to prevent pollution of the lungs.

The bronchioles further branch off into many tiny terminal bronchioles. Terminal bronchioles are the smallest air tubes in the lungs and terminate at the alveoli of the lungs. Like bronchioles, the terminal bronchioles are elastic, capable of dilating or contracting to control airflow into the alveoli.

The alveoli, the functional units of the lungs, permit gas exchange between the air in the lungs and the blood in the capillaries of the lungs. Alveoli are found in small clusters called alveolar sacs at the end of the terminal bronchiole. Each alveolus is a hollow, cup-shaped cavity surrounded by many fine capillaries. The alveolar epithelium covers >99% of the internal surface area of the lungs (Wang et al. Proc Natl Acad Sci USA. 2007 Mar. 13; 104(11): 4449-54).

Adult lungs are very complicated organs containing at least 40-60 different cell types including fibroblasts (Mc-Qualter & Bertoncello. Stem Cells. 2012 May; 30(5): 811-6).

The walls of each alveolus are lined with simple squamous epithelial cells known as alveolar cells, ciliated cells, secretory cells, mainly nonciliated bronchiolar secretory cells which express Secretoglobin 1A member 1 (Scgb1a1+ club cells) (Kidiyoor et al., Gene and Cell Therapy: Therapeutic Mechanisms and Strategies 761 (Nancy Smyth Templeton ed., 4$^{th}$ ed. 2015)), and mesenchymal cell types including resident fibroblasts, myofibroblasts, and perivascular cells that wrap around capillaries (pericytes) (Barkauskas & Noble. Am J Physiol Cell Physiol. 2014 Jun. 1; 306(11): C987-96). The term "club cells" as used herein refers to dome-shaped cells with short microvilli, found in the bronchioles of the lungs. Club cells are the epithelial progenitor cells of the small airways. Club cells were formerly known as "Clara cells." A thin layer of connective tissue underlies and supports the alveolar cells. Present within this connective tissue are fibroblasts, the least specialized cells in the connective tissue family, which are found dispersed in connective tissue throughout the body, and play a key role in the wound healing process (Alberts et al. Molecular Biology of the Cell. 4$^{th}$ Ed. New York: Garland Science; 2002. Fibroblasts and Their Transformations: The Connective-Tissue Cell Family, 1300-1301). Surrounding the connective tissue on the outer border of the alveolus are capillaries. A respiratory membrane is formed where the walls of a capillary touch the walls of an alveolus. At the respiratory membrane, gas exchange occurs freely between the air and blood through the extremely thin walls of the alveolus and capillary.

There are two major types of alveolar cells, type 1 alveolar epithelial cells (AEC1s), and type 2 alveolar epithelial cells (AEC2s). AEC1s are large flat cells through which the exchange of $CO_2/O_2$ takes place; they cover approximately 95% of the alveolar surface, comprise approximately 40% of the alveolar epithelium, and 8% of the peripheral lung cells; in contrast, AEC2s are small, cuboidal cells that cover approximately 5% of the alveolar surface, comprise 60% of the alveolar epithelium, and 15% of the peripheral lung cells, and are characterized by their ability to synthesize and secrete surfactant protein C (SPC) and by the distinct morphological appearance of inclusion bodies known as lamellar bodies (Wang et al. Proc Natl Acad Sci USA. 2007 Mar. 13; 104(11): 4449-54; Barkauskas & Noble. Am J Physiol Cell Physiol. 2014 Jun. 1; 306(11): C987-96). AEC2s function: 1) to synthesize, store, and secrete surfactant, which reduces surface tension, preventing collapse of the alveolus; 2) to transport ions from the alveolar fluid into the interstitium, thereby minimizing alveolar fluid and maximizing gas exchange; 3) to serve as progenitor cells for AEC1s, particularly during reepithelialization of the alveolus after lung injury; and 4) to provide pulmonary host defense by synthesizing and secreting several complement proteins including C3 and C5 (Strunk et al. J Clin Invest. 1988; 81: 1419-1426; Rothman et al. J Immunol. 1990; 145: 592-598; Zhao et al. Int J Mol Med. 2000; 5: 415-419) as well as numerous cytokines and interleukins that modulate lymphocyte, macrophage, and neutrophil functions (Mason. Respirology. 2006 January; 11 Suppl: S12-5; Wang et al. Proc Natl Acad Sci USA. 2007 Mar. 13; 104(11): 4449-54).

Septal cells and macrophages are also found inside the alveoli. Septal cells produce alveolar fluid that coats the inner surface of the alveoli. Alveolar fluid is a surfactant that moistens the alveoli, helps maintain the elasticity of the lungs, and prevents the thin alveolar walls from collapsing. Macrophages in the alveoli keep the lungs clean and free of infection by capturing and phagocytizing pathogens and other foreign matter that enter the alveoli along with inhaled air.

The lungs receive air from the external environment through the process of negative pressure breathing, which requires a pressure differential between the air inside the alveoli and atmospheric air. Muscles surrounding the lungs, such as the diaphragm, intercostal muscles, and abdominal muscles, expand and contract to change the volume of the thoracic cavity. Muscles expand the thoracic cavity and decrease the pressure inside the alveoli to draw atmospheric air into the lungs, in a process known as inhalation or inspiration. Muscles contract the size of the thoracic cavity to increase the pressure inside of the alveoli and force air out of the lungs, in a process known as exhalation or expiration.

External respiration is the process of exchanging oxygen and carbon dioxide between the air inside the alveoli and the blood in the capillaries of the lungs. Air inside the alveoli contains a higher partial pressure of oxygen compared to that in the blood in the capillaries. Conversely, blood in the lungs' capillaries contains a higher partial pressure of carbon dioxide compared to that in the air in the alveoli. These partial pressures cause oxygen to diffuse out of the air and into the blood through the respiratory membrane. At the same time, carbon dioxide diffuses out of the blood and into the air through the respiratory membrane. The exchange of oxygen into the blood and carbon dioxide into the air allows the blood leaving the lungs to provide oxygen to the body's cells, while depositing carbon dioxide waste into the air.

The lungs are a frequent target of infection, including those caused by viruses, bacteria, or fungal organisms, and are subject to myriad diseases and conditions. Lung diseases affecting the airways include, without limitation, asthma (an inflammatory disease of the lungs characterized by reversible (in most cases) airway obstruction), bronchitis (inflammation of the mucous membrane of the bronchial tubes), chronic obstructive pulmonary disease (general term used for those diseases with permanent or temporary narrowing of small bronchi, in which forced expiratory flow is slowed, especially when no etiologic or other more specific term can be applied), cystic fibrosis (a congenital metabolic disorder in which secretions of exocrine glands are abnormal, excessively viscid mucus causes obstruction of passageways, and the sodium and chloride content of sweat are increased throughout the patient's life), and emphysema (a lung condition characterized by increase beyond the normal in the size of air spaces distal to the terminal bronchiole (those parts containing alveoli), with destructive changes in their walls and reduction in their number).

Lung diseases affecting the alveoli include, without limitation, acute respiratory distress syndrome (acute lung injury from a variety of causes, characterized by interstitial and/or alveolar edema and hemorrhage as well as perivascular pulmonary edema associated with hyaline membrane formation, proliferation of collagen fibers, and swollen epithelium with increased pinocytosis), emphysema, lung cancer (any of various types of malignant neoplasms affecting the lungs), pneumonia (inflammation of the lung parenchyma characterized by consolidation of the affected part, the alveolar air spaces being filled with exudate, inflammatory cells, and fibrin), pulmonary edema (an accumulation of an excessive amount of watery fluid in cells or intercellular tissues affecting the lungs, usually resulting from mitral stenosis or left ventricular failure), pneumoconiosis (inflammation commonly leading to fibrosis of the lungs caused by the inhalation of dust incident to various occupations), and tuberculosis (a specific disease caused by infection by *Mycobacterium tuberculosis*, the tubercle *bacillus*, which can affect almost any tissue or organ of the body, the most common seat of the disease being the lungs).

Lung diseases affecting the interstitium, the thin lining between the alveoli, include, without limitation, pneumonia, pulmonary edema, and interstitial lung disease, a broad collection of lung conditions including, without limitation, autoimmune diseases (disorders in which the loss of function or destruction of normal tissue arises from humoral or cellular immune responses to the body's own tissue constituents), idiopathic pulmonary fibrosis (an acute to chronic inflammatory process or interstitial fibrosis of the lung of unknown etiology), and sarcoidosis (a systemic granulomatous disease of unknown cause, especially involving the lungs with resulting interstitial fibrosis, but also involving lymph nodes, skin, liver, spleen, eyes, phalangeal bones, and parotid glands).

Lung diseases affecting blood vessels of the lung include, without limitation, pulmonary embolism (obstruction or occlusion of pulmonary arteries by an embolus, most frequently by detached fragments of thrombus from a leg or pelvic vein) and pulmonary hypertension (high blood pressure in the pulmonary circuit).

Lung diseases affecting the pleura include, without limitation, pleural effusion (increased fluid within the pericardial sac), pneumothorax (the presence of free air or gas in the pleural cavity), and mesothelioma (a rare neoplasm derived from the lining of the cells of the pleura and peritoneum which grows as a thick sheet covering the viscera, and is composed of spindle cells or fibrous tissue which may enclose glandlike spaces lined by cuboidal cells).

Lung diseases affecting the chest wall include, without limitation, obesity hypoventilation syndrome (a combination of severe, grotesque obesity, somnolence, and general debility, theoretically resulting from hypoventilation induced by the obesity) and neuromuscular disorders, including, without limitation, amyotrophic lateral sclerosis (a fatal degenerative disease involving the corticobulbar, corticospinal, and spinal motor neurons, manifested by progressive weakness and wasting of muscles innervated by the affected neurons) and myasthenia gravis (a disorder of neuromuscular transmission marked by fluctuating weakness and fatigue of certain voluntary muscles, including those innervated by brainstem motor nuclei).

Regenerative Cells of the Lungs

The adult lung comprises at least 40-60 different cell types of endodermal, mesodermal, and ectodermal origin, which are precisely organized in an elaborate 3D structure with regional diversity along the proximal-distal axis. In addition to the variety of epithelial cells, these include cartilaginous cells of the upper airways, airway smooth muscle cells, interstitial fibroblasts, myofibroblasts, lipofibroblasts, and pericytes as well as vascular, microvascular, and lymphatic endothelial cells, and innervating neural cells. The regenerative ability of lung epithelial stem/progenitor cells in the different regions of the lung are thought to be determined not only by their intrinsic developmental potential but also by the complex interplay of permissive or restrictive cues provided by these intimately associated cell lineages as well as the circulating cells, soluble and insoluble factors and cytokines within their niche microenvironment (McQualter & Bertoncello. Stem Cells. 2012 May; 30(5); 811-16).

The crosstalk between the different cell lineages is reciprocal, multidirectional, and interdependent. Autocrine and paracrine factors elaborated by mesenchymal and endothelial cells are required for lung epithelial cell proliferation and differentiation (Yamamoto et al. Dev Biol. 2007 Aug. 1; 308(1) 44-53; Ding et al. Cell. 2011 Oct. 28; 147(3): 539-53), while endothelial and epithelial cell-derived factors also regulate mesenchymal cell proliferation and differentiation, extracellular matrix deposition and remodeling, and adhesion-mediated signaling (Crivellato. Int J Dev Biol. 2011; 55(4-5): 365-75); Grinnell & Harrington. Pulmonary endothelial cell interactions with the extracellular matrix. In: Voelkel N F, Rounds S, eds. The Pulmonary Endothelium: Function in Health and Disease. Chichester, West Suxssex: Wiley-Blackwell, 2009: 51-72). Chemotactic factors elaborated by these cell lineages also orchestrate the recruitment of inflammatory cells, which participate in the remodeling of the niche and the regulation of the proliferation and differentiation of its cellular constituents (McQualter & Bertoncello. Stem Cells. 2012 May; 30(5); 811-16).

Lung Mesenchymal Stem/Progenitor Cells

Tracheal and distal embryonic lung mesenchyme have been demonstrated to have inductive properties for the regional specification of the embryonic epithelium (Shannon & Deterding. Epithelial-mesenchymal interactions in lung development. In: McDonald J A, ed. Lung Biology in Health and Disease. Vol. 100. New York: Marcel Dekker Inc, 1997, pp. 81-118.). During lung development, mesenchymal stromal cells at the distal tip of the branching epithelium are known to secrete fibroblast growth factor (FGF)-10, which influences the fate and specificity of early lung epithelial progenitor cells (Bellusci et al. Development. 1997 December; 124(23): 4867-78; Ramasamy et al. Dev Biol. 2007 Jul. 15; 307(2): 237-47). FGF-10 is a component of a multifaceted epithelial-mesenchymal cell signaling network involving BMP, Wnt, and Shh pathways which coordinate the proliferation and differentiation of progenitor cells in the developing lung (reviewed in Morrisey & Hogan. Dev Cell. 2010 Jan. 19; 18(1): 8-23). Lineage tracing studies have also revealed that FGF-10$^{pos}$ mesenchymal cells residing at the branching tip of the epithelium function as stem/progenitor cells for smooth muscle cells, which become distributed along the elongating airways (De Langhe et al. Dev Biol. 2006 Nov. 1; 299(1): 52-62; Mailleuix et al. Development. 2005 May; 132(9): 2157-66). In other studies, mesenchymal stromal cells adjacent to the trachea and extrapulmonary bronchi have also been shown to give rise to bronchiolar smooth muscle cells (Shan et al. Dev Dyn. 2008; 237: 750-5). Collectively, these studies suggest that at least two distinct populations of mesenchymal stromal cells endowed with epithelial modulating properties emerge during development.

Several studies have identified resident mesenchymal stromal cells in adult lungs with the capacity for adipogenic, chondrogenic, osteogenic, and myogenic differentiation. These cells have been clonally expanded from heterogeneous populations of mixed lineage cells defined by their ability to efflux Hoechst 33342 (Giangreco et al. Am J Physiol Lung Cell Mol Physiol. 2004; 286: L624-30; Summer et al. Am J Respir Cell Mol Biol. 2007; 37: 152-9), by their capacity for outgrowth from lung explant cultures (Hoffman et al. Stem Cells Dev. 2011; 20: 1779-92) or by their characteristic expression of Sca-1 (McQualter et al. Stem Cells. 2009; 27: 612-22; Hegab et al. Stem Cells Dev. 2010; 19: 523-36). In addition, further enrichment of CD45$^{neg}$ CD31$^{neg}$ Sca-1$^{pos}$ mesenchymal stromal cells has been achieved based on their lack of EpCAM expression, which selectively labels epithelial lineage cells (McQualter et al. Proc Natl Acad Sci USA 2010; 107: 1414-19). Resolution of the mesenchymal and epithelial lineages has revealed that the endogenous lung mesenchymal stromal cell population is necessary and sufficient to support the proliferation and differentiation of bronchiolar epithelial stem/progenitor cells in co-culture (Id.). This suggests that adult mesenchymal stromal cells share similar epithelial inductive properties to their embryonic counterparts and are an important element of the epithelial stem/progenitor cell niche in the adult lung. This concept is also supported by recent in vivo studies showing that following naphthalene injury of club cells, parabronchial mesenchymal cells secrete FGF-10 to support epithelial regeneration from surviving epithelial stem/progenitor cells (Volckaert et al. J Clin Invest. 2011; 121: 4409-19).

Lung Endothelial Progenitor Cells

Endothelial-epithelial cell interactions and angiogenic and angiocrine factors elaborated in the lung epithelial stem/progenitor cell microenvironment also play a role in the regulation of endogenous lung epithelial stem/progenitor cell regeneration and repair (Yamamoto et al. Dev Biol. 2007 Aug. 1; 308(1) 44-53; Ding et al. Cell. 2011 Oct. 28; 147(3): 539-53; Crivellato. Int J Dev Biol. 2011; 55(4-5): 365-75); Grinnell & Harrington. Pulmonary endothelial cell interactions with the extracellular matrix. In: Voelkel N F, Rounds S, eds. The Pulmonary Endothelium: Function in Health and Disease. Chichester, West Suxssex: Wiley- Blackwell, 2009: 51-72). For example, it has been reported that the coculture of human vascular endothelial cells with a human bronchial epithelial cell line promotes the generation of branching bronchioalveolar epithelial structures in a 3D culture system (Frazdottir et al. Respir Res. 2010; 11: 162). While considerable progress has been made in understanding the heterogeneity, functional diversity, and pathophysiological behavior of lung vascular and microvascular endothelial cells, the immunophenotypic profiling, quantitation, and functional analysis of lung endothelial progenitor cells (EPC) lags far behind. As for EPC derived from human umbilical cord blood, bone marrow, and mobilized peripheral blood (Timmermans et al. J Cell Mol Med. 2009; 13: 87-102), the rarity of EPC in the lung, their lack of distinguishing markers, and the inability to discriminate circulating EPC and tissue resident EPC have been major impediments in assessing the contribution of endogenous lung EPC in lung vascular repair, and lung regeneration and remodeling (Thebaud & Yoder. Pulmonary endothelial progenitor cells. In: Voelkel N F, Rounds S, eds. The Pulmonary Endothelium: Function in Health and Disease. Chichester, West Sussex: Wiley, 2009: 203-16; Yoder. Proc Am Thorac Soc. 2011; 8: 466-70).

Lung macrovascular and microvascular endothelial cells can be resolved on the basis of their preferential binding to the lectins *Helix pomatia* and *Griffonia simplicifolica*, respectively (King et al. Microvasc Res. 2004; 67: 139-51), but there are no other cell surface markers that can discriminate mature lung endothelial cells and EPC (Yoder. Proc Am Thorac Soc. 2011; 8: 466-70). In addition, the rarity of EPC has necessitated the ex vivo expansion and passaging of adherent heterogeneous rat (Alvarez et al. Am J Physiol Lung Cell Mol Physiol. 2008; 294: L419-30) or mouse (Schniedermann et al. BMC Cell Biol. 2010; 11:50) lung endothelial cells in liquid culture prior to quantitation and flow cytometric and functional analysis of lung-derived EPC in in vitro assays. These assays suggest that the lung microvasculature is a rich source of EPC. However, the incidence, immunophenotypic and functional properties of EPC in the primary explanted endothelial cells compared with their ex vivo manipulated, selected, and expanded counterparts remains indeterminate. The ability of these endogenous lung EPCs to contribute to vascular repair and remodeling in vivo is also unproven (Yoder. Proc Am Thorac Soc. 2011; 8: 466-70). Recent studies suggest it likely that both circulating EPC and resident lung EPC contribute to endothelial cell regeneration and repair (Balasubramian et al. Am J Physiol Lung Cell Mol Physiol. 2010; 298: L315-23; Duong et al. Angiogenesis. 2011: 411-22; Chamoto et al. Am J Respir Cell Mol Biol. 2012 March; 46(3): 283-9).

General Principles of Wound Healing

The term "wound healing" refers to the processes by which the body repairs trauma to any of its tissues, especially those caused by physical means and with interruption of continuity.

A wound-healing response can be viewed as comprising four separate phases, comprising: 1) an initial phase post injury involving hemostasis; 2) a second phase involving inflammation; 3) a third phase involving granulation and proliferation; and 4) a fourth phase involving remodeling and maturation. The culmination of the wound-healing response results in the replacement of normal tissue structures with fibroblastic mediated scar tissue. Processes involved in the wound healing response, however, can go awry and produce an exuberance of fibroblastic proliferation, which can result in tissue damage, including hypertrophic scarring (a widened or unsightly scar that does not extend the original boundaries of the wound).

Initial Phase—Hemostasis

An initial injury results in an outflow of blood and lymphatic fluid. This is also the process during which the initial reparative blood clot is created. Both the intrinsic coagulation pathways, so called because all of the components are intrinsic to plasma, and the extrinsic coagulation pathways are activated. The intrinsic and extrinsic systems converge to activate the final common pathways causing fibrin formation. It is generally recognized that these systems function together and interact in vivo.

The intrinsic coagulation pathway is initiated when blood contacts any surface except normal endothelial and blood cells. This pathway, also known as the contact activation pathway, begins with formation of the primary complex on collagen by high-molecular weight kininogen (HMWK), prekallikrein, and coagulation factor (Factor) XII (Hageman factor). Prekallikrein is converted to kallikrein and Factor XII becomes Factor XIIa. Factor XIIa converts Factor XI into Factor XIa. Factor XIa activates Factor IX, which, with its co-factor FVIIIa form the tenase complex, which activates Factor X to Factor Xa.

The extrinsic coagulation pathway, also known as the tissue factor pathway, generates a thrombin burst and is initiated when tissue thromboplastin activates Factor VII. Upon vessel injury, tissue factor (TF), a nonenzymatic lipoprotein cofactor that greatly increases the proteolytic efficiency of Factor VIIa, is exposed to the blood and enzyme coagulation factor VII (proconvertin) circulating in the blood. Once bound to TF, Factor VII is activated to Factor VIIa by different proteases, including thrombin (Factor IIa), Factors Xa, IXa, XIIa and the Factor VIIa-TF complex itself. The Factor VIIa-TF complex activates Factors IX and X. The activation of Factor Xa by the Factor VIIa-TF complex almost immediately is inhibited by tissue factor pathway inhibitor (TFPI). Factor Xa and its cofactor Va form the prothrombinase complex which activates the conversion of prothrombin to thrombin. Thrombin then activates other components of the coagulation cascade, including Factors V and VIII (which activates Factor XI, which, in turn, activates Factor IX), and activates and releases Factor VIII from being bound to von Willebrand Factor (vWF). Factors VIIa and IXa together form the "tenase" complex, which activates Factor X, and so the cycle continues.

As currently understood, coagulation in vivo is a 3-step process centered on cell surfaces. In the first step, coagulation begins primarily by initiation with tissue factor, which is present on the subendothelium, tissues not normally exposed to blood, activated monocytes and endothelium when activated by inflammation. Factors VII and VIIa bind to tissue factor and adjacent collagen. The factor VIIa-tissue factor complex activates factor X and IX. Factor Xa activates factor V, forming a prothrombinase complex (factor Xa, Va and calcium) on the tissue factor expressing cell. In the second step, coagulation is amplified as platelets adhere to the site of injury in the blood vessel. Thrombin is activated by platelet adherence and then acts to fully activate platelets, enhance their adhesion and to release factor V from the platelet a granules. Thrombin on the surface of activated platelets activates factors V, VIII and XI, with subsequent activation of factor IX. The tenase complex (factors IXa, VIIIa and calcium) now is present on platelets where factor Xa can be produced and can generate another prothrombinase complex on the platelet so that there can be large-scale production of thrombin. Propagation, the third step, and is a combination of activation of the prothrombinase complexes that allow large amounts of thrombin to be generated from prothrombin. More platelets can be recruited, as well as activation of fibrin polymers and factor XIII.

The inflammatory phase (see below) begins during the hemo stasis phase. Thrombocytes, as well as recruited white blood cells, release numerous factors to ramp up the healing process. Alpha-granules liberate platelet-derived growth factor (PDGF), platelet factor IV, and transforming growth factor beta (TGF-β). The processes of inflammation, collagen degradation and collagenogenesis, myoblastic creation from transformed fibroblasts, growth of new blood vessels, and reepithelialization are mediated by a host of cytokines and growth factors. The interleukins strongly influence the inflammatory process. Vascular endothelial growth factor (VEGF) and other factors enhance blood vessel formation, and some have multiple roles, such as fibroblast growth factor (FGF)-2, which affects not only the process of angiogenesis but also that of reepithelialization. Vasoactive amines, such as histamine and serotonin, are released from dense bodies found in thrombocytes. PDGF is chemotactic for fibroblasts and, along with TGF-β, is a potent modulator of fibroblastic mitosis, leading to prolific collagen fibril construction in later phases. Fibrinogen is cleaved into fibrin, and the framework for completion of the coagulation process is formed. Fibrin provides the structural support for cellular constituents of inflammation. This process starts immediately after the insult and may continue for a few days.

Second Phase: Inflammation

The early component of the inflammatory phase is predominated by the influx of the polymorphonuclear leukocytes (PMNs) and the later component of the inflammatory phase is predominated by monocytes/macrophages.

Within the first 6-8 hours, PMNs engorge the wound. TGF-β facilitates PMN migration from surrounding blood vessels, from which they extrude themselves from these vessels. These cells cleanse the wound, clearing it of debris. The PMNs attain their maximal numbers in 24-48 hours and commence their departure by hour 72. Other chemotactic agents are released, including FGF, TGF-β and TGF-α, PDGF, and plasma-activated complements C3a and C5a (anaphylactic toxins). They are sequestered by macrophages or interred within the scab or eschar (Id.; Habif. Dermatologic surgical procedures. Clinic Dermatology: A Color Guide to Diagnosis and Therapy. 3$^{rd}$ ed. 1996. 809-810).

As the process continues, monocytes also exude from surrounding blood vessels. Once they leave the vessel, these are termed macrophages. The macrophages continue the cleansing process, manufacture various growth factors during days 3-4, and orchestrate the multiplication of endothelial cells with the sprouting of new blood vessels, duplication of smooth muscle cells, and the creation of the milieu created by the fibroblast. Many factors influencing the wound healing process are secreted by macrophages, including TGFs, cytokines and interleukin (IL)-1, tumor necrosis factor (TNF), and PDGF.

Third Phase: Granulation and Proliferation

The granulation and proliferation phase consists of an overall and ongoing process, comprising subphases termed the "fibroplasia, matrix deposition, angiogenesis and re-epithelialization" subphases (Cho & Lo. Dermatol Clin. 1998 January; 16(1): 25-47).

By days 5-7, fibroblasts have migrated into the wound, laying down new collagen of subtypes I and III. Early in normal wound healing, type III collagen predominates but is later replaced by type I collagen.

Tropocollagen is the precursor of all collagen types and is transformed within the cell's rough endoplasmic reticulum, where proline and lysine are hydroxylated. Disulfide bonds are established, allowing 3 tropocollagen strands to form a triple left-handed triple helix, termed procollagen. As the procollagen is secreted into the extracellular space, peptidases in the cell membrane cleave terminal peptide chains, creating true collagen fibrils.

The wound is suffused with glycosaminoglycans (GAGs) and fibronectin produced by fibroblasts. These GAGs include heparin sulfate, hyaluronic acid, chondroitin sulfate, and keratin sulfate. Proteoglycans are GAGs that are bonded covalently to a protein core and contribute to matrix deposition.

Angiogenesis results from parent vessel offshoots. The formation of new vasculature requires extracellular matrix and basement membrane degradation followed by migration, mitosis, and maturation of endothelial cells. Basic FGF and vascular endothelial growth factor are believed to modulate angiogenesis.

Re-epithelization occurs with the migration of cells from the periphery of the wound and accessory or adjoining tissues. This process commences with the spreading of cells within 24 hours. Division of peripheral cells occurs in hours 48-72, resulting in a thin epithelial cell layer, which bridges the wound. Epidermal growth factors are believed to play a key role in this aspect of wound healing.

This succession of subphases can last up to 4 weeks in the clean and uncontaminated wound.

Fourth Phase: Remodeling and Maturation

After the third week, the wound undergoes constant alterations, known as remodeling, which can last for years after the initial injury occurred. Collagen is degraded and deposited in an equilibrium-producing fashion, resulting in no change in the amount of collagen present in the wound. The collagen deposition in normal wound healing reaches a peak by the third week after the wound is created. Contraction of the wound is an ongoing process resulting in part from the proliferation of specialized fibroblasts termed myofibroblasts, which provide mechanical support and integrity to the tissue after initial injury. Wound contraction occurs to a greater extent with secondary healing (i.e., healing by second intention, which describes a wound left open and allowed to close by reepithelialization and contraction by myofibroblasts) than with primary healing (i.e., healing by first intention, which describes a wound closed by approximation of wound margins or by placement of a graft or flap, or wounds created and closed in the operating room, unlike via reepithelialization and contraction by myofibroblasts). Maximal tensile strength (the greatest longitudinal stress a substance can bear without tearing apart) of the wound is achieved by the 12th week, and the ultimate resultant scar has only 80% of the tensile strength of the original skin that it has replaced. At the end of tissue repair, the reconstructed ECM takes over the mechanical load and myofibroblasts disappear by massive apoptosis (Tomasek et al. Nat Rev Mol Cell Biol. 2002 May; 3(5): 349-63).

Fibroblastic Cells and Myofibroblast Differentiation in Normal Conditions

Under normal conditions, fibroblastic cells exhibit few or no actin-associated cell-cell and cell-matrix contacts and little ECM production (Tomasek et al. Nat Rev Mol Cell Biol. 2002 May; 3(5): 349-63), but after tissue injury, they become activated to migrate into the damaged tissue and to synthesize ECM components (Hinz. J Invest Dermatol. 2007 March; 127(3): 526-37) by cytokines locally released from inflammatory and resident cells (Werner & Grose. Physiol Rev. 2003 July; 83(3): 835-70) or from malignant epithelial cells (De Wever & Mareel. J Pathol. 2003 July; 200(4): 429-47).

Another important stimulus for this phenotypic transition is the change of the mechanical microenvironment; whereas fibroblasts in intact tissue are generally stress-shielded by the crosslinked ECM, this protective structure is lost in the continuously remodeled ECM of injured tissue (Tomasek et al. Nat Rev Mol Cell Biol. 2002 May; 3(5): 349-63). In response to mechanical challenge, fibroblasts acquire contractile stress fibers that are first composed of cytoplasmic actins (Tomasek et al. Nat Rev Mol Cell Biol. 2002 May; 3(5): 349-63), hallmarking the "protomyofibroblast." Stress fibers are connected to fibrous ECM proteins at sites of integrin-containing cell-matrix junctions (Hinz. Eur J Cell Biol. 2006 April; 85(3-4): 175-81) and between cells via de novo established N-cadherin-type adherens junctions (Hinz et al. Mol Biol Cell. 2004 September; 15(9): 4310-20).

In culture, protomyofibroblasts are a stable phenotype, representing an intermediate step in most in vivo conditions where they proceed toward the "differentiated myofibroblast" that is characterized by de novo expression of α-smooth muscle actin (α-SMA), its most commonly used molecular marker, and by increased production of ECM proteins. Expression of α-SMA in stress fibers confers to the differentiated myofibroblast at least a twofold stronger contractile activity compared with α-SMA-negative fibroblasts in culture (Hinz et al. Am J Pathol. 2007 June; 170(6): 1807-16).

At least three local events are needed to generate α-SMA-positive differentiated myofibroblasts: 1) accumulation of biologically active transforming growth factor (TGF) β1; 2) the presence of specialized ECM proteins like the ED-A splice variant of fibronectin; and 3) high extracellular stress, arising from the mechanical properties of the ECM and cell remodeling activity (Tomasek et al. Nat Rev Mol Cell Biol. 2002 May; 3(5): 349-63). Mechanoperception is mediated by specialized cell-matrix junctions, called "fibronexus" in vivo and "supermature focal adhesions" (FAs) in vitro (Hinz. Eur J Cell Biol. 2006 April; 85(3-4): 175-81). Analogously, small N-cadherin-type cell-cell adhesions develop into larger OB-cadherin (cadherin-11)-type junctions during generation of the differentiated myofibroblast in vitro and in vivo (Hinz et al. Mol Biol Cell. 2004 September; 15(9): 4310-20; Hinz et al. Am J Pathol. 2007 June; 170(6): 1807-16).

The main myofibroblast inducer TGFβ1 up-regulates expression of fibronectin and its integrin receptors in lung fibroblasts; this is closely linked to the activation/phosphorylation of focal adhesion kinase essential for the induction of myofibroblast differentiation (Thannickal et al. J Biol Chem. 2003 Apr. 4; 278(14): 12384-9). At the end of tissue repair, the reconstructed ECM again takes over the mechanical load and myofibroblasts disappear by massive apoptosis (Tomasek et al. Nat Rev Mol Cell Biol. 2002 May; 3(5): 349-63); stress release is a powerful promoter of myofibroblast apoptosis in vivo (Hinz et al. Am J Pathol. 2007 June; 170(6): 1807-16).

After injury, the main myofibroblast progenitor appears to be the locally residing fibroblast, which transiently differentiates into a protomyofibroblast, characterized by α-SMA-negative stress fibers. In the lung, the epithelial-mesenchymal transition ("EMT"), the biologic process that allows an epithelial cell to undergo multiple biochemical changes that enable it to assume a mesenchymal cell phenotype (Kalluri & Weinberg. J Clin Invest. 2009 Jun. 1; 119(6): 1420-28)), may provide an additional mechanism to generate fibroblasts (Hinz et al. Am J Pathol. 2007 June; 170(6): 1807-16).

Pulmonary Fibrosis

Pulmonary fibrosis, an interstitial lung disease, is a general term used to describe an increased accumulation of extracellular matrix ("ECM") in the distal lung, rendering the lung stiff and compromising its ability to facilitate normal gas exchange. Patients typically present with the insidious onset of shortness of breath with exertion as the disease often goes unnoticed in its early stages. Pulmonary fibrosis can be associated with a number of underlying diseases (such as connective tissue/rheumatologic disease) or environmental exposures (asbestosis), or it can be idiopathic, i.e., of unknown cause, in nature (Barkauskas & Nobel. Am J Physiol Cell Physiol. 2014 Jun. 1; 306(11): C987-96).

Progressive tissue fibrosis is a major cause of morbidity, and idiopathic pulmonary fibrosis (IPF) is a terminal illness characterized by unremitting ECM deposition in the lung with very limited choice of therapies (Noble et al. J Clin Invest. 2012 August; 122(8): 2756-62). Although certain mediators have been identified as initiating progressive fibrosis, the mechanisms that contribute to the disease are unknown.

IPF, a chronic, terminal disease that manifests over several years, is the most common form of fibrotic lung disease with a prevalence of 14.0-42.7 cases per 100,000 individuals in the United States (depending on the case definition used) and a median survival of 2.5-3.5 yr (Raghu et al. Am J Respir Crit Care Med. 2006 Oct. 1; 174(7):810-6). It is characterized by excess ECM components and scar tissue within the lungs, and exercise-induced breathlessness and chronic dry cough are the prominent symptoms. IPF is viewed as a disease of aging, with the median age at diagnosis being in the mid-60s. There are few effective therapies for IPF short of lung transplant (Meltzer and Nobel. Orphanet J Rare Dis. 2008 Mar. 26; 3: 8. Doi: 10, 1186/1750-1172-3-8). Because a pharmacologic therapy capable of halting or at least slowing the progression of the disease has been elusive, there are intense efforts to better understand the factors that trigger and perpetuate this disease.

IPF belongs to a family of lung disorders known as interstitial lung diseases ("ILD"), or more accurately, the diffuse parenchymal lung diseases ("DPLD"). Within this broad category of diffuse lung diseases, IPF belongs to the subgroup known as idiopathic interstitial pneumonia ("IIP"). By definition, the etiology of IIP is unknown. There are seven distinct IIPs, differentiated by specific clinical features and pathological patterns (Katzenstein et al. Am J Respir Crit Care Med. 2008 April; 157(4 Pt 1): 1301-15). IPF is the most common form of IIP, and is associated with the pathologic pattern known as usual interstitial pneumonia (UIP). The UIP pattern of fibrosis is characterized by two features: 1) Spatial or geographic heterogeneity, which refers to a patchy distribution of dense lung scarring with areas of less affected or normal lung tissue; and 2) Temporal heterogeneity, which refers to areas of densely collagenized fibrosis with variable smooth muscle proliferation alternating with active fibroblast foci (Smith et al. J Clin Pathol. 2013 October; 66(1): 896-903). Therefore, IPF is often referred to as IPF/UIP. IPF is usually fatal, with an average survival of approximately three years from the time of diagnosis (Collard et al. Am J Respir Crit Care Med. 2003 Sep. 1; 168(5): 538-42; Flaherty, et al. Am J Respir Crit Care Med. 2003 Sep. 1; 168(5): 543-8; Latsi et al. Am J Respir Crit Care Med. 2003 Sep. 1; 168(5): 531-7).

IPF arises in the alveolar regions of the lung, a region that consists of AEC2s, and AEC1s, as well as a number of mesenchymal cell types. It is hypothesized that cross talk between the alveolar epithelium and its associated mesenchyme is dysregulated in IPF pathogenesis, and this leads to the unchecked proliferation of extracellular matrix-producing cells. Evidence from genetic analysis of rare familial cases of IPF suggests that defects that incite the development of the disease can originate in the alveolar epithelium (Barkauskas & Noble. Am J Physiol Cell Physiol. 2014 Jun. 1; 306(11): C987-96).

Examples of non-medication based interventions for IPF include pulmonary rehabilitation, long-term oxygen therapy, mechanical ventilation, and lung transplantation. Of these treatments, the only intervention that improves survival in select patients with IPF is lung transplantation (Rafii et al. J Thorac Dis. 2013; 5(1): 48-73). However, lung transplantation is not without significant risks, including infection, given the need for immunosuppression, acute and chronic graft rejection, and airway stenosis (Id.).

Many proposed medication based treatments have failed to date (Id.). These include anti-inflammatory or immunomodulatory therapies, such as corticosteroid monotherapy, azathioprine, cyclophosphamide, everolimus; anticoagulants and therapies targeting the coagulation cascade, such as warfarin, heparin, and prednisolone; endothelin receptor antagonists and vasodilators, such as bosentan, ambrisentan, macitentan, and sildenafil; and antifibrotics and cytokine/kinase inhibitors, such as interferon-gamma, etanercept, imatinib, and CC-930 (Id.). Many of these failures have been associated with a high degree of side effects, which would be expected for medications of these classes, and limited therapeutic effects.

To date, two therapeutic medications have been FDA approved for the treatment of IPF. Esbriet® (pirfenidone), a small molecule antifibrotic that acts on multiple pathways, including the transforming growth factor beta (TGF-β) pathway, and Ofev® (nintedanib), a small molecule inhibitor of the receptors for tyrosine kinases, fibroblast growth factor (FGF), platelet-derived growth factor (PDGF), and vascular endothelial growth factor (VEGF). Although these medications have side effects and do not appear to be able to reverse IPF, they have been shown to significantly slow the progression of the disease.

Recently, microRNAs have shown promise as a therapeutic tool in the treatment of IPF. MicroRNAs (miRNAs) include a broad class of small evolutionarily conserved noncoding RNAs that have important roles in a variety of patho-physiological processes by blocking translation or promoting degradation of complementary target mRNAs (Wynn & Ramalingam. Nat Med. 2012 Jul. 6; 18(7): 1028-40). Although unique subsets of miRNAs have been identified in various fibrotic diseases, a much smaller subset of miRNAs have emerged as regulators of the fibrotic process. For example, miR-21 is expressed in the lungs of individuals with IPF, and mice treated with miR-21 antisense probes were protected from bleomycin-induced pulmonary fibrosis (Liu et al. J Exp Med. 2010 Aug. 2; 207(8): 1589-97). Mechanistically, miR-21 is thought to promote fibrosis by regulating TGF-β1 and MAP kinase signaling in activated myofibroblasts (Id.), and miR-29 also seems to promote fibrosis in human cells by directly regulating type I collagen expression (Ogawa et al. Biochem Biophys Res Commun. 2010 Jan. 1; 391(1): 316-21). In addition, miR-29 has been found to be down regulated in various forms of fibrosis, including IPF. Animal studies injecting a miR-29 mimic into mice has demonstrated promising results even in cases of "established fibrosis." (Fox. Drug Discovery & Development http://www.dddmag.com/new s/2014/10/reversing-idiopathic-pulmonary-fibrosis).

Wound Healing in Pulmonary Fibrosis

Pulmonary fibrosis is hypothesized to develop because epithelial injury and/or cellular stress is/are met by a dysregulated mesenchymal response, leading to deposition of excess collagen and other ECM components into the fibrotic lung (Barkauskas & Noble. Am J Physiol Cell Physiol. 2014 Apr. 16; 306L C987-96).

The wound healing response is dysregulated in pulmonary fibrosis, and disruptions to the highly coordinated wound-repair processes result in pathological scar formation and excessive deposition of ECM components, such as collagen (Chambers. Eur Respir Rev. 2008; 17(109): 130-7). It is thought that in pulmonary fibrosis, aberrant activation of alveolar epithelial cells provokes the migration, proliferation, and activation of mesenchymal cells with the formation of fibroblastic/myofibroblastic foci, leading to the exaggerated accumulation of extracellular matrix with the irreversible destruction of lung tissue (Harari & Caminati. Allergy. 2010 May; 65(5):537-53).

Following injury or "wear and tear" to the alveolar epithelium in otherwise normal lungs, dead or damaged alveolar epithelial cells are replaced by descendants of AEC2s that self-renew and differentiate to AEC1s. It is hypothesized that Scgb1a1+ club secretory cells and/or basal cells serve as a source of AEC2s following injury. These repair processes effectively cover denuded basal lamina, and in the normal healing process, fibrosis does not occur (Barkauskas & Noble. Am J Physiol Cell Physiol. 2014 Jun. 1; 306(11): C987-96). However, in pulmonary fibrosis, abnormal AEC2s are observed, usually overlying fibroblast foci (Rock et al. Proc Natl Acad Sci USA. 2011 Dec. 27; 108(52): E1475-83). The abnormal, hyperplastic morphology of the AEC2s in IPF is thought to relate to cellular stress and the failure to regenerate AEC1s lost by injury or wear and tear. The inability of defective AEC2s to cover the basement membrane denuded by the loss of AEC1s, results the release of profibrotic signals and may perpetuate the development of fibroblast foci (Id.).

In addition to activating the coagulation cascade, platelets and damaged epithelial and endothelial cells release a variety of chemotactic factors that recruit inflammatory monocytes and neutrophils to the site of tissue damage (Wynn & Ramalingam. Nat Med. 2012 Jul. 6; 18(7): 1028-40).

Various growth factors and cytokines secreted by innate inflammatory cells (including macrophages, neutrophils, mast cells and eosinophils) have emerged as potential targets for antifibrotic therapy (Id.). Tumor necrosis factor-α (TNF-α) and interleukin-1β (IL-1β), in particular, have been identified as important targets in a variety of fibrotic diseases (Zhang et al. J Immunol. 1993 May 1; 150(9): 4188-96). Mice that overexpress TNF-α or IL-1β in the lung develop highly progressive pulmonary fibrosis (Miyazaki et al. J Clin Invest. 1995 July; 96(1): 250-9; Kolb et al. J Clin Invest. 2001 June; 107(12): 1529-36). Studies have also shown an essential role for TNF-α in the development of silica- and bleomycin-induced pulmonary fibrosis in mice (Piguet et al. Nature. 1990 Mar. 15; 344(6263): 245-7; Piguet et al. J Exp Med. 1989 Sep. 1; 170(3): 655-63). In support of these experimental findings, patients with idiopathic or systemic sclerosis-associated pulmonary fibrosis have high levels of TNF-α (Piguet et al. Am J Pathol. 1993 September; 143(3): 651-5). Other studies have documented profibrotic activity for IL-1β and NALP3/ASC inflammasome signaling in macrophages (Gasse et al. J Clin Invest. 2007 December;

117(12): 3786-99). Pulmonary fibrosis induced by bleomycin and silica is reduced in IL-1β-deficient mice (Bujak et al. Arch Immunol Ther Exp (Warsz). 2009 May-June; 57(3): 165-76; Jones et al. Nephrol Dial Transplant. 2009; 24: 3024-32; Kamari et al. J Hepatol. 2011 November; 55(5): 1086-94). Like TNF-α, IL-1β is a potent proinflammatory mediator that exacerbates parenchymal-cell injury. It also induces EMT and myofibroblast activation through a TGF-β1-mediated mechanism (Fan et al. Am J Kidney Dis. 2001 April; 37(4): 820-31), confirming that it functions as a potent upstream driver of fibrosis. IL-1β and TNF-α also increase expression of IL-6, which shows autocrine growth-factor activity in fibroblasts. Studies suggest that the cellular source of TGF-β1 dictates its activity, with TGF-β1 derived from macrophages generally showing wound-healing and profibrotic activity and TGF-β1 secreted from CD4+T regulatory cells ($T_{reg}$ cells) functioning as an anti-inflammatory and antifibrotic mediator (Kitani et al. J Exp Med. 2003 Oct. 20; 198(8): 1179-88). Mice deficient in TGF-β1 develop numerous autoimmune disorders and are more susceptible to cancer (Id.).

The CD4+$T_H$17 cell subset that expresses the proinflammatory cytokine IL-17A is emerging as a driver of fibrosis. IL-17A expression has been implicated in the pathogenesis of pulmonary fibrosis (Wilson et al. J Exp Med. 2010 Mar. 15; 207(3): 535-52). In many cases, IL-17A expression is associated with persistent neutrophilia (Laan et al. J Immunol. 1999 Feb. 15; 162(4): 2347-52), and it has been suggested that exaggerated neutrophil recruitment contributes to the development of tissue damage and fibrosis by inducing apoptosis in vascular endothelial cells (Zhu et al. Clin Immunol. 2011 November; 141(2): 152-60). Neutrophil recruitment is also an important predictor of early mortality in IPF patients (Kinder et al. Chest. 2008 January; 133(1): 226-32). Mechanistic studies investigating the IL-17 pathway of fibrosis in mice have identified the proinflammatory cytokines IL-10 and IL-23 as important upstream initiators of profibrotic $T_H$17 responses (Wilson et al. J Exp Med. 2010 Mar. 15; 207(3): 535-52; Gasse et al. PLoS One. 2011; 6(8): e23185). A link between IL-17A and TGF-β1 has also been identified (Wilson et al. J Exp Med. 2010 Mar. 15; 207(3): 535-52). In addition to its role in promoting neutrophilic inflammation, IL-17A has been shown to directly induce expression of matrix metalloproteinase-1 in primary human cardiac fibroblasts (Cortez et al. Am J Physiol Heart Circ Physiol. 2007 December; 293(6): H3356-65), suggesting that IL-17A promotes fibrosis by both exacerbating the upstream inflammatory response and regulating the downstream activation of fibroblasts (Wynn & Ramalingam. Nat Med. 2012 Jul. 6; 18(7): 1028-40).

IL-13 has emerged as a dominant mediator of fibrotic tissue remodeling in several experimental and natural models of fibrosis (Chiaramonte et al. J Clin Invest. 1999 September; 104(6): 777-85). IL-13 production has been implicated in the development of IPF (Murray et al. Int J Biochem Cell Biol. 2008; 40(10): 2174-82). Mechanistically, IL-13 has been hypothesized to induce fibrosis by stimulating the production and activation of TGF-β (Lee et al. J Exp Med. 2001 Sep. 17; 194(6): 809-21). Other studies have suggested that IL-13 can promote fibrosis independently of TGF-β (Liu et al. J Immunol. 2011 Sep. 1; 187(5): 2814-23; Kaviratne et al. J Immunol. 2004 Sep. 15; 173(6): 4020-9) by directly activating the synthetic and proliferative properties of fibroblasts, epithelial cells and smooth-muscle cells (Kuperman et al. Nat Med. 2002 August; 8(8): 885-9; Lee et al. Am J Respir Cell Mol Biol. 2001 October; 25(4): 474-85). Unlike IL-17A—which seems to promote fibrosis indirectly by inducing tissue damage and inflammation—IL-13 and TGF-β show direct fibrotic activity. $T_H$2 cells that produce IL-13 and $T_{reg}$ cells that express TGF-β are also known to inhibit $T_H$17 responses (Wilson et al. Gastroenterology. 2011 January; 140(1): 254-64), suggesting dual roles for IL-13 and TGF-β in the wound-healing response, as both cytokines suppress inflammation while promoting fibrosis. The profibrotic activity of IL-13 is controlled by the abundance of the IL-13Rα1 signaling receptor and IL-13Rα2 decoy receptor expressed on target cells such as myofibroblasts (Ramalingam et al. Nat Immunol. 2008 January; 9(1): 25-33; Chiaramonte et al. J Exp Med. 2003 Mar. 17; 197(6): 687-701). When decoy receptor expression is low or absent, IL-13-dependent fibrosis is exacerbated (Mentink-Kane et al. Gastroenterology. 2011 December; 141(6): 2200-9). However, mice deficient in IL-13Rα2 are more resistant to IL-1β- and IL-17-driven inflammation, probably because of the enhanced IL-13 activity (Wilson et al. Gastroenterology. 2011 January; 140(1): 254-64), suggesting that IL-13Rα2 functions as a key regulator of both $T_H$17-mediated inflammation and $T_H$2-driven fibrosis (Mentink-Kane & Wynn. Immunol Rev. 2004 December; 202: 191-202).

Mechanistically, IFN-γ is believed to inhibit fibrosis, at least in part, by antagonizing the profibrotic activity of TGF-β1. IFN-γ inhibits the TGF-β-induced phosphorylation of the signal transducer Smad3 and subsequent activation of TGF-β-responsive genes (Ulloa et al. Nature 1999 Feb. 25; 397(6721): 710-3). IFN-γ also acts through a pathway dependent on Janus-associated kinase (Jak1) and the transcription factor Stat1 and induces expression of Smad7, which can prevent the interaction of Smad3 with the TGF-β receptor, thus further attenuating TGF-β-induced signaling. IFN-γ also directly inhibits fibroblast proliferation, TGF-β1-induced expression of the genes encoding procollagen I and procollagen III, and collagen synthesis in activated myofibroblasts. IFN-γ also prevents the $T_H$2 cytokine-induced differentiation of CD14+ peripheral blood monocytes into fibroblast-like cells called fibrocytes, which are believed to participate in the development of fibrosis in many organ systems Shao et al. J Leukoc Biol. 2008 June; 83(6): 1323-33). By virtue of its ability to stimulate IFN-γ production in $T_H$1 and natural killer cells, IL-12 has shown similar antifibrotic activity in vivo in mice (Wynn et al. Nature. 1995 Aug. 17; 376(6541): 594-6; Keane et al. Am J Physiol Lung Cell Mol Physiol. 2001 July; 281(1): L92-7). Despite an abundance of in vitro and in vivo evidence supporting an antifibrotic role for $T_H$1-type immunity, clinical studies investigating the therapeutic potential of IFN-γ in the treatment of IPF, systemic sclerosis and other fibrotic disorders have so far been mostly unsuccessful (King et al. Lancet. 2009 Jul. 18; 374(9685): 222-8).

Circulating myeloid cells respond to a gradient of CCL2 and are recruited to damaged tissues, where they differentiate into macrophages that phagocytose the fibrin clot and cellular debris.

Macrophages, which appear early in the wound-healing response and are major producers of TGF-β, one of the drivers of fibrosis (Wynn & Ramalingam. Nat Med. 2012 Jul. 6; 18(7): 1028-40), have also been implicated in the pathogenesis of fibrosis (Wynn & Ramalingam. Nat Med. 2012 Jul. 6; 18(7): 1028-40). Recent literature indicates that various factors should be taken in account in evaluating macrophage activity (Martinez & Gordon. F1000Prime Rep. 2014; 6: 13). Martinez & Gordon have hypothesized that macrophages do not form stable subsets but respond to a combination of factors present in tissues, and that various pathways interact to form complex, even mixed, macrophage phenotypes (Id.).

Although it is widely recognized that monocytes, macrophages and neutrophils have important roles in the progression and resolution of fibrosis (Wynn & Barron. Semin Liver Dis. 2010 August; 30(3): 245-57), other myeloid-lineage cells (such as mast cells, eosinophils and basophils) have also been implicated in the pathogenesis of fibrosis in multiple organ systems (Wynn & Ramalingam. Nat Med. 2012 Jul. 6; 18(7): 1028-40). Mechanistic studies in rats have suggested that mast cells promote fibrosis by recruiting inflammatory leukocytes and by producing profibrotic mediators (Levick et al. Hypertension. 2009 June; 53(6): 1041-7). Eosinophils seem to function in a similar fashion and are considered to be important sources of TGF-β1 and IL-13 (Reiman et al. Infect Immun. 2006 March; 74(3): 1471-9; Minshall et al. Am J Respir Cell Mol boil. 1997 September; 17(3): 326-33). Eosinophils have been most commonly associated with the development of pulmonary fibrosis (Humbles et al. Science. 2004 Sep. 17; 305(5691): 1776-9. Bronchoalveolar-lavage eosinophilia has also been identified as a predictive biomarker of progressive lung disease in IPF and pulmonary fibrosis associated with collagen vascular disorder (Peterson et al. Chest. 1987 July; 92(1): 51-6). Although basophils have a less clear role in the development of fibrosis than the other myeloid-cell populations, they have been implicated in the pathogenesis of myelofibrosis and are frequently found in greater numbers in patients with interstitial lung disease (Gilbert. Prog Clin Biol Res. 1984; 154: 3-17).

ECM fragments, including hyaluronan, have also been shown to be important drivers of fibrosis by stimulating chemokine and proinflammatory cytokine production by inflammatory monocytes and macrophages (Li et al. J Exp Med. 2011 Jul. 4; 208(7): 1459-71). HA fragments require both TLR2 and TLR4 to stimulate mouse macrophages to produce inflammatory chemokines and cytokines; mice deficient in both TLR2 and TLR4 show an impaired transepithelial migration of inflammatory cells, increased tissue injury, elevated lung epithelial cell apoptosis and decreased survival. (Jiang, D et al., "The role of Toll-like receptors in non-infectious lung injury<" (2006) Cell Res. 16: 693-701).

While in normal wound healing, myofibroblasts are lost via apoptosis when the tissue integrity has been sufficiently restored to be mechanically coherent (Darby et al. Lab Invest. 1990 July; 63(1): 21-9); Desmouliere et al. Am J Pathol. 1995 January; 146(1): 56-66), in the wound healing response in pulmonary fibrosis, myofibroblasts remain, failing to undergo apoptosis, and in turn lead to ongoing pathology of accumulation of collagen and other ECM components, and scarring (Darby et al. Clin Cosmet Investig Dermatol. 2014; 7: 301-11). In other words, in pulmonary fibrosis, there is a defect in the granulation and proliferation and remodeling phases; if the remodeling phase of the granulation tissue fails to happen (neither apoptosis of the cells present in the granulation tissue, myofibroblasts, and vascular cells, nor the reorganization of the ECM), myofibroblasts may persist, leading to pathological situations characterized by pulmonary fibrosis (Id.).

Fibroblastic Cells and Myofibroblast Differentiation in Fibrotic Conditions

Fibroblasts and myofibroblasts from IPF patients have been shown to have distinct properties, including the ability to invade the ECM. A hallmark and defining pathological feature of IPF is the formation of fibroblastic foci, which are the accumulation of myofibroblasts in the interstitium of the lung juxtaposed to the alveolar epithelium with destruction of the adjoining alveolar basement membrane (Selman & Pardo. Respir Res. 2002; 3: 3). The destruction of alveolar basement membrane was also observed in experimental lung fibrosis (Fukuda et al. Am J Pathol. 1985 March; 118(3): 452-75; Vaccaro et al. Am Rev Respir Dis. 1985 October; 132(4): 905-12). In view of the many characteristics that encompass features of fibrosis, such as the elaboration of ECM and expression/activation of TGFβ1 (Zhang et al. Am J Pathol. 1994 July; 145(1): 114-25); Zhang et al. J Immunol. 1994 Nov. 15; 153(10): 4733-41), the persistence of the myofibroblast is thought to be of significance in the propagation of fibrosis in pulmonary fibrosis. Early studies of the origin of the myofibroblast in lung injury and fibrosis suggest several possibilities based on observations of its cytoskeletal phenotype, tissue localization, and in vitro studies. Based on evidence that myofibroblasts arise de novo and on the kinetics of the induction of α-SMA expression, perivascular and peribronchiolar adventitial fibroblasts, i.e., the local fibroblasts have been suggested as precursors (Zhang et al. Am J Pathol. 1994 July; 145(1): 114-25), but it has also been reported that circulating fibrocytes (expressing CD45, CD34, collagen I, and CXCR4) can migrate to sites of tissue injury and differentiate into myofibroblasts (Abe et al. J Immunol. 2001 Jun. 15; 166(12): 7556-62; Phillips et al. J Clin Invest. 2004 August; 114(3): 438-46). It has been suggested that such newly appearing myofibroblasts, characterized by α-SMA and/or desmin, expression, may be responsible for the increased lung collagen gene expression in pulmonary fibrosis (Zhang et al. Am J Pathol. 1994 July; 145(1): 114-25).

The mechanism underlying the source of myofibroblasts in pulmonary fibrosis is complex; it has been determined that the presence of Smad3, an intracellular signal transducer for TGF-β1, may have an essential role in myofibroblast differentiation (Ramirez et al. Am J Transplant. 2006 September; 6(9): 2080-8; Hu et al. Am J Respir Cell Mol boil. 2007 January; 36(1): 78-84). However, regulation of the α-SMA gene is quite complex (Giannone & Sheetz. Trends Cell Biol. 2006 April; 16(4): 213-23; Ramirez et al. Am J Transplant. 2006 September; 6(9): 2080-8; Hu et al. Am J Respir Cell Mol boil. 2007 January; 36(1): 78-84). Additional transcription factors, including C/EBPβ (CCAAT/enhancer-binding protein (3), GKLF (gut-enriched Krüppel-like factor), Sp1/Sp3, c-myb, and the downstream effector component of Notch signaling, have been implicated to regulate this gene in a complex and interactive manner, and in addition to inducers, suppressors such as the liver-enriched inhibitory protein isoform of C/EBPβ may serve to keep the precursor fibroblast in an undifferentiated state under normal homeostasis (Hinz et al. Am J Pathol. 2007 June; 170(6): 1807-16). Epigenetic modifications in fibroblasts also contribute to the pathogenesis of fibrosis by stably altering the activation status of myofibroblasts (Wynn & Ramalingam. Nat Med. 2012 Jul. 6; 18(7): 1028-40).

In pulmonary fibrosis, myofibroblasts are found in abundance in areas of high ECM expression and represent the predominant source of heightened ECM and cytokine gene expression (Zhang et al. Am J Pathol. 1994 July; 145(1): 114-25). The myofibroblast is a factor in alveolar epithelial apoptosis, denudation, and retardation of epithelial regeneration (Waghray et al. FASEB J. 2005 May; 19(7): 854-6). Thus, in addition to its potential contribution to reduction in lung tissue compliance, the myofibroblast is likely to play significant roles in promoting ECM deposition, release of inflammatory mediators, and epithelial injury, all of which are considered to be key factors in perpetuating the cycle of injury and fibrosis. As noted above, in pulmonary fibrosis, myofibroblasts fail to undergo apoptosis, as in the normal wound healing response, which leads to ongoing pathology of accumulation of collagen and other ECM components, and scarring (Darby et al. Clin Cosmet Investig Dermatol. 2014; 7: 301-11).

TGFβ1 can induce p38 mitogen-activated protein kinase pathway activation with subsequent activation of the pro-survival phosphatidylinositol 3-kinase-AKT pathway (Horowitz et al. J Biol Chem. 2004 Jan. 9; 279(2): 1359-67). Deficiency in PTEN, a phosphatidylinositol 3-kinase-AKT pathway inhibitor, is associated with increased myofibroblast differentiation (White et al. Am J Respir Crit Care Med. 2006 Jan. 1; 173(1): 112-21). Thus, in addition to promoting myofibroblast differentiation, combinatorial activation of the adhesion-dependent focal adhesion kinase pathway and the soluble growth factor-mediated AKT pathway confers apoptosis/anoikis (programmed cell death induced by anchorage-dependent cells detaching from surrounding ECM) resistance to TGFβ1-differentiated myofibroblasts (Horowitz et al. Cell Signal. 2007 April; 19(4): 761-71).

IPF Fibroblasts Possess a Malignant Phenotype with an Increased Capacity for Invasion It has been proposed that fibroblasts in the IPF lung acquire a phenotype that is reminiscent of malignant cells (Barkauskas & Noble. Am J Physiol Cell Physiol. 2014 Jun. 1; 306(11): C987-96). Fibroblasts from the IPF lung display enhanced migratory capacity when assessed in a chemotaxis chamber with platelet-derived growth factor (PDGF) as the chemoattractant. Fibroblasts from tissues with more dense fibrosis displayed capacity for migration compared with fibroblasts isolated from earlier stage disease (Suganuma et al. Thorax. 1995 September; 50(9): 984-9). IPF fibroblasts, compared with fibroblasts from normal human lung, display slower growth rates, higher rates of apoptosis, and a profibrotic secretory phenotype (Ramos et al. Am J Respir Cell Mol Biol. 2001 May; 24(5): 591-8). In addition, fibrotic lung fibroblasts, unlike normal fibroblasts and more consistent with cancer-derived cells, are able to survive in the absence of attachment and interaction with extracellular matrix and neighboring cells, displaying anchorage-independent growth in soft agar (Torry et al. J Clin Invest. 1994 April; 93(4): 1525-32).

IPF Fibroblasts Demonstrate Impaired Mechanosensitive Signaling

It has long been viewed that myofibroblasts, with their contractile properties, are key effector cells in wound healing (Barkauskas & Noble. Am J Physiol Cell Physiol. 2014 Jun. 1; 306(11): C987-96). After facilitating wound closure, these cells typically disappear from granulation tissue, presumably via a de-differentiation mechanism (Kisseleva et al. Proc Natl Acad Sci USA. 2012 Jun. 12; 109(24): 9448-53), a clearance mechanism (Friedman. Proc Natl Acad Sci USA. 2012 Jun. 12; 109(24): 9230-1; Krizhanovsky et al. Cell. 2008 Aug. 22; 134(4): 657-67), or a combination of both. In IPF, myofibroblasts are believed to persist inappropriately, leading to progressive fibrosis. It has been shown that mechanical stimuli (e.g., stiff extracellular matrix with myofibroblasts generating high contractile forces) can be converted to fibrogenic signals (e.g., liberation of TGF-β1), which, in turn, maintains the myofibroblastic phenotype (Wipff et al. J Cell Biol. 2007 Dec. 17; 179(6): 1311-23). An intrinsic mechanotransduction mechanism that promotes myofibroblast differentiation regulated by nuclear translocation of MKL1 (myocardin-related transcription factor-A, a mechanosensitive transcription factor that is involved in activating the fibrotic gene program) that results in stiff matrix-promoting αSMA gene expression by normal lung fibroblasts (Huang et al. Am J Respir Cell Mol Biol. 2012 September; 47(3): 340-8) has been described. These experiments were done by comparing (myo)fibroblast behavior on polyacrylamide hydrogels of differing stiffness. This intrinsic mechanotransduction is mediated by the Rho kinase (ROCK) pathway, which regulates myofibroblast contractility, differentiation, and survival experiments (Zhou et al. J Clin Invest. 2013 March; 123(3): 1096-108). These experiments also demonstrated that preexisting myofibroblasts can be shuttled to an apoptotic fate if their contractile properties are disrupted (Barkauskas & Noble. Am J Physiol Cell Physiol. 2014 Jun. 1; 306(11): C987-96).

Mechanisms and Pathways of Fibrosis

Because ECM-secreting myofibroblasts are central to the pathogenesis of fibrotic diseases, fibrosis research has focused on elucidating the molecular and immunological mechanisms that initiate, maintain and terminate the differentiation of quiescent fibroblasts into actively proliferating, ECM-producing myofibroblasts (Wynn & Ramalingam. Nat Med. 2012 Jul. 6; 18(7): 1028-40). The mechanisms that control progressive fibrosis, however, are largely unknown (Li et al. J Exp Med. 2011 Jul. 4; 208(7): 1459-71).

Origin of Profibrotic Fibroblasts

The origin of fibrotic fibroblasts has been of great interest in understanding the pathogenesis of tissue fibrosis (Dulauroy et al. Nat Med. 2012 August; 18(8): 1262-70; Hung et al. Am J Respir Crit Care Med. 2013 Oct. 1; 188(7): 820-30; LeBleu et al. Nat Med. 2013 February; 19(2): 227-31; Rock et al. Proc Natl Acad Sci USA. 2011 Dec. 27; 108(52): E1475-83). Fibrotic fibroblasts in IPF are extremely heterogeneous (Jordana et al. Am Rev Respir Dis. 1988 March; 137(3): 579-84.), suggesting they may be raised from different cell types, or represent different stages of activation, or are influenced by their milieu (Zeisberg and Kalluri. Am J Physiol Cell Physiol. 2013 Feb. 1; 304(3): C216-25.). The heterogeneous nature of fibroblasts has also been demonstrated in mouse models (Rock et al. Proc Natl Acad Sci USA. 2011 Dec. 27; 108(52): E1475-83). A common, long-sought-after, marker for fibroblasts has not been identified because of this heterogeneity (Zeisberg and Kalluri. Am J Physiol Cell Physiol. 2013 Feb. 1; 304(3): C216-25), and the major source of profibrotic fibroblasts has not yet been discovered.

Markers such as α smooth muscle actin (α SMA, encoded by ACTA2 gene, the actin isoform that predominates within smooth-muscle cells and plays an important role in fibrogenesis (Cherng et al. J Am Sci. 2008: 4(4): 7-9)), FSP1/S100A4 (fibroblast-specific protein 1/S100A4-positive protein, a marker of fibroblasts in different organs undergoing tissue remodeling (Osterreicher et al. Proc Natl Acad Sci USA. 2010 Nov. 23; 108(1): 308-13)), Vimentin (a major constituent of the intermediate filament (IF) family of proteins, known to maintain cellular integrity and provide resistant against stress (Satelli & Li. Cell Mol Life Sci. 2011 September; 68(18): 3033-46)), Desmin, and PDGFRB (platelet-derived growth factor receptor, beta polypeptide, a tyrosine kinase receptor for members of the PDGF family) are either not exclusively expressed by fibroblasts or specific to all fibroblasts (Krenning et al. J Cell Physiol. 2010 November; 225(3): 631-7; Rock et al., Proc Natl Acad Sci USA. 2011 Dec. 27; 108(52): E1475-83).

It has been suggested that several cellular sources contribute to fibrotic fibroblasts. For example, it has been suggested that circulating fibrocytes or other bone marrow-derived progenitor cells of extrapulmonary origin might be able to migrate to active fibrotic lesions and become fibrotic cells (Andersson-Sjoland et al. Int J Biochem Cell Biol. 2008; 40(10) 2129-40; Hashimoto et al. J Clin Invest. 2004 January; 113(2): 243-52; Phillips et al. J Clin Invest. 2004 August; 114(3): 438-46). Experimental fibrosis models have led to the proposal that epithelial cells (Degryse et al. Am J Physiol Lung Cell Mol Physiol. 2010 October; 299(4): L442-52; Kim et al. Proc Natl Acad Sci USA. 2006 Aug. 29; 103(35): 13180-5; Tanjore et al. Am J Respir Crit Care Med. 2009 Oct. 1; 180(7): 657-65) or endothelial cells (Hashimoto et al. Am J Respir Cell Mol Biol. 2010 August; 43(2): 161-72; LeBleu et al. Nat Med. 2013 August; 19(8): 1047-53; Li and Jimenez. Arthritis Rheum. 2011 August; 63(8): 2473-83) may be able to transform to stromal cells in experimental fibrosis models. However, a genetic tracing approach showed that lung epithelial cells such as Sftpc-lineage AEC2s, as well as Scgb1a1-lineage club cells, do not give rise to fibroblasts (Rock et al. Proc Natl Acad Sci USA. 2011 Dec. 27; 108(52): E1475-83). Genetic fate-mapping methods have confirmed that pericytes proliferate during fibrogenesis, where the pericytes were trace-labeled with either NG2, FoxJ1 or Foxd1(Hung et al. Am J Respir Crit Care Med. 2013 Oct. 1; 188(7): 820-30 Rock et al. Proc Natl Acad Sci USA. 2011 Dec. 27; 108(52): E1475-83). However, neither these cells nor their progeny express high levels of the myofibroblast marker αSMA; expression of αSMA marks myofibroblasts and smooth muscle cells. Some perivascular Gli1+ cells with distinct characteristics of mesenchymal stem cells (MSCs) can differentiate into myofibroblasts in tissue fibrosis (Kramann et al. Cell Stem Cell. 2015 Jan. 8; 16(1): 51-66).

A mesenchymal transcription factor, T-box protein 4 (Tbx4), which is expressed early during embryonic development and controls limb identity (Takeuchi et al. Nature. 1999 Apr. 29; 398(6730): 810-4)) and airway branching (Arora et al. PLos Genet. 2012; 8(8): e1002866) has been identified as a possible source of fibrotic fibroblasts. Tbx4, a member of the T-box family of transcription factors, is involved in multiple biological processes, including angiogenesis, morphogenesis of an epithelium, DNA-templated transcription and regulation of transcription, multicellular organismal development, lung development, limb morphogenesis, and skeletal system morphogenesis; Tbx4 has been found to interact with over 150 different proteins (Papaioannou. Development. 2014 October; 141(20): 3819-33; http://www.genecards.org/cgi-bin/carddisp.pl?gene=TBX4).

Experiments involving the ablation of TBx4+ cells or the disruption of Tbx4 signaling attenuated bleomycin-induced lung fibrosis in in vivo mouse studies. The inventors have shown, by in vivo different mesenchymal marker tracking, multi-color clonal cell labeling, specific cell ablation, and gene deletion in a cell type specific fashion, that Tbx4 lineage cells give rise to fibroblasts, smooth muscle cells, pericytes and endothelial cells in the lung. Tbx4+ cells expanded, proliferated, and formed clonal-like patches within fibrotic foci, and are the major source of αSMA+ fibrotic fibroblasts. Specific deletion of Tbx4+ cells or Tbx4 gene in either collagen- or α-SMA-expressing fibrotic fibroblasts significantly attenuated lung fibrosis, revealing the involvement of Tbx4 in the TGF-β pathway with regards to fibroblast activation and differentiation during tissue fibrosis.

Intrinsic, Autocrine and Epigenetic Mechanisms Regulate Fibrosis

Hyaluronan (HA) is a nonsulfated glycosaminoglycan produced by mesenchymal cells and a variety of tumor cells and has been suggested to contribute to tumor metastasis through interactions with its cognate cell surface receptor CD44 (Arch et al. Science. 1992 Jul. 31; 257(5070): 682-5; Toole, Nat Rev Cancer. 2004 July; 4(7): 528-39). HA is nearly ubiquitous in its distribution, being present in the interstitial spaces of most animal tissues. Accumulation of HA has been shown to be a characteristic of disorders that are associated with progressive tissue fibrosis (Bjermer et al. Thorax. 1989 February; 44(2): 126-31). HA has also been shown to accumulate in the lungs of rats after bleomycin-induced injury, and has a role in regulating the inflammatory response (Jiang et al. Nat Med. 2005 November; 11(11): 1173-9; Noble et al. Physiol Rev. 2011 January; 91(1): 221-64). Three HA synthase genes (HAS1-3) have been identified. Targeted deletion of HAS2 generates an embryonic lethal phenotype caused by impaired cardiac development (Camenisch et al. J Clin Invest. 2000 August; 106(3): 349-60).

CD44 is a ubiquitous cell-surface glycoprotein involved in myriad processes, comprising over 25 signaling super pathways (www.genecards.org/cgi-bin/carddisp.pl?gene-CD44). CD44 is a major cell surface receptor for HA and plays an important role in inflammatory cell recruitment (Mikecz et al. Nat Med. 1995 June; 1(6): 558-63; Siegelman et al. J Leukoc Biol. 1999 August; 66(2): 315-21) and activation (Nobel et al. J Clin Invest. 1993 June; 91(6): 2368-77; DeGrendele et al. Science. 1997 Oct. 24; 278 (5338): 672-5), as well as tumor growth and metastasis (Lesley et al. Adv Immunol. 1993; 54: 271-335). CD44 is necessary for hematopoietic cells to clear HA from sites of inflammation (Teder et al. Science. 2002 Apr. 5; 296(5565: 155-8), and is critical for the recruitment of fibroblasts to injury sites (Acharya et al., J Cell Sci. 2008 May 1; 121(Pt 9): 1393-402.).

The inexorable course of progressive fibrosis in IPF has led to the theory that fibroblasts may take on properties similar to metastatic cancer cells that overexpress HA. Consistent with this concept is a recent study showing that IPF fibroblasts have abnormalities in translational control (Larsson et al. PLoS One. 2008 Sep. 16; 3(9): e3220) that can be found in cancer cells. One of the seminal properties of metastatic cancer cells is the ability to invade basement membrane. It has been suggested that fibrotic fibroblasts and myofibroblasts drive fibrogenesis by invasion and destruction of basement membrane and that HA-CD44 interactions may regulate this process.

Mechanical modifications to the ECM and cell-intrinsic changes in fibroblasts and epithelial cells have been shown to contribute to the progression of fibrosis by maintaining the activation of the following fibrogenic pathways (Wynn & Ramalingam. Nat Med. 2012 Jul. 6; 18(7): 1028-40).

The Wnt-β-Catenin Signaling Pathway

The Wnt-β-catenin signaling pathway is constitutively activated in AEC2s in mouse models of pulmonary fibrosis and in patients diagnosed with IPF and chronic obstructive pulmonary disease (Baarsma et al. PLoS One. 2011; 6(9): e25450). This ubiquitous pathway is involved in organ development, tissue homeostasis, cell growth, renewal, and regeneration, and is intimately involved in tumorigenesis (Valenta et al. EMBO J. 2012 Jun. 13; 31(12): 2714-36). Wnt-1 is involved in over 30 signaling super pathways, and β-catenin is involved in nearly 100 signaling super pathways (www.genecards.org/cgi-bin/carddisp.pl?gene=WNT1; www.genecards.org/cgi-bin/carddisp.pl?gene=CTNNB1).

Mechanistically, Wnt-1—inducible signaling protein 1 (WISP-1) has been shown in mice to increase the proliferation of AEC2s, and to promote EMT in the lung (Wynn & Ramalingam. Nat Med. 2012 Jul. 6; 18(7): 1028-40).

WISP-1 also increases the synthesis of ECM components in mouse and human lung fibroblasts (Jiang et al. J Hepatol. 2006 September; 45(3): 401-9). Blocking studies demonstrated that bleomycin-induced pulmonary fibrosis is highly dependent on the Wnt-1 pathway (Konigshoff et al. J Clin Invest. 2009 April; 119(4): 772-87).

As tissues become more fibrotic, the increased tissue stiffness and decreased elasticity result in mechanical stress, which has been shown to exacerbate tissue injury and perpetuate the activation of local fibroblasts expressing α-smooth muscle actin (α-SMA) (Hinz et al. Mol Biol Cell. 2001 September; 12(9): 2730-41). Two in vitro studies in mouse and porcine cells have suggested that mechanical stress contributes to aberrant wound healing and fibrosis by inducing EMT in AEC2s via a mechanism driven by TGF-β1, Wnt-β-catenin and hyaluronan (Heise et al. J Biol Chem. 2011 May 20; 286(20): 17435-44; Chen et al. Arterioscler Thromb Vasc Biol. 2011 March; 31(3): 590-7). Fibroblasts that are activated as a result of increased tissue or substrate stiffness also seem to maintain their activated phenotype when returned to healthy 'soft' tissues (Balestrini et al. Integr Biol (Camb). 2012 April; 4(4): 410-21), suggesting that mechanical sensing by fibroblasts can permanently alter their behavior in favor of a fibrotic phenotype. It has been suggested that the differentiation of fibroblasts into ECM-producing myofibroblasts is controlled by the combined actions of IL-1β, TGF-β1 and mechanical tension (Hinz. Curr Rheumatol Rep. 2009 April; 11(2): 120-6). Increased compression, shear forces and hydrostatic pressures associated with portal hypertension and vascular remodeling can also perpetuate myofibroblast activation (Wynn & Ramalingam. Nat Med. 2012 Jul. 6; 18(7): 1028-40).

Biomarkers in IPF

Researchers have made efforts to identify diagnostic and predictive biomarkers to improve the drug development in IPF, especially in view of the devastating effects and lethality of IPF and its unknown origin (Zhang & Kaminski. Curr Opin Pulm Med. 2012 September; 18(5):441-6).

Diagnostic Biomarkers

In the context of peripheral blood markers, multiple molecules have been shown to distinguish patients with IPF from controls. These include KL-6 (a high molecular weight glycoprotein used as a serum marker for interstitial lung diseases (Yokoyama et al. Respirology. 2006 March; 11(2): 164-8), surfactant proteins SP-A and SP-D (collagenous glycoproteins investigated at biomarkers for IPF (Greene et al. Eur Respir J. 2002 March; 19(3): 439-46)), matrix metalloproteases MMP-1 and MMP-7 (interstitial collagenases investigated as biomarkers for IPF (Rosas et al. PLoS Med. 2008 Apr. 29; 5(4): e93)), SPP1 (glycoprotein observed to be upregulated in human IPF (Pardo et al. PLoS Med. 2005 September; 2(9): e251)) and YKL-40 (a mammalian chitinase-like protein observed to be upregulated in IPF (Furuhashi et al. Respir Med. 2010 August; 104(8): 1204-10). However, the diagnostic utility of any of these molecules is in doubt as the majority of the studies usually only compared IPF to control individuals, and when smoking controls or other interstitial lung diseases ("ILDs") were analyzed, they often had increased levels of the markers (Zhang & Kaminski. Curr Opin Pulm Med. 2012 September; 18(5): 441-6).

Disease Susceptibility Biomarkers

Multiple mutations associated with familial and sporadic forms of IPF have been reported including mutations in surfactant (Thomas et al. Am J. Respir Crit Care Med. 2002 May 1; 165(9): 1322-8; Lawson et al. Thorax. 2004 November; 59(11): 977-80; Wang et al. Am J Hum Genet. 2009 January; 84(1): 52-9) and telomerase proteins (Armanios et al. N Engl J Med. 2007 Mar. 29; 356(13): 1317-26; Tsakiri et al. Proc Natl Acad Sci USA. 2007 May 1; 104(18): 7552-7). Polymorphisms within TERT (telomerase reverse transcriptase) have also been identified [single nucleotide polymorphism (SNP) in intron 2 of the TERT gene—rs2736100] in a genome-wide association (GWA) study including a derivation cohort of 159 sporadic IPF patients and 934 controls as well as a replication cohort of 83 sporadic IPF cases and 535 controls (Mushiroda et al. J Med Genet. 2008 October; 45(10): 654-6). Leukocyte telomere shortening was found in 24% of familial pulmonary fibrosis and 23% of sporadic IPF cases when compared to control individuals ($P=2.6\times10-8$) (Cronkhite et al. Am J Respir Crit Care med. 2008 Oct. 1; 178(7): 729-37) in a study that contained 201 control individuals, 59 probands with familial pulmonary fibrosis and 73 sporadic pulmonary fibrosis cases without TERT or TERC (telomerase RNA component) mutations. Other genetic variants have been described in IPF, including genes encoding ELMOD2 (a GPTase-activating protein (Hodgson et al. Am J Hun Genet. 2006 July; 79(1): 149-54)), IL-1 (cytokine involved in immune and inflammatory responses (Hutyrova et al. Am j Respir Crit Care Med. 2002 Jan. 15; 165(2): 148-51)), CR-1 (complement receptor 1, a transmembrane glycoprotein, (Zorzetto et al. Am J Respir Crit Care Med. 2003 Aug. 1; 168(3): 330-4)), IL12p40 and IFN-γ (IL-12 p40 subunit and IFN-γ (Latsi et al. Respir Res. 2003. 4:6)), NOD2/CARD15 (an intracellular innate immune sensor (Zorzetto et al. Sarcoidosis Vasc Diffuse Lung Dis. 2005 October; 22(3): 180-5)), MMP-1 (matrix metalloproteinase-1 (Checa et al. Hum Genet. 2008 December; 124(5): 465-72), ENA-78 (epithelial neutrophil activating peptide 78), IP-10 (interferon-inducible protein 10), and VEGF (vascular endothelial growth factor), (Liu et al. Zhonghua Yiu Xue Za Zhi. 2009 Oct. 20; 89(38): 2690-4), CD16b (Fey receptor Mb (Bournazos et al. Lung. 2010 December; 188(6): 475-81)), IL-8 (interleukin 8 (Ahn et al. Respir Res. 2011 Jun. 8; 12:73)) and HER2 (human epidermal growth factor receptor 2 (Martinelli et al. Mol Biol Rep. 2011 October; 38(7): 4613-7)), but the majority have not been replicated. Recently, a SNP in the putative promoter of MUCSB (rs35705950) that was associated with familial interstitial pneumonia (minor allele frequency of 34%, $P=1.2\times10^{-15}$) and IPF (minor allele frequency of 38%, $P=2.5\times10^{-37}$) has been identified; in controls, the minor allele frequency was 9% (Seibold et al. N Engl J Med. 2011 Apr. 21; 364(16): 1503-12). The odds ratio was 6.2 [95% confidence interval (CI) 3.7-10.4] for familial interstitial pneumonia and 8.3 (95% CI 5.8-11.9) for IPF (Id.). These findings were simultaneously confirmed by other researchers in an independent case-control study that included 341 IPF and 801 control individuals (Zhang et al. N Engl J Med. 2011 Apr. 21; 364(16): 1576-7). The minor-allele frequency was 34.3% in patients with IPF and 11.1% in controls (allelic association, $P=7.6\times10-40$) (Id.).

Prognostic Biomarkers

High blood concentrations of KL-6, also known as MUC-1, repeatedly have been shown to be predictive of decreased survival in IPF (Zhang & Kaminski. Curr Opin Pulm Med. 2012 September; 18(5): 441-6). Most studies have been limited by cohort size and lack replication, but are still highly consistent and support the use of KL-6 in disease stratification (Ishikawa et al. Respir Investig. 2012 March; 50(1): 3-13. Other studies have shown that serum CCL18 (chemokine (C-C motif) ligand 18) levels were able to predict outcomes in IPF (higher serum CCL18 concentrations were predictive of decreased total lung capacity, decreased forced vital capacity and increased mortality (Prasse et al. Am J Respir Crit Care Med. 2009 Apr. 15; 179(8): 717-23)), that high serum SP-A concentrations was a predictor of early mortality in IPF (Kinder et al. Chest. 2009 June; 135(6): 1557-63), and that high serum concentrations of YKL-40 distinguished two groups with distinct survival patterns with the hazard ratio for serum YKL-40 (cut-off 79 ng/ml) as 10.9 (95% CI 1.9-63.8, P<0.01) (Korthagen et al. Respir Med. 2011 January; 105(1): 106-13). Researchers using a targeted proteomic approach screened 95 proteins in the plasma of 140 IPF patients (derivation cohort) and validated the results in a replication cohort (101 patients) (Richards et al. Am J Respir Crit Care Med. 2012 Jan. 1; 185(1): 67-76). High plasma concentrations of MMP-7, ICAM-1 and IL-8 were predictive of poor overall survival in both cohorts (Id.). The derivation cohort was used to derive a personal clinical and molecular mortality prediction index (PCMI) using the step AIC approach (Venables & Ripley. Modern applied statistics with S. New York: Springer; 2002). This index [PCMI=114×I(Male)+2×(100%−FVC % predicted)+3×(100%−Dlco % predicted)+111×I(MMP-7≥4.3 ng/ml)] was highly predictive of mortality in the replication cohort with a C-index for early mortality of 84 (Richards et al. Am J Respir Crit Care Med. 2012 Jan. 1; 185(1): 67-76).

Similarly, changes in circulating blood cell populations have been associated with outcome. Recent studies have demonstrated in a cohort of 51 patients that increases in circulating fibrocytes predicted poor prognosis (Moeller et al. Am J Respir Crit Care Med. 2009 Apr. 1; 179(7): 588-94) and other researchers have observed that downregulation of CD28 in circulating CD4 T cells was a marker of poor prognoses in a cohort of 89 IPF patients (Gilani et al. PLoS One. 2010 Jan. 29; 5(1): e8959.

Disease Activity Markers

There is no real definition of the disease activity of IPF. It is conceivable that KL-6, SP-A and MMP-7 are markers of alveolar epithelial cell injury and CCL-18 a marker of alveolar macrophage activation; however, at present, markers for some of the processes that happen in IPF such as deposition of excess collagen have not yet been discovered. Mechanistically, the biomarker that may be tied most closely to disease pathogenesis is MMP-7, a pluripotent matrix metalloprotease expressed in alveolar type II cells. MMP-7 is a WNT/β-catenin pathway target molecule (He et al. J Am Soc Nephrol. 2012 February; 23(2): 294-304), suggesting that increases of MMP-7 are reflective of aberrant WNT/β catenin that has been described in IPF (Chilosi et al. Am J Pathol. 2003 May; 162(5): 1495-502; Konigshoff et al. J Clin Invest. 2009 April; 119(4): 772-87). MMP-7 knockout mice are relatively protected from bleomycin-induced fibrosis, suggesting that it is mechanistically involved in the fibrosis pathways (Zuo et al. Proc Natl Acad Sci USA. 2002 Apr. 30; 99(9): 6292-7). However, at present, there is no data to support MMP-7 as a marker of disease activity (Id.).

Acute exacerbations of IPF (AE-IPF) are episodes of decline in respiratory status without an identifiable cause (Collard et al. Am J Respir Crit Care Med. 2007 Oct. 1; 176(7): 636-43), that lead to significant mortality (Song et al. Eur Respir J. February; 37(2): 356-63). Of the previous markers mentioned, KL-6 has been mostly widely studied in this context (Ishikawa et al. Respir Investig. 2012 March; 50(1): 3-13; Collard et al. Am J Physiol Lung Cell Mol Physiol. 2010 July; 299(1): L3-7; Satoh et al. J Intern Med. 2006 November; 260(5): 429-34). It appears that AE-IPF are associated with increases in blood KL-6, although the mechanisms have not yet been elucidated. Comparisons of gene expression in the lungs of patients with AE-IPF lungs to stable IPF (Konishi et al. Am J Respir Crit Care med. 2009 Jul. 15; 180(2): 167-75) has identified 579 differentially expressed genes, and did not find any indication of infectious or inflammatory cause. Researchers have found increases in α-defensins, a group of innate antimicrobial peptides, in the mRNA levels as well as in the plasma protein level of AE-IPF patients, suggesting that they should be evaluated as biomarkers for acute exacerbations (Zasloff. Nature. 2002 Jan. 24; 415(6870): 389-95).

Drug Efficacy Biomarkers

There are no drug efficacy biomarkers in IPF (Zhang & Kaminski. Curr Opin Pulm Med. 2012 September; 18(5): 441-6).

Utility and Limitations of Animal Models in the Study of IPF

Bleomycin, a chemotherapeutic agent used in the treatment of certain human cancers, has been the most commonly used agent to induce pulmonary fibrosis in animal models of the disease. Bleomycin can be administered through a variety of routes including intratracheal (most common), intraperitoneal, oropharyngeal aspiration, and via osmotic pump. It induces DNA strand breaks (Lown & Sim. Biochem Biophys Res Commun. 1977 Aug. 22; 77(4): 1150-7) and oxidative injury (Sausville et al. Biochem Biophys Res Commun. 1976 Dec. 6; 73(3): 814-22), thus leading to epithelial injury, inflammation, and ultimately fibrosis (Barkauskas & Noble. Am J Physiol Cell Physiol. 2014 Jun. 1; 306(11): C987-96).

The bleomycin model is well-documented and the best characterized murine model in use today to demonstrate efficacy of a particular drug or protein kinase inhibitor in the post-inflammatory/pre-fibrotic/fibro-preventive stages (Vittal, R. et al., *J Pharmacol Exp Ther.*, 321(1):35-44, 2007; Vittal, R. et al., *Am J Pathol.*, 166(2):367-75, 2005; Hecker L. et al., *Nat Med.*, 15(9):1077-81, 2009).

The antibiotic bleomycin was originally isolated from *Streptomyces verticillatus* (Umezawa, H. et al., *Cancer* 20: 891-895, 1967), and was subsequently found to be effective against squamous cell carcinomas and skin tumors (Umezawa, H., *Fed Proc*, 33: 2296-2302, 1974); however, its usefulness as an anti-neoplastic agent was limited by dose-dependent pulmonary toxicity resulting in fibrosis (Muggia, F. et al., *Cancer Treat Rev*, 10: 221-243, 1983). The delivery of bleomycin via the intratracheal route (generally 1.25-4 U/kg, depending on the source) has the advantage that a single injection of the drug produces lung injury and resultant fibrosis in rodents (Phan, S. et al., *Am Rev Respir Dis* 121: 501-506, 1980; Snider, G. et al., *Am Rev Respir Dis.* 117: 289-297, 1978; Thrall, R. et al., *Am J Pathol*, 95: 117-130, 1979). Intratracheal delivery of the drug to rodents results in direct damage initially to alveolar epithelial cells. This event is followed by the development of neutrophilic and lymphocytic pan-alveolitis within the first week (Janick-Buckner, D. et al., *Toxicol Appl Pharmacol.*, 100(3):465-73, 1989). Subsequently, alveolar inflammatory cells are cleared, fibroblast proliferation is noted, and extracellular matrix is synthesized (Schrier D. et al., *Am Rev Respir Dis.*, 127(1):63-6, 1983). The development of fibrosis in this model can be seen biochemically and histologically by day 14 with maximal responses generally noted around days 21-28 (Izbicki G. et al., *Int J Exp Pathol.*, 83(3):111-9, 2002; Phan, S. et al., *Chest.*, 83(5 Suppl):44S-45S, 1983). Beyond 28 days, however, the response to bleomycin is more variable. Original reports suggest that bleomycin delivered intratracheally may induce fibrosis that progresses or persists for 60-90 days (Thrall R. et al., *Am J Pathol.*, 95(1):117-30, 1979; Goldstein R., et al., *Am Rev Respir Dis.*, 120(1):67-73, 1979; Starcher B. et al., *Am Rev Respir Dis.*, 117(2):299-305, 1978); however, other reports demonstrate a self-limiting response that begins to resolve after this period (Thrall R. et al., *Am J Pathol.*, 95(1):117-30, 1979; Phan, S. et al., *Chest,* 83(5 Suppl): 44S-45S, 1983; Lawson W. et al., *Am J Pathol.* 2005; 167(5):1267-1277). While the resolving nature of this model does not mimic human disease, this aspect of the model offers an opportunity for studying fibrotic resolution at these later time points.

The pathology generated by intratracheal bleomycin is not fully representative of IPF histology. The diagnostic criteria for IPF (usual interstitial pneumonia) are threefold: 1) nonuniform pattern of disease involvement with normal lung interspersed with diseased lung, 2) architectural distortion (honeycomb change and/or scar), and 3) presence of fibroblast foci, presumed to be indicative of current ongoing disease. These structures are covered by hyperplastic AEC2s (Katzenstein et al. Hum Pathol. 2008 September; 39(9): 1275-94). While not a diagnostic criterion, human IPF specimens also typically include areas of alveolar collapse with incorporation of basal lamina (Myers & Katzenstein. Chest. 1988 December; 94(6): 1309-11). While experimental bleomycin fibrosis can recapitulate alveolar collapse and cystic air spaces 14 days after intratracheal instillation (Moore et al. Am J Respir Cell Mol Biol), it is also typically characterized by significant neutrophilic inflammation, and there rarely exist examples of the hyperplastic AEC2s that are pathognomonic for the human disease (Degryse et al. Am J Physiol Lung Cell Mol Physiol. 2010 October; 299(4): L442-52; Moore et al. Am J Respir Cell Mol Biol. 2013 August; 49(2): 167-79; Barkauskas & Noble. Am J Physiol Cell Physiol. 2014 Jun. 1; 306(11): C987-96).

Unlike IPF, however, the fibrosis generated after intratracheal bleomycin is not progressive. Following intratracheal bleomycin, collagen content (as assessed by hydroxyproline assay) peaks around 21-28 days postinjury (Izbicki et al. Int J Exp Pathol. 2002 June; 83(3): 111-9). Recent reports and personal experience with this model suggest that the fibrosis induced by a single exposure to bleomycin is self-limited and can display some resolution/regression during the weeks following the injury (Chung et al. Am J Respir Cell Mol Biol. 2003 September; 29(3 Pt 1): 375-80; Lawson et al. Am J Pathol. 2005 November; 167(5): 1267-77; Rock et al. Proc Natl Acad Sci USA. 2011 Dec. 27; 108(52): E1475-83; Barkauskas & Noble. Am J Physiol Cell Physiol. 2014 Jun. 1; 306(11): C987-96).

Investigators have tried to optimize the bleomycin fibrosis model to better replicate the histology associated with human IPF. In one such study, a repetitive bleomycin model was developed in an attempt to recapitulate the recurrent alveolar injury that is hypothesized to drive IPF pathogenesis. Degryse et al. (Am J Physiol Lung Cell Mol Physiol. 2010 October; 299(4): L442-52) describe a model in which they administered intratracheal bleomycin biweekly up to eight times. The histology from this repetitive injury model revealed prominent hyperplastic AEC2s in areas of fibrosis as well as more of a temporally heterogeneous pattern of lung injury (i.e., fibrotic scar next to hyperplastic AEC2s next to normal tissue). Further, the fibrosis that developed seemed to persist until at least 10 weeks after the last bleomycin dose. While the histological results of this model do seem more consistent with human IPF, the time-intensive nature of this model may limit its applicability in the laboratory (Barkauskas & Noble. Am J Physiol Cell Physiol. 2014 Jun. 1; 306(11): C987-96).

Despite its imperfections, the bleomycin model of pulmonary fibrosis remains the most common in the study of fibrotic lung disease. Other fibrosis generating models include the following (reviewed in Moore et al. Am J Physiol Lung Cell Mol Physiol. 2008 February; 294(2): L152-60): granulomatous inflammation (Jakubzick et al Am J Pathol. 2003 May; 162(5): 1475-86), fluorescein isocyanate (Kolodsick et al. J Immunol. 2004 Apr. 1; 172(7): 4068-76; Roberts et al. J Pathol. 1995 July; 176(3): 309-18), irradiation-induced (McDonald et al. Radiother Oncol. 1993 March; 26(3): 212-8), adenosine deaminase deficiency (Chunn et al. Am J Physiol Lung Cell Mol Physiol. 2006 March; 290(3): L579-87), and murine gamma-herpesvirus (which is typically used to augment a fibrotic response to another stimulus) (Gangadharan et al. J Leukoc Biol. 2008 July; 84(1): 50-8; Lok et al. Eur Respir J. 2002 November; 20(5): 1228-32). While many investigators are now designing experiments with human IPF tissue/cells, the field at large still relies heavily on murine models of the disease. A murine model of IPF that recapitulates the disease more faithfully than bleomycin would be most welcome (Barkauskas & Noble. Am J Physiol Cell Physiol. 2014 Jun. 1; 306(11): C987-96).

To date, only limited treatments or therapies exist for the treatment of IPF, and there is a substantial unmet need for effective treatments that can alter the course of IPF by slowing or reversing disease progression. Many clinical trials have ended unsuccessfully after showing negligible patient benefit or high incidence of side effects.

The described invention involves a validated therapeutic target for the development of drugs for patients with progressive tissue fibrosis.

SUMMARY OF EMBODIMENTS

The disclosure provides a method of treating a lung injury at risk of progressing to a fibrotic lung disease in a subject in need thereof. In one aspect, the method comprises administering to the subject a therapeutic amount of IL-6 polypeptide, hyaluronan (HA), compositions thereof, mimetics thereof, pharmaceutically acceptable salts thereof, or combinations thereof, wherein the therapeutic amount is effective to increase renewal of alveolar epithelial cell 2 (AEC2) stem cells, to repair the injury, to reduce lung fibrosis, or a combination thereof.

The disclosure also provides a method of increasing alveolar epithelial cell 2 (AEC2) stem cell renewal in a lung to reduce progression of a lung injury to a fibrotic disease in a subject in need thereof. In one aspect, the method comprises administering to the subject a therapeutic amount of IL-6 polypeptide, hyaluronan (HA), compositions thereof, mimetics thereof, pharmaceutically acceptable salts thereof, or combinations thereof.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1A-FIG. 1F show that $Tlr4^{-/-}$ mice demonstrate higher mortality and more severe fibrosis after bleomycin-induced lung injury. FIG. 1A is a graph showing Tlr4 expression in the lungs of untreated and bleomycin-treated wild-type (WT) mice at day 7 after bleomycin treatment, as assessed by RT-PCR (n=3 mice per group). Data are mean±s.e.m. ****$P<0.0001$ by Student's t-test. FIG. 1B shows a survival analysis of Tlr4$^{-/-}$ mice (n=35) and WT mice (n=34) over a 21-day period after intratracheal treatment with bleomycin (2.5 units per kg body weight (U/kg)). *P<0.05 by log-rank test. FIG. 1C are representative images (n=4 images per group, and 24 images in total) of trichrome staining, and FIG. 1D shows quantification of hydroxyproline contents (saline: WT, n=5; Tlr4$^{-/-}$, n=4; bleomycin 1.25 U/kg: WT, n=6; Tlr4$^{-/-}$, n=9; bleomycin 2.5 U/kg: WT, n=4; Tlr4$^{-/-}$, n=4; bleomycin, 5 U/kg: WT, n=9; Tlr4$^{-/-}$, n=12) in lungs from Tlr4$^{-/-}$ and WT mice 21 days after bleomycin injury. Data are mean±s.e.m. *P<0.05; **P<0.01; by two-way analysis of variance (ANOVA) followed by Sidak's multiple-comparison test. FIG. 1E shows representative images (n=4 images (of n=3 mice) per group) of anti-α-SMA immunostaining in the lungs of WT (top) and Tlr4$^{-/-}$ (bottom) mice 21 days after bleomycin (2.5 U/kg) injury. FIG. 1F is a graph showing Acta2 expression in the lungs of bleomycin-treated Tlr4$^{-/-}$ (n=4) and WT (n=4) mice, as assessed by qPCR. Data are mean±s.e.m. *P<0.05 by Student's t-test. Scale bars, 200 μm.

FIG. 2A is a survival curve of Tlr2$^{-/-}$ and WT mice treated with bleomycin 2.5 U/Kg (n=10 each; P>0.05 by the log-rank test). FIG. 2B is a graph showing hydroxyproline levels in lung tissues of Tlr2 (n=5) and WT mice (n=9) harvested at day 21 after bleomycin (P>0.05 by Student t-test).

FIG. 3A is a graph showing BAL cell count and differential count of Tlr4$^{-/-}$ mice and WT controls after bleomycin treatment at indicated time points. For day 0, WT n=4, Tlr4$^{-/-}$ n=5; day 1, WT n=4, Tlr4$^{-/-}$ n=4; day 3, WT n=5, Tlr4$^{-/-}$ n=5; day 5, WT n=5, Tlr4$^{-/-}$ n=5; day 10, WT n=8, Tlr4$^{-/-}$ n=4. FIG. 3B-FIG. 3C show MIP-2 and TGF-β levels in BAL of Tlr4$^{-/-}$ mice and WT controls at indicated time points. For day 0, WT n=4, Tlr4$^{-/-}$ n=5; day 1, WT n=4, Tlr4$^{-/-}$ n=4; day 3, WT n=5, Tlr4$^{-/-}$ n=5; day 5, WT n=5, Tlr4$^{-/-}$ n=5; day 10, WT n=8, Tlr4$^{-/-}$ n=4. ****P<0.0001 by two-way ANOVA followed by Sidak's multiple comparison test.

FIG. 4A depicts cell surface TLR4 expression examined on AEC2s, macrophages, and fibroblasts isolated from unchallenged Tlr4$^{-/-}$ and WT mice with flow cytometry. FIG. 4B shows cell surface TLR2 expression examined on AEC2s isolated from WT and Tlr2 mouse lungs. In FIG. 4C, cell surface HA of AEC2s from WT and Tlr2$^{-/-}$ (upper panel), or WT and Tlr4$^{-/-}$ (lower panel), were analyzed and compared. Blank control (−HABP, black line) was included. FIG. 4D shows the strategy of flow cytometry analysis of single cells from mouse lung homogenates and gating for type II cells. Viable cells were selected as 7-AAD$^-$ cells (R2) from total single cell digestion (R1). Total epithelial cells (R3) were defined as EpCAM$^+$Lin$^-$ (CD31$^-$CD34$^-$CD45$^-$). CD24$^-$Sca-1$^-$AEC2s (R4) were gated from R3. FIG. 4E shows GFP expression of flow gated CD24$^-$Sca-1$^-$AEC2s (EpCAM$^+$Lin$^-$CD24$^-$Sca-1$^-$) from uninjured SFTPC-GFP mouse lung. FIG. 4F shows percentages of CD24$^-$Sca-1$^-$ AEC2s in total GFP$^+$ cells from uninjured SFTPC-GFP mouse lung. FIG. 4G shows Tomato expression of flow gated CD24$^-$Sca-1$^-$AEC2s from uninjured SFTPC-CreER; Rosa-Tomato mouse lung. FIG. 4H shows percentages of CD24$^-$Sca-1$^-$AEC2s in total Tomato$^+$ cells from uninjured SFTPC-CreER;Rosa-Tomato mouse lung. FIG. 4I shows SP-C staining of flow sorted CD24$^-$Sca-1$^-$AEC2s from uninjured WT mouse lungs showing 96.67% cells were SP-C positive. Scale bar, 50 μm.

FIG. 5A-FIG. 5D show how Tlr4$^{-/-}$ deficiency leads to loss of AEC2s in mouse lungs after bleomycin-induced injury. FIG. 5A shows representative flow cytometry analysis of the change in the CD24$^-$Sca-1$^-$AEC2 population gated from total lung epithelial cells (EpCAM$^+$Lin$^-$) in bleomycin-treated WT mice (day 0, n=3; day 3, n=4; day 7, n=6; day 14, n=5; day 21, n=4). FIG. 5B is a graph showing the numbers of CD24$^-$Sca-1$^-$AEC2s recovered from the lungs of bleomycin-treated Tlr4$^{-/-}$ and WT mice at indicated time points (day 0: n=3 each; day 3: n=4 each; day 7: WT, n=6; Tlr4$^{-/-}$, n=4; day 14: n=5 each). Data are mean±s.e.m. *P<0.05 by Student's t-test. FIG. 5C is a graph showing Tlr4 expression in CD24$^-$Sca-1$^-$AEC2s flow-sorted from bleomycin-treated WT mice at the indicated time points, as assessed by RT-PCR (n=4 mice per group). Data are mean±s.e.m. P<0.01; **P<0.0001; by one-way ANOVA followed by Sidak's multiple-comparison test. FIG. 5D shows representative flow cytometry analysis of CD24$^-$Sca-1$^-$AEC2s in Tlr4$^{-/-}$ and WT mouse lungs at day 0 (n=3 mice per group) and day 14 (n=5 mice per group) after bleomycin treatment.

FIG. 6A are representative images (n=3 images per mouse lung; n=3 mice per group) of co-staining of SFTPC and BrdU in lung sections from WT (top) and Tlr4$^{-/-}$ (bottom) mice 5 days after bleomycin treatment. Arrows indicate overlapping staining. Scale bars, 50 μm. FIG. 6B is a graph showing quantification of SFTPC$^+$BrdU$^+$ in the total SFTPC$^+$ population from the lungs of WT (n=6) and Tlr4$^{-/-}$ (n=5) mice. FIG. 6C show representative images (n=9 images per group) of co-staining and FIG. 6D shows the quantification of SFTPC$^+$Ki67$^+$ in the SFTPC cell population in lung sections from WT (n=3) and Tlr4$^{-/-}$ (n=3) mice after bleomycin treatment. Scale bars, 50 μm. FIG. 6E is a representative image (n=6 colonies) of WT AEC2s stained for SFTPC and T1α. Scale bar, 20 μm. FIG. 6F is a graph showing replating colony-forming efficiencies (CFEs) of CD24$^-$Sca-1$^-$AEC2s from bleomycin-treated WT mice (passage (P) 0, n=8; P1, n=3; P2, n=3). FIG. 6G is a graph showing CFEs of CD24$^-$Sca-1$^-$AEC2s of Tlr4$^{-/-}$ (n=3) and WT mice (n=3) 3 days after bleomycin. FIG. 6H is a graph of the colony sizes of CD24$^-$Sca-1$^-$ AEC2s from Tlr4$^{-/-}$ (n=44) and WT mice (n=39). FIG. 6I is a graph showing CFEs of CD24$^-$Sca-1$^-$AEC2s with or without Healon treatment (WT, n=5 mice per group; Tlr4$^{-/-}$, n=3 mice per group). FIG. 6J is a graph showing CFEs of uninjured WT AEC2s after treatment with medium only (n=4), Healon (n=5), or Healon and pep-1 (n=3). Data are mean±s.e.m. P<0.01; *P<0.001; ****P<0.0001.

FIG. 7A is a graph showing the colony-forming efficiency (CFE) of CD24$^-$Sca-1$^-$AEC2s sorted from uninjured Tlr4$^{-/-}$ and WT mice determined at day 12 post plating (WT n=4, Tlr4$^{-/-}$ n=3, P>0.05).

FIG. 7B is a graph showing the percent of apoptotic cells in gated EpCAM$^+$Lin$^-$ epithelial cells from lungs of Tlr4$^{-/-}$ and WT mice 3 days after bleomycin (WT n=5, Tlr4$^{-/-}$ n=6; *P<0.05 by Student t-test). Apoptosis was determined by staining 7-AAD and Annexin V of single cell lung homogenates.

FIG. 8A is a series of pictures showing mouse lung histology (H&E staining) of SFTPC-Cre;Has2$^{flox/flox}$ mice and littermates (Has2$^{flox/flox}$) at 4 weeks and 9 weeks of age. FIG. 8B is a series of pictures showing mouse lung histology (H&E staining) of SFTPC-Cre and WT controls at 10 weeks old. FIG. 8C is a graph showing HA concentration in BAL of uninjured SFTPC-Cre;Has2$^{flox/flox}$ (n=4) and Has2$^{flox/flox}$ mice (n=4). FIG. 8D is a graph showing the numbers of CD24$^-$Sca-1$^-$AEC2 recovered from SFTPC-Cre;Has2$^{flox/flox}$ mice (n=3) and Has2$^{flox/flox}$ (n=4) at 9 weeks of age. FIG. 8E is a graph showing the percent of apoptotic cells in gated EpCAM$^+$ Lin$^-$ (CD31$^-$CD34$^-$CD45$^-$) cells from day 3 bleomycin treated lungs of SFTPC-Cre;Has2$^{flox/flox}$ (n=4) and littermate controls (n=6) (*P<0.05 by Student t-test).

FIG. 9A is a graph showing cell surface expression of HA in CD24$^-$Sca-1$^-$AEC2s from SFTPC-Cre;Has2$^{flox/flox}$ and Has2$^{flox/flox}$ mice (n=3 per group). FIG. 9B is a graph showing HA concentration in CD24$^-$Sca-1$^-$AEC2s from SFTPC-Cre;Has2$^{flox/flox}$ (n=3), Has2$^{flox/flox}$ (n=3) and WT (n=3) mice. FIG. 9C is a graph showing the numbers of CD24$^-$Sca-1$^-$AEC2s recovered from SFTPC-Cre;Has2$^{flox/flox}$ (n=4) and Has2$^{flox/flox}$ (n=6) mice 3 days after bleomycin treatment. FIG. 9D is a graph showing the percentage of Ki67$^+$AEC2s in the CD24$^-$Sca-1$^-$AEC2 population from SFTPC-Cre;Has2$^{flox/flox}$ (n=9) and SFTPC-Cre (n=9) mice 3 days after bleomycin treatment. FIG. 9E is a graph showing the colony-forming efficiency (CFE) of CD24$^-$Sca-1$^-$AEC2s sorted from SFTPC-Cre; Has2$^{flox/flox}$ (n=3) and Has2$^{flox/flox}$ (n=3) 3 days after bleomycin. FIG. 9F is a graph showing the CFEs of CD24$^-$Sca-1$^-$AEC2s sorted from SFTPC-Cre;Has2$^{flox/flox}$ (n=4 per group) and Has2$^{flox/flox}$ (medium, n=5; Healon, n=4) mice 3 days after bleomycin treatment. FIG. 9G shows survival curves of SFTPC-Cre;Has2$^{flox/flox}$ (n=27) and Has2$^{flox/flox}$ littermates (n=31) after bleomycin treatment. FIG. 9H is a graph showing the hydroxyproline contents in the lungs of SFTPC-Cre;Has2$^{flox/flox}$ (day 0, n=5; day 21, n=6) and Has2$^{flox/flox}$ (day 0, n=7; day 21, n=10) mice. FIG. 9I shows representative images (n=2 images per mouse lung; n=3 mice per group) of trichrome staining of lung sections from SFTPC-Cre;Has2$^{flox/flox}$ (bottom) and Has2$^{flox/flox}$ (top) mice harvested on day 21 after bleomycin treatment. Scale bars, 200 μm. Data are mean±s.e.m. *P<0.05; P<0.01; *P<0.001; ****P<0.0001.

FIG. 10G is a graph showing the quantification of CD24$^-$Sca-1$^-$AEC2s recovered (buffer, n=8; rIL-6, n=4) (top), Ki67 staining of AEC2s (buffer, n=6; rIL-6, n=8) (middle) and total BALF protein (n=4 per group) (bottom) from bleomycin-treated Tlr4$^{-/-}$ mice after treatment with rIL-6 or buffer. Hydroxyproline contents of bleomycin-treated Tlr4$^{-/-}$ (FIG. 10H) (buffer, n=4; rIL-6, n=9) or SFTPC-Cre;Has2$^{flox/flox}$ (FIG. 10I) (buffer, n=9; rIL-6, n=6) mice after treatment with rIL-6 or buffer. Data are mean±s.e.m. *P<0.05; P<0.01; *P<0.001; ****P<0.0001.

FIG. 11A is a graph showing Il6 expression extracted from the Affymetrix array data which CD24$^-$Sca-1$^-$AEC2s were flow sorted from either untreated lungs or the lungs 4 days after bleomycin. The CD24$^-$Sca-1$^-$AEC2s were pooled from multiple mouse lungs each category. Negative value, down-regulated in Tlr4$^{-/-}$ AEC2s compared to WT AEC2s. FIG. 11B is a graph showing Il6 expression in flow sorted CD24$^-$Sca-1$^-$AEC2s confirmed with RT-PCR (for day 0, WT n=6, Tlr4$^{-/-}$ n=5; for day 4, n=4 each; *P<0.001 by two-way ANOVA followed by Sidak's multiple comparison test). FIG. 11C is a graph showing the effect of STAT3 inhibitor (Stat3i, S3I-201) in IL-6-promoted AEC2 colony formation (IL-6 n=4, all other groups n=3 each, **P<0.0001 by one-way ANOVA followed by Sidak's multiple comparison test). FIG. 11D-FIG. 11E are graphs showing AEC2 cell apoptosis and BAL cell counts of bleomycin day 7 Tlr4$^{-/-}$ mice treated with IL-6 protein (n=4) or control buffer (n=3) at one day before and one day and three days after bleomycin. FIG. 11D shows the percent of apoptotic cells in gated CD24$^-$Sca-1$^-$AEC2s (P>0.05). FIG. 11E shows the numbers of BAL cells (P>0.05 by Student t-test). FIG. 11F shows Tlr4$^{-/-}$ mice treated with bleomycin or with additional IL-6 protein treatment at one day before and one day and three days after bleomycin treatment. Percent of survived mice were recorded for 21 days (buffer group n=14, IL-6 group n=10, *P<0.05 by the log-rank test). FIG. 11G shows WT mice treated with anti-IL-6 antibodies or control IgG at one day before and one day and three days after bleomycin treatment (indicated with arrows). Percent of mice survived were records for 21 days after bleomycin (IgG group n=19, IL-6 Ab n=24, **P<0.01 by the log-rank test).

FIG. 12A shows how human AEC2s were defined as Lin$^-$ (CD31$^-$CD45$^-$)EpCAM$^+$HTII-280$^+$ cells (R3). FIG. 12B are graphs showing TLR4 expression on HTII280$^+$ AEC2s isolated from healthy donor lungs (left) and IPF lungs (right). The results were confirmed with cells from five normal and three IPF subjects. FIG. 12C are graphs showing TLR2 expression on HTII-280$^+$AEC2s isolated from healthy donor lungs (left) and IPF lungs (right). The results were confirmed with three normal and three IPF subjects. FIG. 12D are representative images of colonies of HTII-280$^+$AEC2s isolated from a normal donor, and stained with SFTPC (red) and HTII-280 (green). Scale bars, 20 μm. FIG. 12E is a graph showing CFEs of normal and IPF HTII-280$^+$ AEC2s treated with or without Healon (HA) 200 μg/ml (M, media; n=3 each group, **P<0.01 by one-way ANOVA followed by Sidak's multiple comparison test). The results were repeated with AEC2s from three IPF subjects. FIG. 12F is a graph showing CFEs of IPF AEC2s with indicated concentrations of HA treatments (M for media, n=6, at 400 n=4, at 600 n=6, at 800 n=4, ns, not significant, *P<0.05 by one-way ANOVA followed by Sidak's multiple comparison test).

FIG. 13A-FIG. 13J show loss of cell surface HA and impaired renewal capacity of AEC2s from patients with IPF. FIG. 13A shows representative flow cytometry analysis of HTII-280$^+$AEC2s from the lungs of healthy donors (n=4) (left) or patients with IPF (n=7) (right). FIG. 13B is a graph showing the percentage of HTII-280$^+$AEC2s from the lungs of healthy donors (n=4) or patients with IPF (n=7). FIG. 13C shows representative flow cytometry analysis of cell surface HA on HTII-280$^+$AEC2s from healthy (n=6) (left) or diseased (n=9) (right) lungs. FIG. 13D is a graph showing the quantification of HABP$^+$HTII-280$^+$ AEC2s from healthy (n=6) and diseased (n=9) lungs. FIG. 13E is a graph showing the relative Has2 expression in HTII-280$^+$AEC2s from healthy and diseased lungs, as determined by RT-PCR (n=3 subjects per group). FIG. 13F is a graph showing CFE between HTII-280$^+$AEC2s from one healthy and one diseased lung (n=3 wells per group). The results were repeated with AEC2s from three more healthy controls and five more subjects with IPF. FIG. 13G is a graph showing the colony sizes of HTII-280$^+$AEC2s isolated from the lungs of healthy donors (n=61) and patients with IPF (n=75). FIG. 13H is a graph showing the CFEs of diseased HTII-280$^+$AEC2s that were treated with or without IL-6 (n=3 per group). The results were repeated with AEC2s from two more diseased lungs. FIG. 13I shows flow-gated HA$^{hi}$ and HA$^{lo}$ HTII-280$^+$ AEC2s from healthy donors (n=4) (left) and patients with IPF (n=3) (right). FIG. 13J is a graph showing CFE between HA$^{hi}$ and HA$^{lo}$ AEC2s from lungs of healthy donors (n=4 per group) and patients with IPF (n=3 per group). The results were repeated with cells from two more subjects for each group. Data are mean±s.e.m. *P<0.05; P<0.01; *P<0.001; ****P<0.0001.

FIG. 14A shows AEC2 cells gated as EpCAM$^+$HTII-280$^+$ from 7AAD$^-$Lin$^-$ subpopulation of lung homogenates from less fibrotic area and severely fibrotic area of IPF lung and healthy control lung. The results were repeated with three IPF patient lungs. FIG. 14B is a graph showing CFEs of HTII-280$^+$AEC2 cells isolated from less fibrosis area and severely fibrotic area of IPF lung and healthy lung. (n=3, ns, not significant, by Student t-test). FIG. 14C is a graph showing cell surface HA on HTII-280$^+$AEC2s from less fibrotic area and severely fibrotic area of IPF patients and healthy donors. The results were confirmed with cells from three IPF subjects.

DETAILED DESCRIPTION OF EMBODIMENTS

Figure 1A:
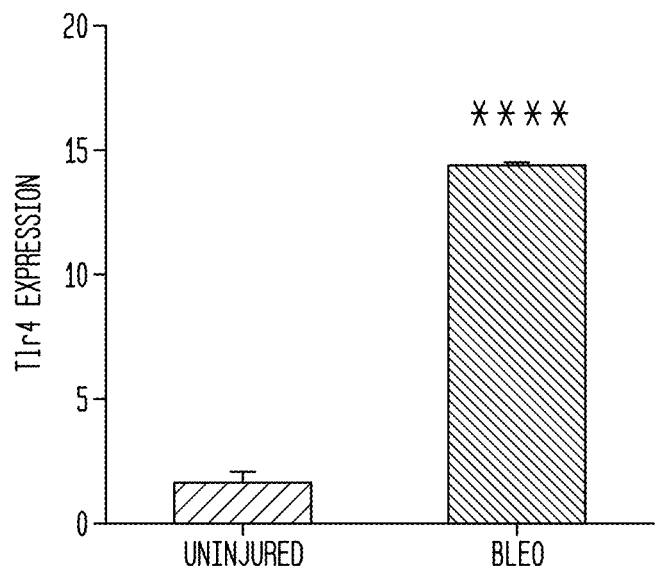

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "peptide" is a reference to one or more peptides and equivalents thereof known to those skilled in the art, and so forth.

As used herein, the term "about" means plus or minus 10% of the numerical value of the number with which it is being used. Therefore, about 50% means in the range of 40%-60%.

"Administering" when used in conjunction with a therapeutic means to administer a therapeutic directly into or onto a target organ, tissue or cell or to administer a therapeutic to a subject, whereby the therapeutic positively impacts the organ, tissue or cell to which it is targeted. Thus, as used herein, the term "administering", when used in conjunction with IL-6 polypeptide or hyaluronan (HA), can include, but is not limited to, providing IL-6 polypeptide or hyaluronan (HA) into or onto the target organ, tissue or cell; providing IL-6 polypeptide or hyaluronan (HA) systemically to a patient by, e.g., intravenous injection, whereby the therapeutic reaches the target organ, tissue or cell; providing IL-6 polypeptide or hyaluronan (HA) in the form of the encoding sequence thereof to the target tissue (e.g., by so-called gene-therapy techniques). "Administering" may be accomplished by parenteral, oral or topical administration, by inhalation, or by such methods in combination with other known techniques.

The terms "animal," "patient," and "subject" as used herein include, but are not limited to, humans and non-human vertebrates such as wild, domestic and farm animals. According to some embodiments, the terms "animal," "patient," and "subject" may refer to humans. According to some embodiments, the terms "animal," "patient," and "subject" may refer to non-human mammals. According to some embodiments, the terms "animal," "patient," and "subject" may refer to any or combination of: dogs, cats, pigs, cows, horses, goats, sheep or other domesticated non-human mammals. According to some embodiments, the subject is a human patient that has been diagnosed or is suspected of having a lung injury at risk of progressing to a fibrotic lung disease. According to some embodiments, the subject is a human patient that has been diagnosed or is suspected of having pulmonary fibrosis. According to some embodiments, the subject is a human patient that has been diagnosed or is suspected of idiopathic pulmonary fibrosis. According to some embodiments, the subject is a human patient that has been diagnosed or is suspected of having a bleomycin-induced lung injury. A "subject in need" of treatment for a particular condition can be a subject having that condition, diagnosed as having that condition, or at risk of developing that condition.

The terms "apoptosis" or "programmed cell death" refer to a highly regulated and active process that contributes to biologic homeostasis comprised of a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

Apoptotic cell death is induced by many different factors and involves numerous signaling pathways, some dependent on caspase proteases (a class of cysteine proteases) and others that are caspase independent. It can be triggered by many different cellular stimuli, including cell surface receptors, mitochondrial response to stress, and cytotoxic T cells, resulting in activation of apoptotic signaling pathways.

The caspases involved in apoptosis convey the apoptotic signal in a proteolytic cascade, with caspases cleaving and activating other caspases that then degrade other cellular targets that lead to cell death. The caspases at the upper end of the cascade include caspase-8 and caspase-9. Caspase-8 is the initial caspase involved in response to receptors with a death domain (DD) like Fas.

Receptors in the TNF receptor family are associated with the induction of apoptosis, as well as inflammatory signaling. The Fas receptor (CD95) mediates apoptotic signaling by Fas-ligand expressed on the surface of other cells. The Fas-FasL interaction plays an important role in the immune system and lack of this system leads to autoimmunity, indicating that Fas-mediated apoptosis removes self-reactive lymphocytes. Fas signaling also is involved in immune surveillance to remove transformed cells and virus infected cells. Binding of Fas to oligimerized FasL on another cell activates apoptotic signaling through a cytoplasmic domain termed the death domain (DD) that interacts with signaling adaptors including FAF, FADD and DAX to activate the caspase proteolytic cascade. Caspase-8 and caspase-10 first are activated to then cleave and activate downstream caspases and a variety of cellular substrates that lead to cell death.

Mitochondria participate in apoptotic signaling pathways through the release of mitochondrial proteins into the cytoplasm. Cytochrome c, a key protein in electron transport, is released from mitochondria in response to apoptotic signals, and activates Apaf-1, a protease released from mitochondria. Activated Apaf-1 activates caspase-9 and the rest of the caspase pathway. Smac/DIABLO is released from mitochondria and inhibits IAP proteins that normally interact with caspase-9 to inhibit apoptosis. Apoptosis regulation by Bcl-2 family proteins occurs as family members form complexes that enter the mitochondrial membrane, regulating the release of cytochrome c and other proteins. TNF family receptors that cause apoptosis directly activate the caspase cascade, but can also activate Bid, a Bcl-2 family member, which activates mitochondria-mediated apoptosis. Bax, another Bcl-2 family member, is activated by this pathway to localize to the mitochondrial membrane and increase its permeability, releasing cytochrome c and other mitochondrial proteins. Bcl-2 and Bcl-xL prevent pore formation, blocking apoptosis. Like cytochrome c, AIF (apoptosis-inducing factor) is a protein found in mitochondria that is released from mitochondria by apoptotic stimuli. While cytochrome C is linked to caspase-dependent apoptotic signaling, AIF release stimulates caspase-independent apoptosis, moving into the nucleus where it binds DNA. DNA binding by AIF stimulates chromatin condensation, and DNA fragmentation, perhaps through recruitment of nucleases.

The mitochondrial stress pathway begins with the release of cytochrome c from mitochondria, which then interacts with Apaf-1, causing self-cleavage and activation of caspase-9. Caspase-3, -6 and -7 are downstream caspases that are activated by the upstream proteases and act themselves to cleave cellular targets.

Granzyme B and perforin proteins released by cytotoxic T cells induce apoptosis in target cells, forming transmembrane pores, and triggering apoptosis, perhaps through cleavage of caspases, although caspase-independent mechanisms of Granzyme B mediated apoptosis have been suggested.

Fragmentation of the nuclear genome by multiple nucleases activated by apoptotic signaling pathways to create a nucleosomal ladder is a cellular response characteristic of apoptosis. One nuclease involved in apoptosis is DNA fragmentation factor (DFF), a caspase-activated DNAse (CAD). DFF/CAD is activated through cleavage of its associated inhibitor ICAD by caspases proteases during apoptosis. DFF/CAD interacts with chromatin components such as topoisomerase II and histone H1 to condense chromatin structure and perhaps recruit CAD to chromatin. Another apoptosis activated protease is endonuclease G (EndoG). EndoG is encoded in the nuclear genome but is localized to mitochondria in normal cells. EndoG may play a role in the replication of the mitochondrial genome, as well as in apoptosis. Apoptotic signaling causes the release of EndoG from mitochondria. The EndoG and DFF/CAD pathways are independent since the EndoG pathway still occurs in cells lacking DFF.

Hypoxia, as well as hypoxia followed by reoxygenation can trigger cytochrome c release and apoptosis. Glycogen synthase kinase (GSK-3) a serine-threonine kinase ubiquitously expressed in most cell types, appears to mediate or potentiate apoptosis due to many stimuli that activate the mitochondrial cell death pathway. Loberg, R D, et al., J. Biol. Chem. 277 (44): 41667-673 (2002). It has been demonstrated to induce caspase 3 activation and to activate the proapoptotic tumor suppressor gene p53. It also has been suggested that GSK-3 promotes activation and translocation of the proapoptotic Bcl-2 family member, Bax, which, upon agregation and mitochondrial localization, induces cytochrome c release. Akt is a critical regulator of GSK-3, and phosphorylation and inactivation of GSK-3 may mediate some of the antiapoptotic effects of Akt.

"Cluster of Differentiation" or "cluster of designation" (CD) molecules are utilized in cell sorting using various methods, including flow cytometry. Cell populations usually are defined using a "+" or a "−" symbol to indicate whether a certain cell fraction expresses or lacks a particular CD molecule.

CD31 (platelet/endothelial cell adhesion molecule; PECAM1) normally is found on endothelial cells, platelets, macrophages and Kupffer cells, granulocytes, T cells, natural killer cells, lymphocytes, megakaryocytes, osteoclasts and neutrophils. CD31 has a key role in tissue regeneration and in safely removing neutrophils from the body. Upon contact, the CD31 molecules of macrophages and neutrophils are used to communicate the health status of the neutrophil to the macrophage.

CD34 is a monomeric cell surface glycoprotein normally found on hematopoietic cells, endothelial progenitor cells, endothelial cells of blood vessels, and mast cells. The CD34 protein is a member of a family of single-pass transmembrane sialomucin proteins and functions as a cell-cell adhesion factor. Studies suggest that CD34 also may mediate the attachment of stem cells to bone marrow extracellular matrix or directly to stromal cells.

CD45 (protein tyrosine phosphatase, receptor type, C; PTPRC) cell surface molecule is expressed specifically in hematopoietic cells. CD45 is a protein tyrosine phosphatase (PTP) with an extracellular domain, a single transmembrane segment, and two tandem intracytoplasmic catalytic domains, and thus belongs to receptor type PTP. Studies suggest it is an essential regulator of T-cell and B-cell antigen receptor signaling that functions by direct interaction with components of the antigen receptor complexes, or by activating various Src family kinases required for antigent receptor signaling. CD45 also suppresses JAK kinases, and thus functions as a regulator of cytokine receptor signaling. The CD45 family consists of multiple members that are all products of a single complex gene. Various known isoforms of CD45 include: CD45RA, CD45RB, CD45RC, CD45RAB, CD45RAC, CD45RBC, CD45RO, and CD45R (ABC). Different isoforms may be found on different cells. For example, CD45RA is found on naïve T cells and CD45RO is found on memory T cells.

Stem cell antigen (Sca-1) is a cell surface protein on bone marrow cells, indicative of HSC and MSC bonemarrow and blood content.

The CD24 gene encodes signal transducer CD24 protein, which may have a pivotal role in cell differentiation of different cell types. Signaling can be triggered by the binding of a lectin-like ligand to the CD24 carbohydrates, and transduced by the release of second messengers derived from the GPI-anchor. CD24 modulates B-cell activation responses. It promotes antigen-dependent proliferation of B-cells, and prevents their terminal differentiation into antibody-forming cells (see Su7zuki, T. et al., J. Immunol. (2001) 166: 5567-77).

The EPCAM gene provides instructions for making a protein known as epithelial cellular adhesion molecule (EpCAM). This protein is found in epithelial cells, which are the cells that line the surfaces and cavities of the body. The EpCAM protein is found spanning the membrane that surrounds epithelial cells, where it helps cells stick to one another (cell adhesion). In addition, the protein in the cell membrane can be cut at a specific location, releasing a piece called the intracellular domain (EpICD), which helps relay signals from outside the cell to the nucleus of the cell. EpICD travels to the nucleus and associates with other proteins, forming a group (complex) that regulates the activity of several genes that are involved in cell growth and division (proliferation), maturation (differentiation), and movement (migration), all of which are important processes for the proper development of cells and tissues. (https://ghr.nlm.nih.gov/gene/EPCAM)

Ki67 is a nuclear protein associated with cellular proliferation that is expressed in S, G1, G2 and M phases of the cell cycle, but is absent from resting cells (G0). During interphase, the antigen can be exclusively detected within the nucleus, whereas in mitosis most of the protein is relocated to the surface of the chromosomes. Scholzen, T., Gerdes, J., J. Cell Phyusiol (2000) 182(3): 311-22.

As used herein, "expression" refers to the process by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. Expression may also refer to the post-translational modification of a polypeptide or protein.

The term "interleukin" is used herein to refer to a cytokine secreted by, and acting on, leukocytes. Interleukins regulate cell growth, differentiation, and motility, and stimulates immune responses, such as inflammation. Examples of interleukins include, interleukin-1 (IL-1), interleukin-1β (IL-1β), interleukin-6 (IL-6), interleukin-8 (IL-8), and interleukin-12 (IL-12).

The interleukin-6 (IL-6) polypeptides to be used in the methods of the described invention may be any of natural IL-6 polypeptides, recombinant IL-6 polypeptides and the derivatives thereof as long as they have an IL-6 activity, particularly human IL-6 activity. Although human IL-6 is based on the DNA sequence as provided below, the production of the protein and proteolytic processing can result in processing variants thereof.

```
HUMAN IL-6, Gene ID: 3569
                                                                SEQ ID NO: 13
       1    acaccatgtt tggtaaataa gtgttttggt gttgtgcaag ggtctggttt cagcctgaag 61    ccatctcaga gctgtctggg tctctggaga ctggagggac aacctagtct agagcccatt 121    tgcatgagac caaggatcct cctgcaagag acaccatcct gagggaagag ggcttctgaa 181    ccagcttgac ccaataagaa attcttgggt gccgacgcgg aagcagattc agagcctaga 241    gccgtgcctg cgtccgtagt ttccttctag cttcttttga tttcaaatca agacttacag 301    ggagagggag cgataaacac aaactctgca agatgccaca aggtcctcct ttgacatccc 361    caacaaagag gtgagtagta ttctcccct tctgccctg aaccaagtgg gcttcagtaa 421    tttcagggct ccaggagacc tggggcccat gcaggtgccc cagtgaaaca gtggtgaaga 481    gactcagtgg caatggggag agcactggca gcacaaggca aacctctggc acagagagca 541    aagtcctcac tgggaggatt cccaaggggt cacttgggag agggcagggc agcagccaac 601    ctcctctaag tgggctgaag caggtgaaga aagtggcaga agccacgcgg tggcaaaaag 661    gagtcacaca ctccacctgg agacgccttg aagtaactgc acgaaatttg aggatggcca 721    ggcagttcta caacagccgc tcacaggag agccagaaca cagaagaact cagatgactg 781    gtagtattac cttcttcata atcccaggct tggggggctg cgatggagtc agaggaaact 841    cagttcagaa catctttggt ttttacaaat acaaattaac tggaacgcta aattctagcc 901    tgttaatctg gtcactgaaa aaaaattttt ttttttcaa aaaacatagc tttagcttat 961    ttttttctc tttgtaaaac ttcgtgcatg acttcagctt tactctttgt caagacatgc 1021    caaagtgctg agtcactaat aaaagaaaaa aagaaagtaa aggaagagtg gttctgcttc 1081    ttagcgctag cctcaatgac gacctaagct gcactttcc ccctagttgt gtcttgccat
```

```
-continued
1141  gctaaaggac gtcacattgc acaatcttaa taaggtttcc aatcagcccc acccgctctg
1201  gccccaccct caccctccaa caaagattta tcaaatgtgg gattttccca tgagtctcaa
1261  tattagagtc tcaaccccca ataaatatag gactggagat gtctgaggct cattctgccc
1321  tcgagcccac cgggaacgaa agagaagctc tatctcccct ccaggagccc agctatgaac
1381  tccttctcca caagtaagtg caggaaatcc ttagccctgg aactgccagc ggcggtcgag
1441  ccctgtgtga gggaggggtg tgtggcccag ggagggctgg cgggcggcca gcagcagagg
1501  caggctccca gctgtgctgt cagctcaccc ctgcgctcgc tcccctccgg cacaggcgcc
1561  ttcggtccag ttgccttctc cctggggctg ctcctggtgt gcctgctgc cttccctgcc
1621  ccagtacccc caggagaaga ttccaaagat gtagccgccc cacacagaca gccactcacc
1681  tcttcagaac gaattgacaa acaaattcgg tacatcctcg acggcatctc agccctgaga
1741  aaggaggtgg gtaggcttgg cgatggggtt gaagggcccg gtgcgcatgc gttcccttg
1801  ccctgcgtg tggccggggg ctgcctgcat taggaggtct ttgctgggtt ctagagcact
1861  gtagatttga ggccaacggg gccgactaga ctgacttctg tatttatcct ttgctggtgt
1921  caggaagttc ctttcctttc tggaaaatgc agaatgggtc tgaaatccat gcccaccttt
1981  ggcatgagct gagggttatt gcttctcagg gcttcctttt ccctttccaa aaaattaggt
2041  ctgtgaagct ccttttttgtc ccccgggctt tggaaggact agaaaagtgc cacctgaaag
2101  gcatgttcag cttctcagag cagttgcagt acttttttggt tatgtaaact caatggctag
2161  gattcctcaa agccattcca gctaagattc atacctcaga gcccaccaaa gtggcaaatc
2221  ataaataggt taaagcatct ccccactttc aatgcaaggt attttggtcc tgtttggtag
2281  aaagaaaaga acacaggagg ggagattggg agcccacact cgaattctgg ttctgccaaa
2341  ccagccttgt gatcttgggt aaattcccta ccacctctgg actccatcag taaaattggg
2401  cgtggactag gtgatctcat agatccttcc tgctggaaca ttctatggct tgaattatat
2461  tctcctaatt attgtcaaaa ttgctgttat taagtatcta ctgtgtgcca ggcactttaa
2521  ataaatattg tgtctaatct tcaaaacaaa tttgcaagga aggttttttgg agataaggaa
2581  actgagactc aggattaagt aacacaccta aagtcacagg tgagcttgga actgaaccca
2641  agtgtgcccc cactccactg gaatttgctt gccaggatgc caatgagttg tagcttcatt
2701  tttcttagag actttcctgg ctgtggttga acaatgaaaa ggccctctag tggtgtttgt
2761  tttagggaca cttaggtgat aacaattctg gtattctttc ccagacatgt aacaagagta
2821  acatgtgtga aagcagcaaa gaggcactgg cagaaaacaa cctgaacctt ccaaagatgg
2881  ctgaaaaaga tggatgcttc caatctggat tcaatgaggt accaacttgt cgcactcact
2941  tttcactatt ccttaggcaa aacttctccc tcttgcatgc agtgcctgta tacatataga
3001  tccaggcagc aacaaaaagt gggtaaatgt aaagaatgtt atgtaaattt catgaggagg
3061  ccaacttcaa gcttttttaa aggcagttta ttcttggaca ggtatggcca gagatggtgc
3121  cactgtggtg agatttttaac aactgtcaaa tgtttaaaac tcccacaggt ttaattagtt
3181  catcctggga aaggtactct cagggccttt tccctctctg gctgccctg gcagggtcca
3241  ggtctgccct ccctccctgc ccagctcatt ctccacagtg agataacctg cactgtcttc
3301  tgattatttt ataaaggag gttccagccc agcattaaca agggcaagag tgcaggaaga
3361  acatcaaggg ggacaatcag agaaggatcc ccattgccac attctagcat ctgttgggct
3421  ttggataaaa ctaattacat ggggcctctg attgtccagt tatttaaaat ggtgctgtcc
3481  aatgtcccaa aacatgctgc ctaagaggta cttgaagttc tctagaggag cagagggaaa
3541  agatgtcgaa ctgtggcaat tttaactttt caaattgatt ctatctcctg gcgataacca
```

-continued

```
3601  attttcccac catctttcct cttaggagac ttgcctggtg aaaatcatca ctggtctttt
3661  ggagtttgag gtatacctag agtacctcca gaacagattt gagagtagtg aggaacaagc
3721  cagagctgtg cagatgagta caaaagtcct gatccagttc ctgcagaaaa aggtgggtgt
3781  gtcctcattc cctcaacttg gtgtggggga agacaggctc aaagacagtt tcctggacaa
3841  ctcagggatg caatgccact tccaaaagag aaggctacac gtaaacaaaa gagtctgaga
3901  aatagtttct gattgttatt gttaaatctt ttttgtttg tttggttggt tggctctctt
3961  ctgcaaagga catcaataac tgtattttaa actatatatt aactgaggtg gattttaaca
4021  tcaatttttta atagtgcaag agatttaaaa ccaaaggcgg ggggcgggc agaaaaaagt
4081  gcatccaact ccagccagtg atccacagaa acaaagacca aggagcacaa aatgattta
4141  agattttagt cattgccaag tgacattctt ctcactgtgg ttgtttcaat tcttttttcct
4201  accttttacc agagagttag ttcagagaaa tggtcagaga ctcaagggtg gaaagaggta
4261  ccaaaggctt tggccaccag tagctggcta ttcagacagc agggagtaga cttgctggct
4321  agcatgtgga ggagccaaag ctcaataaga aggggcctag aatgaaaccc ttggtgctga
4381  tcctgcctct gccatttcta cttaagccag ggtttctcat atgttaacat gcatgggaat
4441  tccctgggca tcttcttgtg gtgtggagtc tgacttagca agcctcgggt gggtttgagg
4501  gtcaaatttc taccaggctt atatccctgg tgatgctgca gaattccagg accacacttg
4561  gaggtttaag gccttccaca agttacttat cccatatggt gggtctatgg aaaggtgttt
4621  cccagtcctc tttacaccac cggatcagtg gtcttcaac agatcctaaa gggatggtga
4681  gagggaaact ggagaaaagt atcagattta gaggccactg aagaacccat attaaaatgc
4741  ctttaagtat gggctcttca ttcatatact aaatatgaac tatgtgccag gcattatttc
4801  atatgacaga atacaaacaa ataagatagt gatgctggtc aggcttggtg gctcatgcct
4861  gtattcccta aactttggga gcctaaggtg agaactcctt gaactcctaa ggccaggagt
4921  tcaagaccag cctggataac atagcaagac ccatctcta caaaaaacca aaaccaaaca
4981  aacaaaaatg atagtggtgc ttccctcagg atgcttgtgg tctaatggga gacagaacag
5041  caaagggatg attagaagtt ggttgctgtg agccaggcac agtgctgata taatcccagc
5101  gctatgggag gctgaggtgg gtggatcatt tgaggccagg agtttaagac cagcctggtc
5161  aacatggtaa aaccccatct ctacttaaaa atacaaaaaa gttagccagg catggtggca
5221  tacacctgta acccagctac tcaggaggct gaggcacatg aatcacttga acccaggagg
5281  cagaggttgc tgtgcaccac tgcactccag cctgggtgac agaacgagac cttgactcaa
5341  aaaaaaaaaa aagaagtttg ttgctatgga agggtcctac tcagagcagg caccccagtt
5401  aatctcattc accccacatt tcacatttga acatcatccc atagcccaga gcatccctcc
5461  actgcaaagg atttattcaa catttaaaca atccttttta ctttcatttt ccttcaggca
5521  aagaatctag atgcaataac caccccctgac ccaaccacaa atgccagcct gctgacgaag
5581  ctgcaggcac agaaccagtg gctgcaggac atgacaactc atctcattct gcgcagcttt
5641  aaggagttcc tgcagtccag cctgagggct cttcggcaaa tgtagcatgg gcacctcaga
5701  ttgttgttgt taatgggcat tccttcttct ggtcagaaac ctgtccactg gcacagaac
5761  ttatgttgtt ctctatggag aactaaaagt atgagcgtta ggacactatt ttaattattt
5821  ttaatttatt aatatttaaa tatgtgaagc tgagttaatt tatgtaagtc atatttatat
5881  ttttaagaag taccacttga aacattttat gtattagttt tgaaataata atggaaagtg
5941  gctatgcagt ttgaatatcc tttgtttcag agccagatca tttcttggaa agtgtaggct
```

```
-continued
6001  tacctcaaat aaatggctaa cttatacata tttttaaaga aatatttata ttgtatttat 6061  ataatgtata aatggttttt ataccaataa atggcatttt aaaaaattca gcaa
```

For use in the subject methods, any of the native IL-6 polypeptides, modifications and variants thereof, or a combination of one or more polypeptides may be used. IL-6 polypeptides of interest include fragments, and can be variously truncated at the carboxyl terminus relative to the full sequence. Such fragments continue to exhibit the characteristic properties of human interleukin 6. Extraneous sequences may be added as long as there is minimal loss of activity. Any variants known in the art and having IL-6 activity may be used in the present methods.

By "naturally occurring" or "wild type," or grammatical equivalents herein is meant an amino acid sequence or a nucleotide sequence that is found in nature and includes allelic variations; that is, an amino acid sequence or a nucleotide sequence that usually has not been intentionally modified. Accordingly, by "non-naturally occurring" or "synthetic" or "recombinant" or grammatical equivalents thereof herein is meant an amino acid sequence or a nucleotide sequence that is not found in nature; that is, an amino acid sequence or a nucleotide sequence that usually has been intentionally modified. It is understood that once a recombinant nucleic acid is made and reintroduced into a host cell or organism, it will replicate non-recombinantly, i.e., using the in vivo cellular machinery of the host cell rather than in vitro manipulations, however, such nucleic acids, once produced recombinantly, although subsequently replicated non-recombinantly, are still considered recombinant for the purpose of the invention.

The sequence of the IL-6 polypeptide may be altered in various ways known in the art to generate targeted changes in sequence. A variant polypeptide will usually be substantially similar, i.e., will differ by at least one amino acid, and may differ by at least two but not more than about ten amino acids. The sequence changes may be substitutions, insertions or deletions. Scanning mutations that systematically introduce alanine, or other residues, may be used to determine key amino acids. Specific amino acid substitutions of interest include conservative and non-conservative changes. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. In one embodiment, the invention contemplates the use of IL-6 variants with one or more non-naturally occurring glycosylation and/or pegylation sites that are engineered to provide glycosyl- and/or PEG-derivatized polypeptides with reduced serum clearance. Also included are modifications of glycosylation, e.g., those made by modifying the glycosylation patterns of a polypeptide during its synthesis and processing or in further processing steps; e.g., by exposing the polypeptide to enzymes that affect glycosylation, such as mammalian glycosylating or deglycosylating enzymes. Also embraced are sequences that have phosphorylated amino acid residues, e.g., phosphotyrosine, phosphoserine, or phosphothreonine.

Included in the subject invention are polypeptides that have been modified using ordinary chemical techniques so as to improve their resistance to proteolytic degradation, to optimize solubility properties, or to render them more suitable as a therapeutic agent. For examples, the backbone of the peptide may be cyclized to enhance stability (see Friedler et al. (2000) *J. Biol. Chem.* 275:23783-23789). Analogs may be used that include residues other than naturally occurring L-amino acids, e.g., D-amino acids or non-naturally occurring synthetic amino acids. The protein may be pegylated to enhance stability.

As used herein "hyaluronan" encompasses hyaluronic acid and its hyaluronate salts, including, but not limited to, sodium hyaluronate, potassium hyaluronate, magnesium hyaluronate and calcium hyaluronate.

The term "immune modulate" or "immunomodulate" and its other grammatical forms refers to the ability of a compound of the present invention to alter (modulate) one or more aspects of the immune system. The immune system functions to protect the organism from infection and from foreign antigens by cellular and humoral mechanisms involving lymphocytes, macrophages, and other antigen-presenting cells that regulate each other by means of multiple cell-cell interactions and by elaborating soluble factors, including lymphokines and antibodies, that have autocrine, paracrine, and endocrine effects on immune cells.

The term "improves" is used to convey that the present invention changes either the appearance, form, characteristics and/or the physical attributes of the subject, organ, tissue or cell to which it is being provided, applied or administered. For example, the change in form may be demonstrated by any of the following alone or in combination: a decrease in one or more symptoms of a disease or disorder; increase in renewal of alveolar epithelial cell 2 (AEC2) cells; repair of a lung injury; reduce lung fibrosis; reduction or elimination of the need for other active agents or therapeutics; and slower progression of fibrotic lung disease.

The term "inhibiting" includes the administration of a compound of the present invention to prevent the onset of the symptoms, alleviating the symptoms, or eliminating the disease, condition or disorder.

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics.

NFκB:

The nuclear factor-kappaB (NF-kappaB)/REL family of transcription factors has a central role in coordinating the expression of a wide variety of genes that control immune responses. Transcription factors of the NF-kappaB family are activated in response to signals that lead to cell growth, differentiation, apoptosis and other events. (Liang, Y et al, "NF-kappaB and its regulation on the immune system," (2004) Cell. Mol. Immunol. 1(5): 343-50)). NF-κB is kept sequestered in the cytoplasm by its inhibitor of KB (IκB). In unstimulated cells, NF-κB/Rel dimers are bound to IκBs and retained in the cytoplasm in an inactive form. Stimulation sequentially leads to phosphorylation, ubiquitination, and proteosomal degradation of IκB, which allows NF-κB to be translocated to the nucleus and to bind to promoter regions of genes. (Grutz, G. (2005) "New Insights into the molecular mechanism of interleukin-10 mediated immunosuppression," J. Leukocyte Biol. 77: 3-15). In diverse cell types, NF-κB is strongly linked to the regulation of apoptosis. (Liang, Y et al, "NF-kappaB and its regulation on the immune system," (2004) Cell. Mol. Immunol. 1(5): 343-50). The canonical NF-κB pathway has been defined primarily in response to TNFα and IL-1 signaling. TNFα and IL-1 are proinflammatory cytokines that play a role in the pathogenesis of chronic inflammatory diseases such as rheumatoid arthritis (RA), inflammatory bowel disease (IBD), asthma, and chronic obstructive pulmonary disease (COPD). Lawrence, T., "The Nuclear Factor NF-κB pathway in inflammation," Cold Spring Harbor Perspectives in Biol. (2009) 1(6): a001651) (citing Holgate, S T, "Cytokine and anticytokine therapy for the treatment of asthma and allergic disease," (2004) Cytokine 28: 152-57; , Chung, K F, "Cytokines as targets in chronic obstructive pulmonary disease," (2006) Curr. Drug Targets 7: 675-81; 2006, Williams, R O et al., "Cytokine inhibitors in rheumatoid arthritis and other autoimmune diseases," (2007) Curr. Opin. Pharacol. 7: 412-17). NF-κB activity at sites of inflammation is associated with activation of the canonical pathway and RelA- or cRel-containing complexes. The alternative NF-κB pathway is characterized by the inducible phosphorylation of p100 by IKKα, leading to activation of RelB/p52 heterodimers. The upstream kinase that activates IKKα in this pathway has been identified as an NIK (NF-κB inducing kinase) (Id., citing Senftleben, U et al., "Activation by IKKα of a second, evolutionary conserved, NFκB signaling pathway," (2001) Science 293: 1495-99).

As used herein, the terms "peptide," "polypeptide" and "protein" are used interchangeably and refer to two or more amino acids covalently linked by an amide bond or non-amide equivalent. The peptides of the invention can be of any length. For example, the peptides can have from about two to about 100 or more residues, such as, 5 to 12, 12 to 15, 15 to 18, 18 to 25, 25 to 50, 50 to 75, 75 to 100, 100 to 200, or more in length. The peptides of the invention include L- and D-isomers, and combinations of L- and D-isomers. The peptides can include modifications typically associated with post-translational processing of proteins, for example, cyclization (e.g., disulfide or amide bond), phosphorylation, glycosylation, carboxylation, ubiquitination, myristylation, or lipidation. According to some embodiments, the peptides of the disclosure comprise only D-isomers. According to some embodiments, the peptides comprise only L-isomers.

The term "pharmaceutically acceptable," is used to refer to the carrier, diluent or excipient being compatible with the other ingredients of the formulation or composition and not deleterious to the recipient thereof. For example, the term "pharmaceutically acceptable" can mean approved by a regulatory agency of the Federal or a state government or listed in the U.S. Pharmacopeia or other generally recognized pharmacopeia for use in animals, and more particularly in humans.

"Signaling" as used herein describes a set of chemical reactions in a cell that occurs when a molecule, such as a hormone, attaches to a receptor. The signal transduction is a cascade of biochemical reactions inside the cell that eventually reach the target molecule or reaction. Thus, signal transduction or signaling as used herein is a method by which molecules inside the cell can be altered by molecules outside the cell.

The signaling chains of the hematopoietin family of cytokine receptors are noncovalently associated with protein tyrosine kinases of the Janus kinase (JAP) family of which there are four members: Jak1, Jak2, Jak2 and Tyk2. Janeway's Immunology, 9$^{th}$ Ed. 2017, Garland Science, New York, Chapter 3, at 1090-110.

Dimerization or clustering of receptor signaling chains brings the JAKs into close proximity, causing phosphorylation of each JAK on a tyrosine residue that stimulates its kinase activity. Activated JAKs then phosphorylate their associated receptors on specific tyrosine residues. This phosphotyrosine, and the specific amino acid sequence surrounding it, creases a binding site that is recognized by SH2 domaons found in other proteins, in particular members of the signal transducers and activators of transcription (STATs) family of transcription factors. There are seven STATS (1-4, 5, 5b and 6), which reide in the cytoplasm in an inactive form until activated by cytokine receptors. The receptor specificity of each STAT is determined by the recognition of the distinctive phosphotyrosine sequence on each activated receptor by the different SH2 domains within the various STAT proteins.

Signal transducer and activator of transcription 3 (STAT3) is a transcription factor encoded by the Stat3 gene. (Levy, D E, and Lee, C-k, "What does Stat3 do?" (2002) J. Clin. Invest. 109(9): 1143-48). Ablation of Stat3 leads to embryonic lethality (Id. Citing Takeda, K. et all, "Tageted disruption of the mouse Stat3 gene3 leads to early embryonic lethality," (1997) Proc. Natl Acad. Sci. USA 94: 3801-3804). STAT3 plays a role in mediating the cell growth, differentiation and survival signals relayed through the IL-6 family of cytokine receptors, and induces distinct sets of target genes in different cells. (Id. citing Hirano, T. et al, "Roles of STAT3 in mediating the cell growth, differentiation and survival signals relayed through the IL-6 family of cytokine receptors" (2000) Oncogene 19: 2548-56). For instance, Stat3 stimulates B cell proliferation, in part, through inhibition of apoptosis, a function mediated by induction of the antiapoptotic gene Bcl-2. Id. In contrast, activation of Stat3 in monocytic cells leads to downregulation of c-myc and c-myb and induction of junB and IRF-1, a pattern of gene regulation consistent with differentiation and growth arrest. Id. A different set of Stat3-dependent genes are upregulated in IL-6-stimulated hepatocytes, genes for the secreted proteins of the acute-phase response. Ic.

As used herein, a "stem cell" is a multipotent or pluripotent cell that (i) is capable of self-renewal; and (ii) can give rise to more than one type of cell through asymmetric cell division. The term "renewal" or "self renewal" as used herein, refers to the process by which a stem cell divides to generate one (asymmetric division) or two (symmetric division) daughter cells having development potential indistinguishable from the mother cell. Self renewal involves both proliferation and the maintenance of an undifferentiated state.

The term "Surfactant Protein C" (SP-C) is used to refer to a protein encoded by the SFTPC gene. In the lung, surfactant lowers surface tension, easing breathing and avoiding lung collapse. The SP-C protein helps spread the surfactant across the surface of the lung tissue, aiding in the surface tension-lowering property of surfactant (see https://ghr.nlm.nih.gov/gene/SFTPC).

As used herein, the term "therapeutic" or "active agent" means an agent utilized to treat, combat, ameliorate, prevent or improve an unwanted condition or disease of a patient. In part, embodiments of the present invention are directed to decreasing one or more symptoms of a fibrotic lung disease, increasing renewal of alveolar epithelial cell 2 (AEC2) cells, increasing repair of a lung injury, reducing lung fibrosis, reducing or eliminating the need for other active agents or therapeutics; and slowing progression of fibrotic lung disease.

A "therapeutically effective amount," "therapeutic amount" or "effective amount" of a composition (e.g., an IL-6 polypeptide or hyaluronan) is a predetermined amount calculated to achieve the desired effect, i.e., to improve or increase AEC2 stem cell renewal, repair a lung injury, and/or to decrease one or more symptoms of IPF. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per day will normally fall within the range of from about 0.001 to about 10 mg/kg, more usually in the range of from about 0.01 to about 1 mg/kg. According to some embodiments, the therapeutically effective dose of IL-6 polypeptide or hyaluronan is about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, and about 1 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of compound of embodiments of this invention is typically an amount such that when it is administered in a physiologically tolerable excipient composition, it is sufficient to achieve an effective systemic concentration or local concentration in the tissue.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50 which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

Therapeutic window, potency and efficacy. The term "potency" as used herein refers to efficacy, effectiveness, or strength of a drug. The potency of a drug is the reciprocal of dose, and has the units of persons/unit weight of drug or body weight/unit weight of drug. Relative potency compares the relative activity of drugs in a series relative to some prototypic member of the series. "Efficacy" connotes the property of a drug to achieve the desired response, and maximum efficacy denotes the maximum achievable effect.

The intensity of effect of a drug (y-axis) can be plotted as a function of the dose of drug administered (X-axis). Goodman & Gilman's The Pharmacological Basis of Therapeutics, Ed. Joel G. Hardman, Lee E. Limbird, Eds., 10th Ed., McGraw Hill, New York (2001), p. 25, 50). These plots are referred to as dose-effect curves. Such a curve can be resolved into simpler curves for each of its components. These concentration-effect relationships can be viewed as having four characteristic variables: potency, slope, maximal efficacy, and individual variation.

The location of the dose-effect curve along the concentration axis is an expression of the potency of a drug. Id. If the drug is to be administered by transdermal absorption, a highly potent drug is required, since the capacity of the skin to absorb drugs is limited.

The slope of the dose-effect curve reflects the mechanism of action of a drug. The steepness of the curve dictates the range of doses useful for achieving a clinical effect.

Maximal or clinical efficacy refers to the maximal effect that can be produced by a drug. Maximal efficacy is determined principally by the properties of the drug and its receptor-effector system and is reflected in the plateau of the curve. In clinical use, a drug's dosage may be limited by undesired effects.

Biological variability. An effect of varying intensity may occur in different individuals at a specified concentration or a drug. It follows that a range of concentrations may be required to produce an effect of specified intensity in all subjects.

Lastly, different individuals may vary in the magnitude of their response to the same concentration of a drug when the appropriate correction has been made for differences in potency, maximal efficacy and slope.

The duration of a drug's action is determined by the time period over which concentrations exceed the MEC. Following administration of a dose of drug, its effects usually show a characteristic temporal pattern. A plot of drug effect vs. time illustrates the temporal characteristics of drug effect and its relationship to the therapeutic window. A lag period is present before the drug concentration exceeds the minimum effective concentration (MEC) for the desired effect. Following onset of the response, the intensity of the effect increases as the drug continues to be absorbed and distributed. This reaches a peak, after which drug elimination results in a decline in the effect's intensity that disappears when the drug concentration falls back below the MEC. The therapeutic window reflects a concentration range that provides efficacy without unacceptable toxicity. Accordingly another dose of drug should be given to maintain concentrations within the therapeutic window.

The term "Toll-like receptors (TLRs)" is used to refer to sensors for microbes present in extracellular spaces. Some are cell surface receptors (e.g., TLR-1, TLR-2, TLR-5, TLR-6), but others (e.g., TLR3, TLR-7, TLR-8, TLR-9) are located intracellularly in the membrane of endosomes, where they detect pathogens or their components that have been taken into cells by phagocytosis, receptor-mediated endocytosis or micropinocytosis. (Janeway's Immunology, $9^{th}$ Ed. 2017, Garland Science, New York, Chapter 2, at 88).

TLR-4 is expressed by several types of immune system cells, including dendritic cells and macrophages, and recognizes the LPS of gram negative bacteria by a mechanism that is partly direct and partly indirect. Systemic injection of LPS causes a collapse of the circulatory and respiratory system (shock), due to an overwhelming secretion of cytokines, particularly TNF-α, causing systemic vascular permeability. To recognize LPS, the ectodomain of TLR-4 uses an accessory protein, MD-2, which initially binds to TLR-4 within the cell and is necessary both for the correct trafficking of TLR-4 to the cell surface and for the recognition of LPS. TLR-4 activation involves two other accessory proteins, LPS-binding protein, present in the blood and in extracellular fluid in tissues, and CD14, which is present on the surface of macrophages, neutrophils and dendritic cells. On its own, CD14 can act as a phagocytic receptor, but on macrophages and dendritic cells it also acts as an accessory protein for TLR-4. Id. at 92.

Mammalian TLRs recognize molecules characteristic of bacteria, fungi and viruses, including the lipoteichoic acids of Gram-positive bacterial cell walls, and the lipopolysaccharide (LPS) of the outer membrane of Gram negative bacteria. Although TLRs have limited specificity compared with the antigen receptors of the adaptive immune system, they can recognize elements of most pathogenic microbes and are expressed by many types of cells, including macrophages, dendritic cells, B cells, stromal cells, and certain epithelial cells. Id. at 88

Signaling by mammalian TLRs in various cell types induces a diverse range of intracellular responses by activating several different signaling pathways that each activate different transcription factors, which, together result in the production of inflammatory cytokines, chemotactic factors, antimicrobial peptides, and the antiviral cytokines interferon α and β. Id. At 92 The outcome of TLR activation can vary depending on the cell type in which it occurs. Id. at 95.

Signaling by mammalian TLRs is activated when binding of a ligand induces formation of a dimer, or induces conformational changes in a preformed TLR dimer. All mammalian TLR proteins have in their cytoplasmic tail a Toll-IL-1 receptor (TIR) domain, which interacts with other T1R-type domains, usually in other signaling molecules, and is also found in the cytoplasmic tail of the receptor for the cytokine interleukin-1-β. Id. at 88 Dimerization brings the cytoplasmic T1R domains together, allowing them to interact with the T1R domains of cytoplasmic adaptor molecules that initiate intracellular signaling. There are four adaptors used by mammalian TLRs: MyD88, MAL (also known as TIRAP), TRIF, and TRAM. The T1R domains of the different TLRs interact with different combinations of these adaptors. Id. At 92-93.

For example, TLR-3 interacts only with TRIF. TLR-21 and TLR2/6 require MyD88/MAL. TLR-4 signaling uses both MyD8/MAL and TRIF/TRAM, which is used during endosomal signaling by TLR-4. The choice of adaptor influences which of the several downstream signals will be activated by the TLR. Id. at 94.

Signaling by most TLRs activates the transcription factor NFκB, several members of the interferon regulatory factor (IRF) transcription factor family through a second pathway, and members of the activator protein 1 (AP-1) family, such as c-Jun, through another signaling pathway involving mitogen-activated protein kinases (MAPKs). NFκB and AP-1 act primarily to induce the expression of proinflammatory cytokines and chemotactic factors. Id. At 94.

The terms "treat," "treated," or "treating" as used herein refers to both therapeutic treatment and/or prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

The described invention relates to methods of using compounds and compositions comprising polypeptides or polysaccharides described herein. These compounds and compositions modulate signaling pathways that provide significant therapeutic benefit in the treatment of a lung injury or fibrotic lung disease. The compounds of the described invention may exist in unsolvated forms as well as solvated forms, including hydrated forms of the polypeptides and polysaccharides disclosed herein. The compounds of the described invention also are capable of forming pharmaceutically acceptable salts, including but not limited to acid addition and/or base addition salts. Furthermore, compounds of the described invention may exist in various solid states including an amorphous form (non-crystalline form), and in the form of clathrates, prodrugs, polymorphs, bio-hydrolyzable esters, racemic mixtures, non-racemic mixtures, or as purified stereoisomers including, but not limited to, optically pure enantiomers and diastereomers. In general, all of these forms can be used as an alternative form to the free base or free acid forms of the compounds, as described above and are intended to be encompassed within the scope of the described invention.

The term "polymorph" is used herein to refer to solid crystalline forms of a compound. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Different physical properties of polymorphs can affect their processing. According to some embodiments, the composition comprises at least one polymorph of any of the compositions disclosed herein.

The compounds and compositions of the described invention described invention can be administered, inter alia, as pharmaceutically acceptable salts, esters, amides or prodrugs.

The term "salts" is used herein to refer to inorganic and organic salts of compounds of the described invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977). The term "salt" refers to acidic salts formed with inorganic and/or organic acids, as well as basic salts formed with inorganic and/or organic bases. Examples of these acids and bases are well known to those of ordinary skill in the art. Such acid addition salts will normally be pharmaceutically acceptable although salts of non-pharmaceutically acceptable acids may be of utility in the preparation and purification of the compound in question. Salts include those formed from hydrochloric, hydrobromic, sulphuric, phosphoric, citric, tartaric, lactic, pyruvic, acetic, succinic, fumaric, maleic, methanesulphonic and benzenesulphonic acids.

According to some embodiments, the pharmaceutical compositions comprise an IL-6 polypeptide, hyaluronan, a mimetic or pharmaceutically acceptable salt thereof, and at least one pharmaceutically acceptable carrier.

The phrase "pharmaceutically acceptable carrier" is art recognized. It is used to mean any substantially non-toxic carrier conventionally useable for administration of pharmaceuticals in which the isolated polypeptide of the present invention will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition. described invention Exemplary carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Suitable pharmaceutical carriers are described in "Remington's Pharmaceutical Sciences" by E. W. Martin, which is incorporated herein by reference in its entirety. According to some embodiments, the pharmaceutically acceptable carrier is sterile and pyrogen-free water. According to some embodiments, the pharmaceutically acceptable carrier is Ringer's Lactate, sometimes known as lactated Ringer's solution.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, .alpha.-tocopherol, and the like; and metal chelating agents, such as citric acid, ethylenediamine tetraacetic acid (EDTA), sorbitol, tartaric acid, phosphoric acid, and the like.

Formulations of the described invention include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 40 percent.

Some examples of suitable carriers, excipients, and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound can be admixed with carriers and diluents, molded into tablets, or enclosed in gelatin capsules. The mixtures can alternatively be dissolved in liquids such as 10% aqueous glucose solution, isotonic saline, sterile water, or the like, and administered intravenously or by injection.

The local delivery of therapeutic amounts of a compound for the treatment of a lung injury or fibrotic lung disease can be by a variety of techniques that administer the compound at or near the targeted site. Examples of local delivery techniques are not intended to be limiting but to be illustrative of the techniques available. Examples include local delivery catheters, site specific carriers, implants, direct injection, or direct applications, such as topical application and, for the lungs, administration by inhalation.

Local delivery by an implant describes the surgical placement of a matrix that contains the pharmaceutical agent into the affected site. The implanted matrix releases the pharmaceutical agent by diffusion, chemical reaction, or solvent activators.

Specific modes of administration will depend on the indication. The selection of the specific route of administration and the dose regimen is to be adjusted or titrated by the clinician according to methods known to the clinician in order to obtain the optimal clinical response. The amount of compound to be administered is that amount sufficient to provide the intended benefit of treatment. The dosage to be administered will depend on the characteristics of the subject being treated, e.g., the particular mammal or human treated, age, weight, health, types of concurrent treatment, if any, and frequency of treatments, and can be easily determined by one of skill in the art (e.g., by the clinician).

Pharmaceutical formulations containing the compounds of the described invention and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels, jellies, and foams;

and parenteral dosage forms which include, but are not limited to, solutions, suspensions, emulsions, and dry powder; comprising an effective amount of a polymer or copolymer of the described invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted.

The compositions or pharmaceutical compositions of the described invention can be formulated for parenteral administration by injection, e.g., by bolus injection or continuous infusion. The compounds can be administered by continuous infusion subcutaneously over a predetermined period of time. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, alter adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragecanth, methyl cellulose, hydroxypropylmethyl-celllose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include, but are not limited to, push-fit capsules made of gelatin, as well as soft, scaled capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compounds for use according to the described invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the described invention can also be formulated in rectal compositions such as suppositories or retention enemas, e.g., containing conventional suppository bases such as cocoa butter or other glycerides.

In addition to the formulations described previously, the compounds of the described invention can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds of the described invention, for example, can be applied to a plaster, or can be applied by transdermal, therapeutic systems that are consequently supplied to the organism.

Pharmaceutical compositions comprising any one or plurality of compounds disclosed herein also can comprise suitable solid or gel phase carriers or excipients. Examples of such carriers or excipients include but are not limited to calcium carbonate, calcium phosphate, various sugars, starches, cellulose derivates, gelatin, and polymers such as, e.g., polyethylene glycols.

For parenteral administration, a composition or pharmaceutical composition can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of analog in 0.9% sodium chloride solution.

The described invention relates to all routes of administration including intramuscular, subcutaneous, sublingual, intravenous, intraperitoneal, intrathecal, intranasal, intratracheal, topical, intradermal, intramucosal, intracavernous, intraocular, intrarectal, into a sinus, gastrointestinal, intraductal, intrathecal, subdural, extradural, intraventricular, intrapulmonary, into an abscess, intraarticular, into a bursa, subpericardial, into an axilla, intrauterine, into the pleural space, intravaginal, intraurethral, intradermal, intrabuccal, transmucosal, transdermal, via inhalation, via nebulizer and via subcutaneous injection. Alternatively, the pharmaceutical composition may be introduced by various means into cells that are removed from the individual. Such means include, for example, microprojectile bombardment and liposome or other nanoparticle device.

Solid dosage forms for oral administration include capsules, tablets, pills, powders and granules. In solid dosage forms, the composition or pharmaceutical compositions are generally admixed with at least one inert pharmaceutically acceptable carrier such as sucrose, lactose, starch, or other generally regarded as safe (GRAS) additives. Such dosage forms can also comprise, as is normal practice, an additional substance other than an inert diluent, e.g., lubricating agent such as magnesium state. With capsules, tablets, and pills, the dosage forms may also comprise a buffering agent. Tablets and pills can additionally be prepared with enteric coatings, or in a controlled release form, using techniques know in the art.

Liquid dosage forms for oral administration include pharmaceutically acceptable emulsions, solutions, suspensions and syrups, with the elixirs containing an inert diluent commonly used in the art, such as water. These compositions can also include one or more adjuvants, such as wetting agent, an emulsifying agent, a suspending agent, a sweetening agent, a flavoring agent or a perfuming agent.

According to some embodiments the pharmaceutical compositions of the claimed invention comprises at least one or a plurality of therapeutics other than the IL-6 polypeptide, hyaluronan, compositions thereof, mimetics thereof, pharmaceutically acceptable salts thereof, or combinations thereof. According to some embodiments, the one or plurality of therapeutics includes one or a combination of immunomodulators, analgesics, anti-inflammatory compounds, anti-fibrotic compounds, proton pump inhibitors, or oxygen therapy.

Examples of immunomodulators include corticosteroids, for example, prednisone, azathioprine, mycophenolate, mycophenolate mofetil, colchicine, and interferon-gamma 1b.

Examples of analgesics include codeine, hydrocodone, oxycodone, methadone, hydromorphone, morphine, and fentanyl.

Examples of anti-inflammatory compounds include aspirin, celecoxib, diclofenac, diflunisal, etodolac, ibuprofen, indomethacin, ketoprofen, ketorolac nabumetone, naproxen, nintedanib, oxaprozin, pirfenidone, piroxicam, salsalate, sulindac, and tolmetin.

Examples of anti-fibrotic compounds are nintedanib and pirfenidone.

Examples of proton pump inhibitors are omeprazole, lansoprazole, dexlansoprazole, esomeprazole, pantoprazole, rabeprazole, and ilaprazole.

According to the foregoing embodiments, the compound, composition or pharmaceutical composition may be administered once, for a limited period of time or as a maintenance therapy over an extended period of time, for example until the condition is ameliorated, cured or for the life of the subject). A limited period of time may be for 1 week, 2 weeks, 3 weeks, 4 weeks and up to one year, including any period of time between such values, including endpoints. According to some embodiments, the composition or pharmaceutical composition may be administered for about 1 day, for about 3 days, for about 1 week, for about 10 days, for about 2 weeks, for about 18 days, for about 3 weeks, or for any range between any of these values, including endpoints. According to some embodiments, the compound, composition or pharmaceutical composition may be administered for more than one year, for about 2 years, for about 3 years, for about 4 years, or longer.

According to the foregoing embodiments, the compound, composition or pharmaceutical composition may be administered once daily, twice daily, three times daily, four times daily or more.

The methods disclosed herein can be used with any of the compounds, compositions, preparations, and kits disclosed herein.

All referenced journal articles, patents, and other publications are incorporated by reference herein in their entirety.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Materials and Methods

Mice. Tlr4$^{-/-}$ and Tlr2$^{-/-}$ mice were obtained (Takeuchi et al., 1999; Kawai et al., 1999), Has2$^{flox/+}$ mice were generated using the Cre-loxP system (Li et al., 2011; Matsumoto et al., 2009), and SFTPC-Cre mice, SFTPC-CreER mice, SFTPC-GFP mice, and Rosa-Tomato$^{flox/flox}$ mice were generated (Barkauskas et al., 2013; Chen et al., 2012; Eblaghie et al., 2006). All mice were backcrossed on the C57Bl/6J background for more than six generations. Although the lungs from SFTPC-Cre mice on a 129/sv background showed abnormal dilated cysts (Jeannotte et al., 2011), SFTPC-Cre transgenic mice, as well as SFTPC-Cre;

Has2^(flox/flox) mice, developed normally, with no readily observable gross or histological abnormalities, consistent with previous reports (Morales-Nebreda et al., 2015). Has2^(flox/flox) homozygous mice were crossed with SFTPC-Cre+ mice to generate SFTPC-Cre+;Has2^(flox/flox) mice. Rosa-Tomato^(flox/flox) mice were crossed with SFTPC-CreER mice to generate SFTPC-CreER+;Rosa-Tomato^(flox/flox) mice. Animals were randomly assigned to treatment groups, and they were age- and sex-matched. 8- to 12-week-old mice of both sexes (male:female ratio ~1:1) were used in the bleomycin lung injury model. Animals for experiments were selected by genotype, and no blinding was performed.

Bleomycin Instillation and Bronchioalveolar Lavage.

Bleomycin instillation and BAL procedures were described previously (Dong et al., 2015; Lovgren et al., 2011). Under anesthesia, the trachea was surgically exposed. 1.25-5 U/kg bleomycin (Hospira, Lake Forest, Ill.) in 25 µl PBS was instilled into the mouse trachea with a 25-G needle inserted between the cartilaginous rings of the trachea. Control animals received saline alone. The tracheostomy site was sutured, and the animals were allowed to recover. Mice were euthanized at different time points, and lung tissue and BAL fluid were collected for experiments. 0.8-ml aliquots of PBS were used for lavage. Cell-free BAL fluid was stored in a −80° C. freezer for cytokine measurement.

Hydroxyproline.

Collagen contents in mouse lungs were measured using a conventional hydroxyproline method (Jiang et al., 2004). Lung tissues were vacuum-dried and hydrolyzed with 6 N hydrochloride acid at 120° C. overnight. Hydroxyproline content was expressed as 'µg per lung', unless specified otherwise. The ability of the assay to completely hydrolyze and recover hydroxyproline from collagen was confirmed using samples containing known amounts of purified collagen.

Cell Lines.

The mouse lung fibroblast cell line, MLg2908, was from ATCC (Catalog CCL-206). *Mycoplasma* contamination was assessed with a MycoFluor *Mycoplasma* Detection Kit (Catalog M7006, Thermo Fisher Scientific), and cells used for experiments were free of *mycoplasma* contamination.

IL-6 Protein and Anti-IL-6 Administration.

Recombinant mouse IL-6 protein (Catalog 406-ML/CF, R&D Systems) was supplied in 50 mM sodium acetate and 1 mM EDTA and was diluted (1:5 or more depending on the stock concentration) in sterile PBS, and 2 µg per mouse in 50 µl was injected intramuscularly at 1 day before and at 1 day and 3 days after bleomycin instillation. Control buffer was made of the same volume of 50 mM sodium acetate and 1 mM EDTA solution and PBS. Mouse anti-IL-6 (MAB406, Clone #MP5-20F3, R&D Systems) or control IgG was reconstituted with sterile PBS. 250 µg per mouse in 250 µl sterile PBS was injected intraperitoneally to mice at 1 day before and at 1 day and 3 days after bleomycin instillation. Recombinant human IL-6 protein (Catalog 206-IL-010, R&D Systems) was reconstituted with sterile PBS containing 0.1% BSA. 200 ng/ml was used for organoid culture of human AEC2s.

RNA Analysis.

RNA was extracted from mouse lung tissues, mouse AEC2s, or human AEC2s using TRIzol reagent. For real-time PCR analysis, 0.5 µg total RNA was used for reverse transcription with the High Capacity cDNA Reverse Transcription Kit (Applied Biosystems, Carlsbad, Calif.). One microliter cDNA was subjected to real-time PCR by using Power SYBR Green PCR Master Mix (Applied Biosystems) and the ABI 7500 fast Real-Time PCR system (Applied Biosystems). The specific primers were designed on the basis of cDNA sequences deposited in the GenBank database. Mouse Tlr4 (NM_021297.2): forward, AAT CCC TGC ATA GAG GTA GTT CC; reverse, GTC TCC ACA GCC ACC AGA TT; with forward primer across exon junction. Mouse Acta2 (NM_007392, encodes α-SMA): forward, GCTGGTGATGATGCTCCCA; reverse, GCCCATTC-CAACCATTACTCC. Mouse Il6 (NM_031168.2): forward, CTCATTCTGCTCTGGAGCCC; reverse, TGCCAT-TGCACAACTCTTTTCT. Mouse Gapdh (NM_008084): forward, ATCATCTCCGCCCCTTCTG; reverse, GGTCAT-GAGCCCTTCCACAAC. Human HAS2 (NM_005328): forward, GCCTCATCTGTGGAGATGGT; reverse, TCCCAGAGGTCCACTAATGC. Human GAPDH: forward, AATGCATCCTGCACCACCAA; reverse, GTAGC-CATATTCATTGTCATA.

| Primer | SEQ ID NO: |
|---|---|
| Mouse Tlr4 (NM_021297.2): | |
| forward, AAT CCC TGC ATA GAG GTA GTT CC | SEQ ID NO: 1 |
| reverse, GTC TCC ACA GCC ACC AGA TT | SEQ ID NO: 2 |
| Mouse Acta2 (NM_007392, encodes α-SMA): | |
| forward, GCTGGTGATGATGCTCCCA | SEQ ID NO: 3 |
| reverse, GTC TCC ACA GCC ACC AGA TT | SEQ ID NO: 4 |
| Mouse Il6 (NM_031168.2): | |
| forward, CTCATTCTGCTCTGGAGCCC | SEQ ID NO: 5 |
| reverse, TGCCATTGCACAACTCTTTTCT | SEQ ID NO: 6 |
| Mouse Gapdh (NM_008084): | |
| forward, ATCATCTCCGCCCCTTCTG | SEQ ID NO: 7 |
| reverse, GGTCATGAGCCCTTCCACAAC | SEQ ID NO: 8 |
| Human HAS2 (NM_005328): | |
| forward, GCCTCATCTGTGGAGATGGT | SEQ ID NO: 9 |
| reverse, TCCCAGAGGTCCACTAATGC | SEQ ID NO: 10 |
| Human GAPDH: | |
| forward, AATGCATCCTGCACCACCAA | SEQ ID NO: 11 |
| reverse, GTAGCCATATTCATTGTCATA | SEQ ID NO: 12 |

The relative expression level of each gene was determined against the Gapdh level in the same sample. The fold change in target-gene expression was calculated by using the $2^{-\Delta\Delta Ct}$ method.

cDNA microarray. CD24−Sca-1−AEC2s were sorted from WT and Tlr4−/− mouse lungs. The CD24−Sca-1−AEC2s were pooled for RNA isolation from multiple mouse lungs for each category (for day 0: n=7 per group; for day 4: WT, n=8; Tlr4−/−, n=7). Standard cDNA microarrays were carried out with GeneChip Mouse 430 2.0 (Affymetrix). Data were processed to subtract background and to normalize within the array using the LOESS normalization by Genespring GX 11 software. The complete microarray data set is available at the National Center for Biotechnology Information Gene Expression Omnibus (http://www.ncbi.nlm.nih.gov/geo/) under accession number GSE68704.

BrdU Labeling.

5-bromo-2'-deoxyuridine (BrdU, 50 mg/kg, from Sigma) was intraperitoneally injected into mice daily from day 1 to day 5 after bleomycin instillation. Mice were euthanized at day 5, 3 hours after the last BrdU injection. Cryosections were used for BrdU and SFTPC co-staining. BrdU-specific antibody was from Accurate Chemical (Clone: BU1/75, Westbury, N.Y.) and was used at 1:100 dilution. SFTPC-specific antibody was from Millipore (Catalog ABC 99) and was used at 1:2,000 dilution.

Histology and Immunofluorescence Staining.

Paraffin-embedded sections and cryosections were used for staining. Trichrome staining was done by following the conventional protocol as described previously (Dong et al., 2015; Jiang et al., 2004). α-SMA in lung tissue was stained with anti-α-SMA (clone 1A4; Dako Cytomation) and followed by visualization with a Vectastain ABC kit (Vector Laboratories). Other primary antibodies used in the study include those specific for: Ki67 (rat anti-mouse-Ki67, 14-5698-82, 1:100, eBioscience), SFTPC (sc-7705, 1:50 dilution, Santa Cruz; or from Millipore, ABC99, 1:2,000), and Pdpn (T1α) (clone 8.1.1, 1:1,000 dilution, DSHB at the University of Iowa) (Barkauskas et al., 2013; Liang et al., 2012).

Stained sections were imaged using a Zeiss AX10 Observer Z1 or Zeiss 780 reverse laser-scanning confocal microscope. The number of SP-C$^+$ cells and SPC$^+$BrdU$^+$ cells, or SPC$^+$ cells and SPC$^+$Ki67$^+$, were counted in three or more random 5× views of each lung section, and the percentage of SPC$^+$BrdU$^+$ or SPC$^+$Ki67$^+$ cells in the total SPC$^+$ cell population of each lung section was calculated and averaged. Three to six mice were used for each experiment group.

Mouse Lung Dissociation and Flow Cytometry.

Single-cell suspensions from mouse lungs were isolated as described (Chen et al., 2012). Mouse lungs were perfused with 5 ml PBS and digested with elastase (4 U/ml; Worthington Biochemical Corporation) and DNase I (100 U/ml; Sigma) to obtain single-cell suspensions for flow cytometry. Primary antibodies to CD31, CD34, CD45, Sca-1, and CD24, and secondary antibody anti-streptavidin were all from eBioscience (San Diego, Calif.). Mouse anti-EpCAM (G8.8, catalog 118215) and anti-Ki67 (catalog 652403) were from BioLegend (San Diego, Calif.). 7-AAD was from BD Biosciences (San Diego, Calif.).

The procedures of staining the cells for flow cytometry and data analysis were described previously (Chen et al., 2012; Liang et al., 2012). In brief, cells were resuspended in Hank's balanced saline solution supplemented with 2% FBS (FBS), 10 mM HEPES, 0.1 mM EDTA, 100 IU/ml penicillin, 100 μg/ml streptomycin (HBSS+ buffer). Labeled primary antibodies including anti-CD31-biotin, anti-CD34-biotin, anti-CD45-biotin, anti-CD24-phycoerythrin (PE), anti-EpCAM-PE-Cy7, and Sca-1-allophycocyanin (APC) were added to cells. Biotin-conjugated antibodies were detected following incubation with streptavidin-APC-Cy7. Dead cells were discriminated by 7-amino-actinomycin D (7-AAD) staining. Flow cytometry was performed using a FACSCanto II flow cytometer and FACSAria III sorter (BD Immunocytometry Systems, San Jose, Calif.) and analyzed using Flow Jo 9.6.4 software (Tree Star, Ashland, Oreg.).

Human Lung Dissociation and FACS.

All human lung experiments were approved by the Cedars-Sinai Medical Center Institutional Review Board (IRB) and were in accordance with the guidelines outlined by the Board. Informed consent was obtained from each subject (IRB: Pro00035396).

Single-cell suspensions from human lungs were isolated as described (Barkauskas et al., 2013). The procedures of staining the cells for flow cytometry and data analysis were described previously (Barkauskas et al., 2013; Liang et al., 2012). Human lung tissues were minced and digested in 2 mg/ml dispase II at 4° C. overnight and for an additional 30 minutes at 37° C. Lung tissues were then digested with elastase and DNase I. Digested lung tissues were passed through 70-μm cell strainers to obtain single-cell suspension for FACS. Anti-human-CD31, anti-human-CD45, and anti-human-EpCAM antibodies were from BioLegend (San Diego, Calif.). Human type II cell marker, HTII-280 (ref. 29) was from L. Dobbs' lab at the University of California, San Francisco (UCSF). Anti-mouse-IgM was from Invitrogen. Biotinylated HA-binding protein (HABP) was from R&D systems (Minneapolis, Minn.). Flow cytometry was performed using a FACSCanto II flow cytometer and FACSAria III sorter (BD Immunocytometry Systems, San Jose, Calif.) and analyzed using Flow Jo 9.6.4 software (Tree Star, Ashland, Oreg.).

Matrigel Culture of Mouse and Human Type 2 Cells.

Flow-sorted mouse CD24$^-$Sca-1$^-$AEC2s or human HTII-280$^+$AEC2s were cultured in Matrigel/medium (1:1) mixture in the presence of MLg2908 lung fibroblast cells (Barkauskas et al., 2013; Chen et al., 2012). 100 μl Matrigel/medium mix containing 3×10$^3$ type 2 cells and 2×10$^5$ MLg2908 cells were plated into each 0.4-μm Transwell insert of a 24-well plate. 400 μl of medium was added in the lower chambers. Medium was described previously (Chen et al., 2012). Matrigel was from BD Biosciences (catalog 354230). Fresh medium was changed every other day. Cultures were maintained in a humidified 37° C. and 5% CO2 incubator. Colonies were visualized with a Zeiss Axiovert40 inverted fluorescent microscope (Carl Zeiss AG, Oberkochen, Germany). The number of colonies with a diameter of ≥50 μm from each insert was counted, and the colony-forming efficiency (CFE) was determined by the number of colonies in each culture as a percentage of the number of input epithelial cells at day 12 after plating.

For passaging experiments, sorted CD24$^-$Sca-1$^-$AEC2s from bleomycin-treated WT mice were plated with lung fibroblasts isolated from CAG-ECFP transgenic (full name B6.129(ICR)-Tg(CAG-ECFP)CK6Nagy/J from Jackson Laboratory) mice. Colonies were dissociated from Matrigel and digested in 0.25% trypsin-EDTA to get single cells. Cells were then sorted via FACS and cyan-negative cells were replated.

For paraffin embedding, the Matrigel discs were fixed with formalin overnight and then removed and transitioned into paraffin by the standard protocol. The paraffin-embedded colony discs were then sliced for staining.

For culture with IL-6 protein or anti-IL-6, sorted type 2 cells were pretreated with IL-6 protein or anti-IL-6 at room temperature for 30 minutes. Type 2 cells were then mixed with fibroblasts in the Matrigel/medium mixture and plated into Transwell inserts. The same concentration of IL-6 protein or IL-6 antibody was added into the Matrigel/medium mix and into the medium placed in the lower chambers.

Organoid Size Measurement.

Organoids derived from flow-sorted mouse CD24$^-$Sca-1$^-$AEC2s or human HTII-280$^+$AEC2s were pictured at day 12 after plating. ZEN pro 2012 software (Zeiss) was used to the measure surface area of the pictured organoids.

Immunofluorescence Staining of Flow-Sorted CD24$^-$Sca-1$^-$AEC2s.

Flow-sorted CD24⁻Sca-1⁻AEC2s were cytospun onto slides with 20,000 cells per slide. Cells were fixed and stained with an SFTPC-specific antibody from Santa Cruz (sc-7705).

Hyaluronan (HA) Concentration.

HA concentration was measured with a HABP-based ELISA-like protocol (Liang et al., 2011).

Enzyme-Linked Immunosorbent Assay (ELISA).

Duoset ELISA kits from R&D systems were used for IL-6, MIP-2, and TGF-β detection, following the manufacturer's instructions.

Healon and HA-Blocking Peptide Pep-1.

Healon GV was purchased from Abbott Medical Optics (Abbot Park, Ill.). Pep-1 was synthesized by Sigma-Genosys and dissolved in DMSO to form a 100 μg/μl stock solution as described previously (Jiang et al., 2005; Mummert et al., 2000). For 3D matrigel culture, sorted type 2 cells were pretreated with Healon (200 μg/ml) or pep-1 (125 μg/ml) at room temperature for 30 minutes. Higher concentrations of Healon (400 μg/ml, 600 μg/ml, and 800 μg/ml) were used for 3D matrigel culture of IPF AEC2s. Cells were then mixed with fibroblasts in Matrigel/medium mix and plated into Transwell inserts. The same concentrations of Healon or Pep-1 were added into the Matrigel/medium mix and medium that were placed in the lower chambers.

Stat3 Inhibitor.

The cell-permeable STAT3 inhibitor S3I-201 was purchased from Santa Cruz Biotechnology (Dallas, Tex.) and dissolved in DMSO to form stock solution of 10 mg/ml (MW 365.36). The dose for treating type 2 cells in colony-formation assays was 50 μM and 100 μM. The same amounts of DMSO were added into the control wells. Flow-sorted type 2 cells were pretreated with the STAT3 inhibitor at 50 μM or 100 μM concentrations, and with IL-6 protein (100 ng/ml), at room temperature for 30 minutes. Cells were then mixed with fibroblasts in Matrigel/medium mix and plated into Transwell inserts. Equal concentrations of the STAT3 inhibitor and IL-6 protein were added into the Matrigel/medium mix and medium placed in the lower chambers.

Cell Surface HA.

Biotinylated HA-binding protein (R&D Systems) and the secondary antibody anti-streptavidin (eBioscience) were used, along with other cell surface markers, for cell surface HA staining. Cells surface HA on gated CD24⁻Sca-1⁻ mouse AEC2s or HTII-280⁺ human AEC2s were analyzed (Jiang et al., 2005).

Statistical Analysis.

Data are expressed as the mean±s.e.m. The sample size for in vivo bleomycin fibrosis studies was based on previous studies in the lab (Li et al., 2011; Lovgren et al., 2011; Jiang et al., 2004; Jiang et al., 2010). No animals were excluded for analysis. All experiments were repeated two or more times. Data were normally distributed, and the variance between groups was not significantly different. Differences in measured variables between the experimental and control group were assessed by using the Student's t-tests or the Mann-Whitney U test. One-way or two-way ANOVA followed by Sidak's multiple-comparison test was used for multiple comparisons. The survival curves were compared using the log-rank test. Results were considered statistically significant at $P<0.05$. GraphPad Prism software was used for statistical analysis.

Results

Tlr4⁻/⁻ Mice are More Susceptible to Bleomycin Injury

Figure 1B:
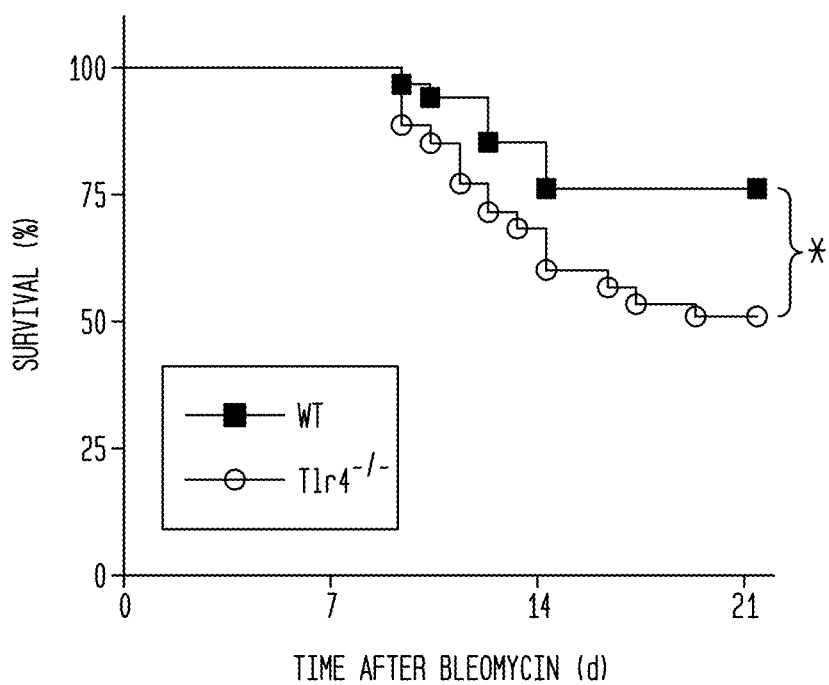
Figure 2A:
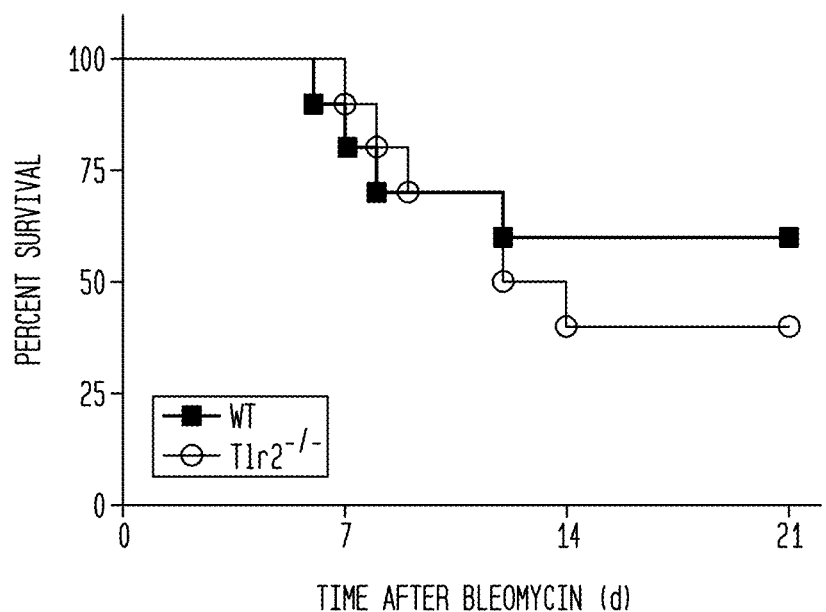
FIG. 2A-FIG. 2B show lung fibrosis of Tlr2 deficient mice.
Figure 2B:
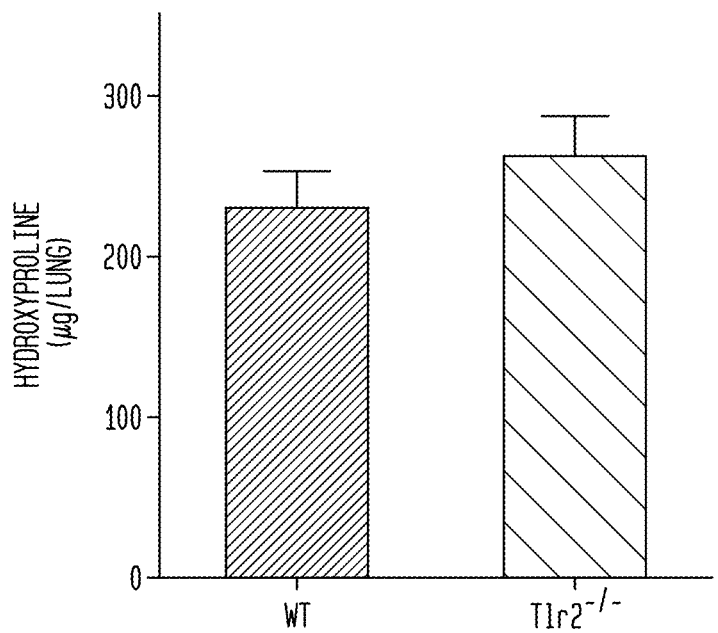

It was previously demonstrated that epithelial cell surface expression of HA, TLR2 and TLR4 is necessary to sustain basal activation of the transcription factor NF-κB and prevent epithelial cell apoptosis (Jiang et al., 2005). Here it was determined whether TLR-HA interactions could provide lung epithelial cells with signals to promote renewal, in addition to preventing apoptosis. Tlr4 expression was higher in the lungs of WT C57Bl/6 mice after bleomycin-induced injury than in the lungs of uninjured controls (FIG. 1A). Also, as compared to WT mice, Tlr4⁻/⁻ mice were more susceptible to bleomycin-induced lung injury (FIG. 1B), and they demonstrated a markedly enhanced fibrotic response to even low doses of bleomycin, as illustrated by enhanced trichrome staining (FIG. 1C) and higher hydroxyproline content in lung tissues 21 days after bleomycin exposure (FIG. 1D). More severe fibrosis in the mutant mice was also accompanied by higher α-smooth muscle actin (α-SMA; encoded by Acta2) staining (FIG. 1E) and elevated Acta2 expression (FIG. 1F), as compared to that in WT mice. The more-fibrotic phenotype seemed to be specific for a TLR4 deficiency, as the enhanced susceptibility to fibrosis was not observed in Tlr2⁻/⁻ mice (FIGS. 2A-B).

Figure 3A:
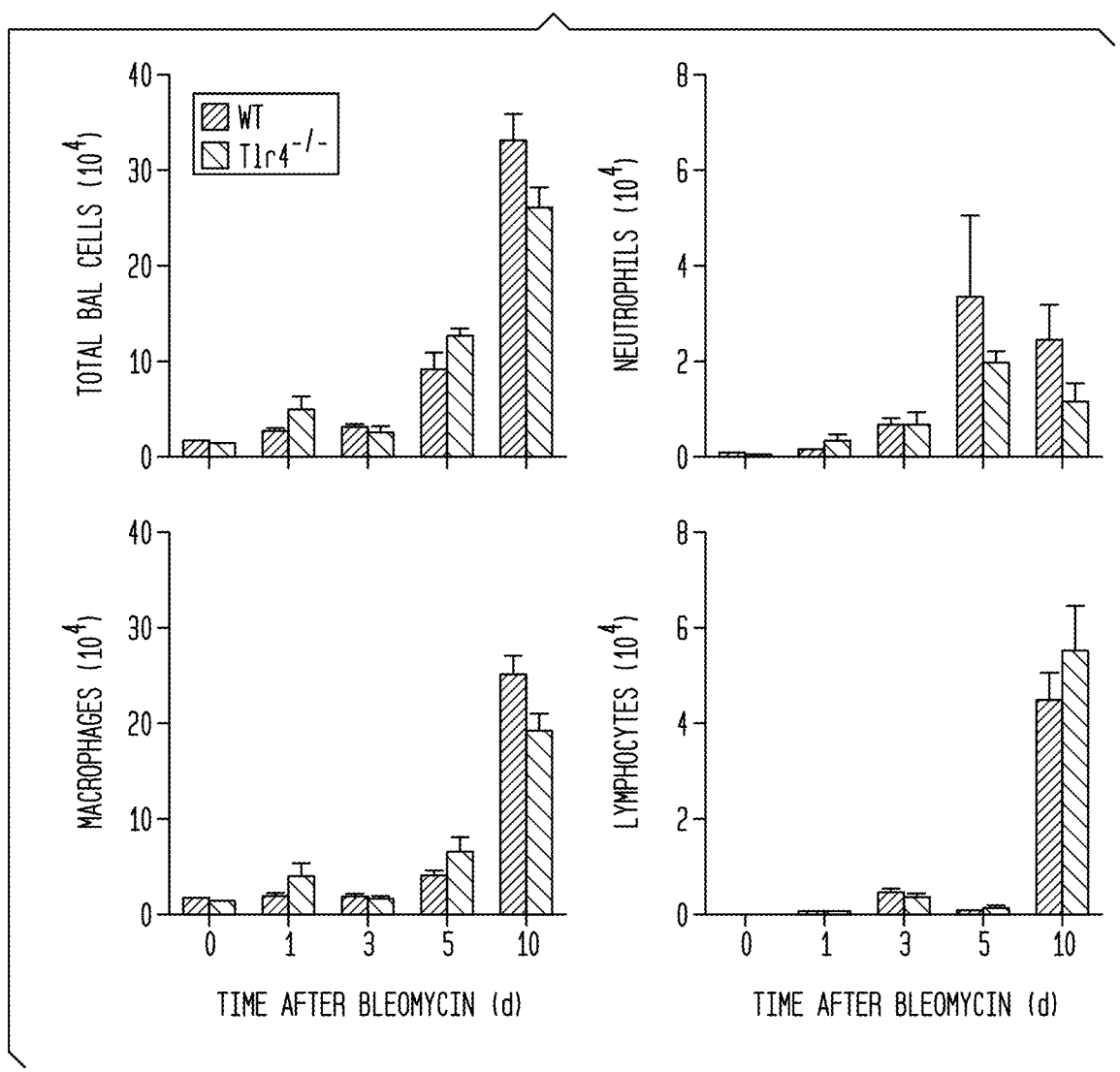
FIG. 3A-FIG. 3C show the inflammatory response to bleomycin injury of Tlr4$^{-/-}$ and WT mice.
Figure 3B:
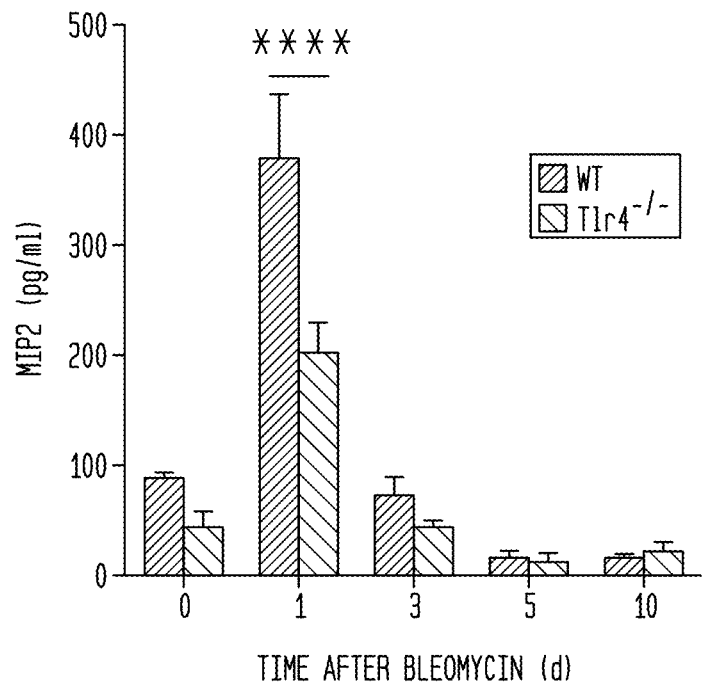
Figure 3C:
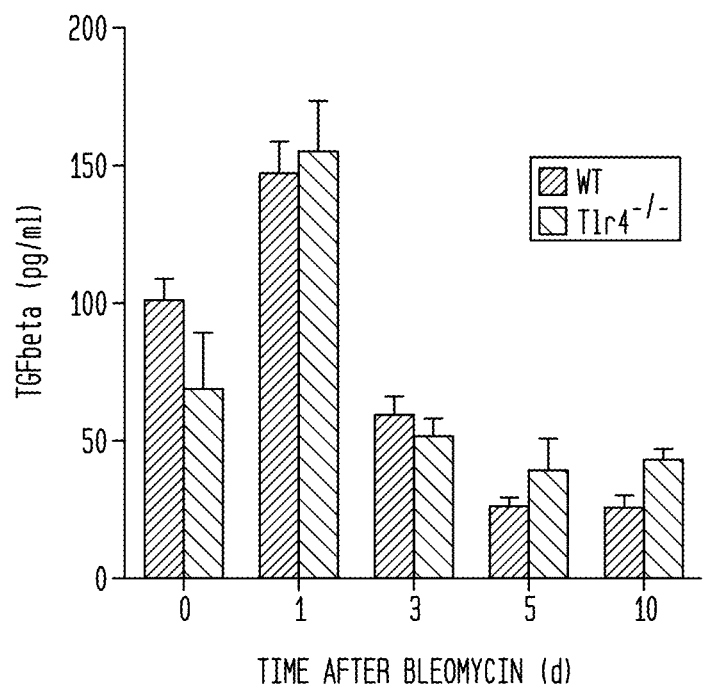

The inflammatory response of Tlr4⁻/⁻ mice to bleomycin-induced lung injury was investigated, and it was found that the number of total bronchoalveolar lavage fluid (BALF) cells, as well as differential inflammatory cell counts, were not different between Tlr4⁻/⁻ and WT mice (FIG. 3A). Furthermore, levels of the chemokine CXCL2 (also called MIP-2) in the BALF of Tlr4⁻/⁻ mice was lower at day 1 after bleomycin treatment than in WT mice (FIG. 3B). Also, there was no difference in transforming growth factor (TGF)-β concentrations in the BALF of Tlr4⁻/⁻ and WT mice (FIG. 3C).

Worse Alveolar Epithelial Cell Injury in Tlr4−/− Mice

Figure 4A:
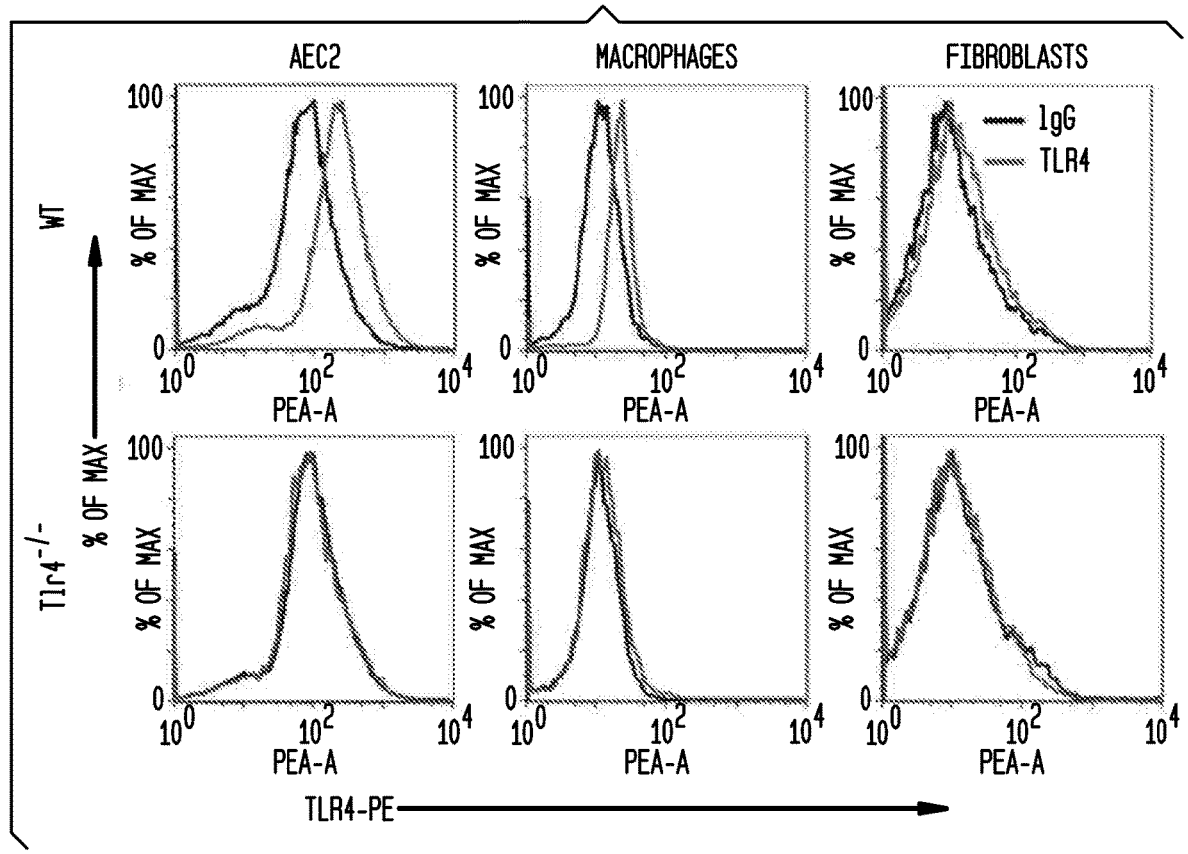
FIG. 4A-FIG. 4I show the identification of CD24$^-$Sca-1$^-$ AEC2s.
Figure 4B:
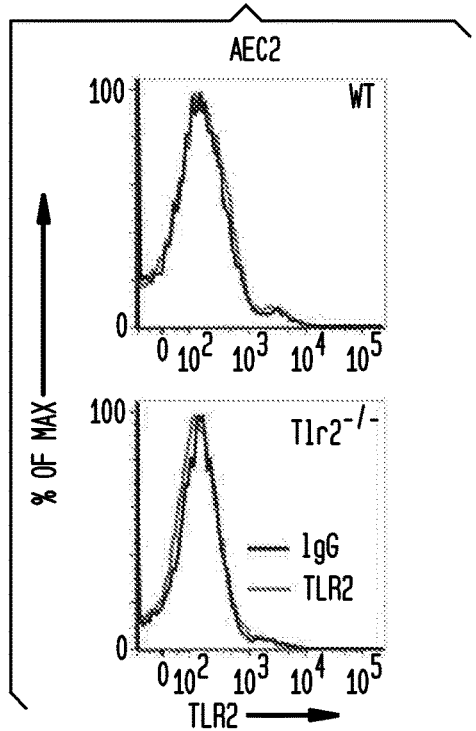
Figure 4C:
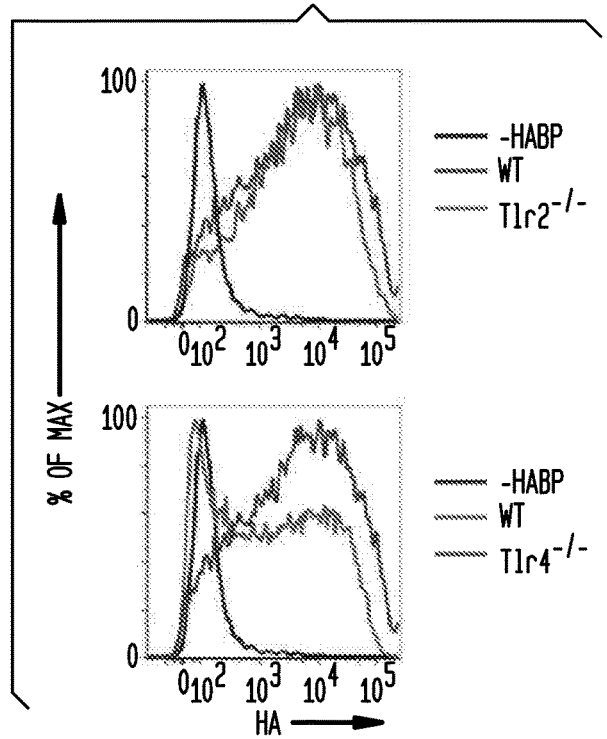

Flow cytometry analysis showed that AEC2s abundantly expressed TLR4 (FIG. 4A). Macrophages also expressed TLR4 as expected, and fibroblasts showed minimal TLR4 expression (FIG. 4A). In contrast, TLR2 expression on AEC2s was minimal (FIG. 4B). Cell surface expression of HA on AEC2s from Tlr2⁻/⁻ mice was as abundant as that of the WT AEC2s, whereas the cell surface expression of HA was markedly lower on the Tlr4⁻/⁻AEC2s than on the WT AEC2s (FIG. 4C).

Figure 4D:
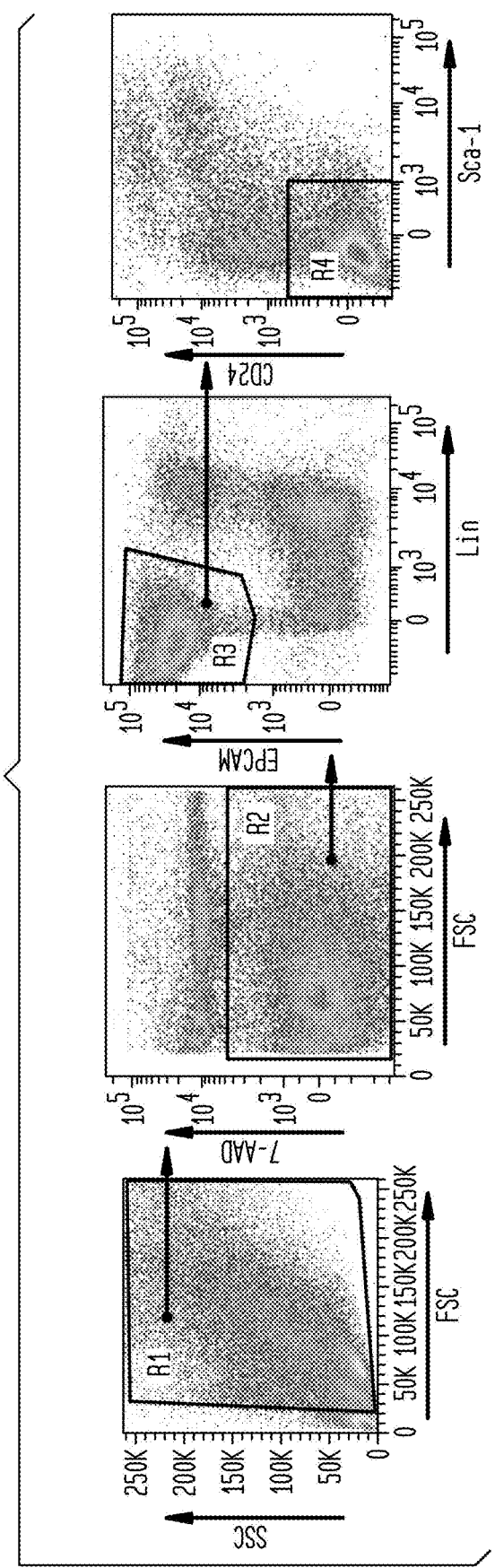
Figure 4E:
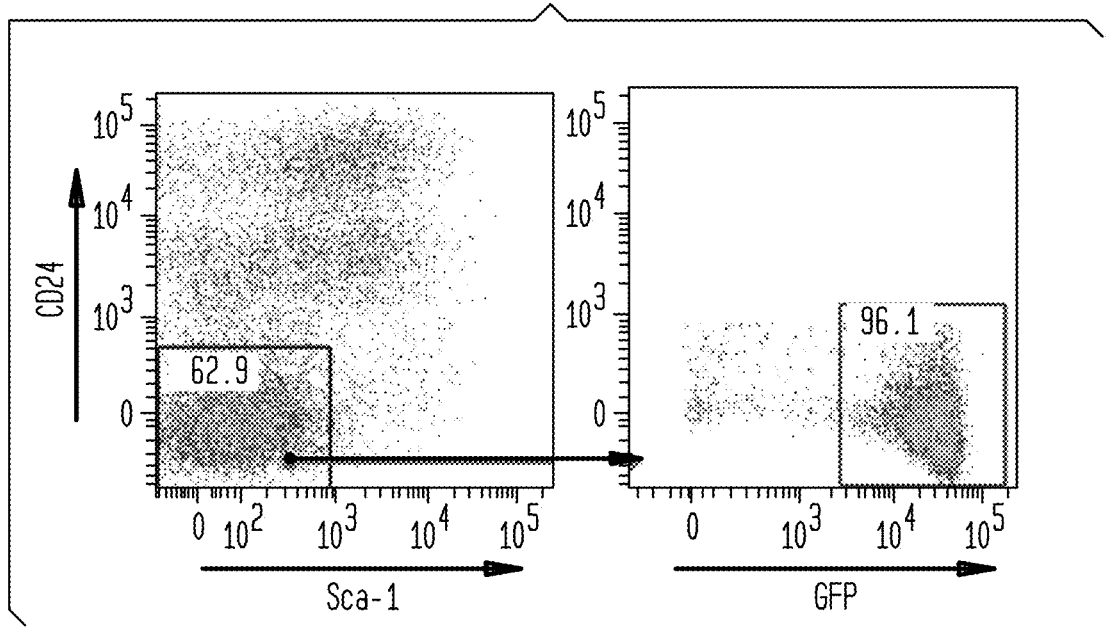
Figure 4F:
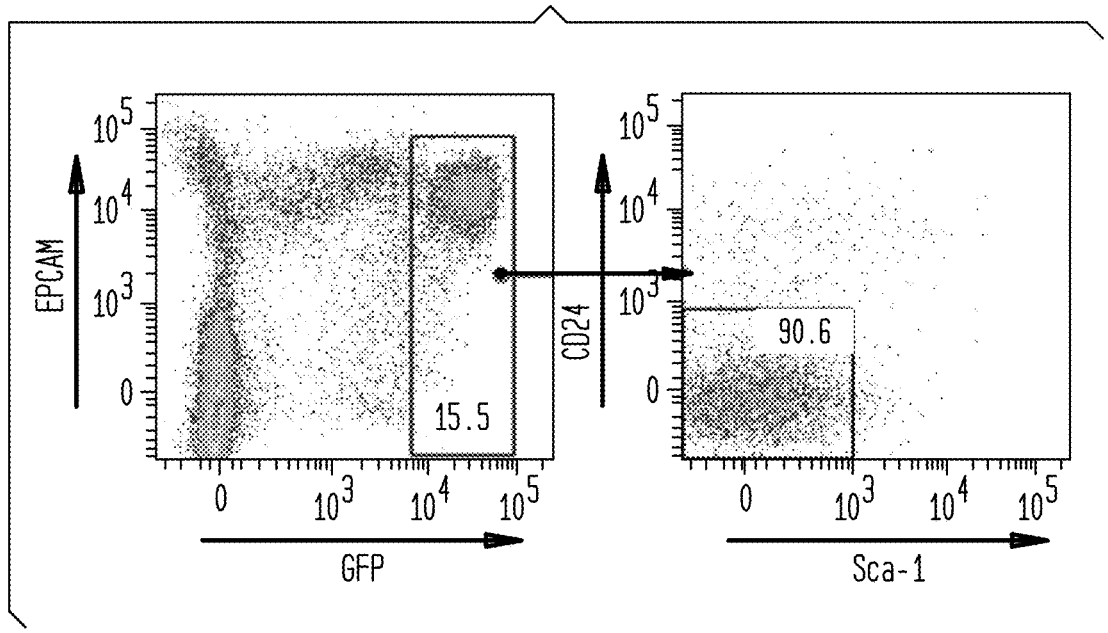
Figure 4G:
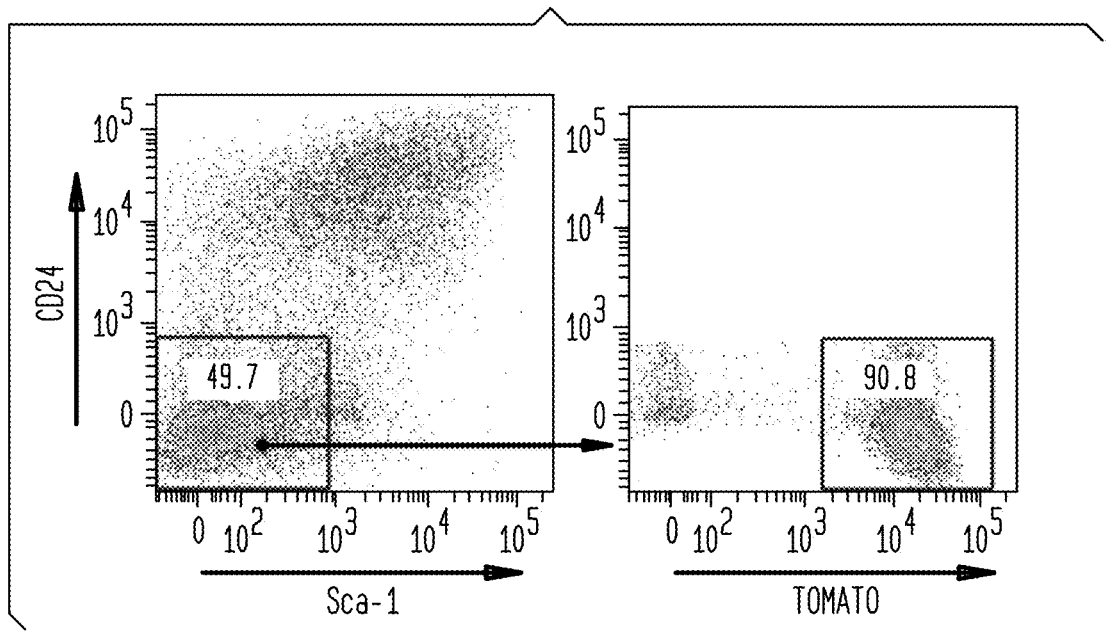
Figure 4H:
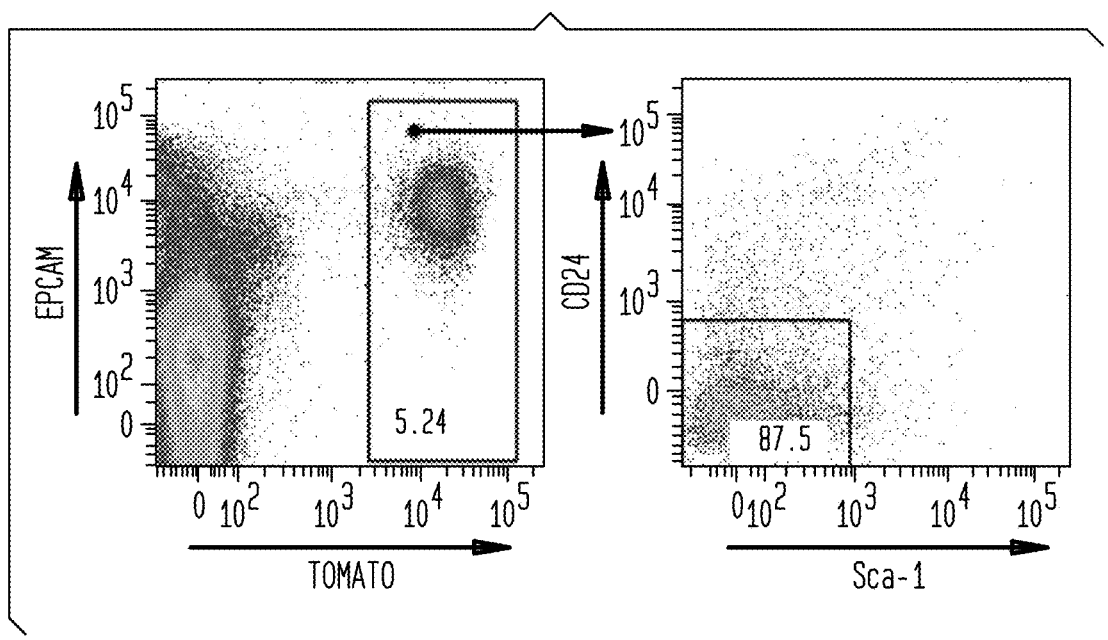
Figure 4I:
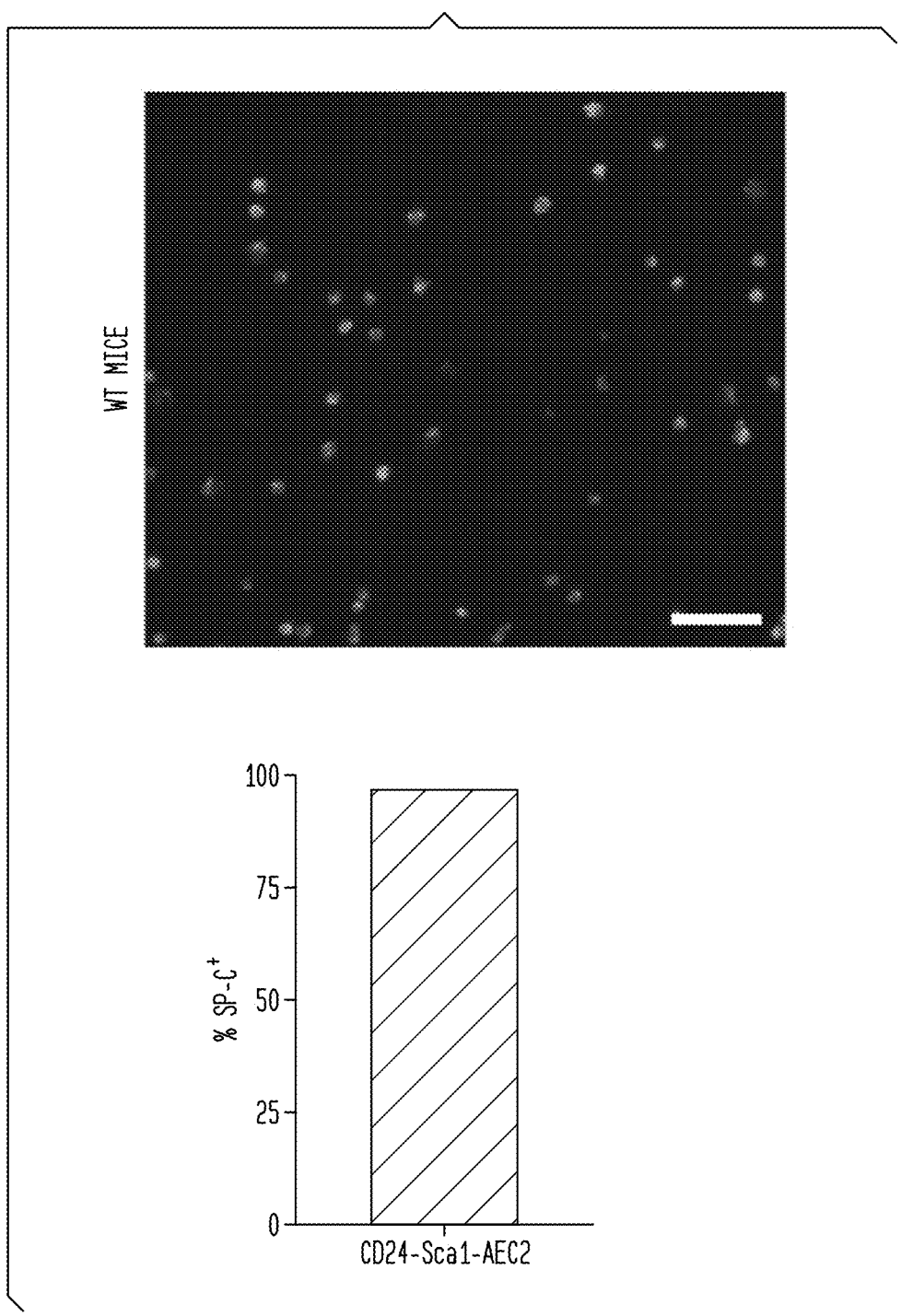

A mouse lung tissue dissociation and fractionation approach was used to generate an epithelial cell population (R3; CD45⁻CD31⁻CD34⁻EpCAM⁺; FIG. 4D) from which an enriched AEC2 fraction was isolated by selection of the CD24⁻Sca1⁻ subset (R4; hereafter designated CD24⁻Sca-1⁻AEC2s; FIG. 4D) (Chen et al., 2012). The gated CD24⁻Sca-1⁻AEC2s were verified as SFTPC⁺ by analyzing lung cells isolated from mice harboring a SFTPC-GFP transgene (FIGS. 4E-F) or by lineage tracing of AEC2s in SFTPC-CreER;Rosa26-Tomato mice, in which AEC2s express the fluorescent protein Tomato after tamoxifen induction (FIGS. 4G-H). In uninjured lungs from SFTPC-GFP transgenic mice, 96.1% of CD24⁻Sca-1⁻AEC2s were GFP positive (FIG. 4E), and 90.6% of GFP⁺ cells sorted into the CD24⁻Sca-1⁻ gate (FIG. 4F). Similarly, in the lungs of uninjured SFTPC-CreER;Rosa26-Tomato mice 1 week after administration of four tamoxifen injections, 90.8% of CD24⁻Sca-1⁻AEC2s were Tomato⁺ (FIG. 4G), and 87.5% of lineage-labeled Tomato⁺ cells sorted into the CD24⁻Sca-1⁻AEC2 gate (FIG. 4H). Immunofluorescence staining showed that 96.67% of FACS-enriched CD24⁻Sca-1⁻AEC2s were SP-C⁺ (FIG. 4I).

Figure 5B:
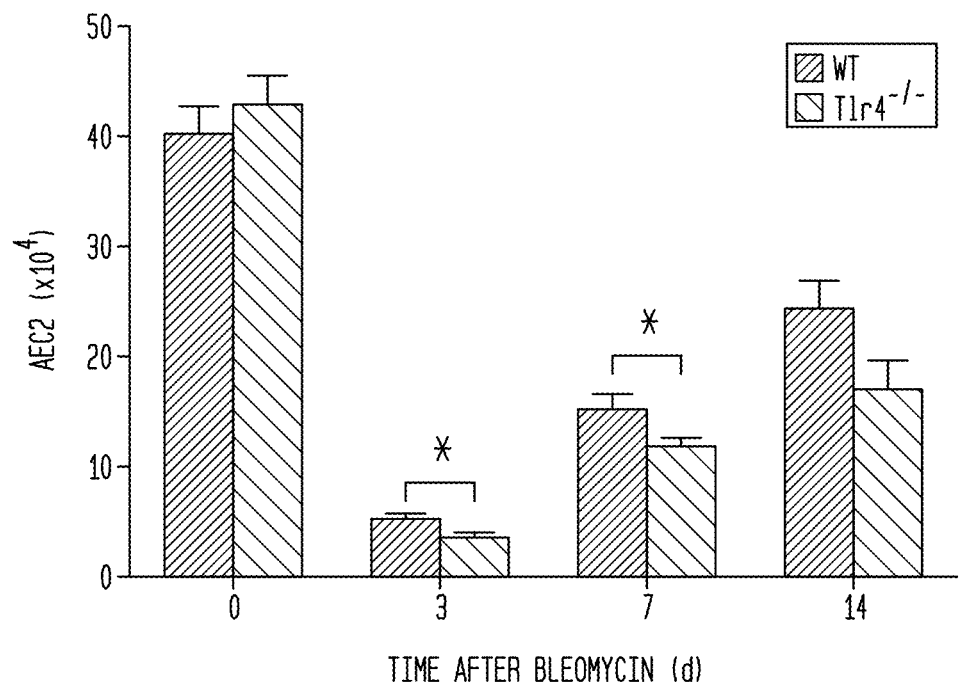
Figure 5C:
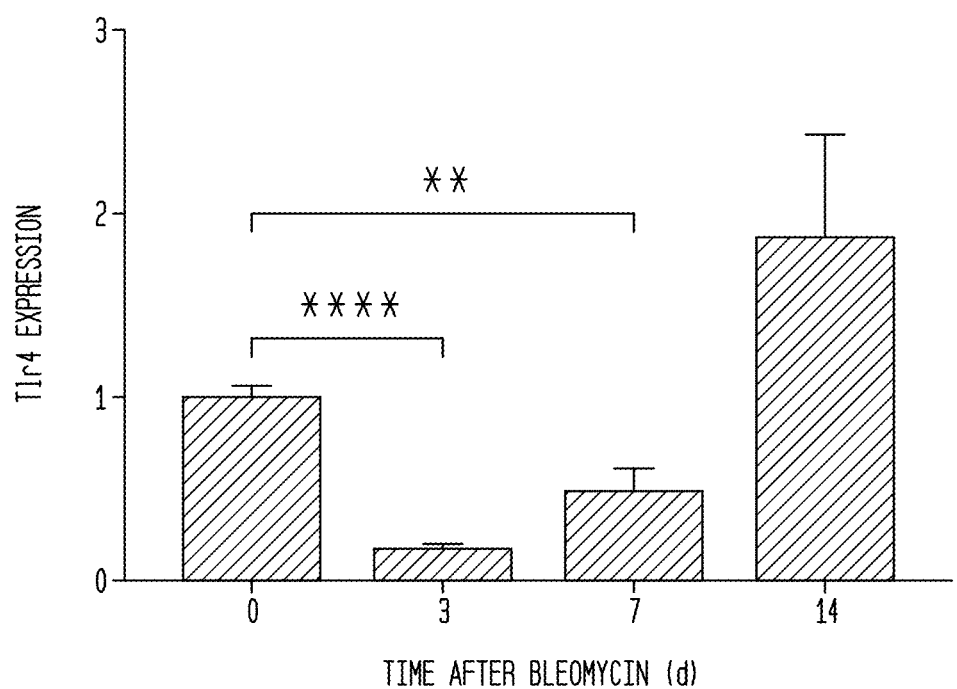
Figure 5D:
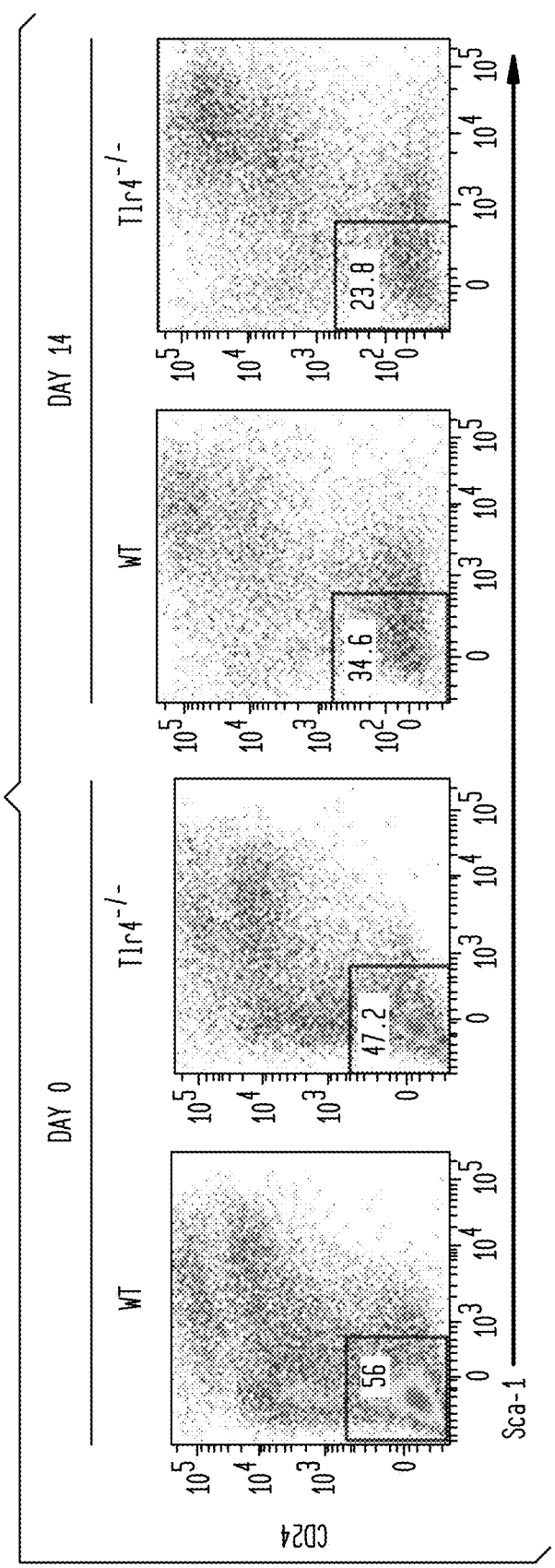

Bleomycin exposure is associated with both a lower percentage of CD24⁻Sca-1⁻AEC2s within the lung epithelial cell fraction (FIG. 5A) and a lower absolute number of CD24⁻Sca-1⁻AEC2s recovered from dissociated lung tissue (FIG. 5B), as compared to those at day 0. The nadir in the lower percentage of CD24⁻Sca-1⁻AEC2s was observed at day 7 (FIG. 5A), and the fewest number of CD24⁻Sca-1⁻ AEC2s were recovered from lungs at day 3 after bleomycin treatment (FIG. 5B). The decline in the percentage of AEC2s and the absolute number were not identical because other cell types in the lung were being differentially affected by the injury. The percentage and number of epithelial cells gradually recovered between day 14 and day 21 after bleomycin treatment (FIG. 5A-B). Tlr4 expression in CD24⁻Sca-1⁻AEC2s were lower at day 3 but were then at equivalent levels by day 14 after bleomycin injury, as compared to that in AEC2s from uninjured lungs (FIG. 5C). The Tlr4 expression pattern correlated with the pattern of CD24⁻Sca-1⁻AEC2 damage and recovery after bleomycin injury. Furthermore, even lower levels of CD24⁻Sca-1⁻AEC2s were observed in bleomycin-injured lungs from Tlr4$^{-/-}$ mice versus WT mice at multiple time points after injury (FIG. 5B, 5D). There was no difference between the numbers of CD24⁻Sca-1⁻AEC2s recovered from the uninjured lungs of Tlr4$^{-/-}$ and WT mice (FIG. 5B). In addition, we observed that a CD24⁻Sca-1⁺ population emerged following bleomycin-induced lung injury (FIG. 5A). The significance of these cells in lung injury is under investigation.

AEC2 Proliferation and Renewal Require TLR4 Signaling

Figure 6A:
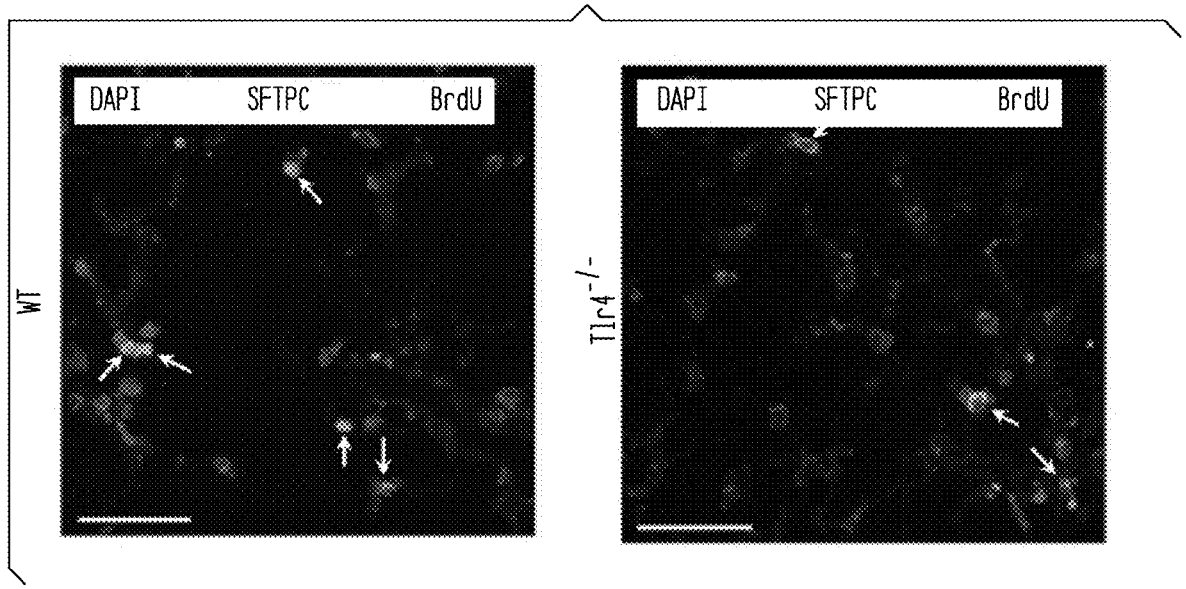
FIG. 6A-FIG. 6J show that AEC2 differentiation and proliferation requires TLR4 signaling.
Figure 6B:
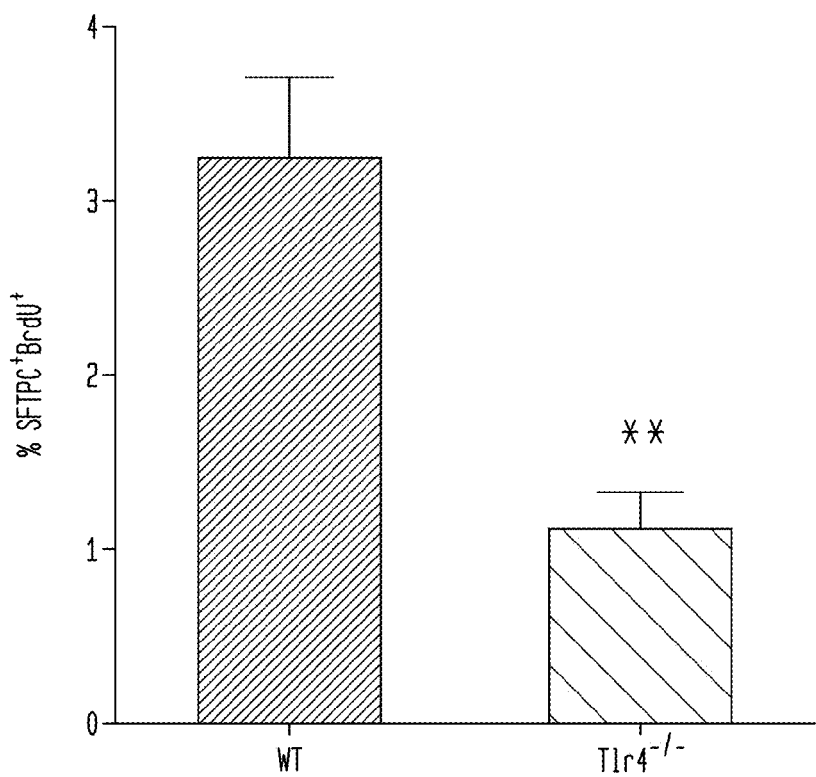
Figure 6C:
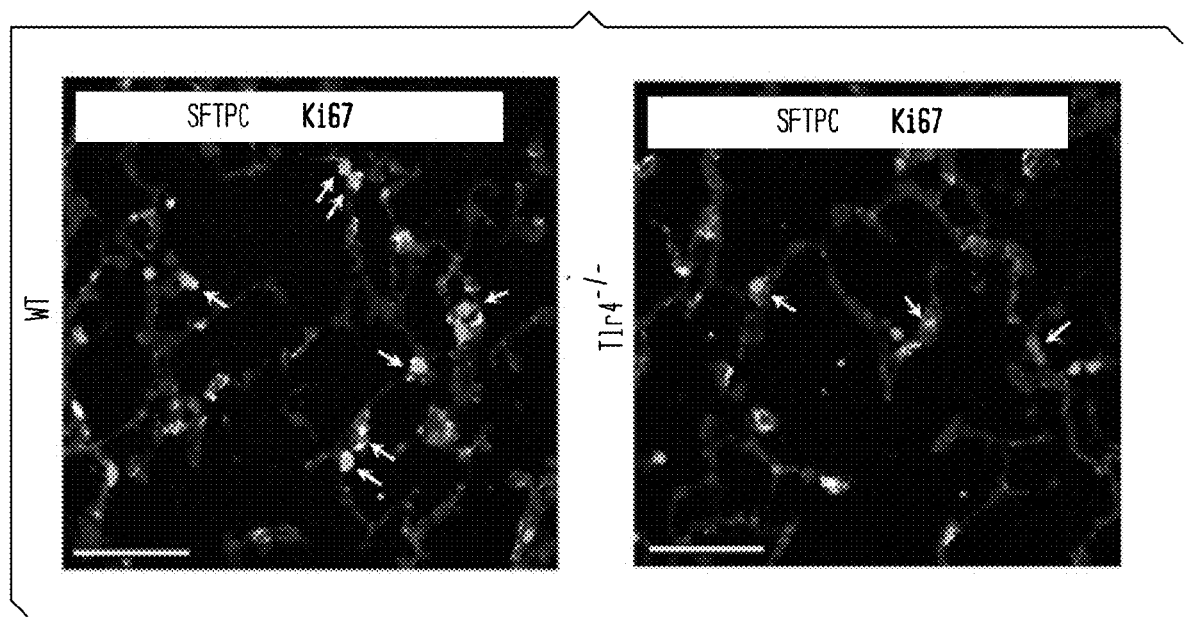
Figure 6D:
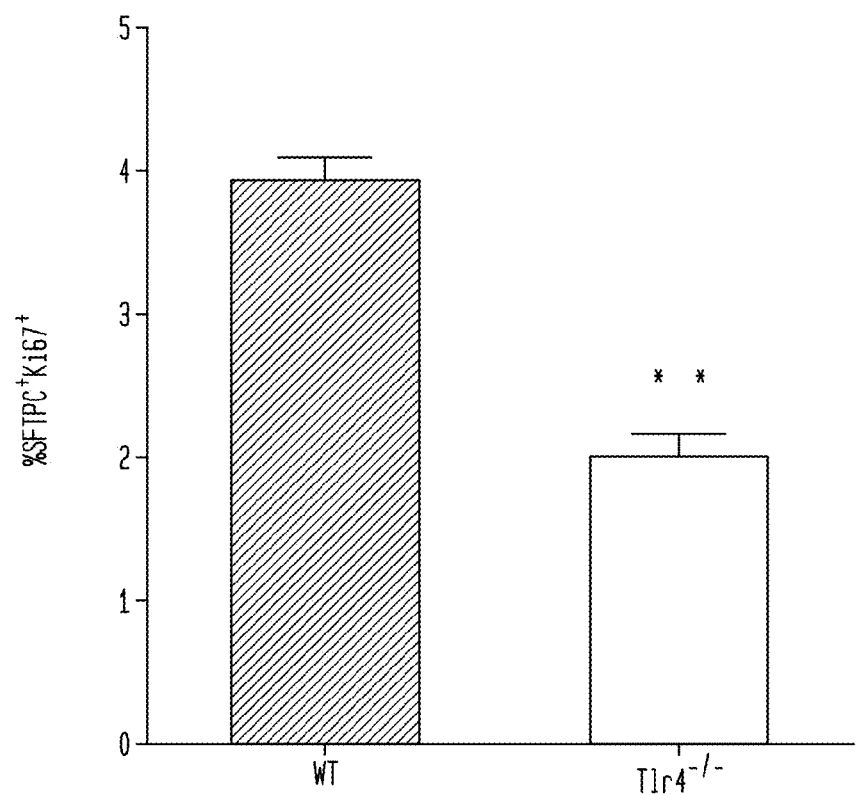

To assess the role of TLR4 on AEC2 proliferation in vivo, 5-bromo-2'-deoxyuridine (BrdU) labeling was performed after bleomycin treatment. Immunofluorescence staining showed fewer SFTPC⁺BrdU⁺ cells in the lungs of Tlr4$^{-/-}$ mice as compared to those in WT mice 5 days after bleomycin treatment (FIG. 6A-B). Similarly, fewer AEC2s in Tlr4$^{-/-}$ mice stained positive for the cell proliferation marker Ki67 than in WT mice (FIG. 6C-D).

Figure 6E:
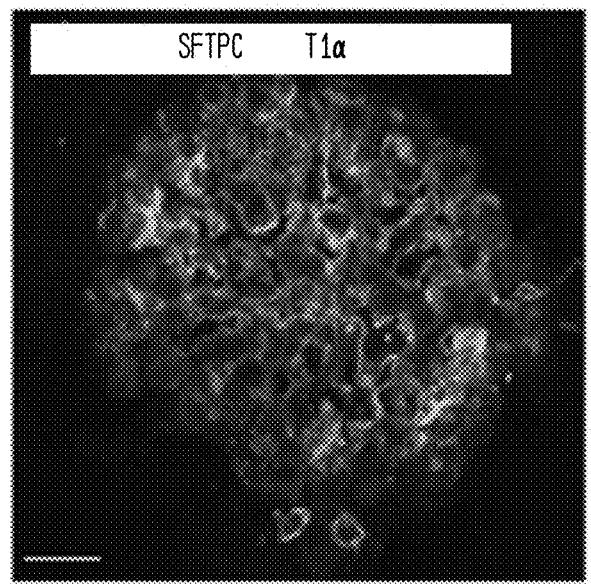
Figure 6F:
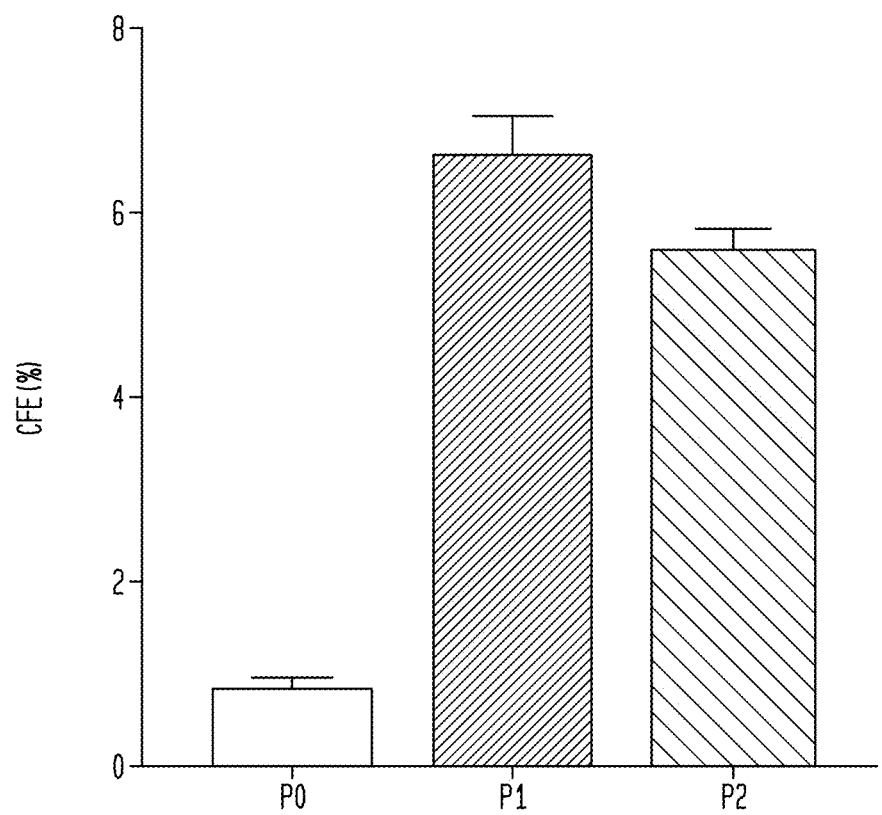
Figure 6G:
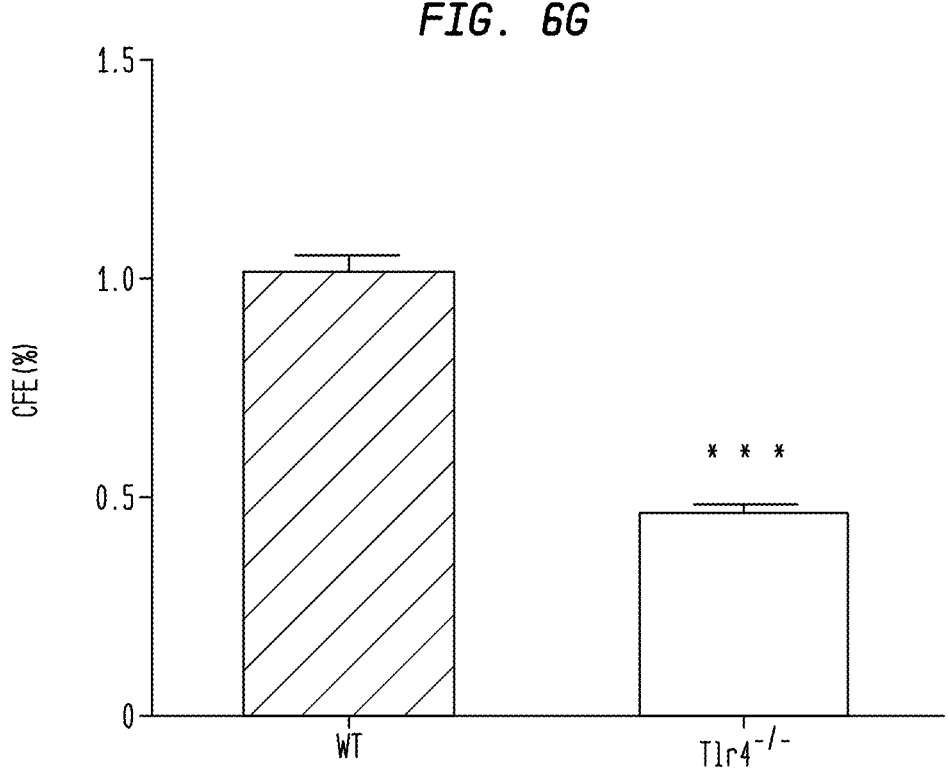
Figure 6H:
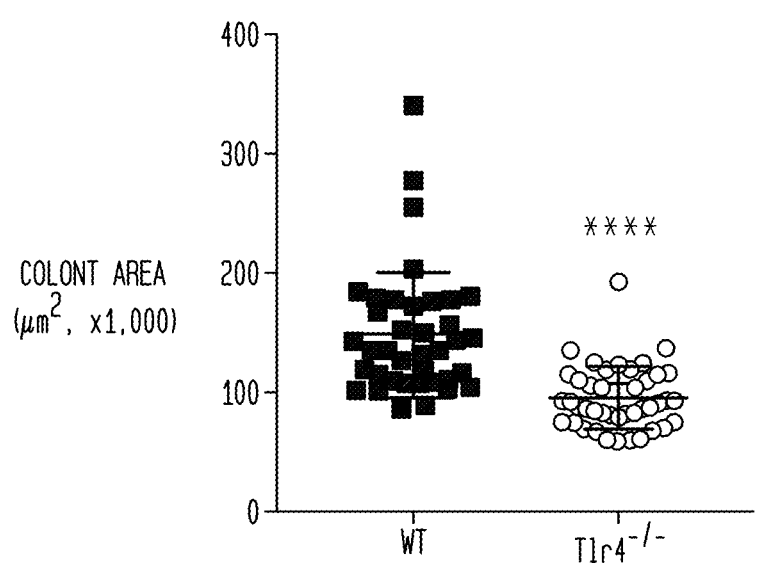
Figure 7A:
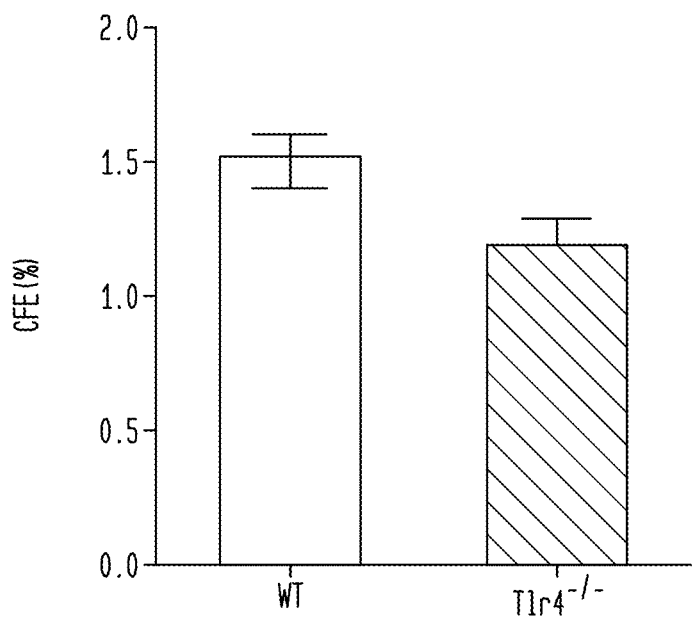
FIG. 7A-FIG. 7B show the characterization of Tlr4$^{-/-}$ AEC2s.

Next the colony-forming efficiency (CFE) of CD24⁻Sca-1⁻AEC2s that were isolated from Tlr4$^{-/-}$ and WT mice were compared at day 3 after bleomycin injury. Flow-sorted CD24⁻Sca-1⁻AEC2s were cocultured with mouse lung fibroblasts (Mlg 2908) embedded in matrigel medium mix for the generation of clonally derived 3D organoids. Immunofluorescence staining showed that the epithelial cells at the periphery of the organoids were SFTPC⁺ and that those within the interior were podoplanin (PDPN; also known as T1α) positive, which are indicative of AEC2 or AEC1 differentiation, respectively (FIG. 6E). Analysis of the replating efficiency of CD24⁻Sca-1⁻AEC2s isolated from the lungs of WT mice 3 days after bleomycin treatment revealed sustained regenerative capacity within passage (P)1 and P2 cells (FIG. 6F). CD24⁻Sca-1⁻AEC2s isolated from the lungs of Tlr4$^{-/-}$ mice 3 days after bleomycin treatment formed markedly fewer (FIG. 6G) and smaller colonies (FIG. 6H) than did CD24⁻Sca-1⁻AEC2s cells isolated from WT lungs, suggesting that the renewal capacity of Tlr4$^{-/-}$ AEC2s was impaired. CFEs were similar between AEC2 cells isolated from uninjured Tlr4$^{-/-}$ and WT lungs (FIG. 7A).

Figure 6I:
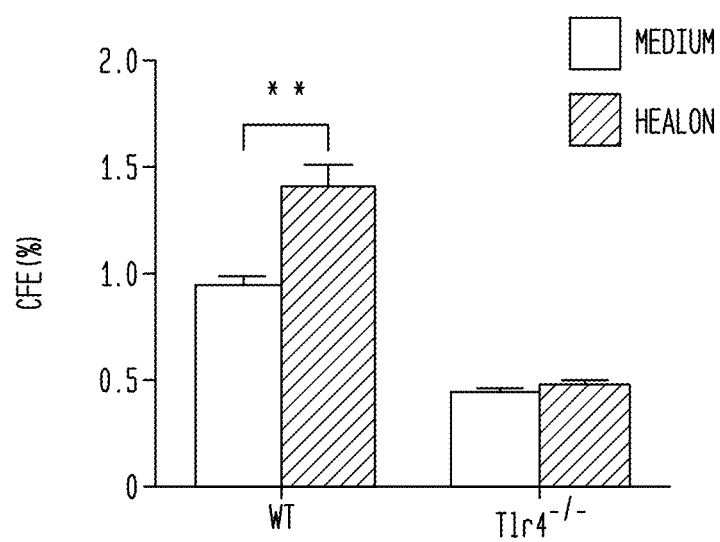
Figure 6J:
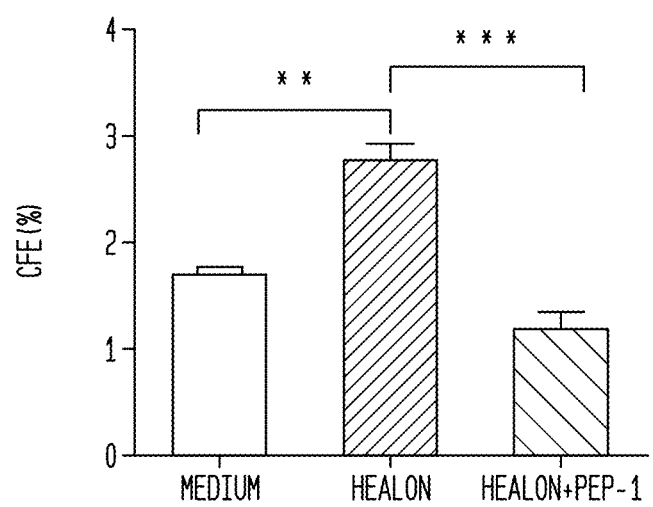
Figure 7B:
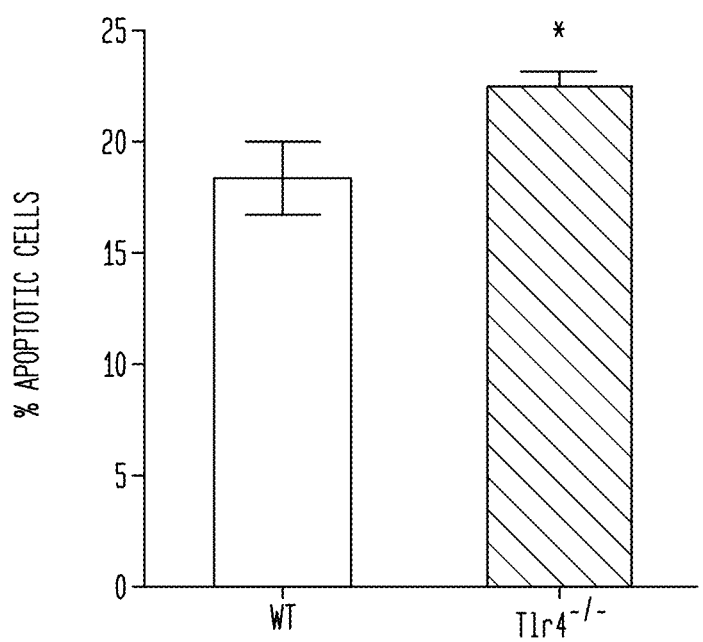

Next the hypothesis that TLR4-promoted AEC2 renewal requires the interaction with HA was tested. Addition of high-molecular-mass HA (referred to as Healon) to the Matrigel medium mix increased the CFE of CD24⁻Sca-1⁻ AEC2s isolated from lungs on day 3 after bleomycin treatment of WT but not Tlr4$^{-/-}$ mice (FIG. 6I). Healon increased the CFE of CD24⁻Sca-1⁻AEC2s from uninjured WT mice, and exposure to the HA-blocking peptide pep-1 (Jiang et al., 2005; Mummert et al., 2000) was able to inhibit the HA-induced increase in CFEs (FIG. 6J). We investigated the apoptosis of epithelial cells in the bleomycin-injured lungs and found that Tlr4$^{-/-}$ mice showed more epithelial cell apoptosis at day 3 after bleomycin treatment than WT mice (FIG. 7B).

HA on AEC2s Regulates AEC2 Renewal and Fibrosis

Figure 8A:
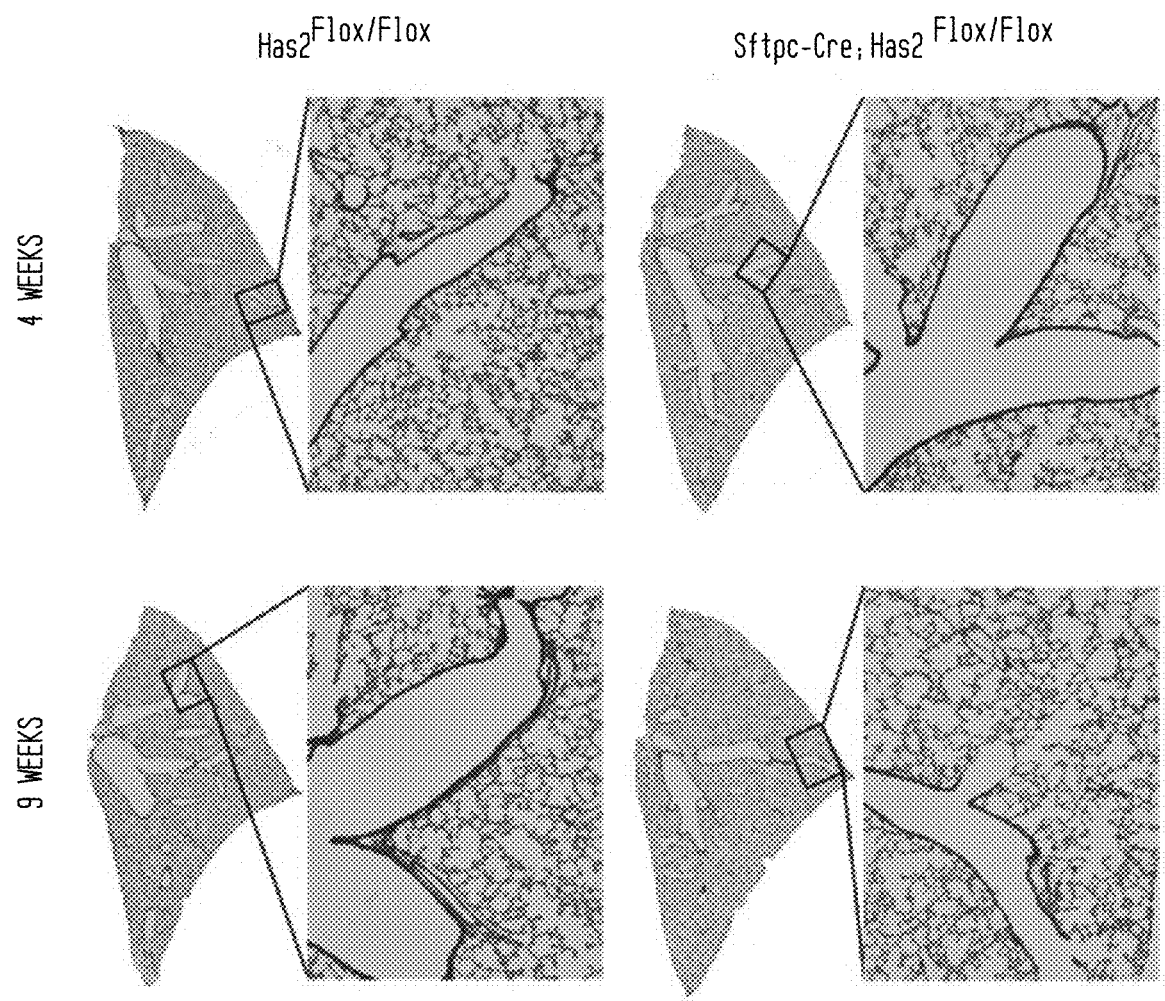
FIG. 8A-FIG. 8E demonstrate the characterization of SFTPC-Cre;Has2$^{flox/flox}$ mice.
Figure 8B:
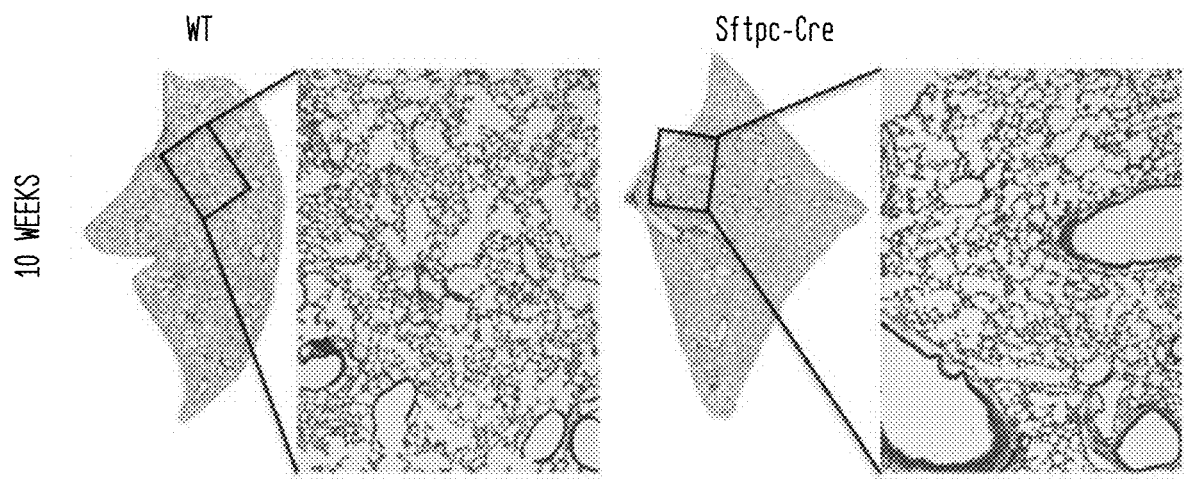
Figure 8C:
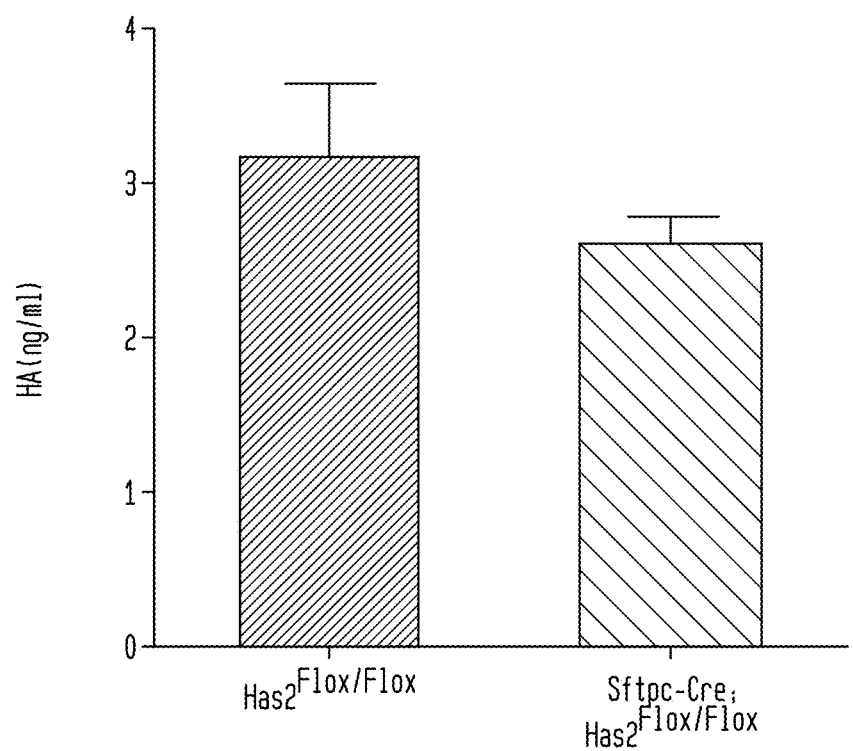
Figure 8D:
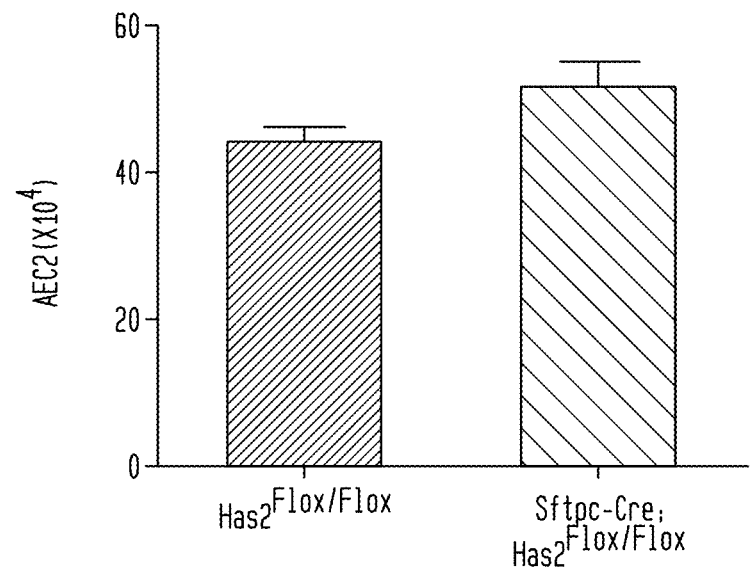
Figure 9A:
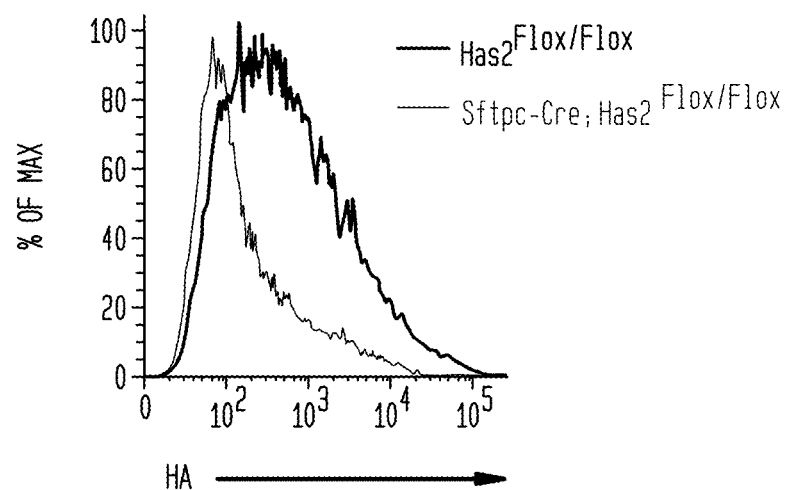
FIG. 9A-FIG. 9I show how Has2-deficient AEC2s have lower colony-forming capacity.
Figure 9B:
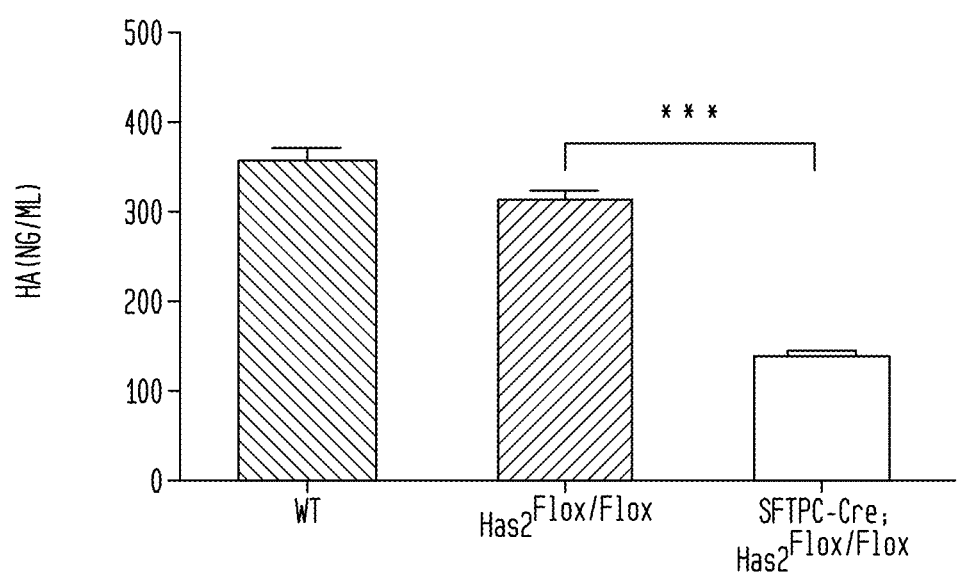

To further define the role of HA in AEC2 renewal, mice harboring loxP-flanked (foxed) alleles of Has2 (hereafter referred to as Has2$^{flox/flox}$ mice) (Li et al., 2011; Matsumoto et al., 2009) were crossed with SFTPC-Cre mice (Eblaghie et al., 2006) to generate SFTPC-Cre;Has2$^{flox/flox}$ mice. The SFTPC-Cre;Has2$^{flox/flox}$ mice have a targeted deletion of Has2 in distal lung epithelial cells, including the AEC2s, throughout lung development (Barkauskas et al., 2013; Chen et al., 2012). The lungs of SFTPC-Cre;Has2$^{flox/flox}$ mice, as well as those of Has2$^{flox/flox}$ and SFTPC-Cre transgenic mice, developed normally with no readily observable gross or histological abnormalities (FIGS. 8A-B). The HA concentrations in the BALF of uninjured SFTPC-Cre; Has2$^{flox/flox}$ mice was slightly lower than those in the BALF of their littermates (FIG. 8C). There was no difference in the numbers of CD24⁻Sca-1⁻AEC2s that were recovered from the uninjured lungs of SFTPC-Cre;Has2$^{flox/flox}$ mice and their littermates (FIG. 8D). Cell surface HA expression was markedly lower on CD24⁻Sca-1⁻AEC2s isolated from SFTPC-Cre;Has2$^{flox/flox}$ mice than on AEC2s isolated from control mice (FIG. 9A). The HA concentrations in the culture medium of CD24⁻Sca-1⁻AEC2s that were isolated from SFTPC-Cre;Has2$^{flox/flox}$ mice were also lower than those in the culture medium of CD24⁻Sca-1⁻AEC2s isolated from their littermates (FIG. 9B).

Figure 8E:
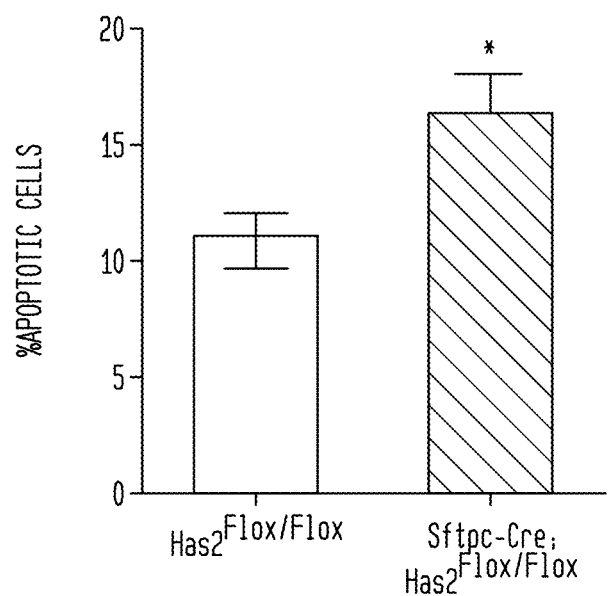
Figure 9C:
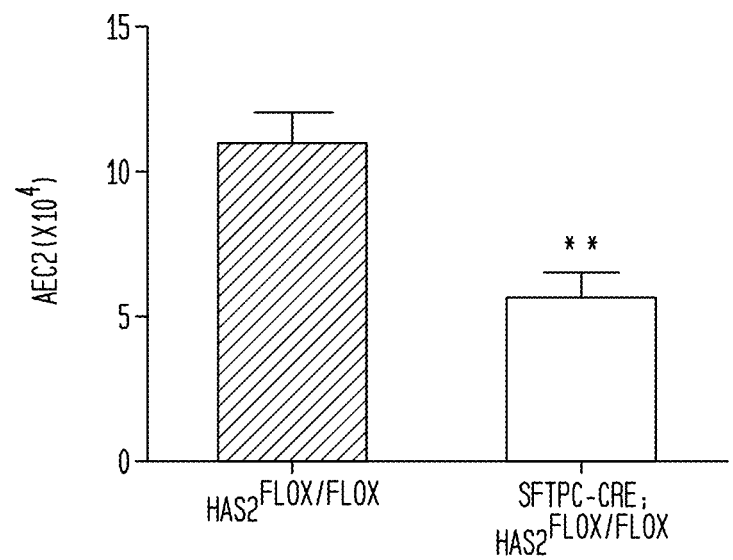
Figure 9D:
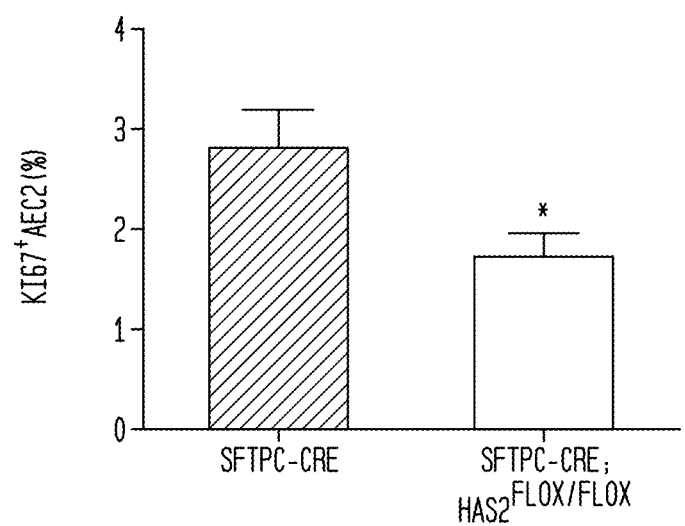
Figure 9E:
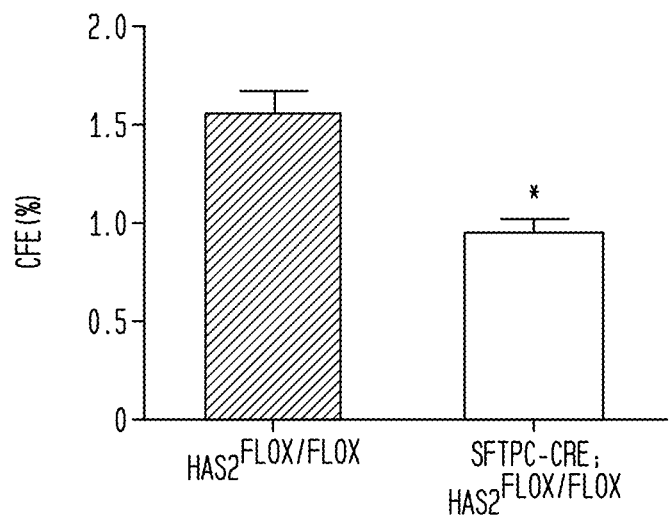
Figure 9F:
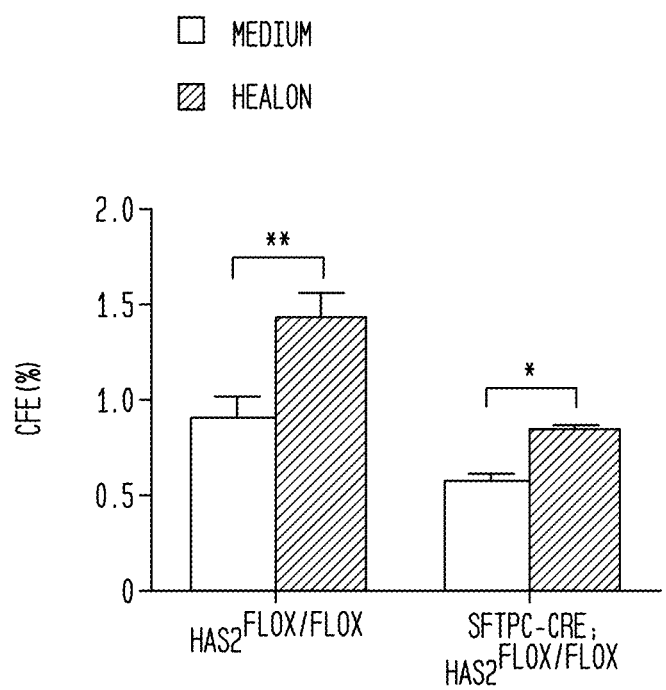

To determine whether lower HA expression affects the renewal capacity of AEC2s, CD24⁻Sca-1⁻AEC2s were isolated from bleomycin-injured mouse lungs and much fewer cells were recovered from the lungs of SFTPC-Cre;Has2$^{flox/flox}$ mice than from their littermates (FIG. 9C). Ki67 staining of gated CD24⁻Sca-1⁻AEC2s from bleomycin-treated SFTPC-Cre;Has2$^{flox/flox}$ mice on day 3 after treatment was lower than that of AEC2s from control mice (FIG. 9D). CD24⁻Sca-1⁻ AEC2s from bleomycin-injured SFTPC-Cre; Has2$^{flox/flox}$ mice showed markedly lower CFEs relative to those of AEC2s from Has2$^{flox/flox}$ littermates (FIG. 9E). EpCAM⁺Lin⁻ epithelial cells from bleomycin-injured SFTPC-Cre;Has2$^{flox/flox}$ mice also showed more apoptosis than the cells from littermate controls (FIG. 8E). Unlike AEC2s isolated from Tlr4$^{-/-}$ mice, AEC2s from bleomycin-injured SFTPC-Cre;Has2$^{flox/flox}$ mice responded to Healon treatment by giving rise to robust colony formation relative to that with the Healon-free Matrigel medium mix (FIG. 9F).

Figure 9G:
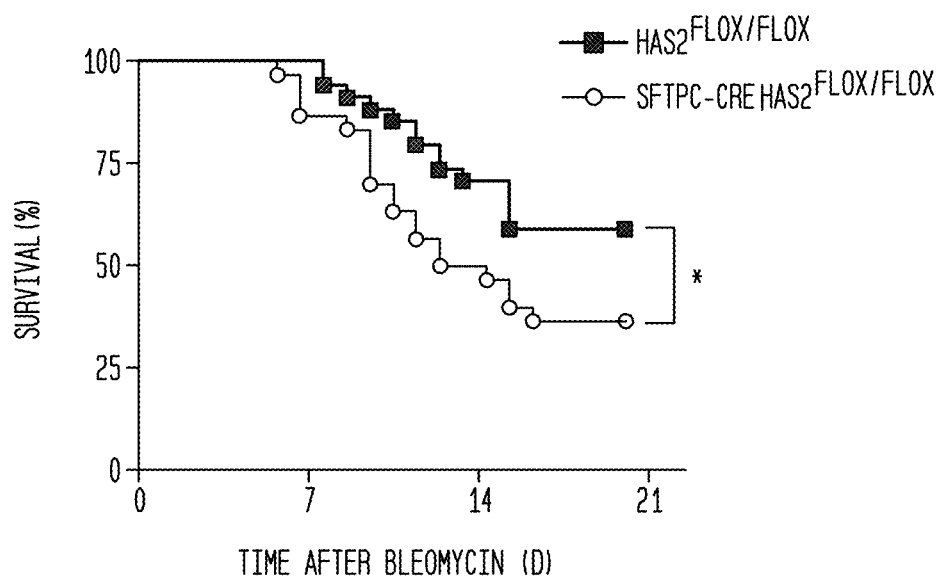
Figure 9H:
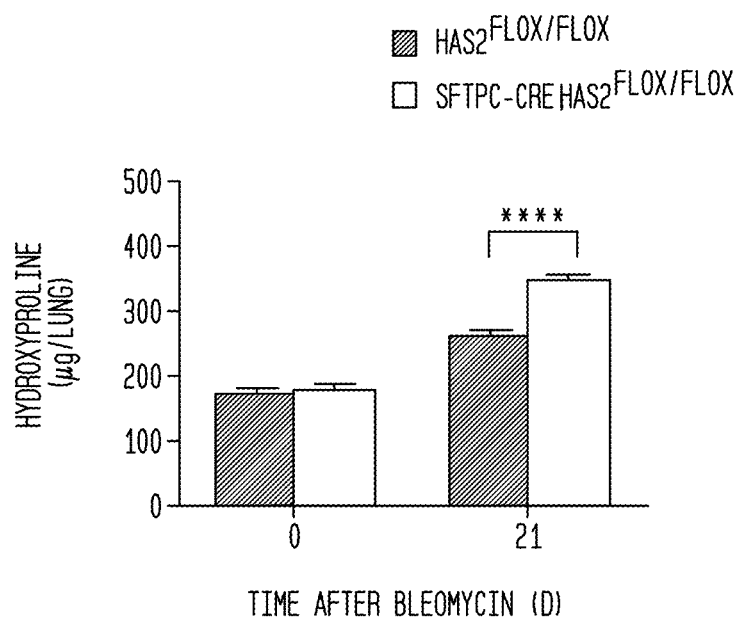
Figure 9I:
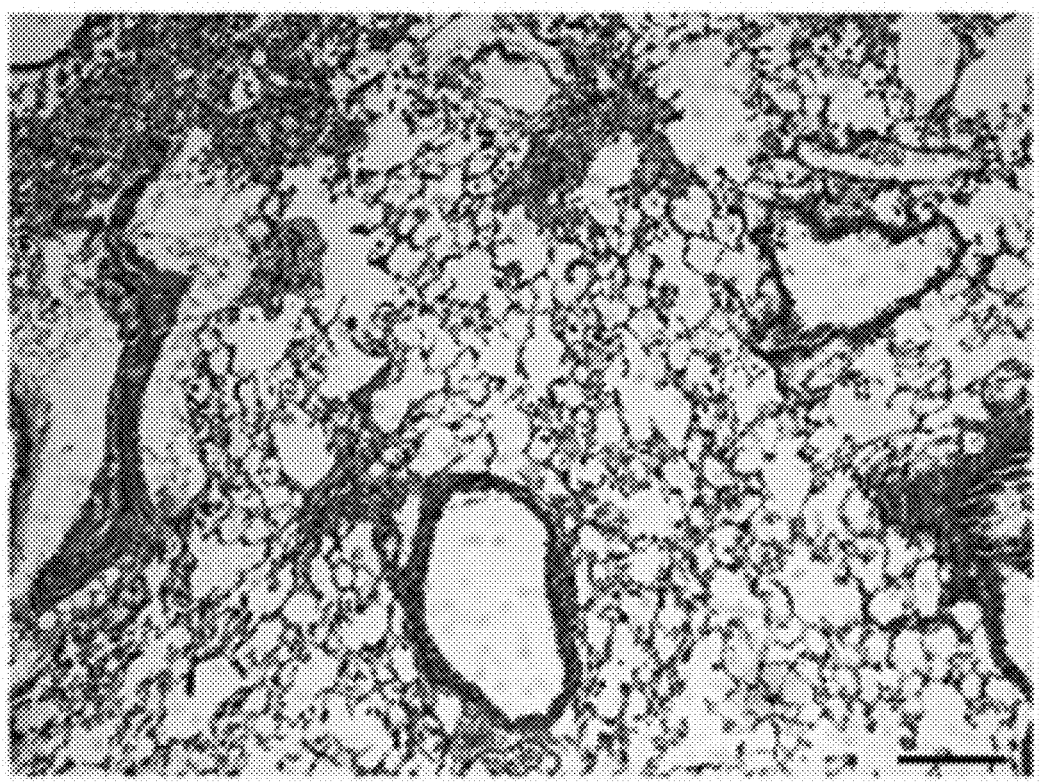
Figure 9I:
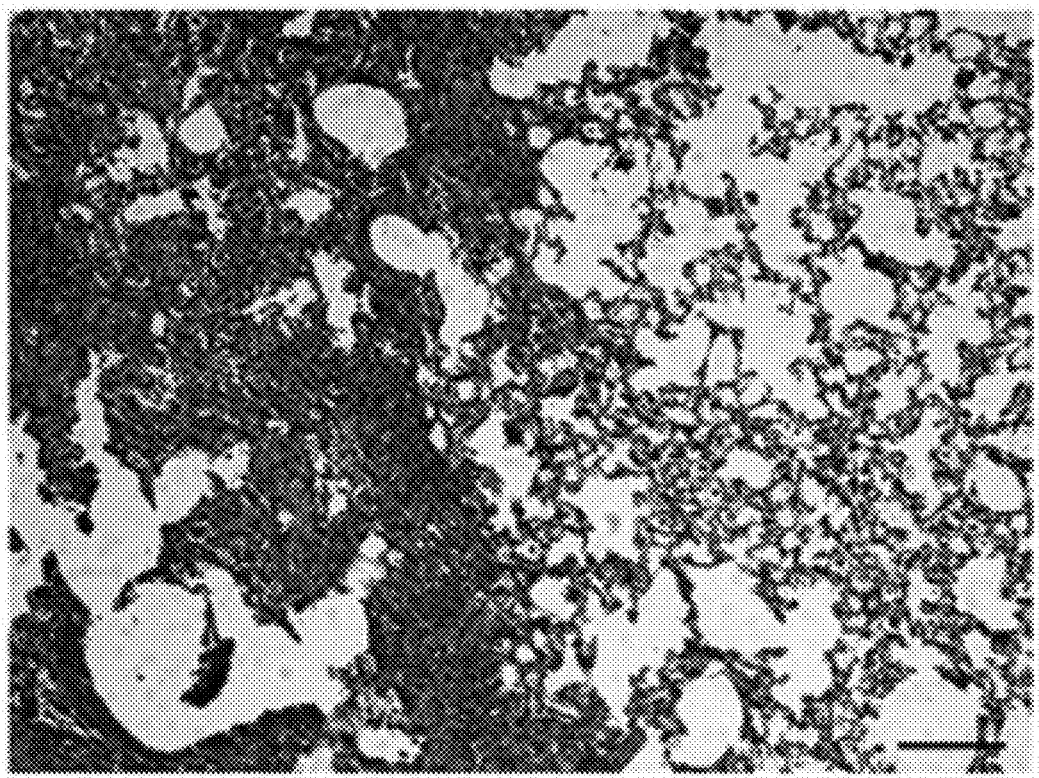

Lower cell surface expression of HA on AEC2s was hypothesized to lead to enhanced susceptibility to bleomycin injury. Indeed, SFTPC-Cre;Has2$^{flox/flox}$ mice showed less survival (FIG. 9G) and more severe lung fibrosis at day 21 after bleomycin treatment as compared to injured littermate controls, as assessed by hydroxyproline content (FIG. 9H) and trichrome staining (FIG. 9I).

IL-6 Promotes AEC2 Renewal

Figure 10A:
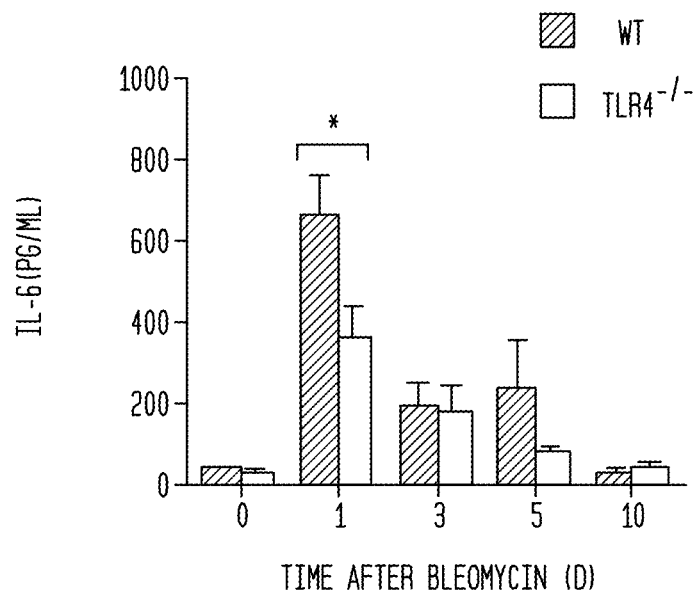
FIG. 10A-FIG. 10I show that IL-6 promotes AEC renewal and limits lung fibrosis. IL-6 concentrations in the BALF of Tlr4$^{-/-}$ and WT mice (FIG. 10A) (day 0: WT, n=3; Tlr4$^{-/-}$, n=5; day 1, n=4 each; day 3, WT n=4, Tlr4$^{-/-}$ n=6; day 5, WT n=5, Tlr4$^{-/-}$ n=4; day 10, WT n=8, Tlr4$^{-/-}$ n=4) or of SFTPC-Cre;Has2$^{flox/flox}$ and their Has2$^{flox/flox}$ littermates (FIG. 10B) (day 0, n=4 per group; day 1, Has2$^{flox/flox}$ n=4; SFTPC-Cre;Has2$^{flox/flox}$, n=5; day 3, Has2$^{flox/flox}$, n=4; SFTPC-Cre;Has2$^{flox/flox}$, n=3) at indicated time points. CFEs of CD24$^-$Sca-1$^-$AEC2s from bleomycin-treated WT mice that were treated with anti-IL-6 or control IgG (FIG. 10C) (n=3 per group) or with rIL-6 (FIG. 10D) (n=6 per group, except n=3 for 10 ng/ml group). M, medium. CFEs of CD24$^-$Sca-1$^-$AEC2s from bleomycin-treated Tlr4$^{-/-}$ and WT mice (FIG. 10E) (medium: WT, n=6; Tlr4$^{-/-}$, n=5; rIL-6, n=3 per group) or from SFTPC-Cre;Has2$^{flox/flox}$ and its Has2$^{flox/flox}$ littermates (FIG. 10F) (n=3 per group) in the presence of rIL-6 (100 ng/ml).
Figure 10B:
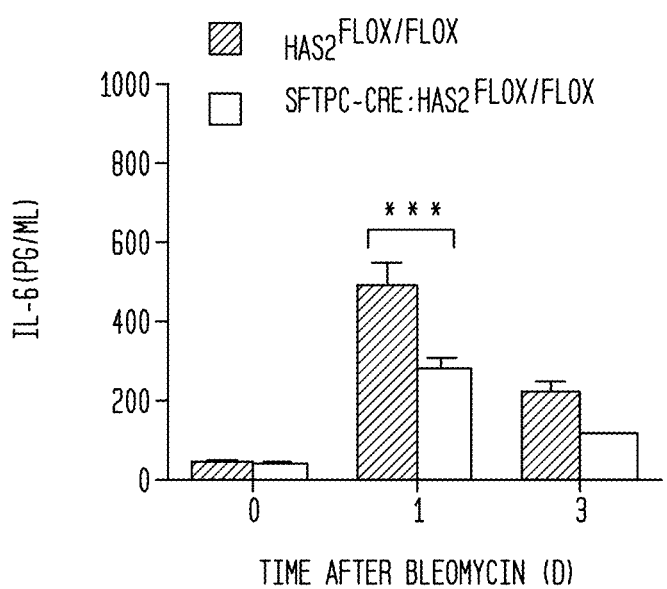
Figure 11A:
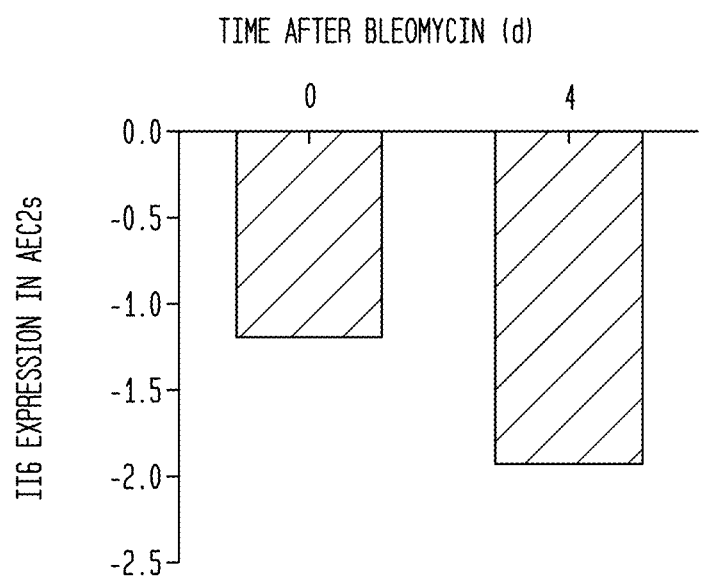
FIG. 11A-FIG. 11G show how IL-6 attenuates bleomycin-induced lung injury.
Figure 11B:
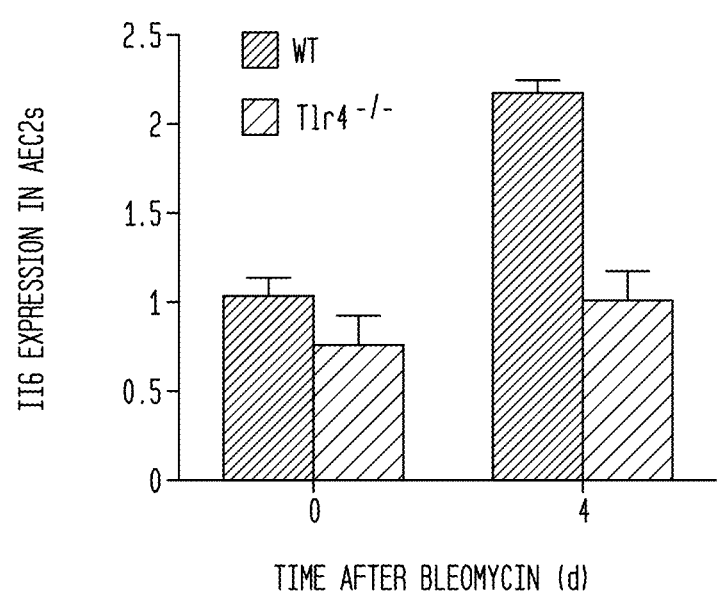

Previous observations that HA-TLR4 interactions are associated with constitutive NF-κB activation in AEC2 cells (Jiang et al., 2005) led to a search for factors downstream of this signaling pathway that might mediate the protective effects of HA and TLR4 on AEC2s. BALF composition was evaluated at various times after injury and it was found that IL-6 was lower in the BALF of both Tlr4$^{-/-}$ and SFTPC-Cre;Has2$^{flox/flox}$ mice, as compared to that in their corresponding controls (FIGS. 10A-B). Microarray analysis also showed that Il6 (which encodes IL-6) was among a cluster of genes whose expression was downregulated in Tlr4$^{-/-}$ versus WT CD24⁻Sca-1⁻AEC2s (FIG. 11A). RT-PCR analysis confirmed that Il6 expression was lower in TLR4-deficient CD24⁻Sca-1⁻AEC2s than in WT AEC2s 4 days after bleomycin treatment (FIG. 11B).

Figure 10C:
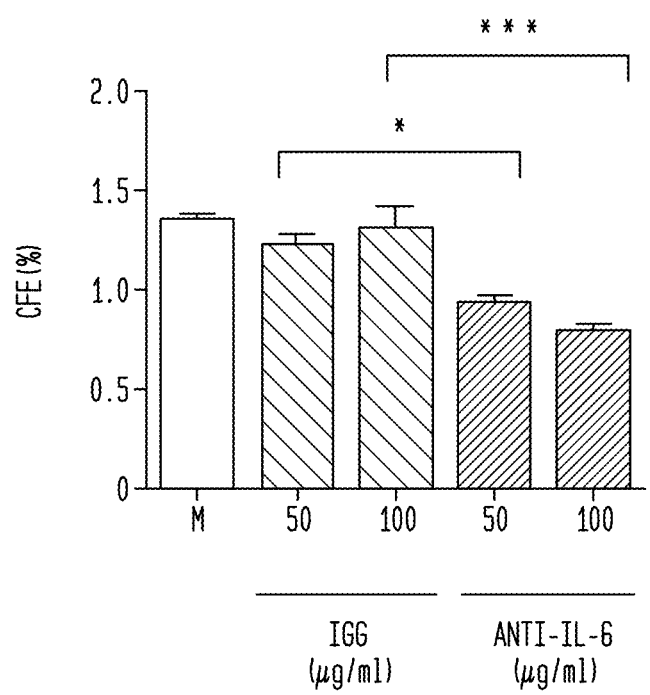
Figure 10D:
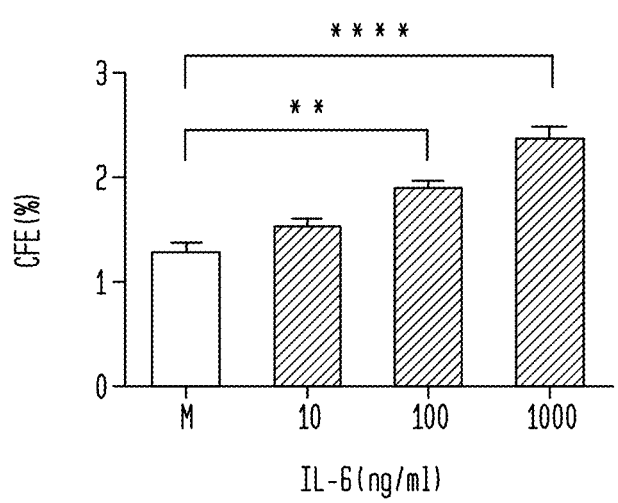
Figure 10E:
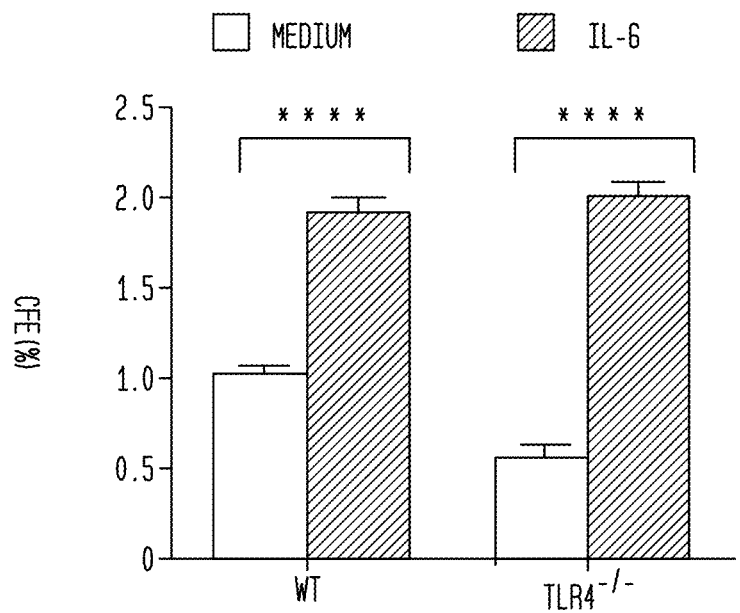
Figure 10F:
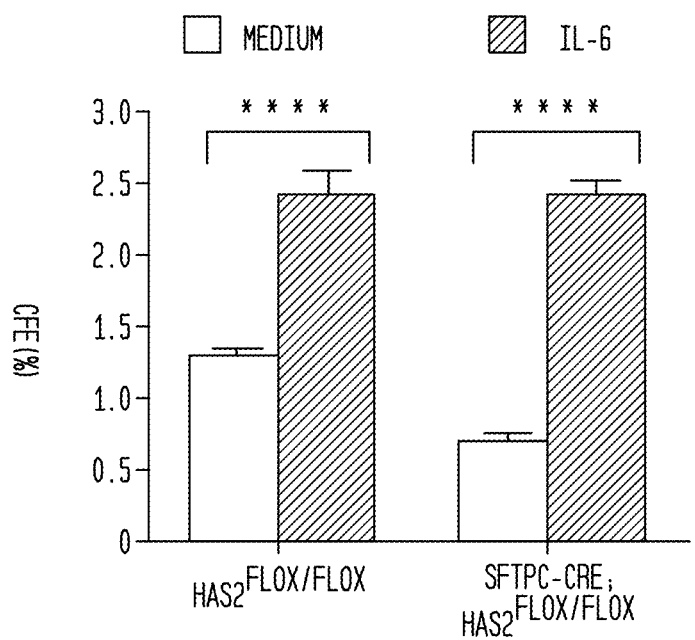
Figure 11C:
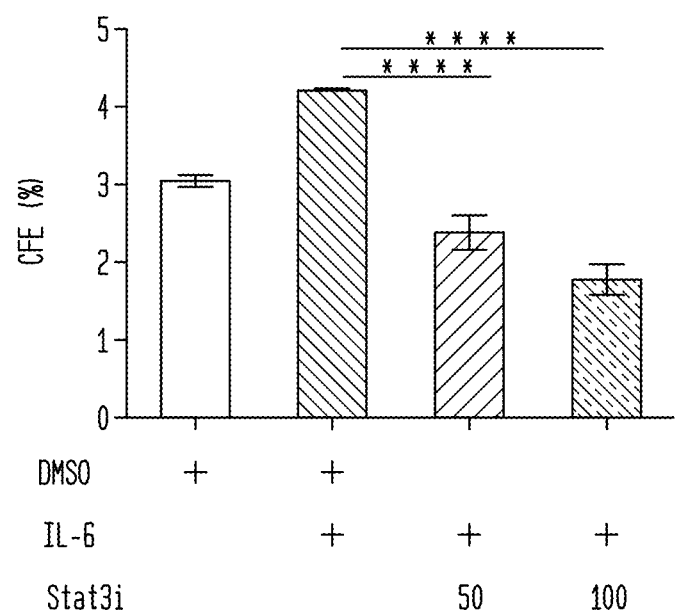

To test the hypothesis that the impaired production of IL-6 might contribute to the impaired renewal capacity of CD24⁻Sca-1⁻AEC2s from Tlr4$^{-/-}$ and SFTPC-Cre;Has2$^{flox/flox}$ mice, the CFEs of CD24⁻Sca-1⁻AEC2s in 3D organoid culture following treatment with either recombinant IL-6 protein (rIL-6) or IL-6-specific antibodies were evaluated. Treatment with anti-IL-6 reduced, whereas treatment with rIL-6 increased, the CFEs of CD24⁻Sca-1⁻AEC2s from bleomycin-treated WT mice in a dose-dependent manner (FIGS. 10C-D). Inhibition of the transcription factor STAT3 abolished the effect of rIL6-promoted colony formation of CD24⁻Sca-1⁻AEC2s (FIG. 11C), suggesting that IL-6 promotes AEC2 renewal through STAT3. In addition, rIL-6 treatment promoted the CFEs of CD24⁻Sca-1⁻AEC2s from both bleomycin-treated Tlr4$^{-/-}$ mice and SFTPC-Cre; Has2$^{flox/flox}$ mice (FIGS. 10E-F).

Figure 10G:
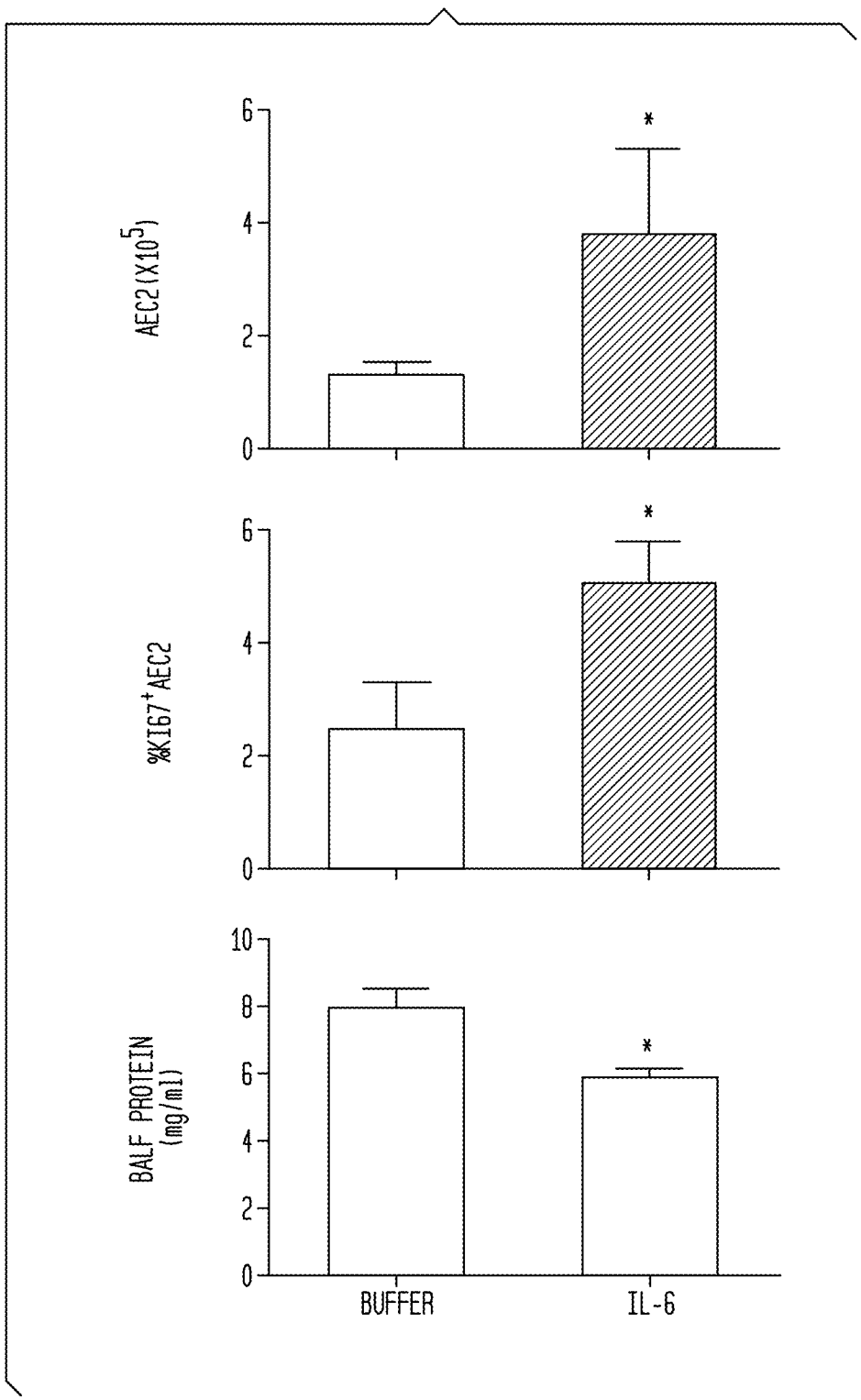
Figure 10H:
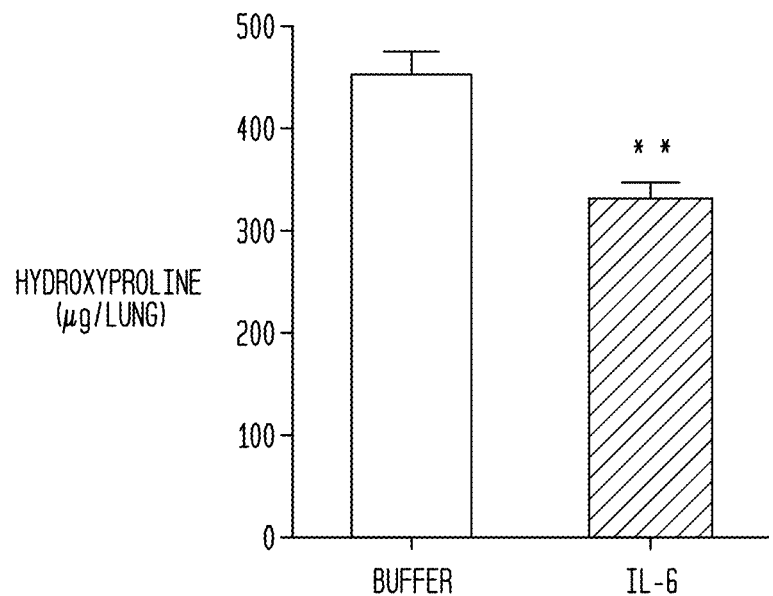
Figure 10I:
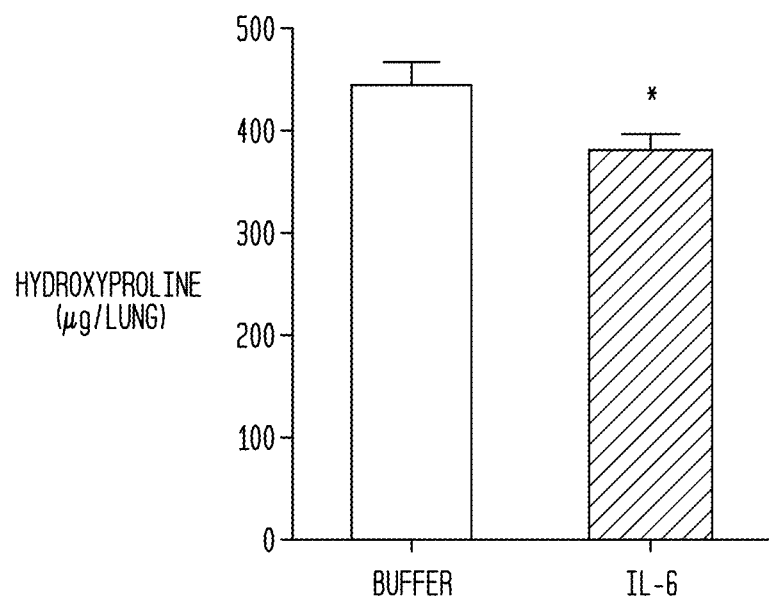
Figure 11D:
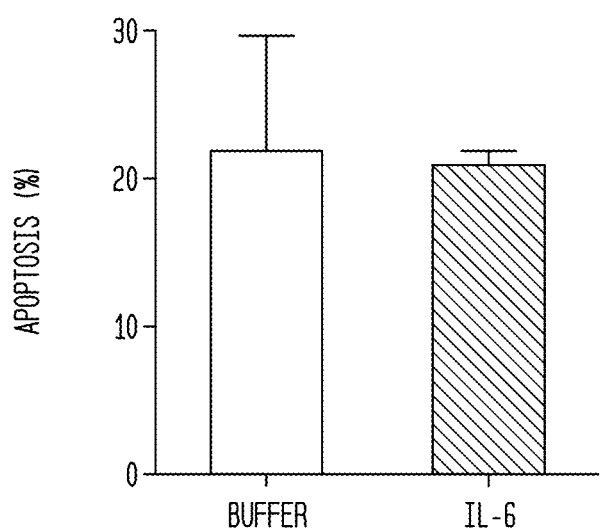
Figure 11E:
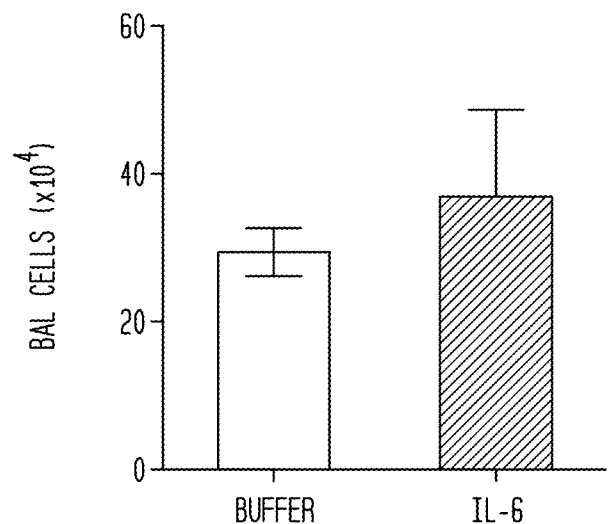
Figure 11F:
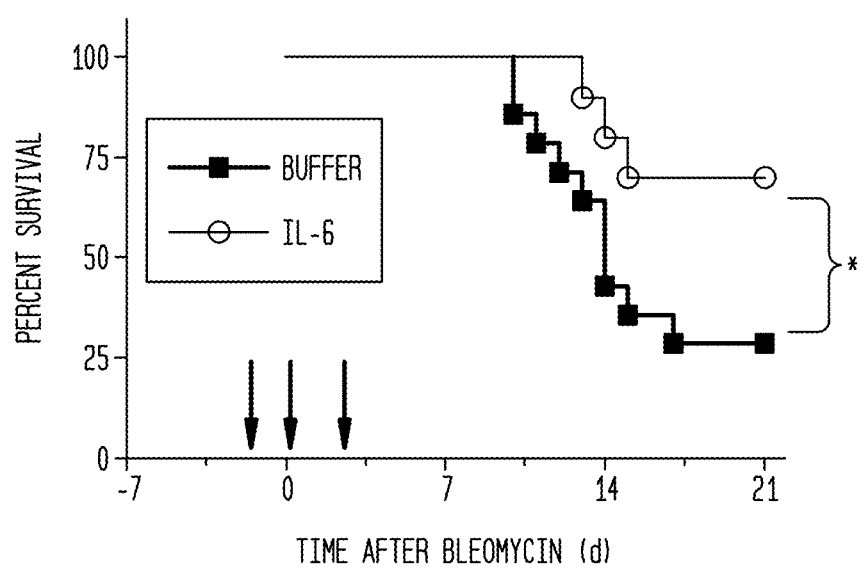
Figure 11G:
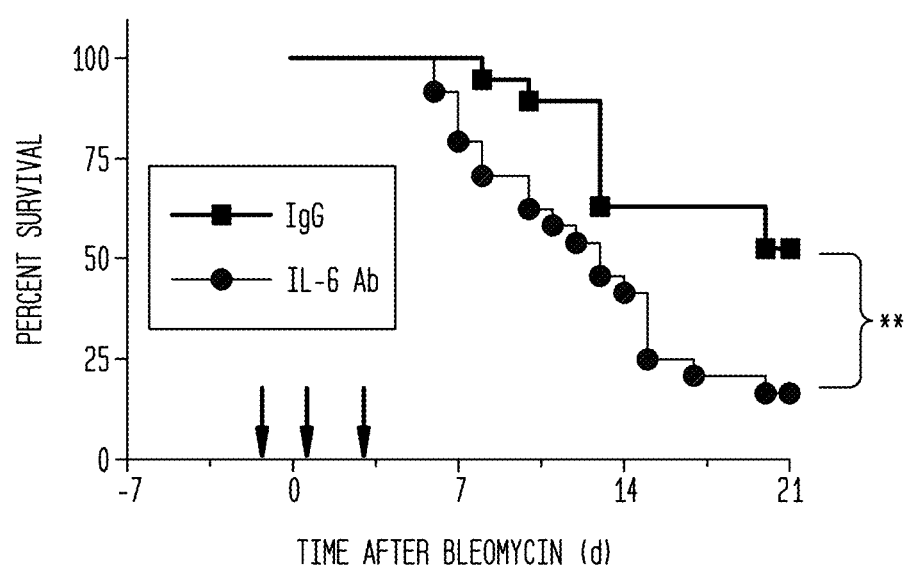

To determine whether IL-6 regulates the fibrotic phenotype in vivo, rIL-6 and anti-IL-6 were delivered to bleomycin-treated mice at the early stage of lung injury. rIL-6 treatment of Tlr4$^{-/-}$ mice resulted in more recovery of CD24⁻Sca-1⁻AEC2s, greater Ki67 staining of CD24⁻Sca-1⁻AEC2s, and lower concentration of total BALF proteins than in Tlr4$^{-/-}$ mice that were treated with a control buffer (FIG. 10G). rIL-6 treatment of Tlr4$^{-/-}$ mice did not affect AEC2 apoptosis (FIG. 11D) and inflammatory cell infiltration relative to those in buffer-treated Tlr4$^{-/-}$ mice (FIG. 11E). Bleomycin-injured Tlr4$^{-/-}$ mice that were treated with rIL-6 showed increased survival as compared to mice that were treated with buffer. In addition, hydroxyproline content was lower in the lungs of Tlr4$^{-/-}$ mice that were treated with bleomycin and rIL-6, as compared to treatment with bleomycin alone (FIG. 10H). Similarly, rIL-6 treatment resulted in lower hydroxyproline content in the lungs of SFTPC-Cre; Has2$^{flox/flox}$ mice that were injured using bleomycin, as compared to those that were treated with buffer (FIG. 10I). Conversely, bleomycin-injured WT mice that were treated with anti-IL-6 showed greater mortality than mice treated with control IgG (FIG. 11G), but we did not observe lower hydroxyproline levels in WT mice treated with anti-IL-6 as compared to the mice that were treated with control IgG (data not shown). Furthermore, delivery of rIL-6 to WT mice did not alter survival or hydroxyproline content, as compared to that for the mice treated with bleomycin alone (data not shown).

AEC2s from Patients with IPF have Lower Cell Surface Expression of HA

Figure 12A:
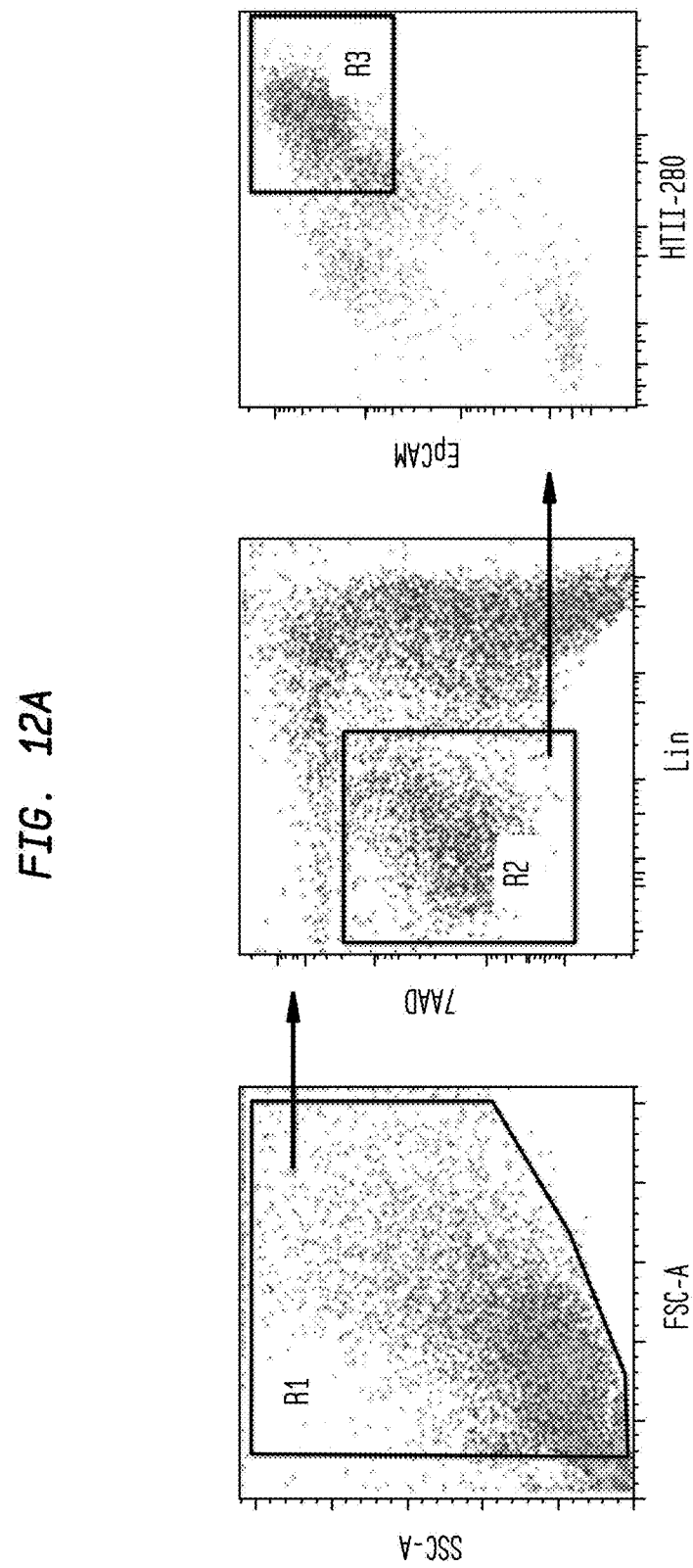
FIG. 12A-FIG. 12F show TLR4 and TLR2 expression of human AEC2s and the effect of exogenous HA on IPF AEC2 renewal.
Figure 13A:
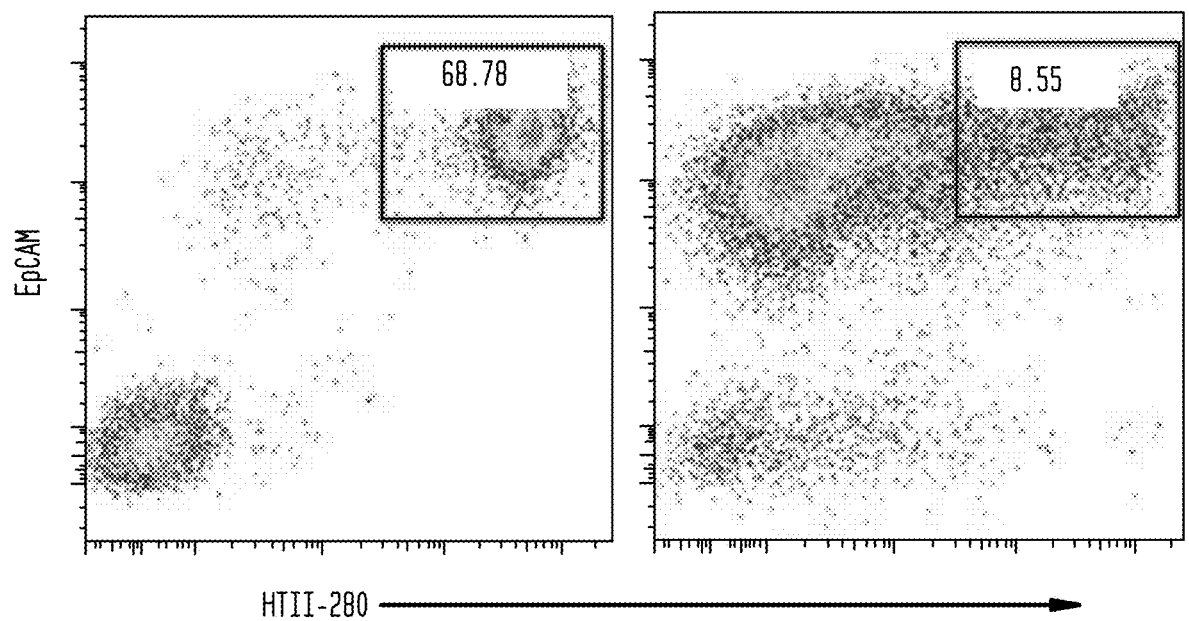
Figure 13B:
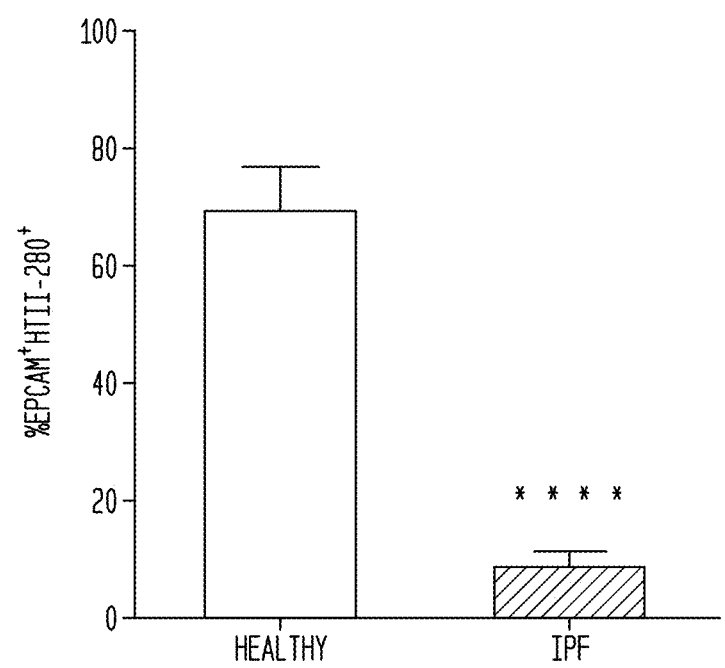
Figure 13C:
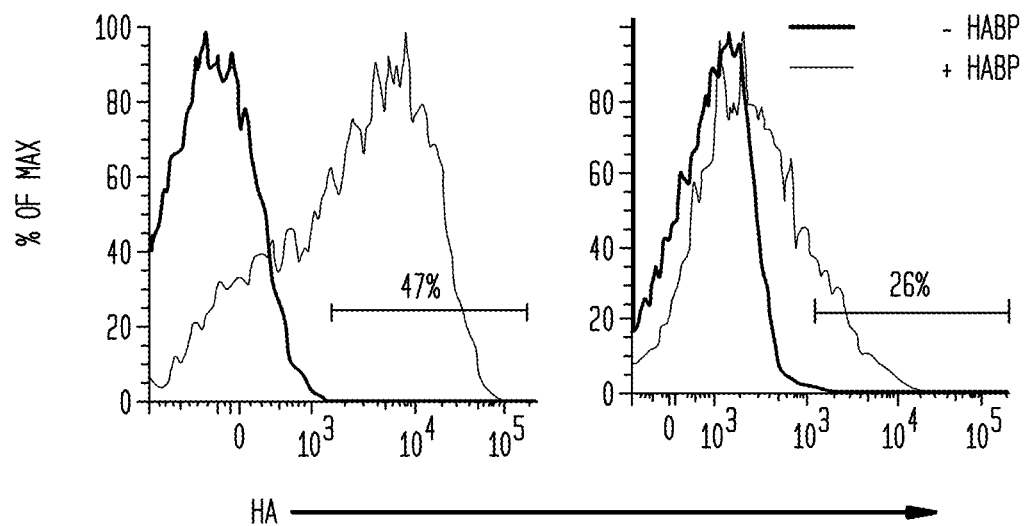
Figure 13D:
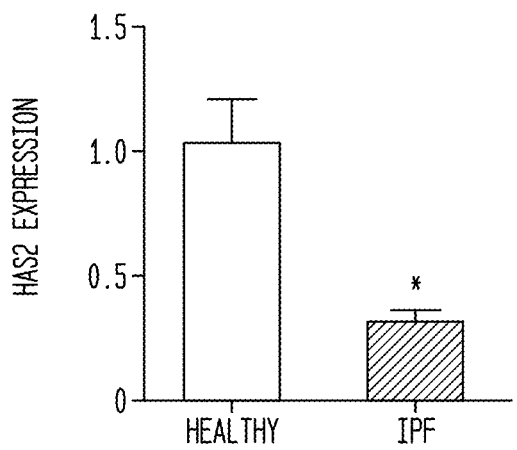
Figure 13E:
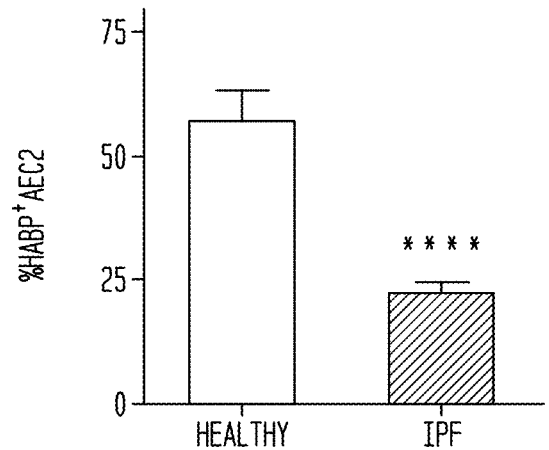

To determine whether our observations in the mouse model of Has2-deficient AEC2s have relevance to human disease, we isolated AEC2s from lung explants of human subjects who had undergone lung transplantation because of IPF. By using cell surface markers (Gonzalez et al., 2010), we were able to sort AEC2s as CD31⁻CD45⁻EpCAM⁺HTII-280⁺ cells from total single-cell suspensions of lung tissues (R3; FIG. 12A). A dramatically lower percentage of EpCAM⁺HTII-280⁺AEC2s were observed within the gated CD31⁻CD45⁻ (Lin⁻) cells in the cell suspension from lung tissue of patients with IPF, relative to those from the lung tissue of healthy donors (FIGS. 13A-B). Cell surface HA expression was markedly diminished on HTII-280⁺AEC2s from explant lung tissues of the individuals with IPF, as compared to that from lung tissue of healthy donors, similar to what was observed in the mouse model (FIGS. 13C-D). Using qPCR, patients with IPF were found to have lower HAS2 expression in HTII-280⁺AEC2s relative to that in the cells from healthy donors (FIG. 13E). These data suggest that the mouse model, which has a targeted deletion of Has2 in distal lung epithelium, recapitulates key aspects of severe pulmonary fibrosis in human disease.

Figure 12B:
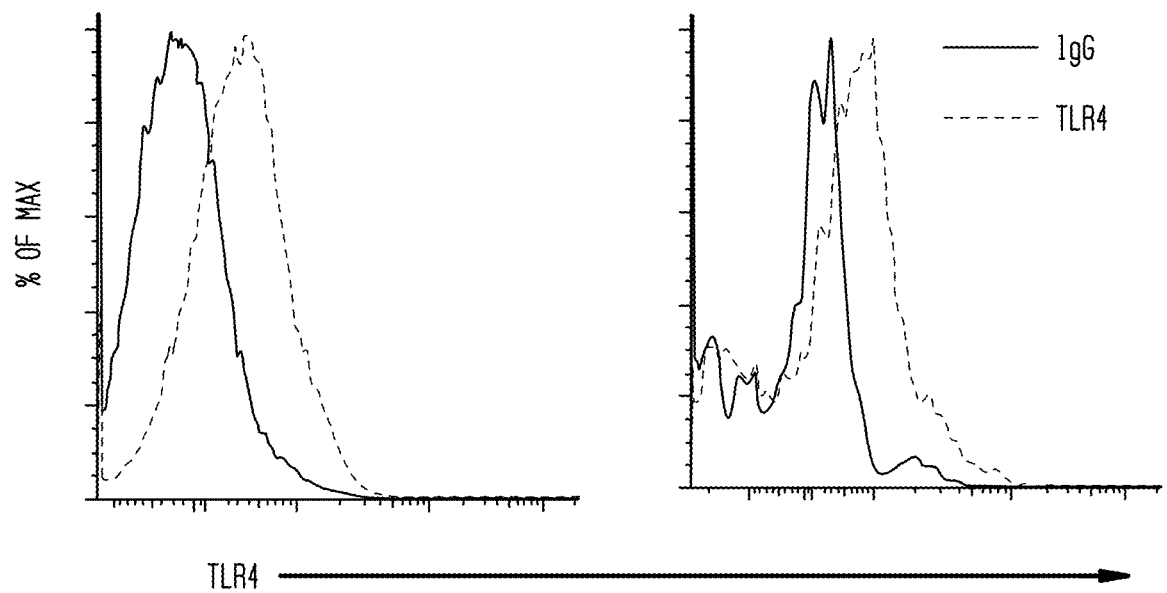
Figure 12C:
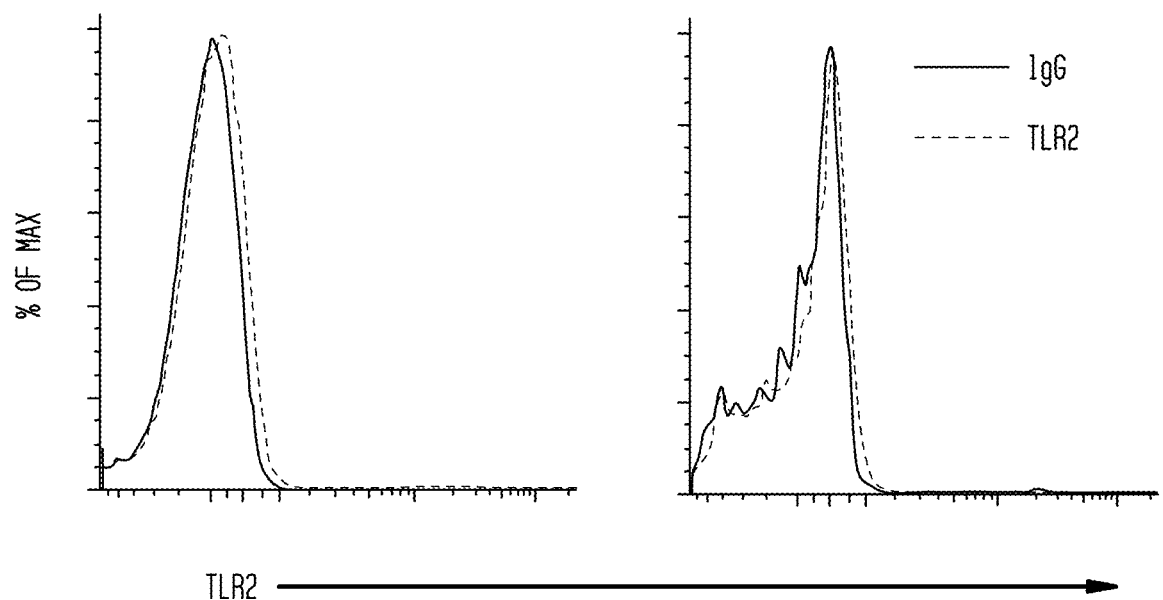

Human HTII-280⁺AEC2s expressed TLR4 (FIG. 12B) but minimal TLR2 (FIG. 12C), consistent with a previous report of TLR4 and TLR2 expression on human alveolar epithelial cells (Armstrong et al., 2004). However, there was no difference in TLR4 expression on HTII-280⁺AEC2s between subjects with IPF and healthy donors (FIG. 12B).

AEC2s from IPF Patients have Impaired Colony Forming Capacity

Figure 12D:
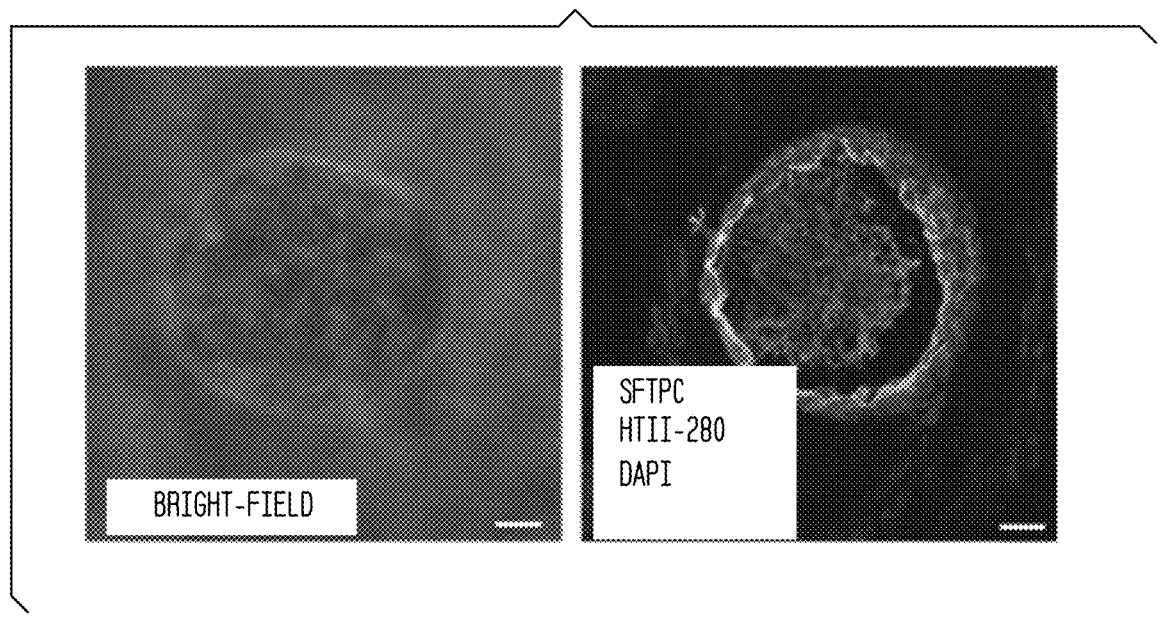
Figure 12E:
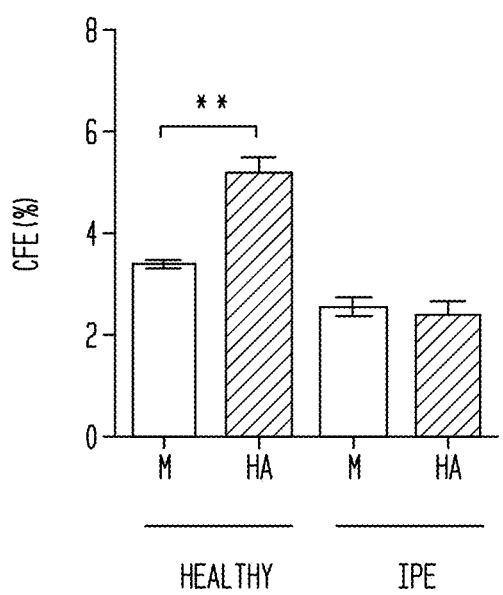
Figure 12F:
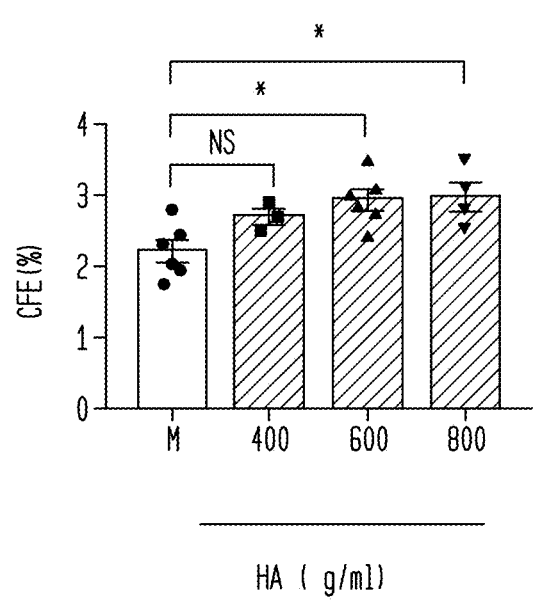

The observation that HTII-280⁺AEC2s from lung tissue of patients with severe pulmonary fibrosis have lower cell surface expression of HA led to the investigation of the renewal capacity of these cells. The renewal capacity of human HTII-280⁺AEC2s were assessed using 3D matrigel culture (FIG. 12D). Similar to what was observed in murine AEC2s that were devoid of cell surface HA, HTII-280⁺ AEC2s from lung tissues of individuals with IPF had lower CFEs (FIG. 13F) and formed smaller colonies (FIG. 13G) relative to AEC2s from the tissue of healthy donors. Furthermore, rIL-6 treatment markedly increased the CFEs of the HTII-280⁺AEC2s that were sorted from diseased lung, as compared to growth of these cells in medium without exogenous IL-6 (FIG. 13H). The concentration (200 µg/ml) of exogenous HA (Healon) that was effective in the murine model increased colony formation of HTII-280⁺AEC2s from healthy lungs but not of AEC2s from the patients with IPF (FIG. 12E). Higher concentrations of Healon were required to augment colony formation of HTII-280⁺AEC2s from IPF lungs (FIG. 12F).

Figure 13I:
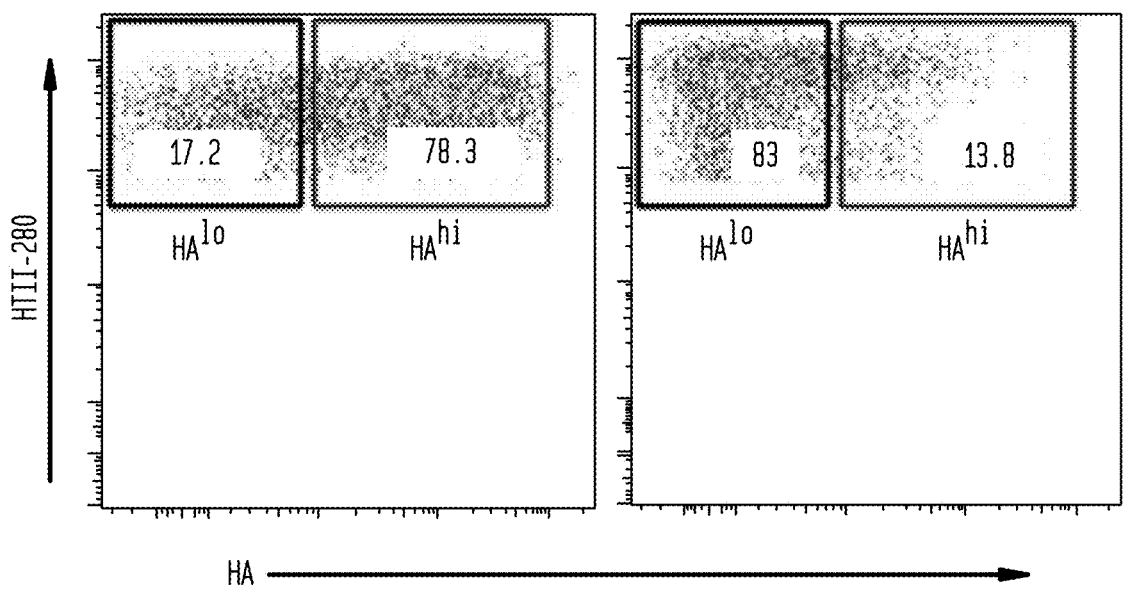
Figure 13J:
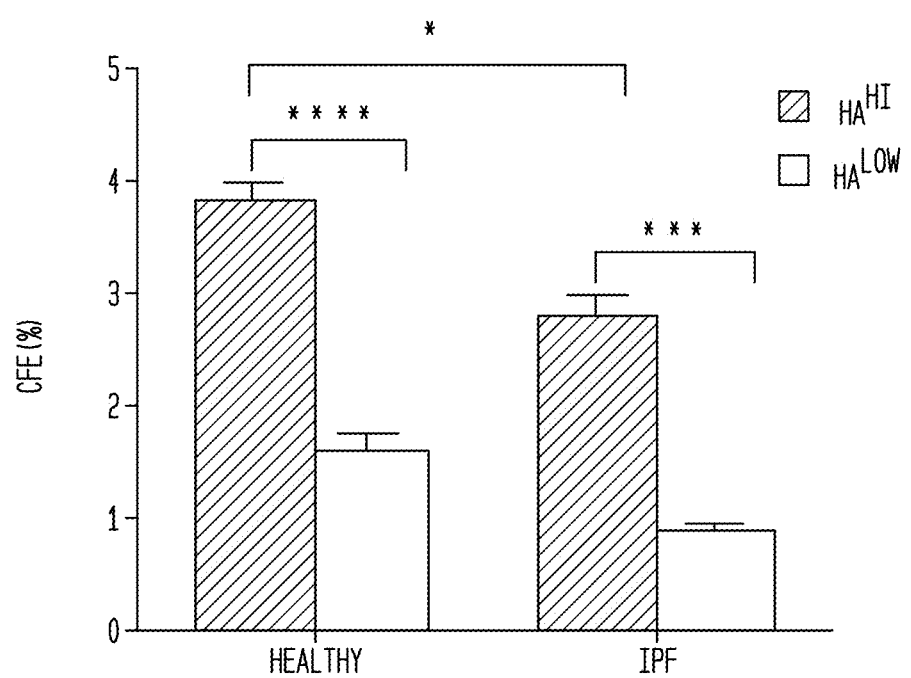

To further investigate whether loss of cell surface expression of HA on HTII-280⁺AEC2 cells in the lungs from the patients with IPF contributed to the impaired renewal capacity of the cells, HTII-280⁺AEC2s that had high HA expression (HA$^{hi}$) and low HA expression (HA$^{lo}$) from the lungs of both patients with IPF and healthy donors were flow-sorted. The majority of HTII-280⁺AEC2s from healthy lung were HA$^{hi}$ cells, and in contrast, only a small portion of HTII-280⁺AEC2s in the diseased lung were HA$^{hi}$ cells (FIG. 13I). HA$^{lo}$ HTII-280⁺AEC2s had lower CFEs than HA$^{hi}$ HTII-280⁺AEC2s from either the diseased or healthy lungs (FIG. 13J). These data indicate that loss of cell surface expression of HA on AEC2s directly contributes to the impaired renewal capacity. However, the HA$^{hi}$ HTII-280⁺ AEC2s from diseased lung still showed lower CFEs relative to those in HA$^{hi}$ HTII-280⁺AEC2s from healthy lungs (FIG. 13J), suggesting there may be other factors contributing to impaired AEC2 renewal in subjects with IPF.

Figure 14A:
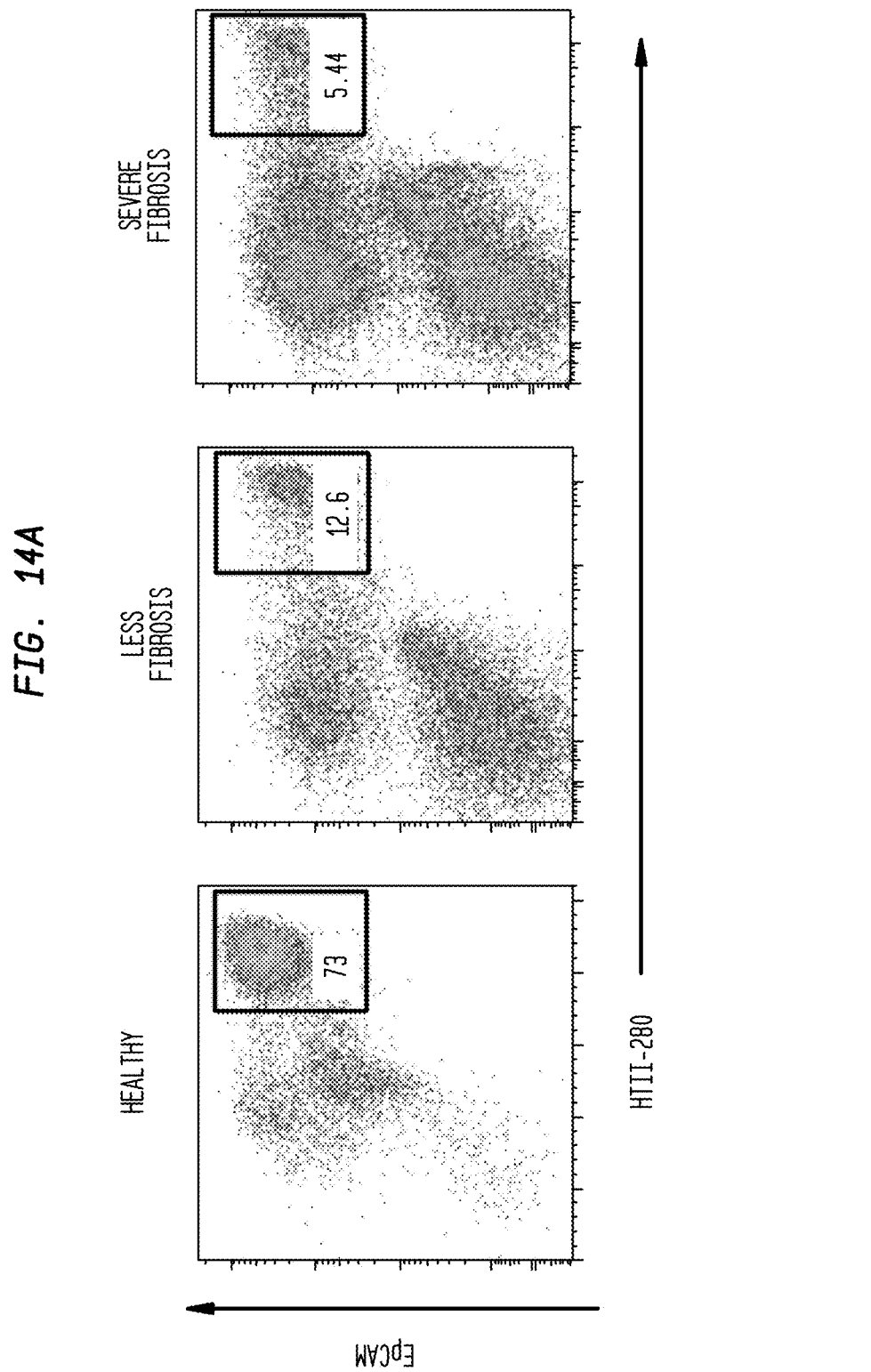
FIG. 14A-FIG. 14C demonstrate that IPF AEC2s from less and severe fibrosis area behave similarly.
Figure 14B:
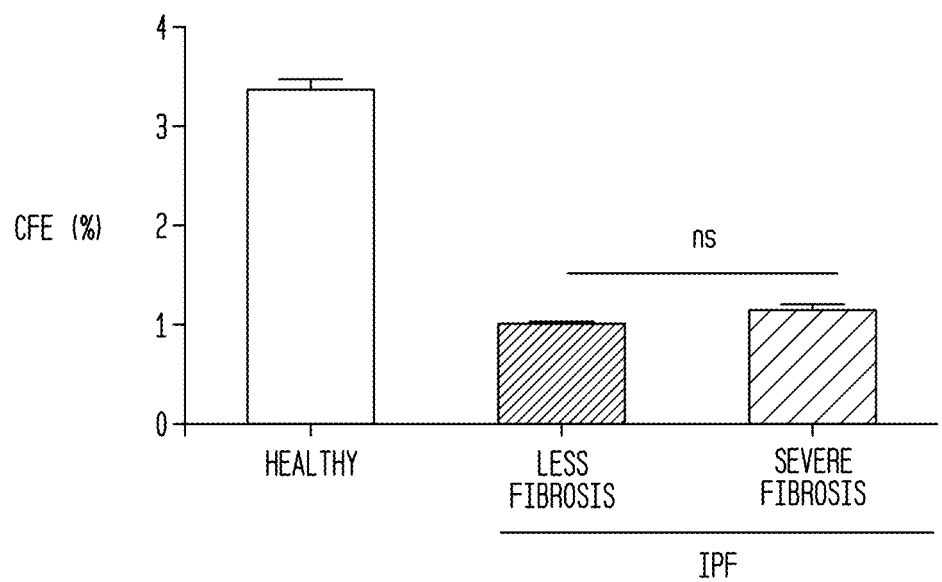
Figure 14C:
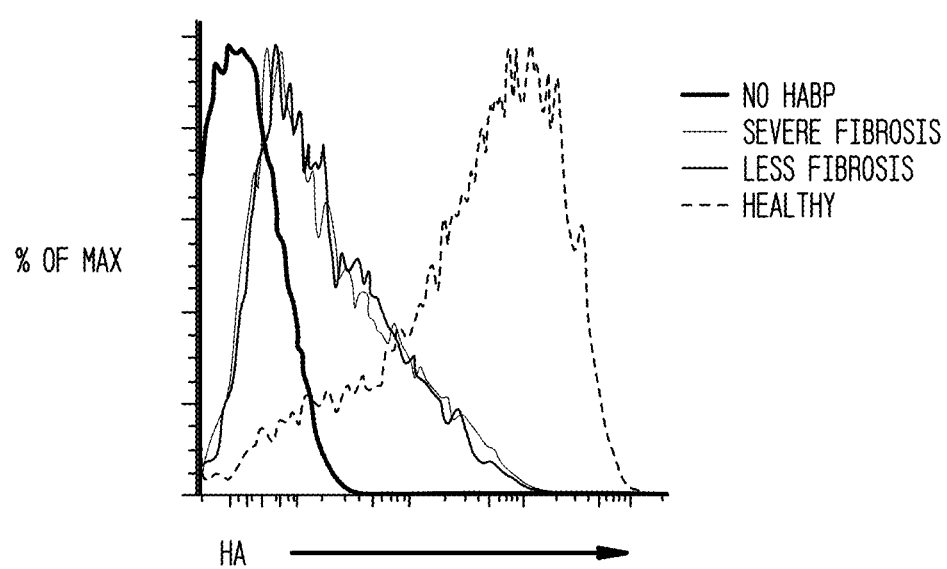

Because IPF is histologically characterized as patchy areas of apparent pulmonary parenchymal fibrosis alternating with relatively normal lung architecture, AEC2s from severely fibrotic areas were tested to see if they behaved differently than those from portions of the lung with less fibrosis in the same lung explant from patients with IPF. Flow cytometry analysis showed that cell suspensions from less fibrotic areas contained relatively higher numbers of HTII-280⁺AEC2s than less severely fibrotic areas within the same lung (FIG. 14A). However, the recovery of HTII-280⁺ AEC2s from the less fibrotic areas was still markedly lower than the recovery from healthy donor lungs (FIG. 13A and FIG. 14A). The CFEs of HTII-280⁺AEC2s showed similar impairment after the AEC2s were isolated from regions that were severely or less severely fibrotic (FIG. 14B). Cell surface HA expression on HTII-280⁺AEC2s was reduced to the same extent regardless of the degree of tissue fibrosis, although there was some variation (FIG. 14C).

Discussion

One of the critical issues in the pathobiology of lung fibrosis is an insufficient understanding of the molecular mechanisms that regulate AEC2 renewal both during tissue homeostasis and after injury. A goal of this study was to dissect the role of innate immune receptors and endogenous extracellular matrix molecules in regulating AEC2 renewal and lung fibrosis. It was found that the endogenous matrix glycosaminoglycan HA and the innate immune receptor TLR4 are required for optimal AEC2 renewal and for limiting fibrosis after lung injury. A loss in cell surface expression of HA was discovered in AEC2s isolated from the lungs of patients with IPF, and that this loss directly contributes to the impaired renewal capacity of such AEC2s.

Previous work demonstrated that HA, as well as TLR4 and TLR2, on epithelial cells were necessary to sustain basal NF-κB activation and prevent epithelial cell apoptosis (Jiang et al., 2005). In this study, the hypothesis that HA and TLR4 on the cell surface are crucial for AEC2 renewal following injury was tested. It was shown that AEC2s with deletion of either Tlr4 or Has2 have lower self-renewal capacity in vitro and lead to greater bleomycin-induced lung injury in vivo. Exogenous HA promoted WT AEC2-mediated organoid formation, but this was not observed with AEC2s from Tlr4$^{-/-}$ mice, suggesting that the interaction between cell-surface-expressed HA and TLR4 is essential for promoting AEC2 renewal.

Epithelial cells from multiple organs—including alveolar epithelial cells (Armstrong et al., 2004), intestinal epithelial cells (Abreu et al., 2001; Neal et al., 2012) and keratinocytes (Pivarcsi et al., 2003)—express innate immune receptors such as TLR4. TLRs have a role not only in immunological responses but also in epithelial protection during homeostasis and after injury. The intestinal epithelial TLR4 and commensal bacteria have a key role in protection against bacterial infection (Rakoff-Nahoum et al., 2006; Rakoff-Nahoum et al., 2004). Evidence is provided here that distal alveolar epithelial TLR4 and HA are crucial in protecting AEC2s from injury and in promoting renewal. These data suggest that cell surface HA may function in a manner similar to commensal bacteria, as the distal alveolar space is devoid of bacteria.

Many downstream signaling events may be altered in the absence of HA-TLR interactions. The described data show that insufficient production of IL-6 resulted from HA or TLR4 deficiency and that this affected the biology of lung repair both in vitro and in vivo. AEC2s isolated from both injured Tlr4$^{-/-}$ and SFTPC-Cre;Has2$^{flox/flox}$ mice demonstrated impaired renewal capacity and that this was significantly reversed by rIL-6 treatment. In addition, exogenous IL-6 treatment during the period of AEC2 vulnerability enhanced AEC2 renewal and partially reversed the fibrotic phenotype in Tlr4$^{-/-}$ and SFTPC-Cre;Has2$^{flox/flox}$ mice in vivo. IL-6 is produced by a variety of cell types, including epithelial cells and macrophages (Oh et al., 2011). The role of IL-6 in lung injury may be multifold. First, IL-6 may be produced in the reparative niche to promote stem cell renewal (Tadokoro et al., 2014; Tebbutt et al., 2002; Zhang et al., 2014). Second, IL-6 is part of a cytokine network that modulates inflammatory responses after bleomycin (Le et al., 2014). Moreover, fibroblasts produce IL-6, and IL-6-STAT3 signaling regulates lung fibrosis (Le et al., 2014; O'Donoghue et al., 2012). It is conceivable that IL-6 has distinct effects on the biology of fibrosis at varying stages of the disease process.

Cell surface HA is significantly lower on AEC2s from patients with IPF than in those from healthy individuals. In contrast, there were no significant differences identified in cell surface TLR4 expression between AEC2s from patients with IPF and healthy donors. One of the reasons for the loss of AEC2 surface HA may be a result of the deficiency in HAS2 gene expression. AEC2s with low HA expression from the lungs of either patients with IPF or healthy individuals had dramatically lower organoid-forming ability, suggesting a direct link between the loss of cell surface HA expression and the impaired renewal capacity of AEC2s. The finding that exogenous HA was able to augment the colony-forming capacity of AEC2s from fibrotic lungs further supports the concept that the loss of cell surface HA is a cause of impaired renewal of AEC2s from diseased lungs. Higher concentrations of HA were required in human AEC2s, suggesting that there are differences with the mouse model system.

These findings support the concept that IPF is primarily a disease of AEC2 stem cell failure. The loss of the HA-synthesizing enzyme in AEC2s was identified as a primary defect leading to the susceptibility to fibrosis. In addition, innate immune receptors were shown to promote epithelial regeneration in addition to the established functions in inflammation. The mouse model using a targeted deletion of Has2 in distal lung epithelium recapitulates key aspects of severe pulmonary fibrosis in human disease. AEC2s isolated from lung explants of patients with chronic obstructive pulmonary disease (COPD), another severe lung disease but with a very different pathology, expressed cell surface HA levels similar to that in AEC2s from healthy donors (data not shown), suggesting that loss of cell surface HA on AEC2s is a unique feature of severe pulmonary fibrosis.

The entire contents of all patents, published patent applications, and other references cited herein are hereby expressly incorporated herein in their entireties by reference.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto

REFERENCES

1. Rakoff-Nahoum, S., Hao, L. & Medzhitov, R. Role of toll-like receptors in spontaneous commensal-dependent colitis. Immunity 25, 319-329 (2006).
2. Rakoff-Nahoum, S., et al. Recognition of commensal microflora by toll-like receptors is required for intestinal homeostasis. Cell 118, 229-241 (2004).
3. Fukata, M. et al. Cox-2 is regulated by Toll-like receptor 4 (TLR4) signaling: role in proliferation and apoptosis in the intestine. Gastroenterology 131, 862-877 (2006).
4. Hogan, B. L. et al. Repair and regeneration of the respiratory system: complexity, plasticity and mechanisms of lung stem cell function. Cell Stem Cell 15, 123-138 (2014).
5. Kotton, D. N. & Morrisey, E. E. Lung regeneration: mechanisms, applications and emerging stem cell populations. Nat. Med. 20, 822-832 (2014).

6. Desai, T. J., Brownfield, D. G. & Krasnow, M. A. Alveolar progenitor and stem cells in lung development, renewal and cancer. Nature 507, 190-194 (2014).
7. Barkauskas, C. E. et al. Type 2 alveolar cells are stem cells in adult lung. J. Clin. Invest. 123, 3025-3036 (2013).
8. Hofer, C. C., et al. Infection of mice with influenza A/WSN/33 (H1N1) virus alters alveolar type II cell phenotype. Am. J. Physiol. Lung Cell. Mol. Physiol. 308, L628-L638 (2015).
9. Liu, Y., et al. Activation of type II cells into regenerative stem-cell-antigen-1+ cells during alveolar repair. Am. J. Respir. Cell Mol. Biol. 53, 113-124 (2015).
10. Rock, J. R. et al. Multiple stromal populations contribute to pulmonary fibrosis without evidence for epithelial-to-mesenchymal transition. Proc. Natl. Acad. Sci. USA 108, E1475-E1483 (2011).
11. Jiang, D. et al. Regulation of lung injury and repair by Toll-like receptors and hyaluronan. Nat. Med. 11, 1173-1179 (2005).
12. Jiang, D., Liang, J., Li, Y. & Noble, P. W. The role of Toll-like receptors in noninfectious lung injury. Cell Res. 16, 693-701 (2006).
13. Jiang, D., Liang, J. & Noble, P. W. Hyaluronan in tissue injury and repair. Annu. Rev. Cell Dev. Biol. 23, 435-461 (2007).
14. Noble, P. W. & Jiang, D. Matrix regulation of lung injury, inflammation and repair: the role of innate immunity. Proc. Am. Thorac. Soc. 3, 401-404 (2006).
15. Jiang, D., Liang, J. & Noble, P. W. Hyaluronan as an immune regulator in human diseases. Physiol. Rev. 91, 221-264 (2011).
16. Camenisch, T. D. et al. Disruption of hyaluronan synthase 2 abrogates normal cardiac morphogenesis and hyaluronan-mediated transformation of epithelium to mesenchyme. J. Clin. Invest. 106, 349-360 (2000).
17. American Thoracic Society. Idiopathic pulmonary fibrosis: diagnosis and treatment. International consensus statement. The joint statement of American Thoracic Society (ATS) and the European Respiratory Society (ERS). Am. J. Respir. Crit. Care Med. 161, 646-664 (2000).
18. Selman, M. et al. Idiopathic pulmonary fibrosis: pathogenesis and therapeutic approaches. Drugs 64, 405-430 (2004).
19. Noble, P. W., Barkauskas, C. E. & Jiang, D. Pulmonary fibrosis: patterns and perpetrators. J. Clin. Invest. 122, 2756-2762 (2012).
20. Amin, R. S. et al. Surfactant protein deficiency in familial interstitial lung disease. J. Pediatr. 139, 85-92 (2001).
21. Thomas, A. Q. et al. Heterozygosity for a surfactant protein C gene mutation associated with usual interstitial pneumonitis and cellular nonspecific interstitial pneumonitis in one kindred. Am. J. Respir. Crit. Care Med. 165, 1322-1328 (2002).
22. Garcia, C. K. Idiopathic pulmonary fibrosis: update on genetic discoveries. Proc. Am. Thorac. Soc. 8, 158-162 (2011).
23. Alder, J. K. et al. Telomere dysfunction causes alveolar stem cell failure. Proc. Natl. Acad. Sci. USA 112, 5099-5104 (2015).
24. Chen, H. et al. Airway epithelial progenitors are region specific and show differential responses to bleomycin-induced lung injury. Stem Cells 30, 1948-1960 (2012).
25. Mummert, M. E., et al. Development of a peptide inhibitor of hyaluronan-mediated leukocyte trafficking. J. Exp. Med. 192, 769-779 (2000).
26. Li, Y. et al. Severe lung fibrosis requires an invasive fibroblast phenotype regulated by hyaluronan and CD44. J. Exp. Med. 208, 1459-1471 (2011).
27. Matsumoto, K. et al. Conditional inactivation of Has2 reveals a crucial role for hyaluronan in skeletal growth, patterning, chondrocyte maturation and joint formation in the developing limb. Development 136, 2825-2835 (2009).
28. Eblaghie, M. C., et al. Evidence that autocrine signaling through Bmpr1a regulates the proliferation, survival and morphogenetic behavior of distal lung epithelial cells. Dev. Biol. 291, 67-82 (2006).
29. Gonzalez, R. F., et al. HTII-280, a biomarker specific to the apical plasma membrane of human lung alveolar type II cells. J. Histochem. Cytochem. 58, 891-901 (2010).
30. Armstrong, L. et al. Expression of functional toll-like receptor-2 and -4 on alveolar epithelial cells. Am. J. Respir. Cell Mol. Biol. 31, 241-245 (2004).
31. Abreu, M. T. et al. Decreased expression of Toll-like receptor 4 and MD-2 correlates with intestinal epithelial cell protection against dysregulated proinflammatory gene expression in response to bacterial lipopolysaccharide. J. Immunol. 167, 1609-1616 (2001).
32. Neal, M. D. et al. Toll-like receptor 4 is expressed on intestinal stem cells and regulates their proliferation and apoptosis via the p53-upregulated modulator of apoptosis. J. Biol. Chem. 287, 37296-37308 (2012).
33. Pivarcsi, A. et al. Expression and function of Toll-like receptors 2 and 4 in human keratinocytes. Int. Immunol. 15, 721-730 (2003).
34. Oh, K. et al. Epithelial transglutaminase 2 is needed for T cell interleukin-17 production and subsequent pulmonary inflammation and fibrosis in bleomycin-treated mice. J. Exp. Med. 208, 1707-1719 (2011).
35. Tadokoro, T. et al. IL-6-STAT3 promotes regeneration of airway ciliated cells from basal stem cells. Proc. Natl. Acad. Sci. USA 111, E3641-E3649 (2014).
36. Tebbutt, N. C. et al. Reciprocal regulation of gastrointestinal homeostasis by SHP2 and STAT-mediated trefoil gene activation in gp130-mutant mice. Nat. Med. 8, 1089-1097 (2002).
37. Zhang, S. et al. Interleukin 6 mediates the therapeutic effects of adipose-derived stromal-stem cells in lipopolysaccharide-induced acute lung injury. Stem Cells 32, 1616-1628 (2014).
38. Le, T. T. et al. Blockade of IL-6 trans-signaling attenuates pulmonary fibrosis. J. Immunol. 193, 3755-3768 (2014).
39. O'Donoghue, R. J. et al. Genetic partitioning of interleukin-6 signaling in mice dissociates Stat3 from Smad3-mediated lung fibrosis. EMBO Mol. Med. 4, 939-951 (2012).
40. Rafii, S. et al. Platelet-derived SDF-1 primes the pulmonary capillary vascular niche to drive lung alveolar regeneration. Nat. Cell Biol. 17, 123-136 (2015).
41. Cao, Z. et al. Targeting of the pulmonary capillary vascular niche promotes lung alveolar repair and ameliorates fibrosis. Nat. Med. 22, 154-162 (2016).
42. Guzy, R. D. et al. Fibroblast growth factor 2 is required for epithelial recovery, but not for pulmonary fibrosis, in response to bleomycin. Am. J. Respir. Cell Mol. Biol. 52, 116-128 (2015).
43. Chapman, H. A. et al. Integrin a6β4 identifies an adult distal lung epithelial population with regenerative potential in mice. J. Clin. Invest. 121, 2855-2862 (2011).

44. Lee, J. H. et al. Lung stem cell differentiation in mice directed by endothelial cells via a BMP4-NFATc1-thrombospondin-1 axis. Cell 156, 440-455 (2014).
45. Treutlein, B. et al. Reconstructing lineage hierarchies of the distal lung epithelium using single-cell RNA-seq. Nature 509, 371-375 (2014).
46. Vaughan, A. E. et al. Lineage-negative progenitors mobilize to regenerate lung epithelium after major injury. Nature 517, 621-625 (2015).
47. Takeuchi, O. et al. Differential roles of TLR2 and TLR4 in recognition of Gram-negative and Gram-positive bacterial cell wall components. Immunity 11, 443-451 (1999).
48. Kawai, T., Adachi, O., Ogawa, T., Takeda, K. & Akira, S. Unresponsiveness of MyD88-deficient mice to endotoxin. Immunity 11, 115-122 (1999).
49. Jeannotte, L. et al. Unsuspected effects of a lung-specific Cre deleter mouse line. Genesis 49, 152-159 (2011).
50. Morales-Nebreda, L. I. et al. Lung-specific loss of a3-laminin worsens bleomycin-induced pulmonary fibrosis. Am. J. Respir. Cell Mol. Biol. 52, 503-512 (2015).
51. Dong, Y. et al. Blocking follistatin-like 1 attenuates bleomycin-induced pulmonary fibrosis in mice. J. Exp. Med. 212, 235-252 (2015).
52. Lovgren, A. K. et al. β-arrestin deficiency protects against pulmonary fibrosis in mice and prevents fibroblast invasion of extracellular matrix. Sci. Transl. Med. 3, 74ra23 (2011).
53. Jiang, D. et al. Regulation of pulmonary fibrosis by chemokine receptor CXCR3. J. Clin. Invest. 114, 291-299 (2004).
54. Liang, J. et al. A macrophage subpopulation recruited by CC chemokine ligand 2 clears apoptotic cells in non-infectious lung injury. Am. J. Physiol. Lung Cell. Mol. Physiol. 302, L933-L940 (2012).
55. Liang, J. et al. Role of hyaluronan and hyaluronan-binding proteins in human asthma. J. Allergy Clin. Immunol. 128, 403-411.e3 (2011).
56. Jiang, D. et al. Inhibition of pulmonary fibrosis in mice by CXCL10 requires glycosaminoglycan binding and syndecan 4. J. Clin. Invest. 120, 2049-2057 (2010).

What is claimed is:

1. A method of treating a lung injury at risk of progressing to a fibrotic lung disease in a subject in need thereof comprising administering to the subject a pharmaceutical composition comprising a therapeutic amount of IL-6 polypeptide, a variant IL-6 polypeptide having no more than ten amino acid differences as compared to an IL-6 polypeptide encoded by SEQ ID NO:13 while retaining IL-6 activity, or pharmaceutically acceptable salts thereof, wherein the therapeutic amount increases renewal of alveolar epithelial cell 2 (AEC2) stem cells, repairs the injury, reduces lung fibrosis, or a combination thereof.

2. The method according to claim 1, wherein the lung injury or fibrotic lung disease is pulmonary fibrosis.

3. The method according to claim 1, wherein the lung injury or fibrotic lung disease is idiopathic pulmonary fibrosis (IPF).

4. The method according to claim 1, wherein the lung injury is a bleomycin-induced lung injury.

5. The method according to claim 1, wherein the method further comprises administering to the subject a therapeutic amount of one or a plurality of immunomodulators, analgesics, anti-inflammatory compounds, anti-fibrotic compounds, proton pump inhibitors, oxygen therapy, or combinations thereof.

6. The method according to claim 5,
i. wherein the immunomodulator is prednisone, azathioprine, mycophenolate, mycophenolate mofetil, colchicine, or interferon-gamma 1b; or
ii. wherein the analgesic is codeine, hydrocodone, oxycodone, methadone, hydromorphone, morphine, or fentanyl; or
iii. wherein the anti-inflammatory compound is aspirin, celecoxib, diclofenac, diflunisal, etodolac, ibuprofen, indomethacin, ketoprofen, ketorolac nabumetone, naproxen, nintedanib, oxaprozin, pirfenidone, piroxicam, salsalate, sulindac, or tolmetin; or
iv. wherein the anti-fibrotic compound is nintedanib or pirfenidone; or
v. wherein the proton pump inhibitor is omeprazole, lansoprazole, dexlansoprazole, esomeprazole, pantoprazole, rabeprazole, or ilaprazole.

7. The method according to claim 1, wherein the IL-6 polypeptide is a recombinant IL-6 polypeptide or pharmaceutically acceptable salt thereof.

8. The method according to claim 1, wherein the therapeutic amount is effective to increase the cell surface expression of hyaluronan in one or a plurality of alveolar epithelial cell 2 (AEC2) cells in the subject.

9. The method according to claim 1, wherein the therapeutic amount increases toll-like receptor 4 (TLR4)-hyaluronan (HA) signaling in the subject.

10. A method of increasing alveolar epithelial cell 2 (AEC2) stem cell renewal in a lung to reduce progression of a lung injury to a fibrotic disease in a subject in need thereof comprising administering to the subject a pharmaceutical composition comprising a therapeutic amount of IL-6 polypeptide, a variant IL-6 polypeptide having no more than ten amino acid differences as compared to an IL-6 polypeptide encoded by SEQ ID NO:13 while retaining IL-6 activity, or pharmaceutically acceptable salts thereof.

11. The method according to claim 10, wherein the lung injury or fibrotic lung disease is pulmonary fibrosis.

12. The method according to claim 10, wherein the lung injury or fibrotic lung disease is idiopathic pulmonary fibrosis (IPF).

13. The method according to claim 10, wherein the lung injury is a bleomycin-induced lung injury.

14. The method according to claim 10, wherein the method further comprises administering to the subject a therapeutic amount of one or a plurality of immunomodulators, analgesics, anti-inflammatory compounds, anti-fibrotic compounds, proton pump inhibitors, oxygen therapy, or combinations thereof.

15. The method according to claim 14,
i. wherein the immunomodulator is prednisone, azathioprine, mycophenolate, mycophenolate mofetil, colchicine, or interferon-gamma 1b; or
ii. wherein the analgesic is codeine, hydrocodone, oxycodone, methadone, hydromorphone, morphine, or fentanyl; or
iii. wherein the anti-inflammatory compound is aspirin, celecoxib, diclofenac, diflunisal, etodolac, ibuprofen, indomethacin, ketoprofen, ketorolac nabumetone, naproxen, nintedanib, oxaprozin, pirfenidone, piroxicam, salsalate, sulindac, or tolmetin; or
iv. wherein the anti-fibrotic compound is nintedanib or pirfenidone; or
v. wherein the proton pump inhibitor is omeprazole, lansoprazole, dexlansoprazole, esomeprazole, pantoprazole, rabeprazole, or ilaprazole.

16. The method according to claim 10, wherein the IL-6 polypeptide is a recombinant IL-6 polypeptide or pharmaceutically acceptable salt thereof.

17. The method according to claim 10, wherein the therapeutic amount increases the cell surface expression of hyaluronan in one or a plurality of alveolar epithelial cell 2 (AEC2s) in the subject.

18. The method according to claim 10, wherein the therapeutic amount increases toll-like receptor 4 (TLR4)-hyaluronan (HA) signaling in the subject.

* * * * *